(12) United States Patent
Jarvis et al.

(10) Patent No.: US 8,575,113 B2
(45) Date of Patent: Nov. 5, 2013

(54) BIR DOMAIN BINDING COMPOUNDS

(75) Inventors: Scott Jarvis, Longueuil (CA); Alain Boudreault, Montreal (CA); Patrick Bureau, Kirkland (CA); James B. Jaquith, Pincourt (CA); Alain Laurent, Montreal (CA); Delphine Labit, LaSalle (CA)

(73) Assignee: Pharmascience Inc., Montreal, Quebec (CA)

( * ) Notice: Subject to any disclaimer, the term of this patent is extended or adjusted under 35 U.S.C. 154(b) by 425 days.

(21) Appl. No.: 12/825,197

(22) Filed: Jun. 28, 2010

(65) Prior Publication Data
US 2010/0292269 A1 Nov. 18, 2010

Related U.S. Application Data

(63) Continuation-in-part of application No. 11/434,166, filed on May 16, 2006, now Pat. No. 7,772,177.

(60) Provisional application No. 60/682,000, filed on May 18, 2005, provisional application No. 60/716,489, filed on Sep. 14, 2005, provisional application No. 60/725,280, filed on Oct. 12, 2005.

(51) Int. Cl.
| | | |
|---|---|---|
| A61K 38/06 | (2006.01) | |
| A61K 38/07 | (2006.01) | |
| A61K 38/00 | (2006.01) | |
| A61P 43/00 | (2006.01) | |

(52) U.S. Cl.
USPC .......................... 514/21.9; 514/18.9

(58) Field of Classification Search
None
See application file for complete search history.

(56) References Cited

U.S. PATENT DOCUMENTS

| | | | |
|---|---|---|---|
| 5,750,646 A | 5/1998 | Coy et al. | |
| 6,110,691 A | 8/2000 | Wang et al. | |
| 6,423,689 B1 | 7/2002 | Booth et al. | |
| 6,608,026 B1 | 8/2003 | Wang et al. | |
| 6,992,063 B2 | 1/2006 | Shi | |
| 7,041,784 B2 | 5/2006 | Wang et al. | |
| 7,094,758 B2 | 8/2006 | Wang et al. | |
| 7,229,617 B2 | 6/2007 | Nasoff et al. | |
| 7,244,851 B2 | 7/2007 | Cohen et al. | |
| 7,309,792 B2 | 12/2007 | Harran et al. | |
| 7,419,975 B2 | 9/2008 | Palermo et al. | |
| 7,456,209 B2 | 11/2008 | Condon et al. | |
| 7,517,906 B2 | 4/2009 | Condon et al. | |
| 7,772,177 B2 * | 8/2010 | Jarvis et al. ................ 514/4.1 |
| 2004/0180828 A1 | 9/2004 | Shi et al. | |
| 2006/0025347 A1 | 2/2006 | Condon et al. | |
| 2006/0194741 A1 | 8/2006 | Condon et al. | |
| 2006/0211627 A1 | 9/2006 | Reed et al. | |
| 2006/0258581 A1 | 11/2006 | Reed et al. | |
| 2007/0032437 A1 | 2/2007 | Shi et al. | |
| 2007/0042428 A1 | 2/2007 | Springs et al. | |
| 2007/0093428 A1 | 4/2007 | Laurent | |
| 2007/0093429 A1 | 4/2007 | Laurent et al. | |
| 2007/0219140 A1 | 9/2007 | Laurent et al. | |
| 2008/0069812 A1 | 3/2008 | Boudreault et al. | |
| 2008/0089896 A1 | 4/2008 | Wang et al. | |
| 2008/0207525 A1 | 8/2008 | Boudreault et al. | |

FOREIGN PATENT DOCUMENTS

| | | |
|---|---|---|
| CA | 2 491 041 A1 | 1/2004 |
| CA | 2 582 734 A1 | 9/2005 |
| CA | 2 560 162 A1 | 10/2005 |
| CA | 2 574 040 A1 | 2/2006 |
| JP | 61183297 A | 8/1986 |
| JP | 04208299 A | 7/1992 |
| WO | WO 92/02545 A1 | 2/1992 |
| WO | WO 92/12168 A1 | 7/1992 |
| WO | WO 00/01726 A1 | 1/2000 |
| WO | WO 02/26775 A2 | 4/2002 |
| WO | WO 02/30959 A2 | 4/2002 |
| WO | WO 02/096930 A2 | 12/2002 |
| WO | WO 03/086470 A2 | 10/2003 |
| WO | WO 2004/005248 A1 | 1/2004 |
| WO | WO 2005/069888 A2 | 8/2005 |
| WO | WO 2005/074989 A2 | 8/2005 |
| WO | WO 2005/084317 A2 | 9/2005 |
| WO | WO 2005/094818 A1 | 10/2005 |
| WO | WO 2005/097791 A1 | 10/2005 |
| WO | WO 2006/010118 A2 | 1/2006 |

(Continued)

OTHER PUBLICATIONS

Zips et al. New Anticancer Agents: In Vitro and In Vivo Evaluation. Review. In vivo. 2005. vol. 19, pp. 1-8.*
Voskoglou-Nomikos et al. Clinical Predictive Value of the in Vitro Cell Line, Human Xenograft, and Mouse Allograft Preclinical Cancer Models. Clinical Cancer Research. 2003. vol. 9, pp. 4227-4239.*
Sporn et al. Chemoprevention of cancer. Carcinogenesis. 2000. vol. 21, No. 3, pp. 525-530.*
Arnt et al., *J. Biol. Chem.*, "Synthetic Smac/DIABLO peptides enhance the effects of chemotherapeutic agents by binding XIAP and cIAP1 in Situ," 277(46): 44236-44243 (2002).
Bertrand et al., *Mol. Cell*, "cIAP1 and cIAP2 facilitate cancer cell survival by functioning as E3 ligases that promote RIP1 ubiquitination," 30: 689-700 (2008).
Bucher et al., *Helv. Chim. Acta.*, 78(4):935-46 (1995).
Chai et al., *Nature*, "Structural and biochemical basis of apoptotic activation by Smac/DIABLO," 406: 855-62 (2000).
Chauhan et al., *Blood*, "Targeting mitochondrial factor Smac/DIABLO as therapy for multiple myeloma (MM)," 109(3): 1220-7 (2007).

(Continued)

*Primary Examiner* — Marcela M Cordero Garcia
(74) *Attorney, Agent, or Firm* — Leydig, Voit & Mayer, Ltd.

(57) ABSTRACT

The present invention is directed towards an isomer, an enantiomer, a diastereoisomer, or a tautomer of a pyrrolidine compound represented by Formula I:

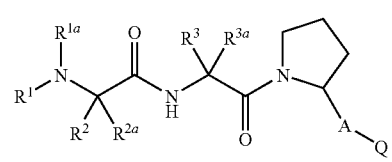

in which the substituents $R^1$, $R^{1a}$, $R^2$, $R^{2a}$, $R^3$, A and Q are defined herein; or a prodrug, or a salt thereof, and which bind to IAP BIR domains. In particular, the compounds are useful in treating proliferative disorders such as cancer.

25 Claims, No Drawings

(56) References Cited

FOREIGN PATENT DOCUMENTS

| | | |
|---|---|---|
| WO | WO 2006/014361 A1 | 2/2006 |
| WO | WO 2006/017295 A2 | 2/2006 |
| WO | WO 2006/020060 A2 | 2/2006 |
| WO | WO 2006/069063 A1 | 6/2006 |
| WO | WO 2006/113376 A1 | 10/2006 |
| WO | WO 2006/122408 A1 | 11/2006 |
| WO | WO 2006/128455 A2 | 12/2006 |
| WO | WO 2006/133147 A2 | 12/2006 |
| WO | WO 2007/048224 A1 | 5/2007 |
| WO | WO 2007/075525 A2 | 7/2007 |
| WO | WO 2007/101347 A1 | 9/2007 |
| WO | WO 2007/104162 A1 | 9/2007 |
| WO | WO 2007/106192 A2 | 9/2007 |
| WO | WO 2007/130626 A2 | 11/2007 |
| WO | WO 2007/131366 A1 | 11/2007 |
| WO | WO 2007/136921 A2 | 11/2007 |
| WO | WO 2008/014229 A2 | 1/2008 |
| WO | WO 2008/014236 A1 | 1/2008 |
| WO | WO 2008/014238 A2 | 1/2008 |
| WO | WO 2008/014240 A2 | 1/2008 |
| WO | WO 2008/014252 A2 | 1/2008 |
| WO | WO 2008/014263 A2 | 1/2008 |
| WO | WO 2008/016893 A1 | 2/2008 |
| WO | WO 2008/045905 A1 | 4/2008 |
| WO | WO 2008/057172 A2 | 5/2008 |
| WO | WO 2008/067280 A2 | 6/2008 |
| WO | WO 2008/073306 A1 | 6/2008 |
| WO | WO 2008/079735 A1 | 7/2008 |
| WO | WO 2008/085610 A1 | 7/2008 |
| WO | WO 2008/128121 A1 | 10/2008 |
| WO | WO 2008/128171 A1 | 10/2008 |
| WO | WO 2008/134679 A1 | 11/2008 |
| WO | WO 2008/144925 A1 | 12/2008 |
| WO | WO 2009/060292 A2 | 5/2009 |
| WO | WO 2009/136290 A1 | 11/2009 |
| WO | WO 2009/140447 A1 | 11/2009 |
| WO | WO 2009/152824 A1 | 12/2009 |
| WO | WO 2009/155709 A1 | 12/2009 |
| WO | WO 2010/015090 A1 | 2/2010 |
| WO | WO 2010/017035 A2 | 2/2010 |
| WO | WO 2010/031171 A1 | 3/2010 |

OTHER PUBLICATIONS

Chen et al., *Bioorg. Med. Chem. Lett.*, "Design, synthesis, and characterization of new embelin derivatives as potent inhibitors of X-linked inhibitor of apoptosis protein," 16(22): 5805-5808 (2006).
Eckelman et al., *Cell Death Differ.*, "The mechanism of peptide-binding specificity of IAP BIR domains," 15(5): 920-8 (2008).
Elmore et al., *Annual Rep. Med. Chem.*, "Inhibitors of Anti-apoptotic Proteins for Cancer Therapy," 40: 245-62 (2006).
Franklin et al., *Biochemistry*, "Structure and function analysis of peptide antagonists of melanoma inhibitor of apoptosis (ML-IAP)," 42: 8223-31 (2003).
Fulda et al., *Nature Medicine*, "Smac agonists sensitize for Apo2L/TRAIL- or anticancer drug-induced apoptosis and induce regression of malignant glioma in vivo," 8: 808-15 (2002).
Gao et al., J. Biol. Chem., "A dimeric Smac/DIABLO peptide directly relieves caspase-3 inhibition by XIAP. Dynamic and cooperative regulation of XIAP by Smac/DIABLO," 282(42): 30718-27 (2007).
Glover et al., *Anal. Biochem.*, "A High-Throughput screen for identification," 320: 157-169 (2003).
Haining et al., *Proc. Natl. Acad. Sci. USA*, "The proapoptotic function of Drosophila HID is conserved in mammalian cells," 96(9): 4936-41 (1999).
IAP from GenBank Accession No. Q13490, pp. 1-6. Accessed Jul. 1, 2008.
Interferon Gamma from GenBank Accession No. NP_776511, pp. 1-3. Accessed Jul. 1, 2008.
Kipp et al., *Biochemistry*, "Molecular targeting of inhibitor of apoptosis proteins based on small molecule mimics of natural binding partners," 41: 7344-9 (2002).

Leban et al., *J. Med. Chem.*, "Potent Gastrin-Releasing Peptide (GRP) Antagonists Derived from GRP(19-27) with a C-Terminal DProΨ[CH$_2$NH]Phe-NH$_2$ and N-Terminal Aromatic Residues," 37(4): 439-445 (1994).
Li et al., *Science*, "A small molecule Smac mimic potentiates Trail- and TNFalpha-mediated cell death," 305(5689): 1471-4 (2004).
Liu et al., *Nature*, "Structural basis for binding of Smac/DIABLO to the XIAP BIR3 domain," 408: 1004-8 (2000).
Marik et al., *J. Peptide. Res.*, "Synthesis and effect of shortened oostatic decapeptide (TMOF) analogs with isosteric structures on reproduction of *Neobellieria bullata*," 57(5): 401-8 (2001).
McCarthy et al., *J. Biol. Chem.*, "Apoptosis induced by *Drosophila* reaper and grim in a human system. Attenuation by inhibitor of apoptosis proteins (cIAPs)," 273(37): 24009-15 (1998).
Nikolovska-Coleska et al., *Anal. Biochem.*, "Development and optimization of a binding assay for the XIAP BIR3 domain using fluorescence polarization," 332: 261-273 (2004).
Nikolovska-Coleska et al., *J. Med. Chem.*, "Discovery of embelin as a cell-permeable, small-molecular weight inhibitor of XIAP through structure-based computational screening of a traditional herbal medicine three-dimensional structure database," 47(10): 2430-40 (2004).
Nikolovska-Coleska et al., *Anal. Biochem.*, "Design and characterization of bivalent Smac-based peptides as antagonists of XIAP and development and validation of a fluorescence polarization assay for XIAP containing both BIR2 and BIR3 domains," 374(1): 87-98 (2008).
Oost et al., *J. Med. Chem.*, "Discovery of potent antagonists of the antiapoptotic protein XIAP for the treatment of cancer," 47(18): 4417-26 (2004).
Park et al., *Bioorg. Med. Chem. Lett.*, "Non-peptidic small molecule inhibitors of XIAP," 15(3): 771-5 (2005).
Petersen et al., *Cancer Cell*, "Autocrine TNFalpha signaling renders human cancer cells susceptible to Smac-mimetic-induced apoptosis," 12(5): 445-56 (2007).
Probst et al., *Cell Death Differ.*, "Smac mimetics increase cancer cell response to chemotherapeutics in a TNF-α-dependent manner," 1-10 (2010).
Richard et al., *Mol. Pharmacol.*, "Agonism, inverse agonism, and neutral antagonism at the constitutively active human neurotensin receptor 2," 60(6): 1392-1398 (2001).
Srinivasula et al., *J. Biol. Chem.*, "Molecular determinants of the caspase-promoting activity of Smac/DIABLO and its role in the death receptor pathway," 275(46): 36152-7 (2000).
Sun et al., *J. Am. Chem. Soc.*, "Structure-Based Design of Potent, Conformationally Constrained Smac Mimetics," 126(51): 16686-87 (2004).
Sun et al., *J. Med. Chem.*, "Structure-based design, synthesis, and evaluation of conformationally constrained mimetics of the second mitochondria-derived activator of caspase that target the X-linked inhibitor of apoptosis protein/caspase-9 interaction site," 47(17): 4147-50 (2004).
Sun et al., *Biorg. Med. Chem. Lett.*, "Structure-based design, synthesis and biochemical testing of novel and potent Smac peptido-mimetics," 15(3): 793-97 (2005).
Sun et al., *Tetrahedron Letters*, "Design and synthesis of a potent biotinylated Smac mimetic," 46: 7015-18 (2005).
Sun et al., *J. Med. Chem.*, "Design, synthesis, and evaluation of a potent, cell-permeable, conformationally constrained second mitochondria derived activator of caspase (Smac) mimetic," 49(26): 7916-20 (2006).
Sun et al., *J. Am. Chem. Soc.*, "Design, synthesis, and characterization of a potent, nonpeptide, cell-permeable, bivalent Smac mimetic that concurrently targets both the BIR2 and BIR3 domains in XIAP," 129(49): 15279-94 (2007).
Sweeney et al., *Biochemistry*, "Determination of the sequence specificity of XIAP BIR domains by screening a combinatorial peptide library," 45(49): 14740-8 (2006).
Terui et al., *Cancer Res.*, "NH2-terminal pentapeptide of endothelial interleukin 8 is responsible for the induction of apoptosis in leukemic cells and has an antitumor effect in vivo," *Cancer Res* 59(22): 5651-5 (1999).

(56) References Cited

OTHER PUBLICATIONS

Varfolomeev et al., *Cell*, "IAP antagonists induce autoubiquitination of c-IAPs, NF-kappaB activation, and TNFalpha-dependent apoptosis," 131(4): 669-81 (2007).

Vince et al., *Cell*, "IAP antagonists target cIAP1 to induce TNFalpha-dependent apoptosis," 131(4): 682-93 (2007).

Voskoglou-Nomikos et al., *Clin. Cancer Res.*, "Clinical Predictive Value of the in vitro Cell Line, Human Xenograft, and Mouse Allograft Preclinical Cancer Models," 9: 4227-4239 (2003).

Vucic et al., *Mol. Cell. Biol.*, "Inhibitor of apoptosis proteins physically interact with and block apoptosis induced by *Drosophila* proteins HID and GRIM," 18(6): 3300-9 (1998).

Weber et al., *Eur. J. Pharmacol.*, "A bombesin receptor subtype-3 peptide increases nuclear oncogene expression in a MEK-1 dependent manner in human lung cancer cells," 412(1): 13-20 (2001).

Wist et al., *Bioorg. Med. Chem.*, "Structure-activity based study of the Smac-binding pocket within the BIR3 domain of XIAP," 15(8): 2935-43 (2007).

Wu et al., *Nature*, "Structural basis of IAP recognition by Smac/DIABLO," 408: 1008-12 (2000).

Wu et al., *Chem. Biol.*, "Development and characterization of nonpeptidic small molecule inhibitors of the XIAP/caspase-3 interaction," 10(8): 759-67 (2003).

XIAP from GenBank Accession No. CAB95312, pp. 1-3. Accessed Jul. 1, 2008.

Zobel et al., *ACS Chem. Biol.*, "Design, Synthesis, and Biological Activity of a Potent Smac Mimetic That Sensitizes Cancer Cells to Apoptosis by Antagonizing IAPs," 1(8): 525-33 (2006).

* cited by examiner

SEQUENCE LISTING

```
<160> NUMBER OF SEQ ID NOS: 9

<210> SEQ ID NO 1
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(20)
<223> OTHER INFORMATION: Xaa is any amino acid
<220> FEATURE:
<221> NAME/KEY: MISC_FEATURE
<222> LOCATION: (22)..(27)
<223> OTHER INFORMATION: Xaa is any amino acid
```

-continued

<220> FEATURE:
<221> NAME/KEY: MISC_FEATURE
<222> LOCATION: (28)..(29)
<223> OTHER INFORMATION: Xaa is any amino acid or is absent

<400> SEQUENCE: 1

Cys Xaa Xaa Cys Xaa Xaa Xaa Xaa Xaa Xaa Xaa Xaa Xaa Xaa Xaa
1               5                   10                  15

Xaa Xaa Xaa Xaa His Xaa Xaa Xaa Xaa Xaa Xaa Xaa Xaa Cys
            20                  25                  30

<210> SEQ ID NO 2
<211> LENGTH: 68
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (9)..(10)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid or is absent
<220> FEATURE:
<221> NAME/KEY: MISC_FEATURE
<222> LOCATION: (14)..(15)
<223> OTHER INFORMATION: Xaa is any amino acid
<220> FEATURE:
<221> NAME/KEY: MISC_FEATURE
<222> LOCATION: (16)..(17)
<223> OTHER INFORMATION: Xaa is any amino acid or is absent
<220> FEATURE:
<221> NAME/KEY: MISC_FEATURE
<222> LOCATION: (18)..(21)
<223> OTHER INFORMATION: Xaa is any amino acid
<220> FEATURE:
<221> NAME/KEY: MISC_FEATURE
<222> LOCATION: (24)..(24)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is any amino acid
<220> FEATURE:
<221> NAME/KEY: MISC_FEATURE
<222> LOCATION: (32)..(33)
<223> OTHER INFORMATION: Xaa is any amino acid
<220> FEATURE:
<221> NAME/KEY: MISC_FEATURE
<222> LOCATION: (35)..(35)
<223> OTHER INFORMATION: Xaa is any amino acid
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (40)..(40)
<223> OTHER INFORMATION: Xaa is any amino acid
<220> FEATURE:
<221> NAME/KEY: MISC_FEATURE
<222> LOCATION: (42)..(47)
<223> OTHER INFORMATION: Xaa is any amino acid
<220> FEATURE:
<221> NAME/KEY: MISC_FEATURE
<222> LOCATION: (49)..(51)
<223> OTHER INFORMATION: Xaa is any amino acid

```
<220> FEATURE:
<221> NAME/KEY: MISC_FEATURE
<222> LOCATION: (53)..(57)
<223> OTHER INFORMATION: Xaa is any amino acid
<220> FEATURE:
<221> NAME/KEY: MISC_FEATURE
<222> LOCATION: (59)..(62)
<223> OTHER INFORMATION: Xaa is any amino acid
<220> FEATURE:
<221> NAME/KEY: MISC_FEATURE
<222> LOCATION: (64)..(64)
<223> OTHER INFORMATION: Xaa is any amino acid
<220> FEATURE:
<221> NAME/KEY: MISC_FEATURE
<222> LOCATION: (66)..(66)
<223> OTHER INFORMATION: Xaa is any amino acid

<400> SEQUENCE: 2

Xaa Xaa Xaa Arg Leu Xaa Thr Phe Xaa Xaa Trp Pro Xaa Xaa Xaa Xaa
1               5                   10                  15

Xaa Xaa Xaa Xaa Xaa Leu Ala Xaa Ala Gly Phe Tyr Tyr Xaa Gly Xaa
            20                  25                  30

Xaa Asp Xaa Val Xaa Cys Phe Xaa Cys Xaa Xaa Xaa Xaa Xaa Xaa Trp
        35                  40                  45

Xaa Xaa Xaa Asp Xaa Xaa Xaa Xaa His Xaa Xaa Xaa Xaa Pro Xaa
    50                  55                  60

Cys Xaa Phe Val
65

<210> SEQ ID NO 3
<211> LENGTH: 497
<212> TYPE: PRT
<213> ORGANISM: Homo sapiens

<400> SEQUENCE: 3

Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
        195                 200                 205
```

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
                275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
    355                 360                 365

Thr Ile Phe Gln Asn Pro Met Val Gln Glu Ala Ile Arg Met Gly Phe
    370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Gln Asp Glu Ser Ser Gln Thr Ser Leu Gln
            420                 425                 430

Lys Glu Ile Ser Thr Glu Glu Gln Leu Arg Arg Leu Gln Glu Glu Lys
    435                 440                 445

Leu Cys Lys Ile Cys Met Asp Arg Asn Ile Ala Ile Val Phe Val Pro
    450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser

<210> SEQ ID NO 4
<211> LENGTH: 616
<212> TYPE: PRT
<213> ORGANISM: Homo sapiens

<400> SEQUENCE: 4

Met His Lys Thr Ala Ser Gln Arg Leu Phe Pro Gly Pro Ser Tyr Gln
1               5                   10                  15

Asn Ile Lys Ser Ile Met Glu Asp Ser Thr Ile Leu Ser Asp Trp Thr
            20                  25                  30

Asn Ser Asn Lys Gln Lys Met Lys Tyr Asp Phe Ser Cys Glu Leu Tyr
        35                  40                  45

Arg Met Ser Thr Tyr Ser Thr Phe Pro Ala Gly Val Pro Val Ser Ser
    50                  55                  60

Leu Ala Arg Ala Gly Phe Tyr Tyr Thr Gly Val Asn Asp Lys Val Lys
65                  70                  75                  80

-continued

```
Cys Phe Cys Cys Gly Leu Met Leu Asp Asn Trp Lys Leu Gly Asp Ser
                85                  90                  95

Pro Ile Gln Lys His Lys Gln Leu Tyr Pro Ser Cys Ser Phe Ile Gln
            100                 105                 110

Asn Leu Val Ser Ala Ser Leu Gly Ser Thr Ser Lys Asn Thr Ser Pro
            115                 120                 125

Met Arg Asn Ser Phe Ala His Ser Leu Ser Pro Thr Leu Glu His Ser
            130                 135                 140

Ser Leu Phe Ser Gly Ser Tyr Ser Ser Leu Ser Pro Asn Pro Leu Asn
145                 150                 155                 160

Ser Arg Ala Val Glu Asp Ile Ser Ser Arg Thr Asn Pro Tyr Ser
                165                 170                 175

Tyr Ala Met Ser Thr Glu Glu Ala Arg Phe Leu Thr Tyr His Met Trp
            180                 185                 190

Pro Leu Thr Phe Leu Ser Pro Ser Glu Leu Ala Arg Ala Gly Phe Tyr
            195                 200                 205

Tyr Ile Gly Pro Gly Asp Arg Val Ala Cys Phe Ala Cys Gly Gly Lys
            210                 215                 220

Leu Ser Asn Trp Glu Pro Lys Asp Asp Ala Met Ser Glu His Arg Arg
225                 230                 235                 240

His Phe Pro Asn Cys Pro Phe Leu Glu Asn Ser Leu Glu Thr Leu Arg
                245                 250                 255

Phe Ser Ile Ser Asn Leu Ser Met Gln Thr His Ala Ala Arg Met Arg
                260                 265                 270

Thr Phe Met Tyr Trp Pro Ser Ser Val Pro Val Gln Pro Glu Gln Leu
            275                 280                 285

Ala Ser Ala Gly Phe Tyr Tyr Val Gly Arg Asn Asp Asp Val Lys Cys
            290                 295                 300

Phe Cys Cys Asp Gly Gly Leu Arg Cys Trp Glu Ser Gly Asp Asp Pro
305                 310                 315                 320

Trp Val Glu His Ala Lys Trp Phe Pro Arg Cys Glu Phe Leu Ile Arg
                325                 330                 335

Met Lys Gly Gln Glu Phe Val Asp Glu Ile Gln Gly Arg Tyr Pro His
            340                 345                 350

Leu Leu Glu Gln Leu Leu Ser Thr Ser Asp Thr Thr Gly Glu Glu Asn
            355                 360                 365

Ala Asp Pro Pro Ile Ile His Phe Gly Pro Gly Glu Ser Ser Ser Glu
            370                 375                 380

Asp Ala Val Met Met Asn Thr Pro Val Val Lys Ser Ala Leu Glu Met
385                 390                 395                 400

Gly Phe Asn Arg Asp Leu Val Lys Gln Thr Val Gln Ser Lys Ile Leu
                405                 410                 415

Thr Thr Gly Glu Asn Tyr Lys Thr Val Asn Asp Ile Val Ser Ala Leu
            420                 425                 430

Leu Asn Ala Glu Asp Glu Lys Arg Glu Glu Lys Glu Lys Gln Ala
            435                 440                 445

Glu Glu Met Ala Ser Asp Asp Leu Ser Leu Ile Arg Lys Asn Arg Met
        450                 455                 460

Ala Leu Phe Gln Gln Leu Thr Cys Val Leu Pro Ile Leu Asp Asn Leu
465                 470                 475                 480

Leu Lys Ala Asn Val Ile Asn Lys Gln Glu His Asp Ile Ile Lys Gln
                485                 490                 495

Lys Thr Gln Ile Pro Leu Gln Ala Arg Glu Leu Ile Asp Thr Ile Leu
            500                 505                 510
```

```
Val Lys Gly Asn Ala Ala Asn Ile Phe Lys Asn Cys Leu Lys Glu
            515                 520                 525

Ile Asp Ser Thr Leu Tyr Lys Asn Leu Phe Val Asp Lys Asn Met Lys
        530                 535                 540

Tyr Ile Pro Thr Glu Asp Val Ser Gly Leu Ser Leu Glu Glu Gln Leu
545                 550                 555                 560

Arg Arg Leu Gln Glu Glu Arg Thr Cys Lys Val Cys Met Asp Lys Glu
                565                 570                 575

Val Ser Val Val Phe Ile Pro Cys Gly His Leu Val Val Cys Gln Glu
            580                 585                 590

Cys Ala Pro Ser Leu Arg Lys Cys Pro Ile Cys Arg Gly Ile Ile Lys
        595                 600                 605

Gly Thr Val Arg Thr Phe Leu Ser
610                 615

<210> SEQ ID NO 5
<211> LENGTH: 555
<212> TYPE: PRT
<213> ORGANISM: Homo sapiens

<400> SEQUENCE: 5

Met Asn Ile Val Glu Asn Ser Ile Phe Leu Ser Asn Leu Met Lys Ser
1               5                   10                  15

Ala Asn Thr Phe Glu Leu Lys Tyr Asp Leu Ser Cys Glu Leu Tyr Arg
                20                  25                  30

Met Ser Thr Tyr Ser Thr Phe Pro Ala Gly Val Pro Val Ser Ser Leu
            35                  40                  45

Ala Arg Ala Gly Phe Tyr Tyr Thr Gly Val Asn Asp Lys Val Lys Cys
        50                  55                  60

Phe Cys Cys Gly Leu Met Leu Asp Asn Trp Lys Arg Gly Asp Ser Pro
65                  70                  75                  80

Thr Glu Lys His Lys Lys Leu Tyr Pro Ser Cys Arg Phe Val Gln Ser
                85                  90                  95

Leu Asn Ser Val Asn Asn Leu Glu Ala Thr Ser Gln Pro Thr Phe Pro
                100                 105                 110

Ser Ser Val Thr Asn Ser Thr His Ser Leu Leu Pro Gly Thr Glu Asn
            115                 120                 125

Ser Gly Tyr Phe Arg Gly Ser Tyr Ser Asn Ser Pro Ser Asn Pro Val
        130                 135                 140

Asn Ser Arg Ala Asn Gln Asp Phe Ser Ala Leu Met Arg Ser Ser Tyr
145                 150                 155                 160

His Cys Ala Met Asn Asn Glu Asn Ala Arg Leu Leu Thr Phe Gln Thr
                165                 170                 175

Trp Pro Leu Thr Phe Leu Ser Pro Thr Asp Leu Ala Lys Ala Gly Phe
            180                 185                 190

Tyr Tyr Ile Gly Pro Gly Asp Arg Val Ala Cys Phe Ala Cys Gly Gly
        195                 200                 205

Lys Leu Ser Asn Trp Glu Pro Lys Asp Asn Ala Met Ser Glu His Leu
210                 215                 220

Arg His Phe Pro Lys Cys Pro Phe Ile Glu Asn Gln Leu Gln Asp Thr
225                 230                 235                 240

Ser Arg Tyr Thr Val Ser Asn Leu Ser Met Gln Thr His Ala Ala Arg
                245                 250                 255

Phe Lys Thr Phe Phe Asn Trp Pro Ser Ser Val Leu Val Asn Pro Glu
            260                 265                 270
```

```
Gln Leu Ala Ser Ala Gly Phe Tyr Tyr Val Gly Asn Ser Asp Asp Val
            275                 280                 285

Lys Cys Phe Cys Cys Asp Gly Leu Arg Cys Trp Glu Ser Gly Asp
            290                 295                 300

Asp Pro Trp Val Gln His Ala Lys Trp Phe Pro Arg Cys Glu Tyr Leu
305                 310                 315                 320

Ile Arg Ile Lys Gly Gln Glu Phe Ile Arg Gln Val Gln Ala Ser Tyr
            325                 330                 335

Pro His Leu Leu Glu Gln Leu Ser Thr Ser Asp Ser Pro Gly Asp
            340                 345                 350

Glu Asn Ala Glu Ser Ser Ile Ile His Phe Glu Pro Gly Glu Asp His
            355                 360                 365

Ser Glu Asp Ala Ile Met Met Asn Thr Pro Val Ile Asn Ala Ala Val
            370                 375                 380

Glu Met Gly Phe Ser Arg Ser Leu Val Lys Gln Thr Val Gln Arg Lys
385                 390                 395                 400

Ile Leu Ala Thr Gly Glu Asn Tyr Arg Leu Val Asn Asp Leu Val Leu
            405                 410                 415

Asp Leu Leu Asn Ala Glu Asp Glu Ile Arg Glu Glu Glu Arg
            420                 425                 430

Ala Thr Glu Glu Lys Glu Ser Asn Asp Leu Leu Leu Ile Arg Lys Asn
            435                 440                 445

Arg Met Ala Leu Phe Gln His Leu Thr Cys Val Ile Pro Ile Leu Asp
450                 455                 460

Ser Leu Leu Thr Ala Gly Ile Ile Asn Glu Gln Glu His Asp Val Ile
465                 470                 475                 480

Lys Gln Lys Thr Gln Thr Ser Leu Gln Ala Arg Glu Leu Ile Asp Thr
            485                 490                 495

Ile Leu Val Lys Gly Asn Ile Ala Ala Thr Val Phe Arg Asn Ser Leu
            500                 505                 510

Gln Glu Ala Glu Ala Val Leu Tyr Glu His Leu Phe Val Gln Gln Asp
            515                 520                 525

Ile Lys Tyr Ile Pro Thr Glu Asp Val Ser Gly Ser Thr Ser Gly Arg
            530                 535                 540

Thr Ile Ala Glu Thr Thr Arg Arg Lys Asn Met
545                 550                 555
```

<210> SEQ ID NO 6
<211> LENGTH: 46
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Glu or Asp
<220> FEATURE:
<221> NAME/KEY: MISC_FEATURE
<222> LOCATION: (9)..(11)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is Val or Ile
<220> FEATURE:
<221> NAME/KEY: MISC_FEATURE

```
<222> LOCATION: (17)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is Val or Ile
<220> FEATURE:
<221> NAME/KEY: MISC_FEATURE
<222> LOCATION: (23)..(23)
<223> OTHER INFORMATION: Xaa is any amino acid
<220> FEATURE:
<221> NAME/KEY: MISC_FEATURE
<222> LOCATION: (25)..(25)
<223> OTHER INFORMATION: Xaa is any amino acid
<220> FEATURE:
<221> NAME/KEY: MISC_FEATURE
<222> LOCATION: (30)..(32)
<223> OTHER INFORMATION: Xaa is any amino acid
<220> FEATURE:
<221> NAME/KEY: MISC_FEATURE
<222> LOCATION: (34)..(35)
<223> OTHER INFORMATION: Xaa is any amino acid
<220> FEATURE:
<221> NAME/KEY: MISC_FEATURE
<222> LOCATION: (38)..(42)
<223> OTHER INFORMATION: Xaa is any amino acid
<220> FEATURE:
<221> NAME/KEY: MISC_FEATURE
<222> LOCATION: (45)..(45)
<223> OTHER INFORMATION: Xaa is any amino acid

<400> SEQUENCE: 6

Glu Xaa Xaa Xaa Xaa Xaa Xaa Xaa Xaa Xaa Cys Lys Xaa Cys Met
1               5                   10                  15

Xaa Xaa Xaa Xaa Xaa Xaa Xaa Phe Xaa Pro Cys Gly His Xaa Xaa Xaa
            20                  25                  30

Cys Xaa Xaa Cys Ala Xaa Xaa Xaa Xaa Xaa Cys Pro Xaa Cys
        35                  40                  45

<210> SEQ ID NO 7
<211> LENGTH: 28
<212> TYPE: DNA
<213> ORGANISM: Homo sapiens

<400> SEQUENCE: 7
ttaataggat ccatcaacgg cttttatc                                      28

<210> SEQ ID NO 8
<211> LENGTH: 19
<212> TYPE: DNA
<213> ORGANISM: Homo sapiens

<400> SEQUENCE: 8
gctgcatgtg tgtcagagg                                                19

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: t-Bu modified
<220> FEATURE:
<221> NAME/KEY: MISC_FEATURE
<222> LOCATION: (8)..(8)
<223> OTHER INFORMATION: t-Bu modified
```

<400> SEQUENCE: 9

Ala Val Pro Phe Tyr Leu Pro Gly Gly
1               5

BIR DOMAIN BINDING COMPOUNDS

CROSS REFERENCE TO RELATED APPLICATIONS

Applicants hereby claim priority from U.S. patent application Ser. No. 60/682,000, filed May 18, 2005; U.S. patent application Ser. No. 60/716,489, filed Sep. 14, 2005; and U.S. patent application Ser. No. 60/725,280, filed Oct. 12, 2005, the entire contents of which are hereby incorporated by reference.

FIELD OF THE INVENTION

The present invention concerns pyrrolidine compounds that bind to IAP BIR domains, and more particularly the BIR2 and BIR3 domains, and are useful to treat proliferative disorders such as cancer.

BACKGROUND OF THE INVENTION

Apoptosis, or programmed cell death, typically occurs in the development and maintenance of healthy tissues in multicellular organisms. Apoptotic pathways are known to play a critical role in embryonic development, viral pathogenesis, cancer, autoimmune disorders, and neurodegenerative diseases, as well as other events. Alterations in an apoptotic response has been implicated in the development of cancer, autoimmune diseases, such as systemic lupus erythematosis and multiple sclerosis, and in viral infections, including those associated with herpes virus, poxvirus, and adenovirus.

Activated caspases, a class of cysteine proteases, are known to initiate apoptosis after they have been activated. In normal cells, the caspases are present as catalytically inactive zymogens. Inhibitors of apoptosis proteins (IAPs) are a family of proteins, which contain one to three baculovirus IAP repeat (BIR) domains, namely BIR1, BIR2, and BIR3, and may also contain a RING zinc finger domain at the C-terminus. The classical human IAPs, XIAP, HIAP1 (also referred to as cIAP2), and HIAP2 (cIAP1) each have three BIR domains, and a carboxy terminal RING zinc finger. Other IAPs, for example NAIP has three BIR domains (BIR1, BIR2 and BIR3), but no RING domain, whereas Livin and ILP2 have a single BIR domain and a RING domain. The prototype X chromosome linked inhibitor of apoptosis (XIAP) can not only inactivate the activated caspases by directly binding to caspases 3, 7, and 9 via the BIR2 and BIR3 domains, but can also remove caspases and the second mitochondrial activator of caspases (Smac) from the cytosol by the ubiquitylation-mediated proteasome pathway via the E3 ligase activity of a RING zinc finger domain. The BIR3 domain of XIAP binds and inhibits caspase-9, which is responsible for initiating the cascade in response to genotoxic damage and many other triggers. The linker-BIR2 domain of XIAP inhibits the activity of caspases-3 and -7, which are two downstream or effector caspases. The BIR domains have also been associated with the interactions of IAPs with tumor necrosis factor-associated factor (TRAFs)-1 and -2, and to TAB1. The IAPs thus function as a 'constraint' on the caspase cascade, thereby preventing or inhibiting active caspases. Because of their central role, the IAPs are capable of suppressing cell death from a wide variety of triggers, including chemotherapeutic drugs and irradiation.

Overexpression of one or more of the IAPs has been documented in most established cancer cell lines, as well as in primary tumor biopsy samples. Chromosome amplification of the 11q21-q23 region, which encompasses both HIAP1 and HIAP2, has been observed in a variety of malignancies, including medulloblastomas, renal cell carcinomas, glioblastomas, and gastric carcinomas. Thus, the IAPs may directly contribute to tumor progression and resistance to pharmaceutical intervention.

Progress in the cancer field has now led to a new paradigm in cancer biology wherein neoplasia is viewed as a failure to execute normal pathways of apoptosis. Normal cells receive continuous feedback from their environment through various intracellular and extracellular factors, and "commit suicide" if removed from this context. Cancer cells, however, gain the ability to ignore or bypass this regulation and continue inappropriate proliferation.

The X-ray crystallographic structure of XIAP BIR2 and BIR3 reveals a critical binding pocket and groove on the surface of each BIR domain. Two mammalian mitochondrial proteins, namely second mitochondria-derived activator of caspases (Smac) and Omi/Htra2, and four *Drosophila* proteins (Reaper, HID, Grim, and Sickle), which interfere with IAP function by binding to these sites on the BIR domain, have been identified. Each of these IAP inhibitors possesses a short amino-terminal tetrapeptide, AXPY or AVPI-like, sequence that fits into this binding pocket and disrupts protein/protein interactions such as IAP-caspase interactions. Although the overall folding of individual BIR domains is believed to be generally conserved, there are alterations in the amino acid sequences that form the binding pocket and groove that suggest that binding affinities might vary between each of the BIR domains.

Cancer therapies, including radiation therapy and chemotherapy, have traditionally been viewed as causing overwhelming cellular injury due to their lack of specificity. Therefore the need to improve the specificity of agents used to treat cancer, and indeed other proliferative disorders, is important because of the benefits in decreasing the side effects associated with administration of these agents.

A number of compounds have been disclosed that demonstrate down regulation of XIAP. The action of the compounds does not appear to be via direct interaction with XIAP. The down regulation of XIAP is likely a result of increased protein degradation.

A number of peptidic and non-peptidic compounds have been described, which bind XIAP BIR3 (Sun et al., Bioorg. Med. Chem. Let. 15 (2005) 793-797; Oost et al., J. Med. Chem., 2004, 47(18), 4417-4426; Park et al., Bioorg. Med. Chem. Lett. 15 (2005) 771-775; Franklin et al., Biochemistry, Vol. 42, No. 27, 2003, 8223-8231; Kip et al., Biochemistry 2002, 41, 7344-7349; Wu et al., Chemistry and Biology, Vol. 10, 759-767 (2003); Glover et al., Analytical Biochemistry, 320 (2003) 157-169); United States published patent application number 20020177557; and United States published patent application number 20040180828).

The aforesaid compounds while they appear to target the BIR3 domain of XIAP, may have limited bioavailability and therefore limited therapeutic application. Moreover, the compounds may not be selective against other IAPs and indeed other BIR domains, such as BIR2; this lack of specificity may lead to unexpected side effects.

Thus, IAP BIR domains continue to remain an attractive target for the discovery and development of novel therapeutic agents, especially for the treatment of proliferative disorders such as cancer.

SUMMARY OF THE INVENTION

We have discovered a novel series of pyrrolidine compounds that enhance cellular apoptosis through IAP modulation. The compounds are less peptidic in character because the proline in the previously described compounds has been replaced with a pyrrolidine and as such have pharmaceutically acceptable stability and bioavailability. The derivatives significantly reduce, or essentially eliminate, the interaction of activated apoptotic proteins, such as caspase 3, caspase 7, and caspase 9, with the BIR domains of mammalian IAPs. Specifically, we have demonstrated that the compounds bind to the BIR domains of mammalian XIAP and promote apoptosis of cancer cells as a single agent or in combination with a chemotherapeutic agent. Moreover, the compounds were shown to modulate XIAP protein in cells and induce the proteolytic processing of XIAP and a change in cellular localization. Advantageously, the compounds described herein have anti-cancer activity in various cancer cell lines such as breast, pancreatic, colon and lung, and may also find application in other diseases where cells are resistant to apoptosis. Moreover, our data indicate that the derivatives also bind to the BIR 3 domains of other IAPs, such as cIAP-1 or cIAP-2, and thus may be useful in the treatment of sepsis, inflammation, cancer and the like. Furthermore, the derivatives of the present invention have improved selectivity for BIR3 and BIR2 of various IAPs compared to previously described compounds Also the compounds of the present invention can be administered in vivo and show anti-cancer activity.

In one aspect of the present invention, there is provided an isomer, an enantiomer, a diastereoisomer, or a tautomer of a compound represented by Formula I:

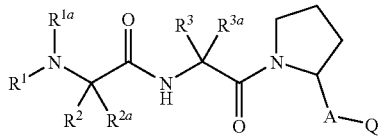

I wherein:
n is 0 or 1;
m is 0, 1 or 2;
p is 1 or 2;
Y is NH, O or S;
$R^1$ and $R^{1a}$ are each independently
　1) H, or
　2) $C_1$-$C_6$ alkyl optionally substituted with one or more $R^6$ substituents;
$R^2$ and $R^{2a}$ are each independently
　1) H, or
　2) $C_1$-$C_6$ alkyl optionally substituted with one or more $R^6$ substituents;
$R^3$ and $R^{1a}$
　1) H, or
　2) $C_1$-$C_6$ alkyl optionally substituted with one or more $R^6$ substituents;
A is
　1) —$CH_2$—,
　2) —$CH_2CH_2$—,
　3) —$C(CH_3)_2$—,
　4) —$CH(C_1$-$C_6$ alkyl)-,
　5) —$CH(C_3$-$C_7$ cycloalkyl)-,
　6) —$C_3$-$C_7$ cycloalkyl-, or
　7) —$CH(C_1$-$C_6$ alkyl-$C_3$-$C_7$ cycloalkyl)-;

Q is
　1) $NR^4R^5$,
　2) $OR^{11}$, or
　3) $S(O)_mR^{11}$; or
Q is

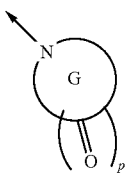

wherein G is a 5, 6 or 7 membered ring which optionally incorporates one or more heteroatoms chosen from S, N or O, the ring being optionally substituted with one or more $R^{12}$ substituents;
$R^4$ and $R^5$ are each independently
　1) H,
　2) haloalkyl,
　3) ←$C_1$-$C_6$ alkyl,
　4) ←$C_2$-$C_6$ alkenyl,
　5) ←$C_2$-$C_4$ alkynyl,
　6) ←$C_3$-$C_7$ cycloalkyl,
　7) ←$C_3$-$C_7$ cycloalkenyl,
　8) ←aryl,
　9) ←heteroaryl,
　10) ←heterocyclyl,
　11) ←heterobicyclyl,
　12) ←—C(O)(O)$_n$—$R^{11}$,
　13) ←C(=Y)$NR^8R^9$, or
　14) ←S(O)$_2$—$R^{11}$,
wherein the alkyl, alkenyl, alkynyl, cycloalkyl, cycloalkenyl is optionally substituted with one or more $R^6$ substitutents; and wherein the aryl, heteroaryl, heterocyclyl, and heterobicyclyl is optionally substituted with one or more $R^{10}$ substituents;
$R^6$ is
　1) halogen,
　2) $NO_2$,
　3) CN,
　4) haloalkyl,
　5) $C_1$-$C_6$ alkyl,
　6) $C_2$-$C_6$ alkenyl,
　7) $C_2$-$C_4$ alkynyl,
　8) $C_3$-$C_7$ cycloalkyl,
　9) $C_3$-$C_7$ cycloalkenyl,
　10) aryl,
　11) heteroaryl,
　12) heterocyclyl,
　13) heterobicyclyl,
　14) $OR^7$,
　15) $S(O)_mR^7$,
　16) $NR^8R^9$,
　17) $NR^8S(O)_2R^{11}$,
　18) $COR^7$,
　19) $C(O)OR^7$,
　20) $CONR^8R^9$,
　21) $S(O)_2NR^8R^9$
　22) $OC(O)R^7$,
　23) $OC(O)Y$—$R^{11}$,
　24) $SC(O)R^7$, or
　25) $NC(Y)NR^8R^9$,
wherein the aryl, heteroaryl, heterocyclyl, and heterobicyclyl is optionally substituted with one or more $R^{10}$ substituents;

$R^7$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $R^8R^9NC(=Y)$, or
13) $C_1$-$C_6$ alkyl-$C_2$-$C_4$ alkenyl, or
14) $C_1$-$C_6$ alkyl-$C_2$-$C_4$ alkynyl,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) $C(O)Y-R^{11}$, or
14) $S(O)_2-R^{11}$,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
or $R^8$ and $R^9$ together with the nitrogen atom to which they are bonded form a five, six or seven membered heterocyclic ring optionally substituted with one or more $R^6$ substituents;
$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8R^9$,
13) $SR^7$,
14) $COR^7$,
15) $C(O)OR^7$,
16) $S(O)_mR^7$,
17) $CONR^8R^9$,
18) $S(O)_2NR^8R^9$,
19) aryl,
20) heteroaryl,
21) heterocyclyl, or
22) heterobicyclyl,
wherein the alkyl, alkenyl, alkynyl, cycloalkyl, and cycloalkenyl is optionally substituted with one or more $R^6$ substituents;

$R^{11}$ is
1) haloalkyl,
2) $C_1$-$C_{12}$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl,
wherein the alkyl, alkenyl, alkynyl, cycloalkyl, cycloalkenyl is optionally substituted with one or more $R^6$ substituents; and wherein the aryl, biphenyl, heteroaryl, heterocyclyl, and heterobicyclyl is optionally substituted with one or more $R^{10}$ substituents;
$R^{12}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl,
10) heterobicyclyl,
11) $C(O)(O)_n-R^{11}$,
12) $C(O)NR^8R^9$,
13) $S(O)_m-R^{11}$, or
14) $C(=Y)NR^8R^9$,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^{13}$ and $R^{14}$ are each independently
1) H, or
2) $C_1$-$C_6$ alkyl; or
$R^{13}$ and $R^{14}$ are combined to form a heterocyclic ring or a heterobicycle ring;
or a prodrug, or a salt thereof; or the compound of Formula I is labeled with a detectable label or an affinity tag.

In another aspect of the present invention, there is provided an intermediate compound represented by Formula 1-v:

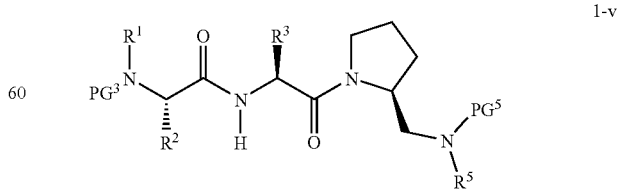

1-v wherein $PG^3$ and $PG^5$ are protecting groups, and $R^1$, $R^2$, $R^3$ and $R^5$ are as defined hereinabove.

In another aspect of the present invention, there is provided an intermediate compound represented by Formula 2-i:

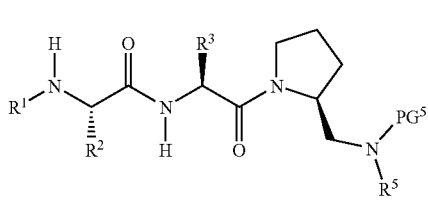

2-i wherein PG⁵ is a protecting group, and R¹, R², R³, and R⁵ are as defined hereinabove.

In another aspect of the present invention, there is provided an intermediate compound represented by Formula 4-i:

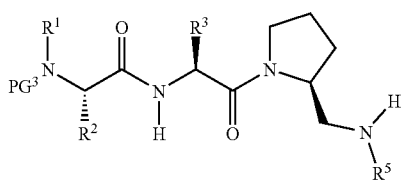

4-i wherein PG³ is a protecting group, and R¹, R², R³, and R⁵ are as defined hereinabove.

In another aspect of the present invention, there is provided an intermediate compound represented by Formula 5-i:

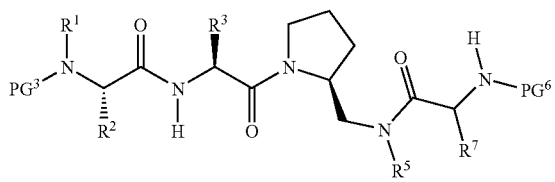

5-i wherein PG³ and PG⁶ are a protecting groups, and R¹, R², R³, R⁵ and R⁷ are as defined hereinabove.

In another aspect of the present invention, there is provided an intermediate compound represented by Formula 5-ii:

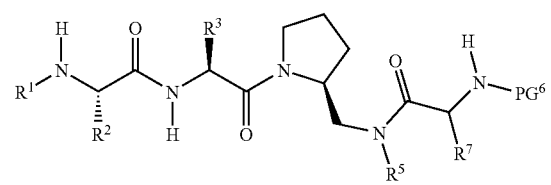

5-ii wherein PG⁶ is a protecting group, and R¹, R², R³, R⁵ and R⁷ are as defined hereinabove.

In another aspect of the present invention, there is provided an intermediate compound represented by Formula 6-i:

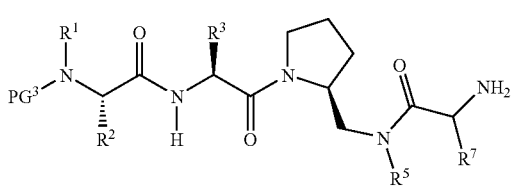

6-i wherein PG³ is a protecting group, and R¹, R², R³, R⁵ and R⁷ are as defined hereinabove.

In another aspect of the present invention, there is provided an intermediate compound represented by Formula 7-ix or Formula 7-x:

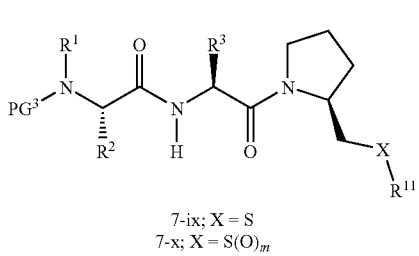

7-ix; X = S
7-x; X = S(O)$_m$ wherein PG³ is a protecting group, and R¹, R², R³, R¹¹, and n are as defined hereinabove.

In another aspect of the present invention, there is provided a process for producing compounds represented by Formula I, described hereinabove, the process comprising: in a solvent, either singly or doubly deprotecting the intermediate of Formula 1-v:

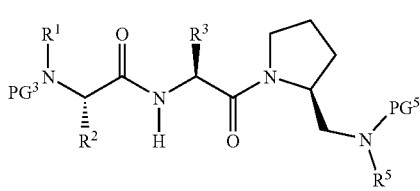

1-v so as to produce compounds of Formula 1, wherein PG³ and PG⁵ are protecting groups, and R¹, R², R³ and R⁵ are as defined hereinabove.

In another aspect of the present invention, there is provided a process for producing compounds represented by Formula I, described hereinabove, the process comprising:
a) coupling an intermediate represented by Formula 4-i:

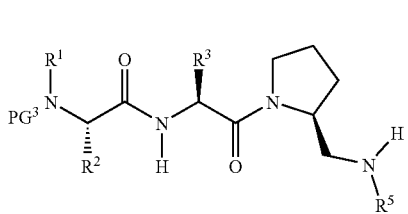

4-i and LG-C(O)—R$^{11}$ or LG-S(O)$_2$—R$^{11}$ in a solvent at room temperature; and b) removing the protecting group so as to form compounds of Formula 1, wherein PG$^3$ is a protecting group, LG is a leaving group, and R$^1$, R$^2$, R$^3$, and R$^5$ are as defined herein.

In another aspect of the present invention, there is provided a process for producing compounds represented by Formula I, described hereinabove, the process comprising: in a solvent, deprotecting the intermediate of Formula 5-ii:

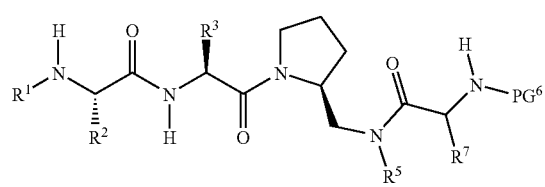

5-ii so as to produce compounds of Formula 1, wherein PG$^6$ is a protecting group, and R$^1$, R$^2$, R$^3$, R$^5$ and R$^7$ are as defined hereinabove.

In another aspect of the present invention, there is provided a process for producing compounds represented by Formula I, described hereinabove, the process comprising: in a solvent, deprotecting the intermediate of Formula 5-i:

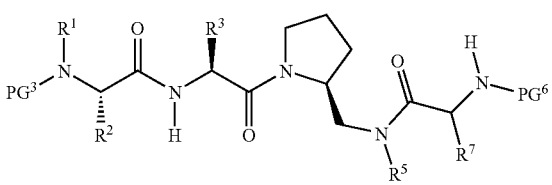

5-i so as to produce compounds of Formula 1, wherein and R$^1$, R$^2$, R$^3$, R$^5$ and R$^7$ are as defined hereinabove.

In another aspect of the present invention, there is provided a process for producing compounds represented by Formula I, described hereinabove, the process comprising:

a) coupling an intermediate represented by Formula 6-i:

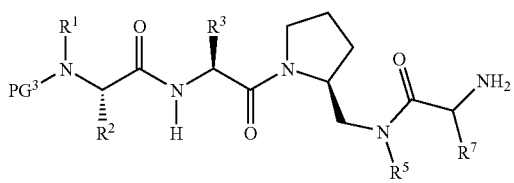

6-i and LG-C(O)—R$^{11}$, LG-S(O)$_2$—R$^{11}$, or R$^{11}$NCO in a solvent at room temperature; and b) removing the protecting group so as to form compounds of Formula 1, wherein PG$^3$ is a protecting group, LG is a leaving group, and R$^1$, R$^2$, R$^3$, R$^5$ and R$^7$ are as defined herein.

In another aspect of the present invention, there is provided a process for producing compounds represented by Formula I, described hereinabove, the process comprising: in a solvent, deprotecting the intermediate of Formula 7-ix or Formula 7-x:

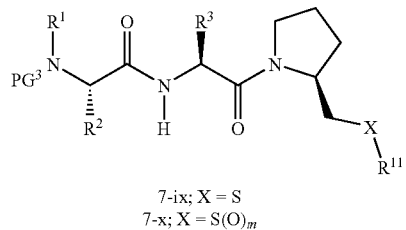

7-ix; X = S
7-x; X = S(O)$_m$ so as to produce compounds of Formula 1, wherein PG$^3$ is a protecting group, and R$^1$, R$^2$, R$^3$, R$^{11}$ and n are as defined hereinabove.

In another aspect of the present invention, there is provided a pharmaceutical composition comprising a compound, as described above, and a pharmaceutically acceptable carrier, diluent or excipient.

In another aspect of the present invention, there is provided a pharmaceutical composition adapted for administration as an agent for treating a proliferative disorder in a subject, comprising a therapeutically effective amount of a compound, as described above.

In another aspect of the present invention, there is provided a method of preparing a pharmaceutical composition, the method comprising: mixing a compound, as described above, with a pharmaceutically acceptable carrier, diluent or excipient.

In another aspect of the present invention, there is provided a method of treating a disease state characterized by insufficient apoptosis, the method comprising: administering to a subject in need thereof, a therapeutically effective amount of a pharmaceutical composition, as described above, so as to treat the disease state.

In another aspect of the present invention, there is provided a method of modulating IAP function, the method comprising: contacting a cell with a compound of the present invention so as to prevent binding of a BIR binding protein to an IAP BIR domain thereby modulating the IAP function.

In another aspect of the present invention, there is provided a method of treating a proliferative disease, the method comprising: administering to a subject in need thereof, a therapeutically effective amount of the pharmaceutical composition, as described above, so as to treat the proliferative disease.

In another aspect of the present invention, there is provided a method of treating a proliferative disease, the method comprising: administering to a subject in need thereof, a therapeutically effective amount of the pharmaceutical composition, as described above, in combination with a death receptor agonist so as to treat the proliferative disease.

In another aspect of the present invention, there is provided a method of treating cancer, the method comprising: administering to a subject in need thereof, a therapeutically effective amount of the pharmaceutical composition, as described above, so as to treat the cancer.

In another aspect of the present invention, there is provided a method of treating cancer, the method comprising: administering to the subject in need thereof, a therapeutically effective amount of a pharmaceutical composition, as described above, in combination or sequentially with an agent selected from:

a) an estrogen receptor modulator,
b) an androgen receptor modulator,
c) retinoid receptor modulator,
d) a cytotoxic agent, e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor,
l) a PPAR-γ agonist,
m) a PPAR-δ. agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug.
s) a proteasome inhibitor;
t) an HDAC inhibitor;
u) an inhibitor of the chemotrypsin-like activity in the proteasome; or
v) E3 ligase inhibitors;
or in combination or sequentially with radiation therapy, so as to treat the cancer.

In still another aspect of the present invention, there is provided a probe, the probe being a compound of Formula I above, the compound being labeled with a detectable label or an affinity tag.

In another aspect of the present invention, there is provided a method of identifying compounds that bind to an IAP BIR domain, the method comprising:
 a) contacting an IAP BIR domain with a probe to form a probe:BIR domain complex, the probe being displaceable by a test compound;
 b) measuring a signal from the probe so as to establish a reference level;
 c) incubating the probe:BIR domain complex with the test compound;
 d) measuring the signal from the probe;
 e) comparing the signal from step d) with the reference level, a modulation of the signal being an indication that the test compound binds to the BIR domain,
 wherein the probe is a compound of Formula I labeled with a detectable label or an affinity label.

In another aspect of the present invention, there is provided a method of identifying compounds that bind to an IAP BIR domain, the method comprising:
 a) contacting an IAP BIR domain with a compound of Formula I or a probe to form either a probe or a compound:BIR domain complex;
 b) measuring the amount the probe or the compound bound to the BIR domain.

In another aspect of the present invention, there is provided a method of measuring the binding of IAP proteins to a BIR binding compound, the method comprising:
 a) contacting an IAP BIR domain with a probe to form a probe:BIR domain complex;
 b) washing non-bound protein;
 c) extracting the bound protein from the probe either with a test compound or eluent,
 wherein the probe is a compound of Formula I labeled with an affinity label.

In another aspect of the present invention, there is provided a method of identifying compounds that bind to a protein containing a BIR domain, the method comprising:
 a) contacting an IAP protein or fragment thereof with ancIAP binding protein to form an IAP protein:BIR domain complex, the IAP protein being displaceable by a test compound.

DETAILED DESCRIPTION OF THE INVENTION

As long as not defined otherwise, all groups, substituents, indices such as, for example, $R^1$, $R^2$, $R^3$, $R^{3a}$, $R^4$, $R^5$, $R^6$, $R^7$, $R^8$, $R^9$, $R^{10}$, $R^{11}$, $R^{12}$, $R^{13}$, $R^{14}$, Y, A, Q, n, m, p have the meanings which are defined hereinabove and hereinbelow. In the following description, typical embodiments of the groups, substituents, and indices according to the present invention are provided.

In an embodiment of the first aspect of the present invention, there is provided an isomer, an enantiomer, a diastereoisomer, or a tautomer of a compound represented by Formula I:

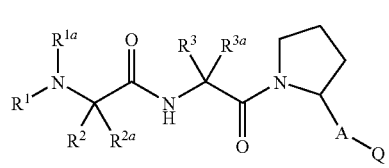

wherein:
n is 0 or 1;
m is 0, 1 or 2;
Y is NH, O or S;
$R^1$ and $R^{1a}$ are each independently
 1) H, or
 2) $C_1$-$C_6$ alkyl optionally substituted with one or more $R^6$ substituents;
$R^2$ and $R^{2a}$ are each independently
 1) H, or
 2) $C_1$-$C_6$ alkyl optionally substituted with one or more $R^6$ substituents;
$R^3$, and $R^{3a}$
 1) H, or
 2) $C_1$-$C_6$ alkyl optionally substituted with one or more $R^6$ substituents;
A is —$CH_2$—;
Q is
 1) $NR^4R^5$,
 2) $OR^{11}$, or
 3) $S(O)_mR^{11}$;
$R^4$ and $R^5$ are each independently
 1) H,
 2) haloalkyl,
 3) ←$C_1$-$C_6$ alkyl,
 4) ←$C_2$-$C_6$ alkenyl,
 5) ←$C_2$-$C_4$ alkynyl,
 6) ←$C_3$-$C_7$ cycloalkyl,
 7) ←$C_3$-$C_7$ cycloalkenyl,
 8) ←aryl,
 9) ←heteroaryl,
 10) ←heterocyclyl,
 11) ←heterobicyclyl,
 12) ←$C(O)(O)_n$—$R^{11}$,
 13) ←$C(=Y)NR^8R^9$, or
 14) ←$S(O)_2$—$R^{11}$,
wherein the alkyl, alkenyl, alkynyl, cycloalkyl, cycloalkenyl is optionally substituted with one or more $R^6$ substitutents; and wherein the aryl, heteroaryl, heterocyclyl, and heterobicyclyl is optionally substituted with one or more $R^{10}$ substituents;
$R^6$ is
 1) halogen,
 2) $NO_2$,
 3) CN,
 4) haloalkyl,
 5) $C_1$-$C_6$ alkyl,
 6) $C_2$-$C_6$ alkenyl, 7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^7$,
15) $S(O)_m R^7$,
16) $NR^8 R^9$,
17) $NR^8 S(O)_2 R^{11}$,
18) $COR^7$,
19) $C(O)OR^7$,
20) $CONR^8 R^9$,
21) $S(O)_2 NR^8 R^9$,
22) $OC(O)R^7$,
23) $OC(O)Y$—$R^{11}$,
24) $SC(O)R^7$, or
25) $NC(Y)NR^8 R^9$,
wherein the aryl, heteroaryl, heterocyclyl, and heterobicyclyl is optionally substituted with one or more $R^{10}$ substituents;
$R^7$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
6) $C_3$-$C_7$ cycloalkenyl,
7) aryl,
8) heteroaryl,
9) heterocyclyl,
10) heterobicyclyl,
11) $R^8 R^9 NC(=Y)$,
12) $C_1$-$C_6$ alkyl-$C_2$-$C_4$ alkenyl, or
13) $C_1$-$C_6$ alkyl-$C_2$-$C_4$ alkynyl,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) $C(O)Y$—$R^{11}$, or
14) $S(O)_2 R^{11}$,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents; or $R^8$ and $R^9$ together with the nitrogen atom to which they are bonded form a five, six or seven membered heterocyclic ring optionally substituted with one or more $R^6$ substituents;
$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8 R^9$,
13) $SR^7$,
14) $COR^7$,
15) $C(O)OR^7$,
16) $S(O)_m R^7$,
17) $CONR^8 R^9$,
18) $S(O)_2 NR^8 R^9$,
19) aryl,
20) heteroaryl,
21) heterocyclyl, or
22) heterobicyclyl,
wherein the alkyl, alkenyl, alkynyl, cycloalkyl, and cycloalkenyl is optionally substituted with one or more $R^6$ substituents;
$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^{13}$ and $R^{14}$ are each independently
1) H, or
2) $C_1$-$C_6$ alkyl; or
$R^{13}$ and $R^{14}$ are combined to form a heterocyclic ring or a heterobicycle ring; or a salt thereof.

Backbone:

One subset of the compounds of Formula I include an isomer, an enantiomer, a diastereoisomer, or a tautomer of compounds of the following Formula 1.1

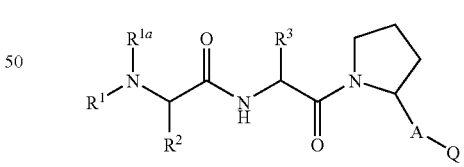

1.1 wherein:
n is 0 or 1;
m is 0, 1 or 2;
Y is NH, O or S;
$R^1$ and $R^{1a}$ are each independently
1) H, or
2) $C_1$-$C_6$ alkyl optionally substituted with one or more $R^6$ substituents;
$R^2$ is
1) H, or
2) $C_1$-$C_6$ alkyl optionally substituted with one or more $R^6$ substituents;

$R^3$ is
1) H, or
2) $C_1$-$C_6$ alkyl optionally substituted with one or more $R^6$ substituents;

A is —$CH_2$—;

Q is
1) $NR^4R^5$,
2) $OR^{11}$, or
3) $S(O)_m R^{11}$;

$R^4$ and $R^5$ are each independently
1) H,
2) haloalkyl,
3) ←$C_1$-$C_6$ alkyl,
4) ←$C_2$-$C_6$ alkenyl,
5) ←$C_2$-$C_4$ alkynyl,
6) ←$C_3$-$C_7$ cycloalkyl,
7) ←$C_3$-$C_7$ cycloalkenyl,
8) ←aryl,
9) ←heteroaryl,
10) ←heterocyclyl,
11) ←heterobicyclyl,
12) ←$C(O)(O)_n$—$R^{11}$,
13) ←$C(=Y)NR^8R^9$, or
14) ←$S(O)_2$—$R^{11}$, wherein the alkyl, alkenyl, alkynyl, cycloalkyl, cycloalkenyl is optionally substituted with one or more $R^6$ substitutents; and wherein the aryl, heteroaryl, heterocyclyl, and heterobicyclyl is optionally substituted with one or more $R^{10}$ substituents;

$R^6$ is
1) halogen,
2) $NO_2$,
3) CN,
4) haloalkyl,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^7$,
15) $S(O)_m R^7$,
16) $NR^8R^9$,
17) $NR^8S(O)_2R^{11}$,
18) $COR^7$,
19) $C(O)OR^7$,
20) $CONR^8R^9$,
21) $S(O)_2NR^8R^9$
22) $OC(O)R^7$,
23) $OC(O)Y$—$R^{11}$,
24) $SC(O)R^7$, or
25) $NC(Y)NR^8R^9$, wherein the aryl, heteroaryl, heterocyclyl, and heterobicyclyl is optionally substituted with one or more $R^{10}$ substituents;

$R^7$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
6) $C_3$-$C_7$ cycloalkenyl,
7) aryl,
8) heteroaryl,
9) heterocyclyl,
10) heterobicyclyl,
11) $R^8R^9NC(=Y)$,
12) $C_1$-$C_6$ alkyl-$C_2$-$C_4$ alkenyl, or
13) $C_1$-$C_6$ alkyl-$C_2$-$C_4$ alkynyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) $C(O)Y$—$R^{11}$, or
1) $S(O)_2$—$R^{11}$, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

or $R^8$ and $R^9$ together with the nitrogen atom to which they are bonded form a five, six or seven membered heterocyclic ring optionally substituted with one or more $R^6$ substituents;

$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8R^9$,
13) $SR^7$,
14) $COR^7$,
15) $C(O)OR^7$,
16) $S(O)_m R^7$,
17) $CONR^8R^9$,
18) $S(O)_2NR^8R^9$,
19) aryl,
20) heteroaryl,
21) heterocyclyl, or
22) heterobicyclyl, wherein the alkyl, alkenyl, alkynyl, cycloalkyl, and cycloalkenyl is optionally substituted with one or more $R^6$ substituents;

$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl, 9) heterocyclyl, or
10) heterobicyclyl,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^{13}$ and $R^{14}$ are each independently
  1) H, or
  2) $C_1$-$C_6$ alkyl; or
$R^{13}$ and $R^{14}$ are combined to form a heterocyclic ring or a heterobicycle ring; or a salt thereof.

Another subset of the compounds of Formula 1 includes an isomer, an enantiomer, a diastereoisomer, or a tautomer of compounds of the following Formula 1.2 and 1.3

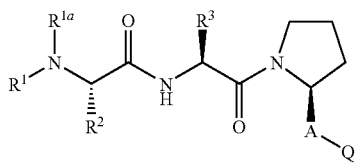
1.2

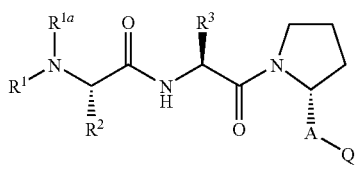
1.3 wherein $R^1$, $R^{1a}$, $R^2$, $R^3$, A and Q are as defined herein; or a prodrug, or a salt thereof; and
wherein compounds of Formula 1.2 are typical.

The invention typically includes an isomer, an enantiomer, a diastereoisomer, or a tautomer of a compound of Formula 1.2

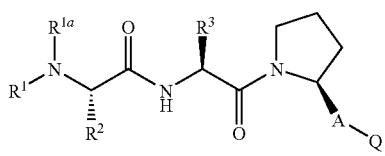
1.2 wherein:
n is 0 or 1;
m is 0, 1 or 2;
Y is NH, O or S;
$R^1$ and $R^{1a}$ are each independently
  1) H, or
  2) $C_1$-$C_3$ alkyl optionally substituted with one $R^6$ substituent;
$R^2$ is
  1) H, or
  2) $C_1$-$C_3$ alkyl optionally substituted with one $R^6$ substituent;
$R^3$ is $C_1$-$C_3$ alkyl optionally substituted with one $R^6$ substituent;
A is —$CH_2$—;
Q is
  1) $NR^4R^5$,
  2) $OR^{11}$, or
  3) $S(O)_m R^{11}$;

$R^4$ and $R^5$ are each independently
  1) H,
  2) haloalkyl,
  3) ←$C_1$-$C_6$ alkyl,
  4) ←$C_2$-$C_6$ alkenyl,
  5) ←$C_2$-$C_4$ alkynyl,
  6) ←$C_3$-$C_7$ cycloalkyl,
  7) ←$C_3$-$C_7$ cycloalkenyl,
  8) ←aryl,
  9) ←heteroaryl,
  10) ←heterocyclyl,
  11) ←heterobicyclyl,
  12) ←$C(O)(O)_n$—$R^{11}$,
  13) ←$C(=Y)NR^8R^9$, or
  14) ←$S(O)_2$—$R^{11}$,
wherein the alkyl, alkenyl, alkynyl, cycloalkyl, cycloalkenyl is optionally substituted with one or more $R^6$ substitutents; and wherein the aryl, heteroaryl, heterocyclyl, and heterobicyclyl is optionally substituted with one or more $R^{10}$ substituents;
$R^6$ is
  1) halogen,
  2) $NO_2$,
  3) CN,
  4) haloalkyl,
  5) $C_1$-$C_6$ alkyl,
  6) $C_2$-$C_6$ alkenyl,
  7) $C_2$-$C_4$ alkynyl,
  8) $C_3$-$C_7$ cycloalkyl,
  9) $C_3$-$C_7$ cycloalkenyl,
  10) aryl,
  11) heteroaryl,
  12) heterocyclyl,
  13) heterobicyclyl,
  14) $OR^7$,
  15) $S(O)_m R^7$,
  16) $NR^8R^9$,
  17) $NR^8S(O)_2R^{11}$,
  18) $COR^7$,
  19) $C(O)OR^7$,
  20) $CONR^8R^9$,
  21) $S(O)_2NR^8R^9$
  22) $OC(O)R^7$,
  23) $OC(O)Y$—$R^{11}$,
  24) $SC(O)R^7$, or
  25) $NC(Y)NR^8R^9$,
wherein the aryl, heteroaryl, heterocyclyl, and heterobicyclyl is optionally substituted with one or more IV substituents;
$R^7$ is
  1) H,
  2) haloalkyl,
  3) $C_1$-$C_6$ alkyl,
  4) $C_2$-$C_6$ alkenyl,
  5) $C_2$-$C_4$ alkynyl,
  6) $C_3$-$C_7$ cycloalkyl,
  6) $C_3$-$C_7$ cycloalkenyl,
  7) aryl,
  8) heteroaryl,
  9) heterocyclyl,
  10) heterobicyclyl,
  11) $R^8R^9NC(=Y)$, or
  12) $C_1$-$C_6$ alkyl-$C_2$-$C_4$ alkenyl, or
  13) $C_1$-$C_6$ alkyl-$C_2$-$C_4$ alkynyl,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) $C(O)Y-R^{11}$, or
2) $S(O)_2-R^{11}$,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents; or $R^8$ and $R^9$ together with the nitrogen atom to which they are bonded form a five, six or seven membered heterocyclic ring optionally substituted with one or more $R^6$ substituents;
$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8R^9$,
13) $SR^7$,
14) $COR^7$,
15) $C(O)OR^7$,
16) $S(O)_mR^7$,
17) $CONR^8R^9$,
18) $S(O)_2NR^8R^9$,
19) aryl,
20) heteroaryl,
21) heterocyclyl, or
22) heterobicyclyl,
wherein the alkyl, alkenyl, alkynyl, cycloalkyl, and cycloalkenyl is optionally substituted with one or more $R^6$ substituents;
$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^{13}$ and $R^{14}$ are each independently
1) H, or
2) $C_1$-$C_6$ alkyl; or $R^{13}$ and $R^{14}$ are combined to form a heterocyclic ring or a heterobicycle ring; or a salt thereof.

One example of the aforesaid compounds of the present invention includes compounds of Formula 1.2a

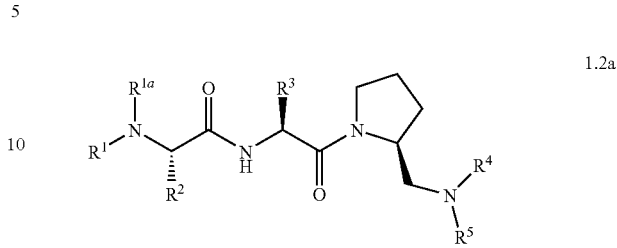

wherein:
n is 0 or 1;
m is 0, 1 or 2;
Y is NH, O or S;
$R^1$ and $R^{1a}$ are each independently
1) H, or
2) $C_1$-$C_6$ alkyl optionally substituted with one $R^6$ substituent;
$R^2$ is
1) H, or
2) $C_1$-$C_6$ alkyl optionally substituted with one $R^6$ substituent;
$R^3$ is
1) H, or
2) $C_1$-$C_6$ alkyl optionally substituted with one $R^6$ substituent;
$R^4$ and $R^5$ are each independently
1) H,
2) haloalkyl,
3) ←$C_1$-$C_6$ alkyl,
4) ←$C_2$-$C_6$ alkenyl,
5) ←$C_2$-$C_4$ alkynyl,
6) ←$C_3$-$C_7$ cycloalkyl,
7) ←$C_3$-$C_7$ cycloalkenyl,
8) ←aryl,
9) ←heteroaryl,
10) ←heterocyclyl,
11) ←heterobicyclyl,
12) ←$C(O)(O)_n-R^{11}$,
13) ←$C(=Y)NR^8R^9$, or
14) ←$S(O)_2-R^{11}$,
wherein the alkyl, alkenyl, alkynyl, cycloalkyl, cycloalkenyl is optionally substituted with one or more $R^6$ substitutents; and wherein the aryl, heteroaryl, heterocyclyl, and heterobicyclyl is optionally substituted with one or more $R^{10}$ substituents;
$R^6$ is
1) halogen,
2) $NO_2$,
3) CN,
4) haloalkyl,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^7$,
15) $S(O)_mR^7$, 16) $NR^8R^9$,
17) $NR^8S(O)_2R^{11}$,
18) $COR^7$,
19) $C(O)OR^7$,
20) $CONR^8R^9$,
21) $S(O)_2NR^8R^9$
22) $OC(O)R^7$,
23) $OC(O)Y\text{---}R^{11}$,
24) $SC(O)R^7$, or
25) $NC(Y)NR^8R^9$, wherein the aryl, heteroaryl, heterocyclyl, and heterobicyclyl is optionally substituted with one or more $R^{10}$ substituents;

$R^7$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
6) $C_3$-$C_7$ cycloalkenyl,
7) aryl,
8) heteroaryl,
9) heterocyclyl,
10) heterobicyclyl,
11) $R^8R^9NC(=Y)$, or
12) $C_1$-$C_6$ alkyl-$C_2$-$C_4$ alkenyl, or
13) $C_1$-$C_6$ alkyl-$C_2$-$C_4$ alkynyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) $C(O)Y\text{---}R^{11}$, or
3) $S(O)_2\text{---}R^{11}$, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents; or $R^8$ and $R^9$ together with the nitrogen atom to which they are bonded form a five, six or seven membered heterocyclic ring optionally substituted with one or more $R^6$ substituents;

$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8R^9$,
13) $SR^7$,
14) $COR^7$,
15) $C(O)OR^7$,
16) $S(O)_mR^7$,
17) $CONR^8R^9$,
18) $S(O)_2NR^8R^9$,
19) aryl,
20) heteroaryl,
21) heterocyclyl, or
22) heterobicyclyl, wherein the alkyl, alkenyl, alkynyl, cycloalkyl, and cycloalkenyl is optionally substituted with one or more $R^6$ substituents;

$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^{13}$ and $R^{14}$ are each independently
1) H, or
2) $C_1$-$C_6$ alkyl; or $R^{13}$ and $R^{14}$ are combined to form a heterocyclic ring or a heterobicycle ring; or a salt thereof.

Another example of compounds of the present invention includes compounds of Formula 1.2b

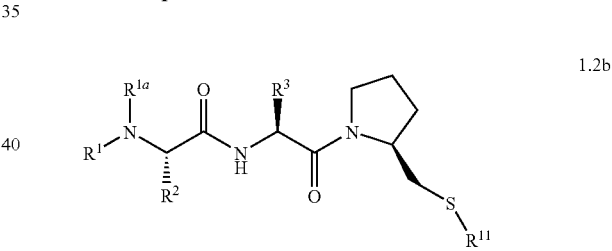

wherein:
n is 0 or 1;
m is 0, 1 or 2;
Y is NH, O or S;
$R^1$ and $R^{1a}$ are both H;
$R^2$ is $CH_3$;
$R^3$ is $CH(CH_3)_2$;
$R^6$ is
1) halogen,
2) $NO_2$,
3) CN,
4) haloalkyl,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^7$, 15) $S(O)_mR^7$,
16) $NR^8R^9$,
17) $NR^8S(O)_2R^{11}$,
18) $COR^7$,
19) $C(O)OR^7$,
20) $CONR^8R^9$,
21) $S(O)_2NR^8R^9$
22) $OC(O)R^7$,
23) $OC(O)Y-R^{11}$,
24) $SC(O)R^7$, or
25) $NC(Y)NR^8R^9$, wherein the aryl, heteroaryl, heterocyclyl, and heterobicyclyl is optionally substituted with one or more $R^{10}$ substituents;

$R^7$ is
1) H,
2) haloalkyl,
3) $C_1-C_6$ alkyl,
4) $C_2-C_6$ alkenyl,
5) $C_2-C_4$ alkynyl,
6) $C_3-C_7$ cycloalkyl,
6) $C_3-C_7$ cycloalkenyl,
7) aryl,
8) heteroaryl,
9) heterocyclyl,
10) heterobicyclyl,
11) $R^8R^9NC(=Y)$, or
12) $C_1-C_6$ alkyl-$C_2-C_4$ alkenyl, or
13) $C_1-C_6$ alkyl-$C_2-C_4$ alkynyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^8$ and $R^9$ are each independently
1) H,
2) haloalkyl,
3) $C_1-C_6$ alkyl,
4) $C_2-C_6$ alkenyl,
5) $C_2-C_4$ alkynyl,
6) $C_3-C_7$ cycloalkyl,
7) $C_3-C_7$ cycloalkenyl,
8) aryl,
9) heteroaryl,
10) heterocyclyl,
11) heterobicyclyl,
12) $C(O)R^{11}$,
13) $C(O)Y-R^{11}$, or
14) $S(O)_2R^{11}$, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents; or $R^8$ and $R^9$ together with the nitrogen atom to which they are bonded form a five, six or seven membered heterocyclic ring optionally substituted with one or more $R^6$ substituents;

$R^{10}$ is
1) halogen,
2) $NO_2$,
3) CN,
4) $B(OR^{13})(OR^{14})$,
5) $C_1-C_6$ alkyl,
6) $C_2-C_6$ alkenyl,
7) $C_2-C_4$ alkynyl,
8) $C_3-C_7$ cycloalkyl,
9) $C_3-C_7$ cycloalkenyl,
10) haloalkyl,
11) $OR^7$,
12) $NR^8R^9$,
13) $SR^7$,
14) $COR^7$,
15) $C(O)OR^7$,
16) $S(O)_mR^7$,
17) $CONR^8R^9$,
18) $S(O)_2NR^8R^9$,
19) aryl,
20) heteroaryl,
21) heterocyclyl, or
22) heterobicyclyl, wherein the alkyl, alkenyl, alkynyl, cycloalkyl, and cycloalkenyl is optionally substituted with one or more $R^6$ substituents;

$R^{11}$ is
1) haloalkyl,
2) $C_1-C_6$ alkyl,
3) $C_2-C_6$ alkenyl,
4) $C_2-C_4$ alkynyl,
5) $C_3-C_7$ cycloalkyl,
6) $C_3-C_7$ cycloalkenyl,
7) aryl,
8) heteroaryl,
9) heterocyclyl, or
10) heterobicyclyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^{13}$ and $R^{14}$ are each independently
1) H, or
2) $C_1-C_6$ alkyl; or $R^{13}$ and $R^{14}$ are combined to form a heterocyclic ring or a heterobicycle ring; or a salt thereof.

Another example of compounds of the present invention includes compounds of Formula 1.2c

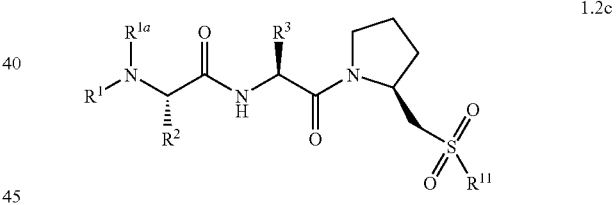

1.2c wherein:
n is 0 or 1;
m is 0, 1 or 2;
Y is NH, O or S;
$R^1$ and $R^{1a}$ are both H;
$R^2$ is $CH_3$;
$R^3$ is $CH(CH_3)_2$;
$R^6$ is
1) halogen,
2) $NO_2$,
3) CN,
4) haloalkyl,
5) $C_1-C_6$ alkyl,
6) $C_2-C_6$ alkenyl,
7) $C_2-C_4$ alkynyl,
8) $C_3-C_7$ cycloalkyl,
9) $C_3-C_7$ cycloalkenyl,
10) aryl,
11) heteroaryl,
12) heterocyclyl,
13) heterobicyclyl, 14) OR$^7$,
15) S(O)$_m$R$^7$,
16) NR$^8$R$^9$,
17) NR$^8$S(O)$_2$R$^{11}$,
18) COR$^7$,
19) C(O)OR$^7$,
20) CONR$^8$R$^9$,
21) S(O)$_2$NR$^8$R$^9$
22) OC(O)R$^7$,
23) OC(O)Y—R$^{11}$,
24) SC(O) R$^7$, or
25) NC(Y)NR$^8$R$^9$,
wherein the aryl, heteroaryl, heterocyclyl, and heterobicyclyl is optionally substituted with one or more R$^{10}$ substituents;
R$^7$ is
  1) H,
  2) haloalkyl,
  3) C$_1$-C$_6$ alkyl,
  4) C$_2$-C$_6$ alkenyl,
  5) C$_2$-C$_4$ alkynyl,
  6) C$_3$-C$_7$ cycloalkyl,
  6) C$_3$-C$_7$ cycloalkenyl,
  7) aryl,
  8) heteroaryl,
  9) heterocyclyl,
  10) heterobicyclyl,
  11) R$^8$R$^9$NC(=Y), or
  12) C$_1$-C$_6$ alkyl-C$_2$-C$_4$ alkenyl, or
  13) C$_1$-C$_6$ alkyl-C$_2$-C$_4$ alkynyl,
wherein the alkyl, alkenyl, alkynyl, cycloalkyl, cycloalkenyl is optionally substituted with one or more R$^6$ substituents; and wherein the aryl, heteroaryl, heterocyclyl, and heterobicyclyl is optionally substituted with one or more R$^{19}$ substituents;
R$^8$ and R$^9$ are each independently
  1) H,
  2) haloalkyl,
  3) C$_1$-C$_6$ alkyl,
  4) C$_2$-C$_6$ alkenyl,
  5) C$_2$-C$_4$ alkynyl,
  6) C$_3$-C$_7$ cycloalkyl,
  7) C$_3$-C$_7$ cycloalkenyl,
  8) aryl,
  9) heteroaryl,
  10) heterocyclyl,
  11) heterobicyclyl,
  12) C(O)R$^{11}$,
  13) C(O)Y—R$^{11}$, or
  14) S(O)$_2$—R$^{11}$,
wherein the alkyl, alkenyl, alkynyl, cycloalkyl, cycloalkenyl is optionally substituted with one or more R$^6$ substituents; and wherein the aryl, heteroaryl, heterocyclyl, and heterobicyclyl is optionally substituted with one or more R$^{10}$ substituents; or R$^8$ and R$^9$ together with the nitrogen atom to which they are bonded form a five, six or seven membered heterocyclic ring optionally substituted with one or more R$^6$ substituents;
R$^{10}$ is
  1) halogen,
  2) NO$_2$,
  3) CN,
  4) B(OR$^{13}$)(OR$^{14}$),
  5) C$_1$-C$_6$ alkyl,
  6) C$_2$-C$_6$ alkenyl,
  7) C$_2$-C$_4$ alkynyl,
  8) C$_3$-C$_7$ cycloalkyl,
  9) C$_3$-C$_7$ cycloalkenyl,
  10) haloalkyl,
  11) OR$^7$,
  12) NR$^8$R$^9$,
  13) SR$^7$,
  14) COR$^7$,
  15) C(O)OR$^7$,
  16) S(O)$_m$R$^7$,
  17) CONR$^8$R$^9$,
  18) S(O)$_2$NR$^8$R$^9$,
  19) aryl,
  20) heteroaryl,
  21) heterocyclyl, or
  22) heterobicyclyl,
wherein the alkyl, alkenyl, alkynyl, cycloalkyl, and cycloalkenyl is optionally substituted with one or more R$^6$ substituents;
R$^{11}$ is
  1) haloalkyl,
  2) C$_1$-C$_6$ alkyl,
  3) C$_2$-C$_6$ alkenyl,
  4) C$_2$-C$_4$ alkynyl,
  5) C$_3$-C$_7$ cycloalkyl,
  6) C$_3$-C$_7$ cycloalkenyl,
  7) aryl,
  8) heteroaryl,
  9) heterocyclyl, or
  10) heterobicyclyl,
wherein the alkyl, alkenyl, alkynyl, cycloalkyl, cycloalkenyl is optionally substituted with one or more R$^6$ substituents; and wherein the aryl, heteroaryl, heterocyclyl, and heterobicyclyl is optionally substituted with one or more R$^{10}$ substituents;
R$^{13}$ and R$^{14}$ are each independently
  1) H, or
  2) C$_1$-C$_6$ alkyl; or
R$^{13}$ and R$^{14}$ are combined to form a heterocyclic ring or a heterobicycle ring; or a salt thereof.

Another example of compound of the present invention includes compounds of Formula 1.2d

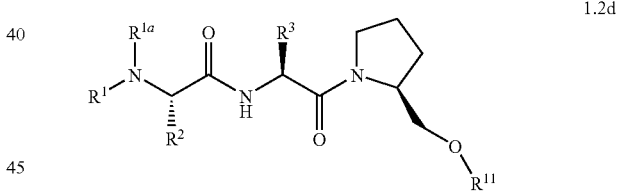

1.2d wherein:
n is 0 or 1;
m is 0, 1 or 2;
Y is NH, O or S;
R$^1$ and R$^{1a}$ are both H;
R$^2$ is CH$_3$;
R$^3$ is CH(CH$_3$)$_2$ or C(CH$_3$)$_2$;
R$^6$ is
  1) halogen,
  2) NO$_2$,
  3) CN,
  4) haloalkyl,
  5) C$_1$-C$_6$ alkyl,
  6) C$_2$-C$_6$ alkenyl,
  7) C$_2$-C$_4$ alkynyl,
  8) C$_3$-C$_7$ cycloalkyl,
  9) C$_3$-C$_7$ cycloalkenyl,
  10) aryl,
  11) heteroaryl,
  12) heterocyclyl, 13) heterobicyclyl,
14) $OR^7$,
15) $S(O)_m R^7$,
16) $NR^8 R^9$,
17) $NR^8 S(O)_2 R^{11}$,
18) $COR^7$,
19) $C(O)OR^7$,
20) $CONR^8 R^9$,
21) $S(O)_2 NR^8 R^9$
22) $OC(O) R^7$,
23) $OC(O)Y—R^{11}$,
24) $SC(O) R^7$, or
25) $NC(Y)NR^8 R^9$,
wherein the aryl, heteroaryl, heterocyclyl, and heterobicyclyl is optionally substituted with one or more $R^{10}$ substituents;
$R^7$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $R^8 R^9 NC(=Y)$, or
13) $C_1$-$C_6$ alkyl-$C_2$-$C_4$ alkenyl, or
14) $C_1$-$C_6$ alkyl-$C_2$-$C_4$ alkynyl,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) $C(O)Y—R^{11}$, or
14) $S(O)_2—R^{11}$,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
or $R^8$ and $R^9$ together with the nitrogen atom to which they are bonded form a five, six or seven membered heterocyclic ring optionally substituted with one or more $R^6$ substituents;
$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8 R^9$,
13) $SR^7$,
14) $COR^7$,
15) $C(O)OR^7$,
16) $S(O)_m R^7$,
17) $CONR^8 R^9$,
18) $S(O)_2 NR^8 R^9$,
19) aryl,
20) heteroaryl,
21) heterocyclyl, or
22) heterobicyclyl,
wherein the alkyl, alkenyl, alkynyl, cycloalkyl, and cycloalkenyl is optionally substituted with one or more $R^6$ substituents;
$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl,
wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^{13}$ and $R^{14}$ are each independently
1) H, or
2) $C_1$-$C_6$ alkyl; or
$R^{13}$ and $R^{14}$ are combined to form a heterocyclic ring or a heterobicycle ring; or a salt thereof.

$R^1$ and $R^{1a}$:

In one subset of the present invention, $R^1$ and $R^{1a}$ are each independently
1) H, or
2) $C_1$-$C_3$ alkyl optionally substituted with one $R^6$ substituent.

In one example of the present invention, $R^1$ and $R^{1a}$ are both H.

In an alternative example in the present invention, $R^1$ is H and $R^{1a}$ is $CH_3$.

$R^2$ and $R^{2a}$:

In one subset of the present invention, it is preferred that $R^2$ and $R^{2a}$ are each independently
1) H, or
2) $C_1$-$C_3$ alkyl optionally substituted with one $R^6$ substituent.

In one example of the present invention, $R^{2a}$ is H and $R^2$ is $C_1$-$C_2$ alkyl.

$R^3$ and $R^{3a}$:

In one subset of the present invention, $R^3$ and $R^{3a}$ are each independently
1) H, or
2) $C_1$-$C_6$ alkyl optionally substituted with one or more $R^6$ substituents.

In one example of the present invention, $R^{3a}$ is H and $R^3$ is $C_1$-$C_6$ alkyl optionally substituted with one or more $R^6$ substituents.

A:

In one subset of the present invention, A is —CH$_2$—.

Q:

In one subset of the present invention, Q is NR$^4$R$^5$ wherein R$^4$ and R$^5$ are each independently
1) H,
2) haloalkyl,
3) ←C$_1$-C$_6$ alkyl,
4) ←C$_2$-C$_6$ alkenyl,
5) ←C$_2$-C$_4$ alkynyl,
6) ←C$_3$-C$_7$ cycloalkyl,
7) ←C$_3$-C$_7$ cycloalkenyl,
8) ←aryl,
9) ←heteroaryl,
10) ←heterocyclyl,
11) ←heterobicyclyl,
12) ←C(O)(O)$_n$—R$^{11}$,
13) ←C(=Y)NR$^8$R$^9$, or
14) ←S(O)$_2$—R$^{11}$, wherein the alkyl, alkenyl, alkynyl, cycloalkyl, cycloalkenyl is optionally substituted with one or more R$^6$ substitutents; and wherein the aryl, heteroaryl, heterocyclyl, and heterobicyclyl is optionally substituted with one or more R$^{10}$ substituents.

In one example of the present invention, R$^4$ and R$^5$ are each independently
1) H,
2) ←C$_1$-C$_6$ alkyl,
3) ←aryl,
4) ←heteroaryl,
5) ←C(O)(O)$_n$—R$^{11}$,
6) ←C(=Y)NR$^8$R$^9$, or
7) ←S(O)$_2$—R$^{11}$, wherein the alkyl is optionally substituted with one or more R$^6$ substitutents; and wherein the aryl, and heteroaryl is optionally substituted with one or more R$^{10}$ substituents.

In another example, R$^4$ is ←C(O)(O)$_n$—R$^{11}$ and R$^5$ is ←C$_1$-C$_6$ alkyl substituted with an R$^6$ substituent.

In an alternative example, R$^4$ is ←C(=Y)NR$^8$R$^9$ and R$^5$ is ←C$_1$-C$_6$ alkyl substituted with an R$^6$ substituent.

In an alternative example, R$^4$ is ←C(O)(O)$_n$—R$^{11}$ and R$^5$ is ←aryl.

Specific examples of compounds of the present invention are provided in Table 1 described hereinafter.

If any variable, such as R$^6$, R$^{10}$ and the like, occurs more than one time in any constituent structure, the definition of the variable at each occurrence is independent at every other occurrence. If a substituent is itself substituted with one or more substituents, it is to be understood that that the one or more substituents may be attached to the same carbon atom or different carbon atoms. Combinations of substituents and variables defined herein are allowed only if they produce chemically stable compounds.

One skilled in the art will understand that substitution patterns and substituents on compounds of the present invention may be selected to provide compounds that are chemically stable and can be readily synthesized using the chemistry set forth in the examples and chemistry techniques well known in the art using readily available starting materials.

It is to be understood that many substituents or groups described herein have functional group equivalents, which means that the group or substituent may be replaced by another group or substituent that has similar electronic, hybridization or bonding properties.

Definitions

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, C$_1$-C$_6$ as in C$_1$-C$_6$— alkyl is defined as including groups having 1, 2, 3, 4, 5 or 6 carbons in a linear or branched arrangement, and C$_1$-C$_4$ as in C$_1$-C$_4$ alkyl is defined as including groups having 1, 2, 3, or 4 carbons in a linear or branched arrangement, and C$_1$-C$_3$ as in C$_1$-C$_3$ alkyl is defined as including groups having 1, 2, or 3 carbons in a linear or branched arrangement. Examples of alkyl as defined above include, but are not limited to, methyl, ethyl, n-propyl, i-propyl, n-butyl, t-butyl, i-butyl, pentyl and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regeochemistry and combinations thereof. For example, C$_2$-C$_6$ as in C$_2$-C$_6$ alkenyl is defined as including groups having 1, 2, 3, 4, 5, or 6 carbons in a linear or branched arrangement, at least two of the carbon atoms being bonded together by a double bond. Examples of C$_2$-C$_6$ alkenyl include ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example C$_2$-C$_4$ as in C$_2$-C$_4$ alkynyl is defined as including groups having 2, 3, or 4 carbon atoms in a chain, at least two of the carbon atoms being bonded together by a triple bond.

As used herein, the term "cycloalkyl" is intended to mean a monocyclic saturated aliphatic hydrocarbon group having the specified number of carbon atoms therein, for example, C$_3$-C$_7$ as in C$_3$-C$_7$ cycloalkyl is defined as including groups having 3, 4, 5, 6, or 7 carbons in a monocyclic arrangement. Examples of C$_3$-C$_7$ cycloalkyl as defined above include, but are not limited to, cyclopropyl, cyclobutyl, cyclopentyl, cyclohexyl and cycloheptyl.

As used herein, the term "cycloalkenyl" is intended to mean a monocyclic saturated aliphatic hydrocarbon group having the specified number of carbon atoms therein, for example, C$_3$-C$_7$ as in C$_3$-C$_7$ cycloalkenyl is defined as including groups having 3, 4, 5, 6, or 7 carbons in a monocyclic arrangement. Examples of C$_3$-C$_7$ cycloalkenyl as defined above include, but are not limited to, cyclopentenyl, and cyclohexenyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

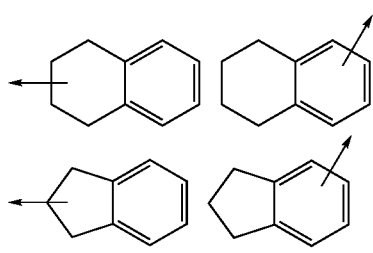

Arrowed lines drawn from the ring system indicate that the bond may be attached to any of the suitable ring atoms.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and

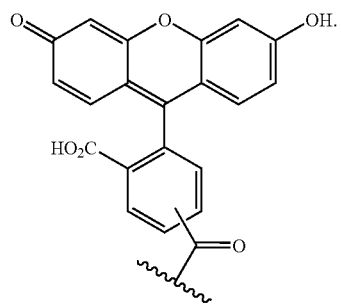

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, pyrazolinyl, and

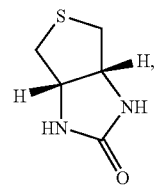

As used herein, the term "heterobicycle" either alone or in combination with another radical, is intended to mean a heterocycle as defined above fused to another cycle, be it a heterocycle, an aryl or any other cycle defined herein. Examples of such heterobicycles include, but are not limited to, coumarin, benzo[d][1,3]dioxole, 2,3-dihydrobenzo[b][1,4]dioxine and 3,4-dihydro-2H-benzo[b][1,4]dioepine.

Examples of

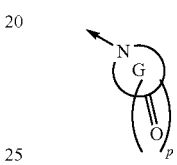

wherein G is a 5, 6 or 7 membered ring which optionally incorporates one or more heteroatoms selected from S, N or O and p is 1 or 2, and is optionally substituted with one or more $R^{12}$ substituents, include, but are not limited to:

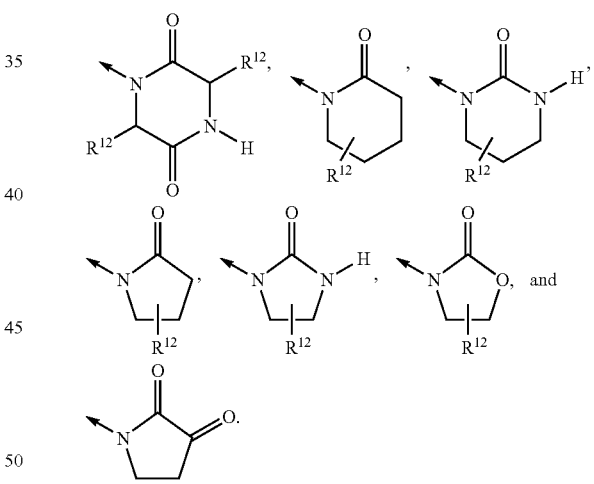

As used herein, the term "heteroatom" is intended to mean O, S or N.

As used herein, the term "detectable label" is intended to mean a group that may be linked to a compound of the present invention to produce a probe or to an IAP BIR domain, such that when the probe is associated with the BIR domain, the label allows either direct or indirect recognition of the probe so that it may be detected, measured and quantified. Examples of detectable labels include, but are not limited to, radioisotopes, fluorescent labels, colorimetric labels, chemiluminescent labels, or enzymatic markers and the like.

As used herein, the term "affinity tag" is intended to mean a ligand or group, which is linked to either a compound of the present invention or to an IAP BIR domain to allow another compound to be extracted from a solution to which the ligand or group is attached. Examples of affinity tags include, but are not limited to, biotin and polyhistidine.

As used herein, the term "probe" is intended to mean a compound of Formula I which is labeled with either a detectable label or an affinity tag, and which is capable of binding, either covalently or non-covalently, to an IAP BIR domain. When, for example, the probe is non-covalently bound, it may be displaced by a test compound. When, for example, the probe is bound covalently, it may be used to form cross-linked adducts, which may be quantified and inhibited by a test compound or extracting media such as Leamli buffer, SDS and the like.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Alternatively, the protecting group may be maintained and represent a substituent of an active compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Examples of protecting groups used throughout include, but are not limited to Fmoc, Bn, Boc and CBz. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

As used herein, the term "amino acid" is intended to mean any of the following α-amino acids:

| Amino acid | Abbreviation |
| --- | --- |
| α-Amino butyric acid | Abu |
| Alanine | Ala |
| Arginine | Arg |
| Aspartic acid | Asp |
| Asparagine | Asn |
| Cysteine | Cys |
| Glutamic acid | Glu |
| Glutamine | Gln |
| Glycine | Gly |
| Isoleucine | Ile |
| Histidine | His |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |

-continued

| Amino acid | Abbreviation |
| --- | --- |
| Tyrosine | Tyr |
| Valine | Val |

As used herein, the term "residue" when referring to α-amino acids is intended to mean a radical derived from the corresponding α-amino acid by eliminating the hydroxyl of the carboxy group and one hydrogen of the α-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively.

As used herein, the term "subject" is intended to mean humans and non-human mammals such as primates, cats, dogs, swine, cattle, sheep, goats, horses, rabbits, rats, mice and the like.

As used herein, the term "prodrug" is intended to mean a compound that may be converted under physiological conditions or by solvolysis to a biologically active compound of the present invention. Thus, the term "prodrug" refers to a metabolic precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable carrier, diluent or excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins or encapsulating polymeric delivery systems, which is acceptable for use in the subject, preferably humans.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable.

These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

As used herein, the term "BIR domain binding" is intended to mean a compound or the action of a compound of the present invention, which blocks or diminishes the binding of IAPs to BIR binding proteins or is involved in displacing BIR binding proteins from an IAP. Examples of BIR binding proteins include, but are not limited to, caspases and mitochondrially derived BIR binding proteins such as Smac, Omi/WTR2A and the like.

As used herein, the term "insufficient apoptosis" is intended to mean a state wherein a disease is caused or continues because cells deleterious to the subject have not apoptosed. This includes, but is not limited to, cancer cells that survive in a subject without treatment, cancer cells that survive in a subject during or following anti-cancer treatment, or immune cells whose action is deleterious to the subject, and includes, neutrophils, monocytes and auto-reactive T-cells.

As used herein, the term "therapeutically effective amount" is intended to mean an amount of a compound of Formula I or a salt thereof, which, when administered to a subject is sufficient to effect treatment for a disease-state associated with insufficient apoptosis. The amount of the compound of Formula I will vary depending on the compound, the condition and its severity, and the age of the subject to be treated, but can be determined routinely by one of ordinary skill in the art having regard to his own knowledge and to this disclosure.

As used herein, the term "treating" or "treatment" is intended to mean treatment of a disease-state associated with insufficient apoptosis, as disclosed herein, in a subject, and includes: (i) preventing a disease or condition associated with insufficient apoptosis from occurring in a subject, in particular, when such mammal is predisposed to the disease or condition but has not yet been diagnosed as having it; (ii) inhibiting a disease or condition associated with insufficient apoptosis, i.e., arresting its development; or (iii) relieving a disease or condition associated with insufficient apoptosis, i.e., causing regression of the condition.

As used herein, the term "treating cancer" is intended to mean the administration of a pharmaceutical composition of the present invention to a subject, preferably a human, which is afflicted with cancer to cause an alleviation of the cancer by killing, inhibiting the growth, or inhibiting the metastasis of the cancer cells.

As used herein, the term "preventing disease" is intended to mean, in the case of cancer, the post-surgical, post-chemotherapy or post-radiotherapy administration of a pharmaceutical composition of the present invention to a subject, preferably a human, which was afflicted with cancer to prevent the regrowth of the cancer by killing, inhibiting the growth, or inhibiting the metastasis of any remaining cancer cells. Also included in this definition is the prevention of prosurvival conditions that lead to diseases such as asthma, MS and the like.

As used herein, the term "apoptosis" or "programmed cell death" is intended to mean the regulated process of cell death wherein a dying cell displays a set of well-characterized biochemical hallmarks that include cell membrane blebbing, cell soma shrinkage, chromatin condensation, and DNA laddering, as well as any caspase-mediated cell death.

As used herein, the term "BIR domain" or "BIR" are used interchangeably throughout and are intended to mean a domain which is characterized by a number of invariant amino acid residue including conserved cysteines and one conserved hisitidine residue within the sequence Cys-(Xaa1)$_2$ Cys-(Xaa1)$_{16}$His-(Xaa1)$_{6-8}$Cys (SEQ ID NO: 1). Typically, the amino acid sequence of the consensus sequence is: Xaa1-Xaa1-Xaa1-Arg-Leu-Xaa1-Thr-Phe-Xaa1-Xaa1-Trp-Pro-Xaa2-Xaa1-Xaa1-Xaa2-Xaa2-Xaa1-Xaa1-Xaa1-Xaa1-Leu-Ala-Xaa1-Ala-Gly-Phe-Tyr-Tyr-Xaa1-Gly-Xaa1-Xaa1-Asp-Xaa1-Val-Xaa1-Cys-Phe-Xaa1-Cys-Xaa1-Xaa1-Xaa1-Xaa1-Xaa1-Xaa1-Trp-Xaa1-Xaa1-Xaa1-Asp-Xaa1-Xaa1-Xaa1-Xaa1-Xaa1-His-Xaa-1-Xaa1-Xaa1-Xaa1-Pro-Xaa1-Cys-Xaa1-Phe-Val (SEQ ID NO: 2), wherein Xaa1 is any amino acid and Xaa2 is any amino acid or is absent. Preferably the sequence is substantially identical to one of the BIR domain sequences provided for XIAP, HIAP1, or HIAP2 herein.

The BIR domain residues are listed below (see Genome Biology (2001) 1-10):

|  | XIAP (SEQ ID NO: 3) | HIAP-1 (SEQ ID NO: 4) | HIAP-2 (SEQ ID NO: 5) |
| --- | --- | --- | --- |
| BIR1 | 21-93 | 41-113 | 24-96 |
| BIR2 | 159-230 | 179-250 | 164-235 |
| BIR3 | 258-330 | 264-336 | 250-322 |
| Seq. # | P98170 | XP-006266 | XP-006267 |

As used herein, the term "ring zinc finger" or "RZF" is intended to mean a domain having the amino acid sequence of the consensus sequence: Glu-Xaa1-Xaa1-Xaa1-Xaa1-Xaa1-Xaa-1-Xaa2-Xaa1-Xaa1-Xaa1-Cys-Lys-Xaa3-Cys-Met-Xaa1-Xaa1-Xaa1-Xaa1-Xaa1-Xaa3-Xaa1-Phe-Xaa1-Pro-Cys-Gly-His-Xaa1-Xaa1-Xaa1-Cys-Xaa1-Xaa1-Cys-Ala-Xaa1-Xaa-1-Xaa1-Xaa1-Xaa1-Cys-Pro-Xaa1-Cys (SEQ ID NO: 6), wherein Xaa1 is any amino acid, Xaa2 is Glu or Asp, and Xaa3 is Val or Ile.

As used herein, the term "IAP" is intended to mean a polypeptide or protein, or fragment thereof, encoded by an IAP gene. Examples of IAPs include, but are not limited to, human or mouse NAIP (Birc 1), HIAP-1 (cIAP2, Birc 3), HIAP-2 (cIAP1, Birc 2), XIAP (Birc 4), survivin (Birc 5), livin (ML-IAP, Birc 7), ILP-2 (Birc 8) and Apollon/BRUCE (Birc 6) (see for example U.S. Pat. Nos. 6,107,041; 6,133, 437; 6,156,535; 6,541,457; 6,656,704; 6,689,562; Deveraux and Reed, Genes Dev. 13, 239-252, 1999; Kasof and Gomes, J. Biol. Chem., 276, 3238-3246, 2001; Vucic et al., Curr. Biol. 10, 1359-1366, 2000; Ashab et al. FEBS Lett., 495, 56-60, 2001, the contents of which are hereby incorporated by reference).

As used herein, the term "IAP gene" is intended to mean a gene encoding a polypeptide having at least one BIR domain and which is capable of modulating (inhibiting or enhancing) apoptosis in a cell or tissue. The IAP gene is a gene having about 50% or greater nucleotide sequence identity to at least one of human or mouse NAIP (Birc 1), HIAP-1 (cIAP2, Birc 3), HIAP-2 (cIAP1, Birc 2), XIAP (Birc 4), survivin (Birc 5), livin (ML-IAP, Birc 7), ILP-2 (Birc 8) and Apollon/BRUCE (Birc 6). The region of sequence over which identity is measured is a region encoding at least one BIR domain and a ring zinc finger domain. Mammalian IAP genes include nucleotide sequences isolated from any mammalian source.

As used herein, the term "$IC_{50}$" is intended to mean an amount, concentration or dosage of a particular compound of the present invention that achieves a 50% inhibition of a maximal response, such as displacement of maximal fluorescent probe binding in an assay that measures such response.

As used herein, the term "$EC_{50}$" is intended to mean an amount, concentration or dosage of a particular compound of the present invention that achieves a 50% inhibition of cell survival.

As used herein, the term "modulate" or "modulating" is intended to mean the treatment, prevention, suppression, enhancement or induction of a function or condition using the compounds of the present invention. For example, the compounds of the present invention can modulate IAP function in a subject, thereby enhancing apoptosis by significantly reducing, or essentially eliminating the interaction of activated apoptotic proteins, such as caspase-3, 7 and 9, with the BIR domains of mammalian IAPs.

As used herein, the term "enhancing apoptosis" is intended to mean increasing the number of cells that apoptose in a given cell population either in vitro or in vivo. The cell population may include, but is not limited to, ovarian cancer cells, colon cancer cells, breast cancer cells, lung cancer cells, pancreatic cancer cells, or T cells and the like. It will be appreciated that the degree of apoptosis enhancement provided by an apoptosis-enhancing compound of the present invention in a given assay will vary, but that one skilled in the art can determine the statistically significant change in the level of apoptosis that identifies a compound that enhances apoptosis otherwise limited by an IAP. Preferably "enhancing apoptosis" means that the increase in the number of cells undergoing apoptosis is at least 25%, more preferably the increase is 50%, and most preferably the increase is at least one-fold. Preferably the sample monitored is a sample of cells that normally undergo insufficient apoptosis (i.e., cancer cells). Methods for detecting the changes in the level of apoptosis (i.e., enhancement or reduction) are described in the Examples and include methods that quantitate the fragmentation of DNA, methods that quantitate the translocation phosphatoylserine from the cytoplasmic to the extracellular side of the membrane, determination of activation of the caspases and methods quantitate the release of cytochrome C and the apoptosis inhibitory factor into the cytoplasm by mitochondria.

As used herein, the term "proliferative disease" or "proliferative disorder" is intended to mean a disease that is caused by or results in inappropriately high levels of cell division, inappropriately low levels of apoptosis, or both. For example, cancers such as lymphoma, leukemia, melanoma, ovarian cancer, breast cancer, pancreatic cancer, and lung cancer, and autoimmune disorders are all examples of proliferative diseases.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms.

Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

Utilities

The compounds of the present invention are useful as IAP BIR domain binding compounds and as such the compounds, compositions and method of the present invention include application to the cells or subjects afflicted with or having a predisposition towards developing a particular disease state, which is characterized by insufficient apoptosis. Thus, the compounds, compositions and methods of the present invention are used to treat cellular proliferative diseases/disorders, which include, but are not limited to, i) cancer, ii) autoimmune disease, iii) inflammatory disorders, iv) proliferation induced post medical procedures, including, but not limited to, surgery, angioplasty, and the like.

The compounds of the present invention may also be useful as antiulcerous agents. Down-regulation of the TRAIL (TNF-alpha-related apoptosis inducing ligand) system, in the context of *H. pylori* infection, may limit exaggerated apoptosis of gastric epithelial cells and destruction of tissue and, therefore, may enable *H. pylori* to maintain its niche, thus the compounds of the present invention may be useful in the treatment of bacterial infection and/or recurrent infection that may have develop due to the down-regulation of the TRAIL system. (see Nou et al. J. Infectious Diseases (2005) 571-8).

The compounds of the present invention may also be useful in the treatment of primary varicosis. Data suggest (see Ducass et al. Eur. J. Vasc. Endovac. Surg (2005) 316-323) that primary varicose veins are associated with inhibition of programmed cell death involving the defect in intrinsic apoptotic pathway. Thus the BIR domain binding compounds of the present invention may be useful in the treatment of this pathology.

The compounds of the present invention may also be useful in the treatment of diseases in which there is a defect in the programmed cell-death or the apoptotic machinery (TRAIL, FAS, apoptosome), such as multiple sclerosis, asthma, artherosclerosis, inflammation, autoimmunity and the like.

The treatment involves administration to a subject in need thereof a compound of the present invention or a pharmaceutically acceptable salt thereof, or a pharmaceutical composition comprising a pharmaceutical carrier and a therapeutically effective amount of a compound of the present invention, or a pharmaceutically acceptable salt thereof.

In particular, the compounds, compositions and methods of the present invention are useful for the treatment of cancer including solid tumors such as skin, breast, brain, lung, testicular carcinomas, and the like. Cancers that may be treated by the compounds, compositions and methods of the invention include, but are not limited to the following:

| Tissue | Example |
|---|---|
| Adrenal gland | neuroblastoma |
| Bone | osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors |
| Cardiac | sarcoma (angiosarcoma, fibrosarcoma, rhabdomyosarcoma, liposarcoma), myxoma, rhabdomyoma, fibroma, lipoma and teratoma |
| Gastrointestinal | esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) |
| Genitourinary tract | kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma teratoma, embryonal carcinoma, teratocarcinoma, choriocarcinoma, sarcoma, interstitial cell carcinoma, fibroma, fibroadenoma, adenomatoid tumors, lipoma) |
| Gynecological | uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) |
| Hematologic | blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] |
| Liver | hepatoma (hepatocellular carcinoma), cholangiocarcinoma, hepatoblastoma, angiosarcoma, hepatocellular adenoma, hemangioma |
| Lung | bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma |
| Nervous system | skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma) |
| Skin | malignant melanoma, basal cell carcinoma, squamous cell carcinoma, Karposi's sarcoma, moles dysplastic nevi, lipoma, angioma, dermatofibroma, keloids |

The compounds of the present invention, or their pharmaceutically acceptable salts or their prodrugs, may be administered in pure form or in an appropriate pharmaceutical composition, and can be carried out via any of the accepted modes of Galenic pharmaceutical practice.

The pharmaceutical compositions of the present invention can be prepared by admixing a compound of the present invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral (subcutaneous injections, intravenous, intramuscular, intrasternal injection or infusion techniques), sublingual, ocular, rectal, vaginal, and intranasal. Pharmaceutical compositions of the present invention are formulated so as to allow the active ingredients contained therein to be bioavailable upon administration of the composition to a subject. Compositions that will be administered to a subject or patient take the form of one or more dosage units, where for example, a tablet may be a single dosage unit, and a container of a compound of the present invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the present invention, or a pharmaceutically acceptable salt thereof, for treatment of a disease-state as described above.

A pharmaceutical composition of the present invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example inhalatory administration.

For oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil such as soybean or vegetable oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

A liquid pharmaceutical composition of the present invention used for either parenteral or oral administration should contain an amount of a compound of the present invention such that a suitable dosage will be obtained. Typically, this amount is at least 0.01% of a compound of the present invention in the composition. When intended for oral administration, this amount may be varied to be between 0.1 and about 70% of the weight of the composition. For parenteral usage, compositions and preparations according to the present invention are prepared so that a parenteral dosage unit contains between 0.01 to 1% by weight of the compound of the present invention.

The pharmaceutical composition of the present invention may be used for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present invention from about 0.1 to about 10% w/v (weight per unit volume).

The pharmaceutical composition of the present invention may be used for rectal administration to treat for example, colon cancer, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the present invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention in solid or liquid form may include an agent that binds to the compound of the present invention and thereby assists in the delivery of the compound. Suitable agents that may act in this capacity include, but are not limited to, a monoclonal or polyclonal antibody, a protein or a liposome.

The pharmaceutical composition of the present invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the present invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the present invention may be prepared by methodology well known in the pharmaceutical art. For example, a pharmaceutical composition intended to be administered by injection can be prepared by admixing a compound of the present invention with sterile saline, distilled water for injection, and the like, so as to form a solution. A surfactant may be added to facilitate the formation of a homogeneous solution or suspension. Surfactants are compounds that non-covalently interact with the compound of the present invention so as to facilitate dissolution or homogeneous suspension of the compound in the aqueous delivery system.

The compounds of the present invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose may be from about 0.1 mg to about 40 mg/kg of body weight per day or twice per day of a compound of the present invention, or a pharmaceutically acceptable salt thereof.

Combination Therapy

The compounds of the present invention, or pharmaceutically acceptable salts thereof, may also be administered simultaneously with, prior to, or after administration of one or more of the therapeutic agents described below. Such combination therapy may include administration of a single pharmaceutical dosage formulation which contains a compound of the present invention and one or more additional agents given below, as well as administration of the compound of the present invention and each of additional agent in its own separate pharmaceutical dosage formulation. For example, a compound of the present invention and another therapeutic agent can be administered to the patient either together in a single oral dosage composition such as a tablet or capsule, or each agent administered in separate oral dosage formulations or via intravenous injection. Where separate dosage formulations are used, the compounds of the present invention and one or more additional agents can be administered at essentially the same time, i.e., concurrently, or at separately staggered times, i.e., sequentially; combination therapy is understood to include all these regimens.

Thus, the present invention also encompasses the use of the compounds of the present invention in combination with radiation therapy or one or more additional agents such as those described in WO 03/099211 (PCT/US03/15861), which is hereby incorporated by reference.

Examples of such additional therapeutic agents include, but are not limited to the following:

a) an estrogen receptor modulator,
b) an androgen receptor modulator,
c) retinoid receptor modulator,
d) a cytotoxic agent,
e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor,
l) a PPAR-$\gamma$ agonist,
m) a PPAR-$\delta$. agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug.
s) a proteasome inhibitor such as Velcade and MG132 (7-Leu-Leu-aldehyde) (see He at al. in Oncogene (2004) 23, 2554-2558);
t) an HDAC inhibitor, such as sodium butyrate, phenyl butyrate, hydroamic acids, cyclin tetrapeptide and the like (see Rosato et al., Molecular Cancer Therapeutics 2003, 1273-1284);
u) an inhibitor of the chemotrypsin-like activity in the proteasome; and
v) E3 ligase inhibitors.

More specifically, the compounds of the present invention can also be used in combination with one or more chemotherapeutic agents that disrupts or stabilizes microtubules is particularly effective in treating cancer and other neoplasms. Microtubule-disrupting agents (e.g., vinca alkaloids) and microtubule-stabilizing agents (e.g., taxanes) are described in greater detail below.

Vinca Alkaloids and Related Compounds

Vinca alkaloids that can be used in combination with the nucleobase oligomers of the invention to treat cancer and other neoplasms include vincristine, vinblastine, vindesine, vinflunine, vinorelbine, and anhydrovinblastine.

Dolastatins are oligopeptides that primarily interfere with tubulin at the vinca alkaloid binding domain. These compounds can also be used in combination with the compounds of the invention to treat cancer and other neoplasms. Dolastatins include dolastatin-10 (NCS 376128), dolastatin-15, ILX651, TZT-1027, symplostatin 1, symplostatin 3, and LU103793 (cemadotin).

Cryptophycins (e.g., cryptophycin 1 and cryptophycin 52 (LY355703)) bind tubulin within the vinca alkaloid-binding domain and induce G2/M arrest and apoptosis. Any of these compounds can be used in combination with the compounds of the invention to treat cancer and other neoplasms.

Other microtubule disrupting compounds that can be used in conjunction with the compounds of the invention to treat cancer and other neoplasms are described in U.S. Pat. Nos. 6,458,765; 6,433,187; 6,323,315; 6,258,841; 6,143,721; 6,127,377; 6,103,698; 6,023,626; 5,985,837; 5,965,537; 5,955,423; 5,952,298; 5,939,527; 5,886,025; 5,831,002; 5,741,892; 5,665,860; 5,654,399; 5,635,483; 5,599,902; 5,530,097; 5,521,284; 5,504,191; 4,879,278; and 4,816,444, and U.S. patent application Publication Nos. 2003/0153505 A1; 2003/0083263 A1; and 2003/0055002 A1, each of which is hereby incorporated by reference.

Taxanes and Other Microtubule Stabilizing Compounds

Taxanes such as paclitaxel, doxetaxel, RPR 109881A, SB-T-1213, SB-T-1250, SB-T-101187, BMS-275183, BRT 216, DJ-927, MAC-321, IDN5109, and IDN5390 can be used in combination with the compounds of the invention to treat cancer and other neoplasms. Taxane analogs (e.g., BMS-184476, BMS-188797) and functionally related non-taxanes (e.g., epothilones (e.g., epothilone A, epothilone B (EPO906), deoxyepothilone B, and epothilone B lactam (BMS-247550)), eleutherobin, discodermolide, 2-epi-discodermolide, 2-des-methyldiscodermolide, 5-hydroxymethyldiscodermolide, 19-des-aminocarbonyldiscodermolide, 9(13)-cyclodiscodermolide, and laulimalide) can also be used in the methods and compositions of the invention.

Other microtubule stabilizing compounds that can be used in combination with the compounds of the invention to treat cancer and other neoplasms are described in U.S. Pat. Nos. 6,624,317; 6,610,736; 6,605,599; 6,589,968; 6,583,290; 6,576,658; 6,515,017; 6,531,497; 6,500,858; 6,498,257; 6,495,594; 6,489,314; 6,458,976; 6,441,186; 6,441,025; 6,414,015; 6,387,927; 6,380,395; 6,380,394; 6,362,217; 6,359,140; 6,306,893; 6,302,838; 6,300,355; 6,291,690; 6,291,684; 6,268,381; 6,262,107; 6,262,094; 6,147,234; 6,136,808; 6,127,406; 6,100,411; 6,096,909; 6,025,385; 6,011,056; 5,965,718; 5,955,489; 5,919,815; 5,912,263; 5,840,750; 5,821,263; 5,767,297; 5,728,725; 5,721,268; 5,719,177; 5,714,513; 5,587,489; 5,473,057; 5,407,674; 5,250,722; 5,010,099; and 4,939,168; and U.S. patent application Publication Nos. 2003/0186965 A1; 2003/0176710

A1; 2003/0176473 A1; 2003/0144523 A1; 2003/0134883 A1; 2002/0016356 A1; 2002/0002292 A1, each of which is hereby incorporated by reference.

A1; 2003/0087888 A1; 2003/0060623 A1; 2003/0045711
A1; 2003/0023082 A1; 2002/0198256 A1; 2002/0193361
A1; 2002/0188014 A1; 2002/0165257 A1; 2002/0156110
A1; 2002/0128471 A1; 2002/0045609 A1; 2002/0022651

Other chemotherapeutic agents that may be administered with a compound of the present invention are listed in the following Table:

| | | |
|---|---|---|
| Alkylating agents | cyclophosphamide | mechlorethamine |
| | lomustine | thiotepa |
| | busulfan | streptozocin |
| | procarbazine | chlorambucil |
| | ifosfamide | temozolomide |
| | altretamine | dacarbazine |
| | melphalan | semustine |
| | estramustine phosphate | carmustine |
| | hexamethylmelamine | |
| Platinum agents | cisplatin | tetraplatin |
| | carboplatinum | BBR-3464 (Hoffmann-La Roche) |
| | oxaliplatin | Ormiplatin |
| | ZD-0473 (AnorMED) | SM-11355 (Sumitomo) |
| | spiroplatinum | iproplatin |
| | lobaplatin (Aeterna) | AP-5280 (Access) |
| | carboxyphthalatoplatinum | |
| | satraplatin (Johnson Matthey) | |
| Antimetabolites | azacytidine | 6-mercaptopurine |
| | tomudex | hydroxyurea |
| | gemcitabine | 6-thioguanine |
| | trimetrexate | decitabine (SuperGen) |
| | capecitabine | cytarabin |
| | deoxycoformycin | clofarabine (Bioenvision) |
| | 5-fluorouracil | 2-fluorodeoxy |
| | fludarabine | cytidine |
| | floxuridine | irofulven (MGI Pharma) methotrexate |
| | pentostatin | DMDC (Hoffmann-La Roche) |
| | 2-chlorodeoxyadenosine | idatrexate |
| | raltitrexed | ethynylcytidine (Taiho) |
| Topoisomerase inhibitors | amsacrine | TAS-103 (Taiho) |
| | rubitecan (SuperGen) | Topotecan |
| | epirubicin | elsamitrucin (Spectrum) dexrazoxanet |
| | exatecan mesylate (Daiichi) | (TopoTarget) |
| | etoposide | J-107088 (Merck & Co) |
| | quinamed (ChemGenex) | pixantrone (Novuspharma) |
| | teniposide or mitoxantrone | BNP-1350 (BioNumerik) |
| | gimatecan (Sigma-Tau) | rebeccamycin analogue (Exelixis) |
| | irinotecan (CPT-11) | CKD-602 (Chong Kun Dang) |
| | diflomotecan (Beaufour-Ipsen) | BBR-3576 (Novuspharma) |
| | 7-ethyl-10-hydroxy-camptothecin | KW-2170 (Kyowa Hakko) |
| Antitumor antibiotics | dactinomycin (actinomycin D) | bleomycinic acid |
| | amonafide | idarubicin |
| | doxorubicin (adriamycin) | bleomycin A |
| | azonafide | rubidazone |
| | deoxyrubicin | bleomycin B |
| | anthrapyrazole | plicamycinp |
| | valrubicin | mitomycin C |
| | oxantrazole | porfiromycin |
| | daunorubicin (daunomycin) | MEN-10755 (Menarini) |
| | losoxantrone | cyanomorpholinodoxorubicin |
| | epirubicin | GPX-100 (Gem Pharmaceuticals) |
| | bleomycin sulfate (blenoxane) | mitoxantrone (novantrone) |
| | therarubicin | |
| Antimitotic agents | paclitaxel | RPR 109881A (Aventis) |
| | SB 408075 (GlaxoSmithKline) | ZD 6126 (AstraZeneca) |
| | docetaxel | TXD 258 (Aventis) |
| | E7010 (Abbott) | PEG-paclitaxel (Enzon) |
| | Colchicines | epothilone B (Novartis) |
| | PG-TXL (Cell Therapeutics) | AZ10992 (Asahi) |
| | vinblastine | T 900607 (Tularik) |
| | IDN 5109 (Bayer) | IDN-5109 (Indena) |
| | Vincristine | T 138067 (Tularik) |
| | A 105972 (Abbott) | AVLB (Prescient NeuroPharma) |
| | Vinorelbine | cryptophycin 52 (Eli Lilly) |
| | A 204197 (Abbott) | azaepothilone B (BMS) |
| | Vindesine | vinflunine (Fabre) |
| | LU 223651 (BASF) | BNP-7787 (BioNumerik) |
| | dolastatin 10 (NCI) | auristatin PE (Teikoku Hormone) |
| | D 24851 (ASTAMedica) | CA-4 prodrug (OXiGENE) |
| | rhizoxin (Fujisawa) | BMS 247550 (BMS) |
| | ER-86526 (Eisai) | dolastatin-10 (NIH) |
| | mivobulin (Warner-Lambert) | BMS 184476(BMS) |
| | combretastatin A4 (BMS) | CA-4 (OXiGENE) |

| | | |
|---|---|---|
| | cemadotin (BASF) | BMS 188797 (BMS) |
| | isohomohalichondrin-B (PharmaMar) | taxoprexin (Protarga) |
| Aromatase inhibitors | Aminoglutethimide | anastrazole |
| | Exemestane | YM-511 (Yamanouchi) |
| | Letrozole | formestane |
| | atamestane (BioMedicines) | |
| Thymidylate synthase inhibitors | pemetrexed (Eli Lilly) | ZD-9331 (BTG) |
| | nolatrexed (Eximias) | CoFactor ™ (BioKeys) |
| DNA antagonists | trabectedin (PharmaMar) | albumin + 32P (Isotope Solutions) |
| | mafosfamide (Baxter International) | O6 benzyl guanine (Paligent) |
| | glufosfamide (Baxter International) | thymectacin (NewBiotics) edotreotide (Novartis) |
| | apaziquone (Spectrum Pharmaceuticals) | |
| Farnesyltransferase inhibitors | arglabin (NuOncology Labs) | perillyl alcohol (DOR BioPharma) |
| | tipifarnib (Johnson & Johnson) | BAY-43-9006 (Bayer) |
| | lonafarnib (Schering-Plough) | |
| Pump inhibitors | CBT-1 (CBA Pharma) | tariquidar (Xenova) |
| | zosuquidar trihydrochloride (Eli Lilly) | biricodar dicitrate (Vertex) |
| | | MS-209 (Schering AG) |
| Histone acetyltransferase inhibitors | tacedinaline (Pfizer) | depsipeptide (Fujisawa) |
| | pivaloyloxymethyl butyrate (Titan) | MS-275 (Schering AG) |
| | SAHA (Aton Pharma) | |
| Metalloproteinase inhibitors | Neovastat (Aeterna Laboratories) | marimastat (British Biotech) BMS-275291 (Celltech) |
| | CMT-3 (CollaGenex) | |
| Ribonucleoside reductase inhibitors | gallium maltolate (Titan) | triapine (Vion) |
| | tezacitabine (Aventis) | didox (Molecules for Health) |
| TNF alpha agonists/antagonists | virulizin (Lorus Therapeutics) | CDC-394 (Celgene) |
| | revimid (Celgene) | |
| Endothelin A receptor antagonist | atrasentan (Abbott) | ZD-4054 (AstraZeneca) |
| | YM-598 (Yamanouchi) | |
| Retinoic acid receptor agonists | fenretinide (Johnson & Johnson) | LGD-1550 (Ligand) |
| | alitretinoin (Ligand) | |
| Immuno-modulators | Interferon | norelin (Biostar) |
| | dexosome therapy (Anosys) | IRX-2 (Immuno-Rx) |
| | oncophage (Antigenics) | BLP-25 (Biomira) |
| | pentrix (Australian Cancer Technology) | PEP-005 (Peplin Biotech) |
| | | MGV (Progenics) |
| | GMK (Progenics) | synchrovax vaccines (CTL Immuno) |
| | ISF-154 (Tragen) | beta.-alethine (Dovetail) |
| | adenocarcinoma vaccine (Biomira) | melanoma vaccine (CTL Immuno) |
| | cancer vaccine (Intercell) | CLL therapy (Vasogen) |
| | CTP-37 (A VI BioPharma) | p21 RAS vaccine (GemVax) |
| Hormonal and antihormonal agents | estrogens | bicalutamide |
| | Prednisone | testosterone propionate; |
| | conjugated estrogens | fluoxymesterone |
| | methylprednisolone | flutamide |
| | ethinyl estradiol | methyltestosterone |
| | prednisolone | octreotide |
| | chlortrianisen | diethylstilbestrol |
| | aminoglutethimide | nilutamide |
| | idenestrol | megestrol |
| | leuprolide | mitotane tamoxifen |
| | hydroxyprogesterone caproate | P-04 (Novogen) |
| | goserelin | Toremofine |
| | medroxyprogesterone | 2-methoxyestradiol (EntreMed) |
| | leuporelin | dexamethasone |
| | testosterone | arzoxifene (Eli Lilly) |
| Photodynamic agents | talaporfin (Light Sciences) | motexafin |
| | Pd-bacteriopheophorbide (Yeda) | gadolinium (Pharmacyclics) |
| | Theralux (Theratechnologies) | hypericin |
| | lutetium texaphyrin (Pharmacyclics) | |
| Tyrosine Kinase Inhibitors | imatinib (Novartis) | C225 (ImClone) |
| | kahalide F (PharmaMar) | ZD4190 (AstraZeneca) |
| | leflunomide (Sugen/Pharmacia) | rhu-Mab (Genentech) |
| | CEP-701 (Cephalon) | ZD6474 (AstraZeneca) |
| | ZD1839 (AstraZeneca) | MDX-H210 (Medarex) |
| | CEP-751 (Cephalon) | vatalanib (Novartis) |
| | erlotinib (Oncogene Science) | 2C4 (Genentech) |
| | MLN518 (Millenium) | PKI166 (Novartis) |
| | canertinib (Pfizer) | MDX-447 (Medarex) |
| | PKC412 (Novartis) | GW2016 (GlaxoSmithKline) |
| | squalamine (Genaera) | ABX-EGF (Abgenix) |
| | phenoxodiol ( ) | EKB-509 (Wyeth) |
| | SU5416 (Pharmacia) | IMC-1C11 (ImClone) |
| | trastuzumab (Genentech) | EKB-569 (Wyeth) |
| | SU6668 (Pharmacia) | |

-continued

| Miscellaneous agents | |
|---|---|
| SR-27897 (CCK A inhibitor, Sanofi-Synthelabo) | gemtuzumab (CD33 antibody, Wyeth Ayerst) |
| BCX-1777 (PNP inhibitor, BioCryst) | CCI-779 (mTOR kinase inhibitor, Wyeth) |
| tocladesine (cyclic AMP agonist, Ribapharm) | PG2 (hematopoiesis enhancer, Pharmagenesis) |
| ranpirnase (ribonuclease stimulant, Alfacell) | exisulind (PDE V inhibitor, Cell Pathways) |
| alvocidib (CDK inhibitor, Aventis) | Immunol ™ (triclosan oral rinse, Endo) |
| galarubicin (RNA synthesis inhibitor, Dong-A) | CP-461 (PDE V inhibitor, Cell Pathways) |
| CV-247 (COX-2 inhibitor, Ivy Medical) | triacetyluridine (uridine prodrug, Wellstat) |
| tirapazamine (reducing agent, SRI International) | AG-2037 (GART inhibitor, Pfizer) |
| P54 (COX-2 inhibitor, Phytopharm) | SN-4071 (sarcoma agent, Signature BioScience) |
| N-acetylcysteine (reducing agent, Zambon) | WX-UK1 (plasminogen activator inhibitor, Wilex) |
| CapCell ™ (CYP450 stimulant, Bavarian Nordic) | TransMID-107.TM. (immunotoxin, KS Biomedix) |
| R-flurbiprofen (NF-kappaB inhibitor, Encore) | PBI-1402 (PMN stimulant, ProMetic LifeSciences) |
| GCS-100 (gal3 antagonist, GlycoGenesys) | |
| 3CPA (NF-kappaB inhibitor, Active Biotech) | PCK-3145 (apoptosis promotor, Procyon) |
| G17DT immunogen (gastrin inhibitor, Aphton) | bortezomib (proteasome inhibitor, Millennium) |
| seocalcitol (vitamin D receptor agonist, Leo) | doranidazole (apoptosis promotor, Pola) |
| efaproxiral (oxygenator, Allos Therapeutics) | SRL-172 (T cell stimulant, SR Pharma) CHS-828 (cytotoxic agent, Leo) |
| 131-I-TM-601 (DNA antagonist, TransMolecular) | TLK-286 (glutathione S transferase inhibitor, Telik) |
| PI-88 (heparanase inhibitor, Progen) | |
| eflornithine (ODC inhibitor, ILEX Oncology) | trans-retinoic acid (differentiator, NIH) |
| tesmilifene (histamine antagonist, YM BioSciences) | PT-100 (growth factor agonist, Point Therapeutics) |
| minodronic acid (osteoclast inhibitor, Yamanouchi) | MX6 (apoptosis promotor, MAXIA) midostaurin (PKC inhibitor, Novartis) |
| histamine (histamine H2 receptor agonist, Maxim) | apomine (apoptosis promotor, ILEX Oncology) bryostatin-1 (PKC stimulant, GPC Biotech) |
| indisulam (p53 stimulant, Eisai) | urocidin (apoptosis promotor, Bioniche) |
| tiazofurin (IMPDH inhibitor, Ribapharm) | CDA-II (apoptosis promotor, Everlife) |
| aplidine (PPT inhibitor, PharmaMar) | Ro-31-7453 (apoptosis promotor, La Roche) |
| cilengitide (integrin antagonist, Merck KGaA) | SDX-101 (apoptosis promotor, Salmedix) |
| rituximab (CD20 antibody, Genentech) | brostallicin (apoptosis promotor, Pharmacia) |
| SR-31747 (IL-1 antagonist, Sanofi-Synthelabo) | ceflatonin (apoptosis promotor, ChemGenex) |

Additional combinations may also include agents which reduce the toxicity of the aforesaid agents, such as hepatic toxicity, neuronal toxicity, nephrotoxicity and the like.

Moreover, our in vitro results suggest that the compounds of the present invention may well work with TRAIL and proteasome inhibitors such as MG132 and Velcade currently used in human clinical trials for multiple myeloma may be used in combination with the compounds of the present invention.

Screening Assays

The compounds of the present invention may also be used in a method to screen for other compounds that bind to an IAP BIR domain. Generally speaking, to use the compounds of the invention in a method of identifying compounds that bind to an IAP BIR domain, the IAP is bound to a support, and a compound of the invention is added to the assay. Alternatively, the compound of the invention may be bound to the support and the IAP is added.

There are a number of ways in which to determine the binding of a compound of the present invention to the BIR domain. In one way, the compound of the invention, for example, may be fluorescently or radioactively labeled and binding determined directly. For example, this may be done by attaching the IAP to a solid support, adding a detectably labeled compound of the invention, washing off excess reagent, and determining whether the amount of the detectable label is that present on the solid support. Numerous blocking and washing steps may be used, which are known to those skilled in the art.

In some cases, only one of the components is labeled. For example, specific residues in the BIR domain may be labeled. Alternatively, more than one component may be labeled with different labels; for example, using $I^{125}$ or $Eu^{3+}$ for the BIR domain, and a fluorescent label for the probe.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity. The compounds may be capable of directly or indirectly altering the IAP biological activity.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining an IAP BIR domain and a probe to form a probe:BIR domain complex in a first sample followed by adding a test compound from a second sample. The binding of the test is determined, and a change, or difference in binding between the two samples indicates the presence of a test compound capable of binding to the BIR domain and potentially modulating the IAP's activity.

In one case, the binding of the test compound is determined through the use of competitive binding assays. In this embodiment, the probe is labeled with an an affinity label such as biotin. Under certain circumstances, there may be competitive binding between the test compound and the probe, with the probe displacing the candidate agent.

In one case, the test compound may be labeled. Either the test compound, or a compound of the present invention, or both, is added first to the IAP BIR domain for a time sufficient to allow binding to form a complex.

Formation of the probe:BIR domain complex typically require Incubations of between 4° C. and 40° C. for between 10 minutes up to 24 hours to allow for high-throughput screening. Any excess of reagents are generally removed or washed away. The test compound is then added, and the presence or absence of the labeled component is followed, to indicate binding to the BIR domain.

In one case, the probe is added first, followed by the test compound. Displacement of the probe is an indication the test compound is binding to the BIR domain and thus is capable of binding to, and potentially modulating, the activity of IAP. Either component can be labeled. For example, the presence of probe in the wash solution indicates displacement by the test compound. Alternatively, if the test compound is labeled, the presence of the probe on the support indicates displacement.

In one case, the test compound may be added first, with incubation and washing, followed by the probe. The absence of binding by the probe may indicate the test compound is bound to the BIR domain. Thus, if the probe is detected on the support, coupled with a lack of test compound binding, may indicate the test compound is capable of binding to the BIR domain.

Modulation is tested by screening for a test compound's ability to modulate the activity of IAP and includes combining a test compound with an IAP BIR domain, as described above, and determining an alteration in the biological activity of the IAP. Therefore in this case, the test compound should both bind to the BIR domain (although this may not be necessary), and alter its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound compound.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; colorimetric labels; enzymatic markers such as luciferase, alkaline phosphatase, or HAP; or radioisotopes such as tritium, $I^{125}$ and the like Affinity tags, which may be useful in performing the screening assays of the present invention include be biotin, polyhistidine and the like.

Synthesis and Methodology

General methods for the synthesis of the compounds of the present invention are shown below and are disclosed merely for the purpose of illustration and are not meant to be interpreted as limiting the processes to make the compounds by any other methods. Those skilled in the art will readily appreciate that a number of methods are available for the preparation of the compounds of the present invention.

Schemes 1 to 6 illustrate general synthetic procedures for the preparation of compounds of the instant invention.

Intermediate 1-v was prepared by the following sequence. The prolinal derivative 1-i was treated with amine $R^5NH_2$, followed by reduction with an appropriate hydride to provide intermediate 1-ii. Protection of the amine with $PG^5$, followed by deprotection of $PG^1$, yields intermediate 1-iii. $PG^2(H)N(R^3)CHCO_2H$ is coupled to 1-iii using amino acid coupling agents, followed by deprotection of $PG^2$ yields intermediate 1-iv. Similarly, $PG^3(R^1)N(R^2)CHCO_2H$ is coupled to 1-iv using amino acid coupling agents yields intermediate 1-v.

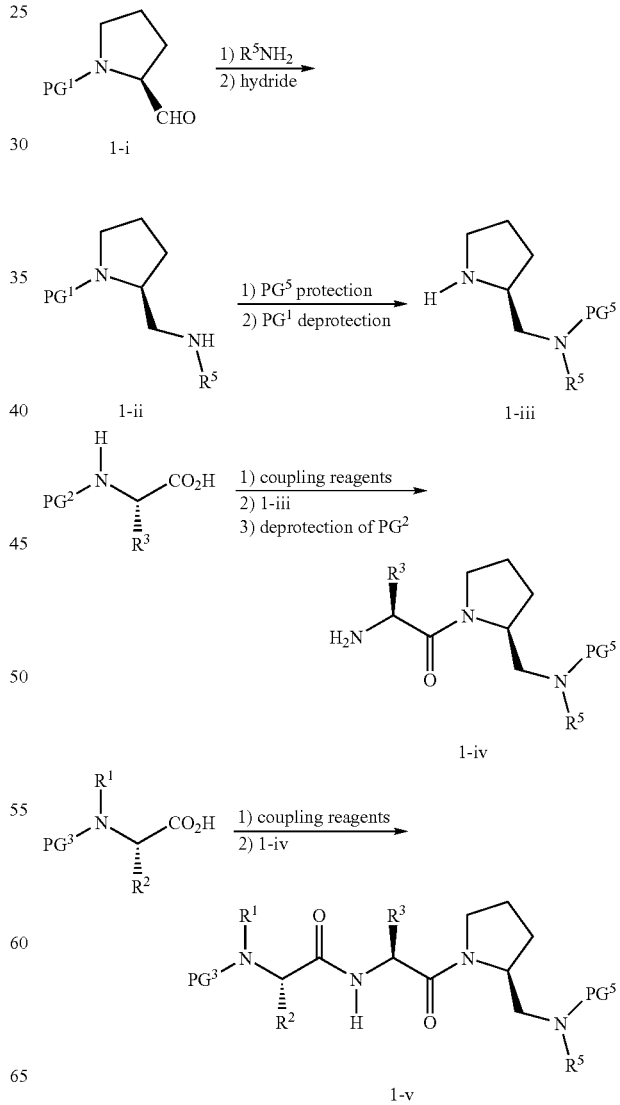

Scheme 1

Deprotection of PG³ provides active compounds of formula 2-i

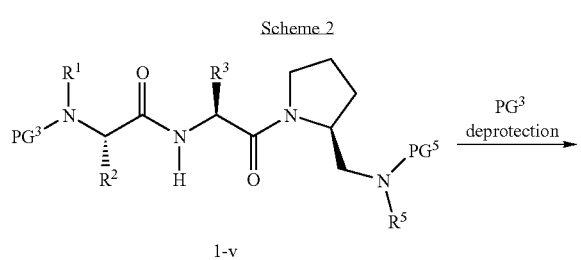

Scheme 2

1-v 2-i

Deprotection of PG⁵ followed by deprotection of PG³, or vise versa, provides active compounds of formula 3-i. In cases where PG³ is the same as PG⁵ a double deprotection can be carried out in one step.

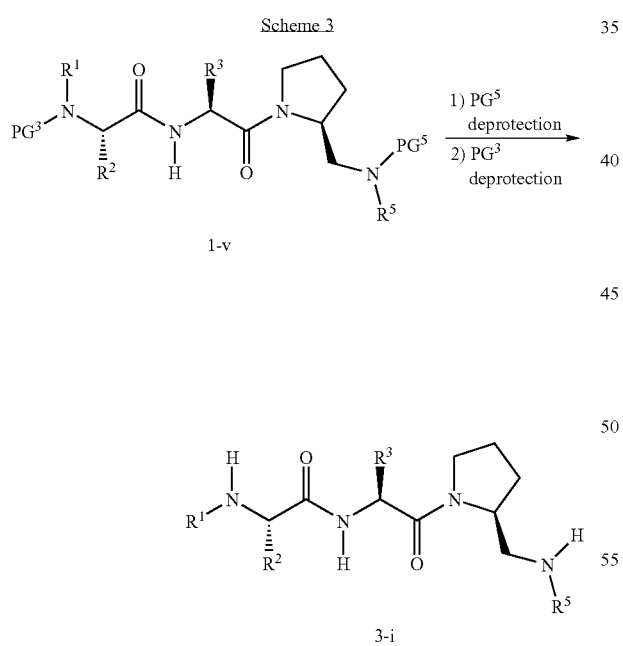

Scheme 3

1-v 3-i

Scheme 4 illustrated the introduction of acyl or sulfonyl moieties at the R⁴ position. Intermediate 1-v can be converted to intermediate 4-i by deprotection of PG⁵. Acylation of 4-i with LG-C(O)R¹¹, followed by deprotection of PG³ provides compounds of formula 4-ii. Similarly, sulfonylation of 4-i with LG-S(O)₂R¹¹, followed by deprotection of PG³ provides compounds of formula 4-iii. In these examples —C(O)R¹¹ and —S(O)₂R¹¹ represent a subset of R⁵ as defined herein.

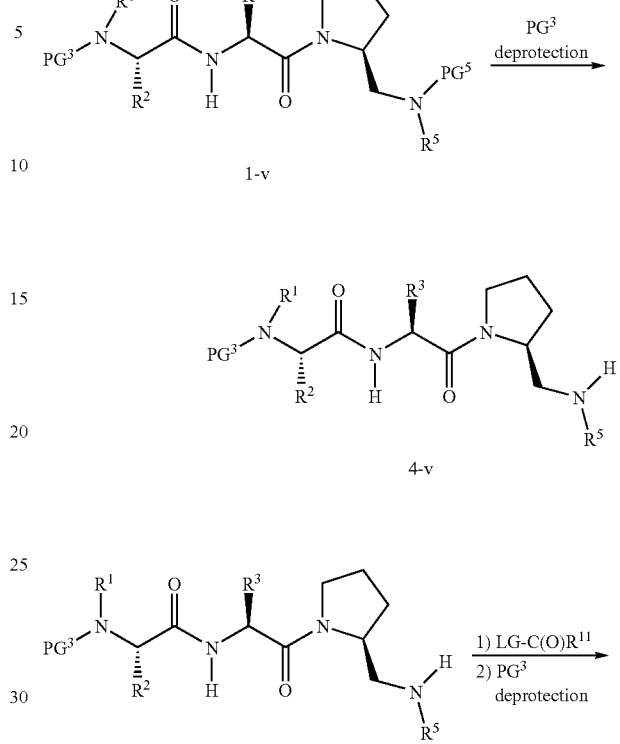

Scheme 4

1-v 4-v 4-v 4-ii 4-i 4-iii

Scheme 5 illustrates the introduction of amino acids at the R⁴ position. Coupling of PG⁶(H)N(R⁷)(H)CCO₂H to intermediate 4-i using amino acid coupling reagents provides intermediate 5-i. Deprotection of PG³ provides compounds of formula 5-ii. Deprotection of PG³ followed by deprotection of PG⁶, or vise versa, provides active compounds of formula 5-iii. In cases where PG³ is the same as PG⁶ a double deprotection can be carried out in one step to convert intermediate 5-i to compound 5-iii.

Scheme 5

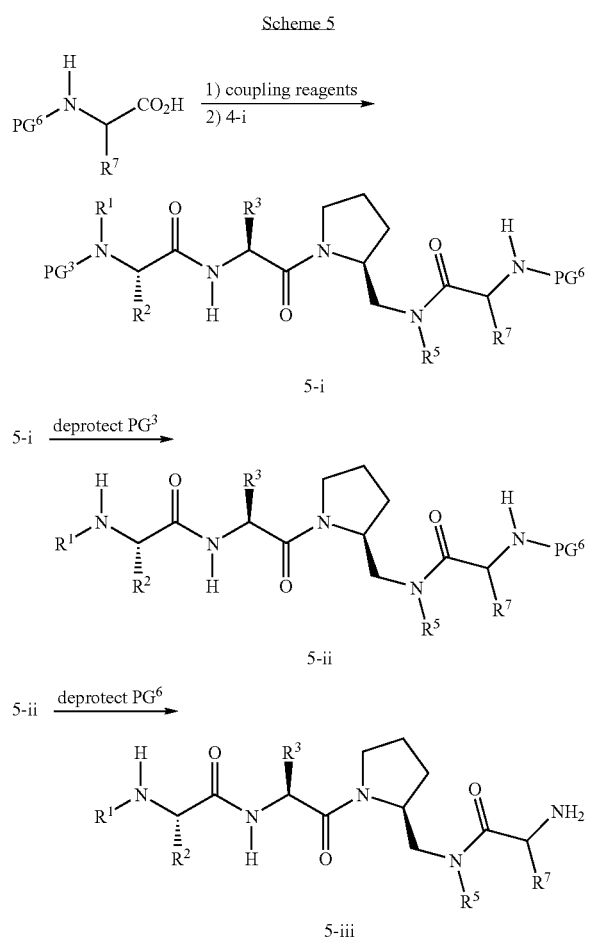

Intermediate 6-i is prepared from intermediate 5-i by deprotection of $PG^6$. Acylation of 6-i with $LG\text{-}C(O)R^{11}$, followed by deprotection of $PG^3$ provides compounds of formula 6-ii. Similarly, sulfonylation of 6-i with $LG\text{-}S(O)_2R^{11}$, followed by deprotection of $PG^3$ provides compounds of formula 6-iii. Treatment of intermediate 6-i with $R^{11}CNO$, followed by deprotection of $PG^6$, provides compounds of formula 6-iv.

In these examples $-C(O)R^{11}$ and $-S(O)_2R^{11}$ represent a subset of $R^4$ as defined herein Scheme 6

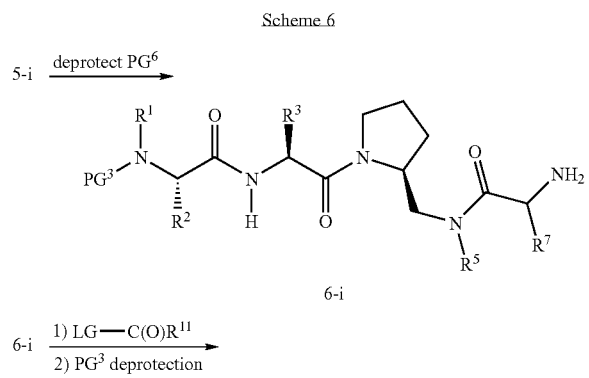

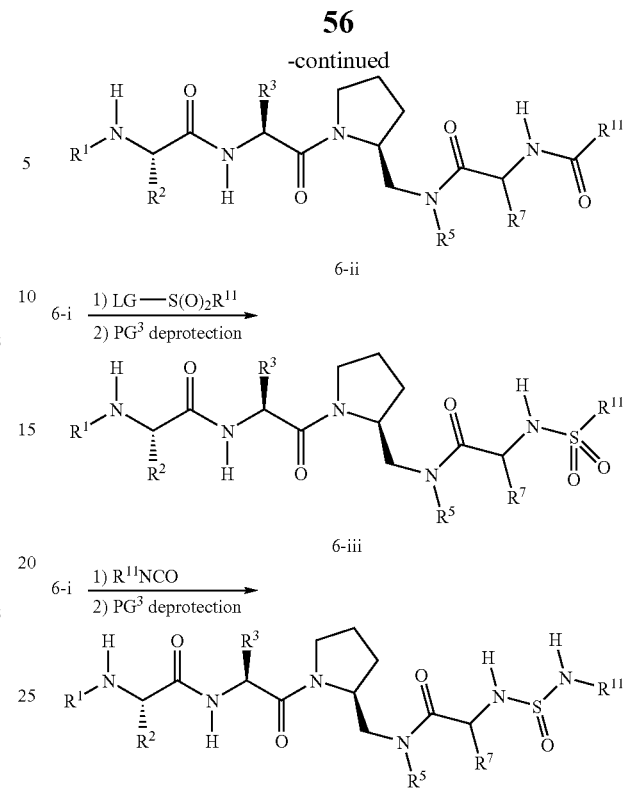

Thioester, sulfoxide and sulfone derivates may be prepared as illustrated in Scheme 7. The alcohol moiety of the prolinol derivative 7-i is converted to a leaving group by, for example, by treated with MsCl to provide intermediate 7-ii. Treatment of intermediate 7-ii with a $HSR^{11}$ provides intermediate 7-iii. Deprotection of $PG^1$ yields intermediate 7-iv. Oxidation of 7-iii to sulfoxide 7-v (m=1) or sulfone 7-v (m=2) is followed by deprotection of $PG^1$ to yield sulfoxide 7-vi (m=1) or sulfone 7-vi (m=2), respectively. $PG^2(H)N(R^3)CHCO_2H$ is coupled to either 7-iv or 7-vi using amino acid coupling agents, followed by deprotection of $PG^2$ yields intermediates 7-vii or 7-vii, respectively. Similarly, $PG^3(R^1)N(R^2)CHCO_2H$ is coupled to intermediates 7-vii or 7-vii using amino acid coupling agents yields intermediates 7-xi or 7-x, respectively. Deprotection of $PG^3$ provides compounds 7-xi or 7-xii, respectively Scheme 7

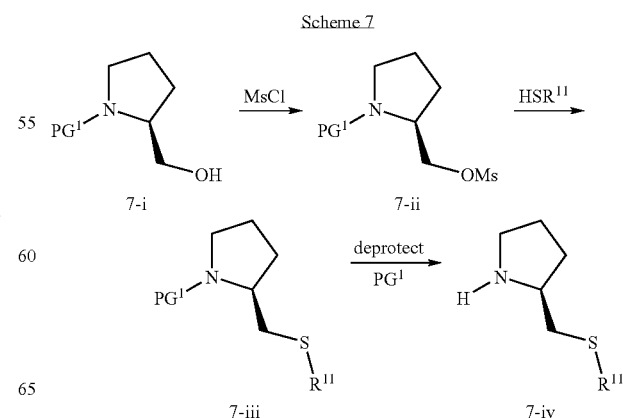

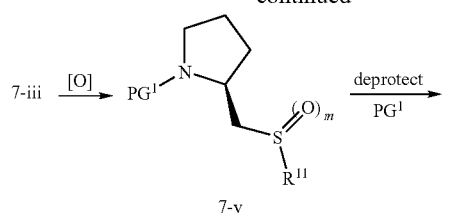

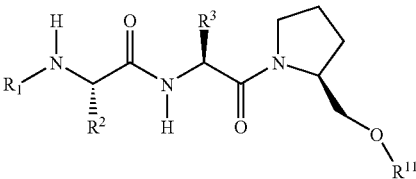

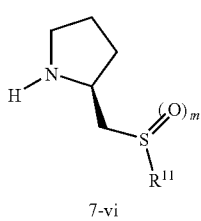

n = 1 or 2

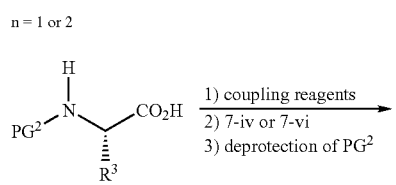

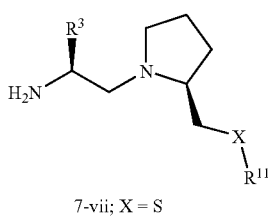

7-vii; X = S
7-viii; X = S(O)$_m$

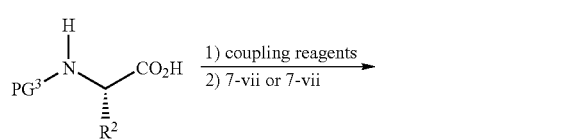

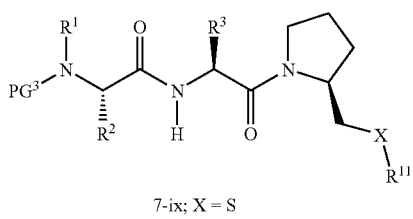

7-ix; X = S
7-x; X = S(O)$_m$ 7-ix or 7-x $\xrightarrow{\text{deprotect}}$ PG$^3$

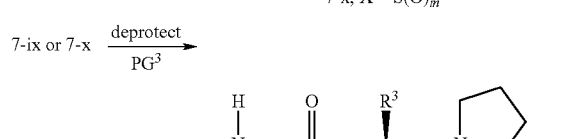

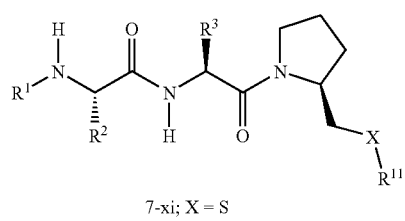

7-xi; X = S
7-xii; X = S(O)$_m$

Similar chemistry may be performed using alcohols (HOR$^{11}$) in the place of thiols (HSR$^{11}$) to provide ether derivatives such as compounds of formula I defined below:

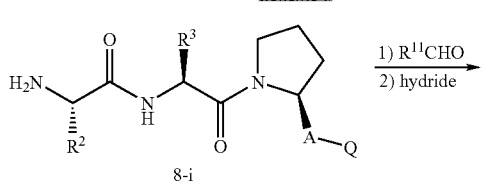

Compounds of formula 8-i may be functionalized on the left hand side by reductive amination by the treatment of compound 8-i with aldehyde R$^1$CHO, and reduction of the resulting imide intermediate with a hydride source, to yield compounds of formula 8-ii.

Scheme 8

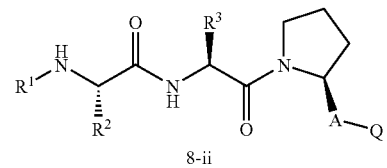

EXAMPLES

The following abbreviations are used throughout:
Boc: t-butoxycarbonyl;
Boc-NMe-Ala-OH: N-butoxycarbonyl-N-methly-alanine
Boc-tBuGly-OH: N-butoxycarbonyl-α-tert-butylglycine
CBz: benzyloxycarbonyl;
DCM: dichloromethane;
DIPEA: diisopropylethylamine;
DMAP: 4-(dimethylamino)pyridine;
DMF: N,N-dimethylformamide;
DTT: dithiothreitol;
EDC: 3-dimethylaminopropyl)-3-ethylcarbodiimide hydrochloride;
EDTA: ethylenediaminetetracetic acid;
Fmoc: N-(9-fluorenylmethoxycarbonyl);
HBTU: O-(benzotriazol-1-yl)-N,N,N',N'-tetramethyluronium hexafluorophosphate;
HCl: hydrochloric acid;
HOAc: acetic acid;
HOBt: 1-hydroxybenzotriazole;
HPLC: high performance liquid chromatography;
LCMS: liquid chromatography-mass spectrometer;
m-CPBA: meta-chloroperbenzoic acid
MeOH: methanol;
MgSO$_4$: magnesium sulfate;
MS: mass spectrum;
NaHCO$_3$: sodium hydrogen carbonate;
Pd/C: palladium on carbon;
TEA: triethylamine;
TFA: trifluoroacetic acid; and
THF: tetrahydrofuran.
1. Synthesis of Intermediate 1-4b Step A:

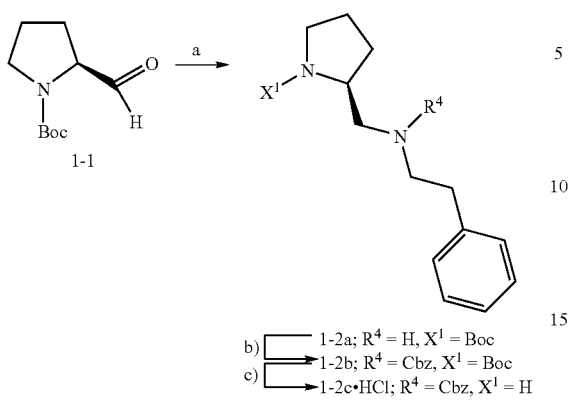

b) ┌── 1-2a; R⁴ = H, X¹ = Boc
   │ → 1-2b; R⁴ = Cbz, X¹ = Boc
c) └── → 1-2c·HCl; R⁴ = Cbz, X¹ = H

Step a)

To a solution of N-(tert-butoxycarbonyl)-L-prolinal 1-1 (10.0 g, 50.2 mmol) in methylene chloride (150 mL) was added phenethylamine (6.52 mL, 50.2 mmol). After stirring for 1 hr sodium triacetoxyborohydride (21.0 g, 100.3 mmol) and methanol (50 mL) were added and the reaction mixture was then stirred at room temperature overnight. Saturated aqueous NaHCO₃ and ethyl acetate were added, the organic layer was separated, washed with brine, dried over MgSO₄, filtered and concentrated in vacuo. Purification by silica gel chromatography eluting with a hexane/EtOAc gradient provided the expected intermediate 1-2a as colorless oil. MS (m/z) M+1=305.2

Step b)

To a solution of 1-2a (8.1 g, 26.6 mmol) in methylene chloride (80 mL) cooled to 0° C. were sequentially added triethylamine (7.4 mL, 53.3 mmol), benzyl chloroformate (4.1 mL, 29.3 mmol) and the reaction mixture was stirred for 3 hrs at room temperature. Saturated aqueous NaHCO₃ and ethyl acetate were added, the organic layer was separated, washed with brine, dried over MgSO₄, filtered and concentrated in vacuo. Purification by silica gel chromatography eluting with a hexane/EtOAc gradient provided the expected intermediate 1-2b as colorless oil.

Step c)

4N HCl in 1,4-dioxane (10 mL) was added to 1-2b (11.5 g, 26.2 mmol) at room temperature and the solution was stirred for 2 hrs at room temperature. Volatiles were removed under reduced pressure and the residue was triturated with diethyl ether to provide the expected intermediate 1-2c·HCl as a white solid. MS (m/z) M+1=339.2

Step B

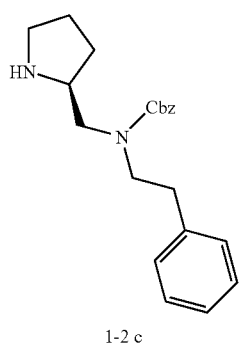

1-2c

-continued

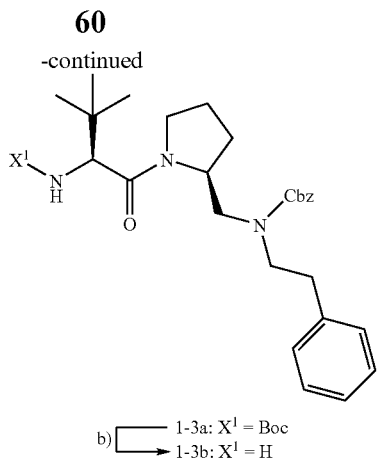

b) ┌── 1-3a: X¹ = Boc
   └── → 1-3b: X¹ = H

Step a)

To a solution of Boc-tBu-Gly-OH (5.7 g, 24.5 mmol) in DMF were sequentially added DIPEA (16.9 mL, 94.3 mmol), HOBt (3.3 g, 24.5 mmol) and HBTU (9.3 g, 24.5 mmol). After stirring for 10 min 1-2c.HCl (6.4 g, 18.8 mmol) was added and the reaction mixture was stirred overnight at room temperature. Water and ethyl acetate were added, the organic layer was separated, washed with 10% citric acid, saturated aqueous NaHCO₃ and brine, dried over MgSO₄, filtered and concentrated in vacuo. Purification by silica gel chromatography eluting with a hexane/EtOAc gradient provided the expected intermediate 1-3a as colorless oil.

Step b)

4N HCl in 1,4-dioxane (10 mL) was added to 1-3a (8.3 g, 15.0 mmol) at room temperature and the solution was stirred for 2 hrs at room temperature. Volatiles were removed under reduced pressure and the residue was triturated with diethyl ether to provide the expected intermediate 1-3b.HCl as a white solid. MS (m/z) M+1=452.3

Step C

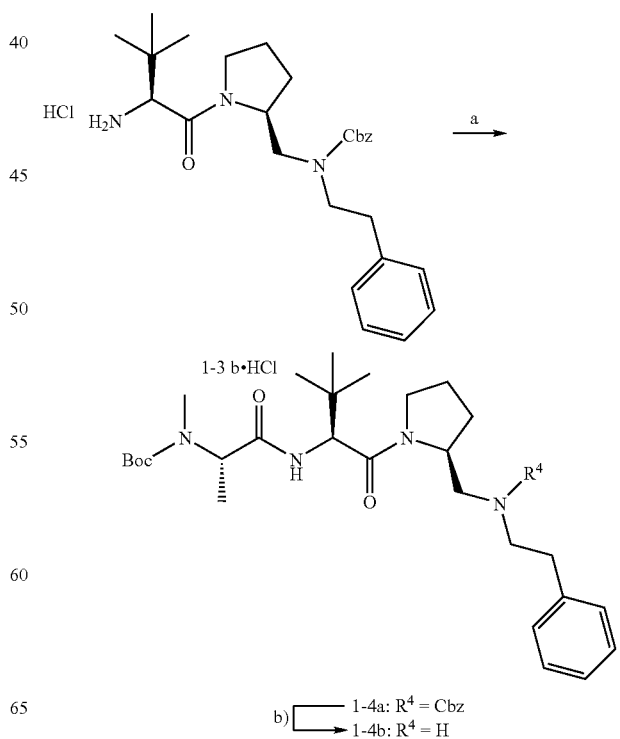

b) ┌── 1-4a: R⁴ = Cbz
   └── → 1-4b: R⁴ = H

Step a)

To a solution of Boc-NMe-Ala-OH (4.2 g, 20.7 mmol) in DMF were sequentially added DIPEA (14.3 mL, 79.8 mmol), HOBt (2.8 g, 20.7 mmol) and HBTU (7.9 g, 20.7 mmol). After stirring for 10 min 1-3b.HCl (7.2 g, 15.9 mmol) was added and the reaction mixture was stirred overnight at room temperature. Water and ethyl acetate were added, the organic layer was separated, washed with 10% citric acid, aqueous NaHCO₃ and brine, dried over MgSO₄, filtered and concentrated in vacuo. Purification by silica gel chromatography eluting with a hexane/EtOAc gradient provided the expected intermediate 1-4-a as colorless oil.

Step b)

To a solution of 1-4-a (3.0 g, 4.7 mmol) in anhydrous MeOH (100 mL) and stirred under N₂ was added 10% Pd/C (200 mg). The reaction mixture was purged with H₂ and stirred for 1 hr. The reaction was then filtered through celite and the filtrate was concentrated in vacuo. Purified by silica gel chromatography eluting with a hexane/EtOAc gradient provided the expected intermediate 1-4b as colorless oil. MS (m/z) M+1=503.4

2. Synthesis of Compound 47.HCl filtered and concentrated in vacuo. Purification by silica gel chromatography eluting with a hexane/EtOAc gradient provided the expected intermediate 2-1 as colorless oil.

Step b)

4N HCl in 1,4-dioxane (10 mL) was added to 2-1 (350 mg, 0.70 mmol) at room temperature and the solution was stirred for 2 hrs at room temperature. Volatiles were removed under reduced pressure and the residue was triturated with diethyl ether to provide the expected compound 47.HCl as a white solid. MS (m/z) M+1=507.3

3. Synthesis of Compound 68.HCl

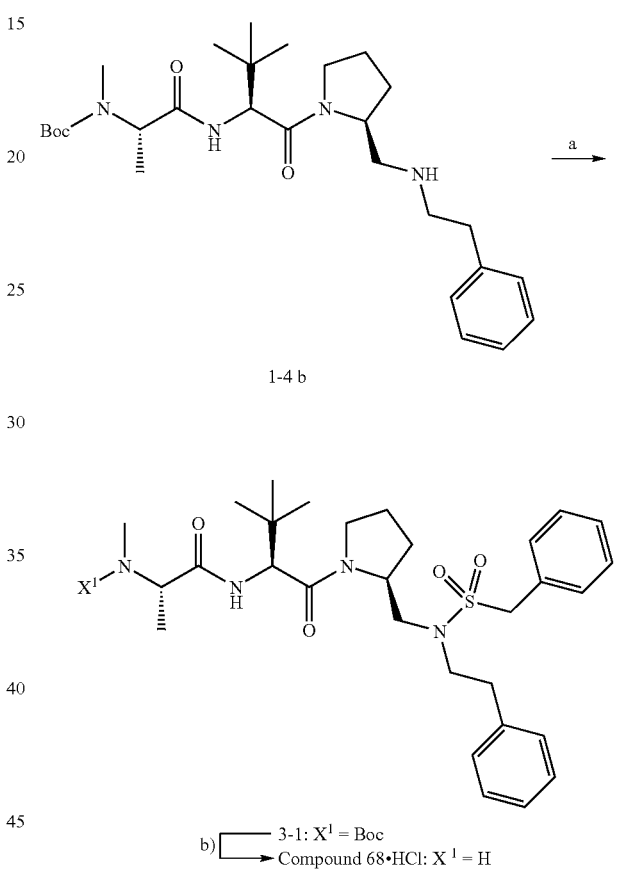

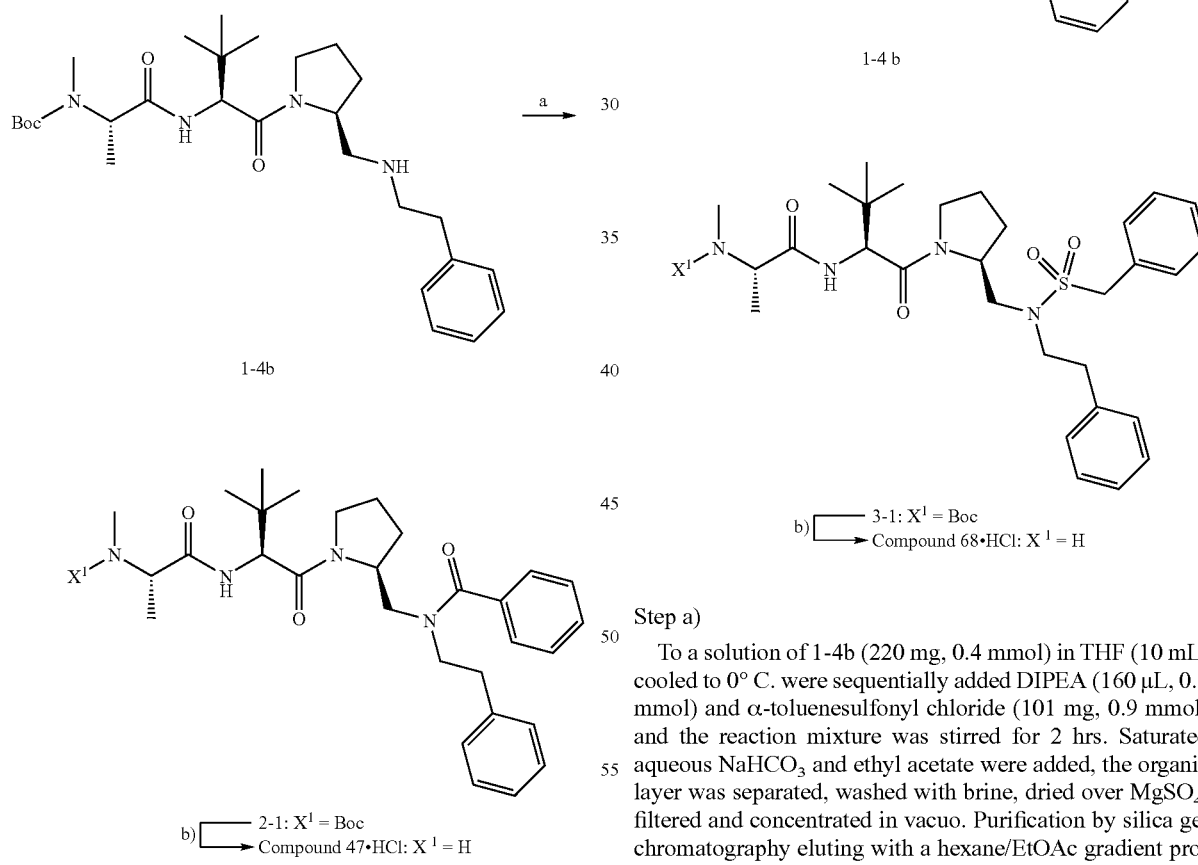

Step a)

To a solution of 1-4b (220 mg, 0.4 mmol) in THF (10 mL) cooled to 0° C. were sequentially added DIPEA (160 μL, 0.8 mmol) and α-toluenesulfonyl chloride (101 mg, 0.9 mmol) and the reaction mixture was stirred for 2 hrs. Saturated aqueous NaHCO₃ and ethyl acetate were added, the organic layer was separated, washed with brine, dried over MgSO₄, filtered and concentrated in vacuo. Purification by silica gel chromatography eluting with a hexane/EtOAc gradient provided the expected intermediate 3-1 as colorless oil.

Step b)

4N HCl in 1,4-dioxane (10 mL) was added to 3-1 (350 mg, 0.53 mmol) at room temperature and the solution was stirred for 2 hrs at room temperature. Volatiles were removed under reduced pressure and the residue was triturated with diethyl ether to provide the expected compound 68.HCl as a white solid. MS (m/z) M+1=507.3

Step a)

To a solution of 1-4b (210 mg, 0.4 mmol) in THF (10 mL) cooled to 0° C. were sequentially added DIPEA (160 μL, 0.8 mmol), benzoyl chloride (75 μL, 0.6 mmol) and the reaction mixture was stirred for 2 hrs at room temperature. Saturated aqueous NaHCO₃ and ethyl acetate were added, the organic layer was separated, washed with brine, dried over MgSO₄, 4. Synthesis of compound 32.2HCl

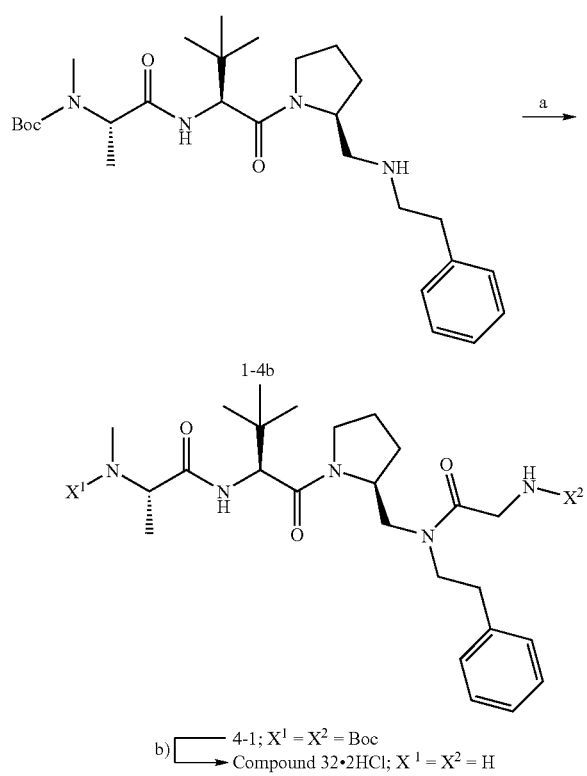

Step a)
To a solution of Boc-Gly-OH (303 mg, 1.7 mmol) in DMF were sequentially added DIPEA (1.2 mL, 6.6 mmol), HOBt (234 mg, 1.7 mmol) and HBTU (656 mg, 1.7 mmol). After stirring for 10 min 1-4b (670 mg, 1.3 mmol) was added and the reaction mixture was stirred overnight at room temperature. Water and ethyl acetate were added, the organic layer was separated, washed with 10% citric acid, saturated aqueous NaHCO$_3$ and brine, dried over MgSO$_4$, filtered and concentrated in vacuo. Purification by silica gel chromatography eluting with a hexane/EtOAc gradient provided the expected intermediate 4-1 as a white solid.

Step b)
4N HCl in 1,4-dioxane (10 mL) was added to 4-1 (250 mg, 0.38 mmol) at room temperature and the solution was stirred for 2 hrs at room temperature. Volatiles were removed under reduced pressure and the residue was triturated with diethyl ether to provide the expected compound 32.2HCl as a white solid. MS (m/z) M+1=460.3

5. Synthesis of Compound 42.2HCl

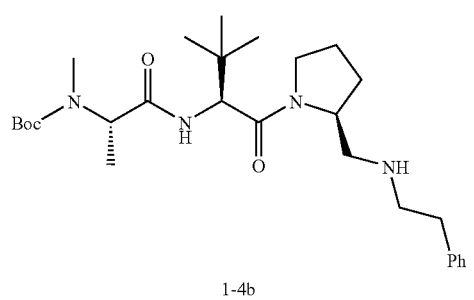

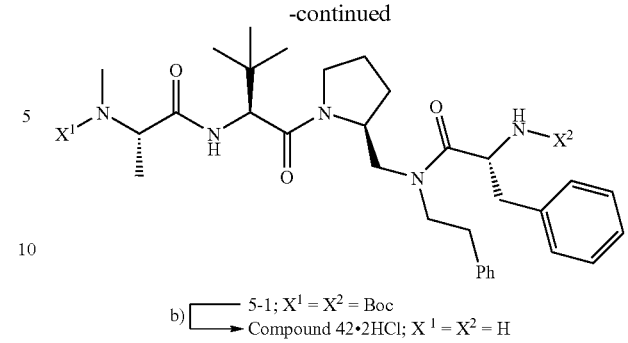

Step a)
To a solution of Boc-D-Phe-OH (207 mg, 0.8 mmol) in DMF were sequentially added DIPEA (300 µL, 1.8 mmol), HOBt (96 mg, 0.7 mmol) and HBTU (204 mg, 0.6 mmol). After stirring for 10 min 1-4b (183 mg, 0.3 mmol) was added and the reaction mixture was stirred overnight at room temperature. Water and ethyl acetate were added, the organic layer was separated, washed with 10% citric acid, saturated aqueous NaHCO$_3$ and brine, dried over MgSO$_4$, filtered and concentrated in vacuo. Purification by silica gel chromatography eluting with a hexane/EtOAc gradient provided the expected intermediate 5-1 as a white solid.

Step b)
4N HCl in 1,4-dioxane (10 mL) was added to 5-1 (217 mg, 0.30 mmol) at room temperature and the solution was stirred for 2 hrs at room temperature. Volatiles were removed under reduced pressure and the residue was triturated with diethyl ether to provide the expected compound 42.2HCl as a white solid. MS (m/z) M+1=550.4

6. Synthesis of Compound 50.2HCl

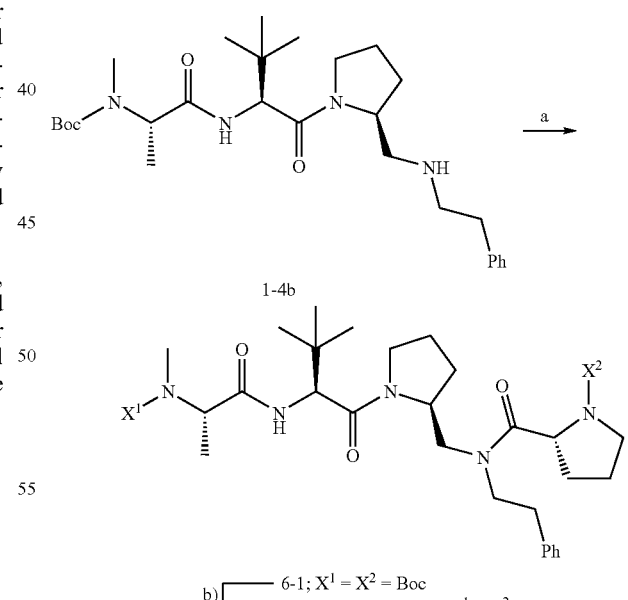

Step a)
To a solution of Boc-D-Pro-OH (130 mg, 0.6 mmol) in DMF were sequentially added DIPEA (300 µL, 1.8 mmol), HOBt (92 mg, 0.6 mmol) and HBTU (230 mg, 0.6 mmol). After stirring for 10 min 1-4b (150 mg, 0.3 mmol) was added and the reaction mixture was stirred overnight at room temperature. Water and ethyl acetate were added, the organic layer was separated, washed with 10% citric acid, saturated aqueous NaHCO₃ and brine, dried over MgSO₄, filtered and concentrated in vacuo. Purification by silica gel chromatography eluting with a hexane/EtOAc gradient provided the expected intermediate 6-1 as a white solid.

Step b)

4N HCl in 1,4-dioxane (5 mL) was added to 6-1 (200 mg, 0.28 mmol) at room temperature and the solution was stirred for 2 hrs at room temperature. Volatiles were removed under reduced pressure and the residue was triturated with diethyl ether to provide the expected compound 50.2HCl as a white solid. MS (m/z) M+1=500.4

7. Synthesis of Compound 54.2HCl

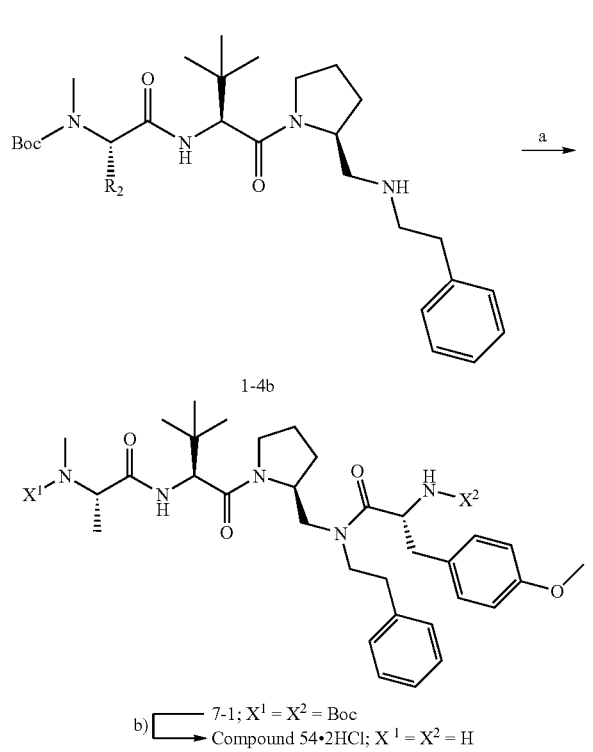

Step a)

To a solution of Boc-D-Tyr(Me)-OH (153 mg, 0.5 mmol) in DMF were sequentially added DIPEA (358 μL, 2.0 mmol), HOBt (70 mg, 0.5 mmol) and HBTU (196 mg, 0.5 mmol). After stirring for 10 min 1-4b (200 mg, 0.4 mmol) was added and the reaction mixture was stirred overnight at room temperature. Water and ethyl acetate were added, the organic layer was separated, washed with 10% citric acid, saturated aqueous NaHCO₃ and brine, dried over MgSO₄, filtered and concentrated in vacuo. Purification by silica gel chromatography eluting with a hexane/EtOAc gradient provided the expected intermediate 7-1 as a white solid.

Step b)

4N HCl in 1,4-dioxane (5 mL) was added to 7-1 (234 mg, 0.30 mmol) at room temperature and the solution was stirred for 2 hrs at room temperature. Volatiles were removed under reduced pressure and the residue was triturated with diethyl ether to provide the expected compound 54.2HCl as a white solid. MS (m/z) M+1=580.4

8. Synthesis of Compound 55.3HCl

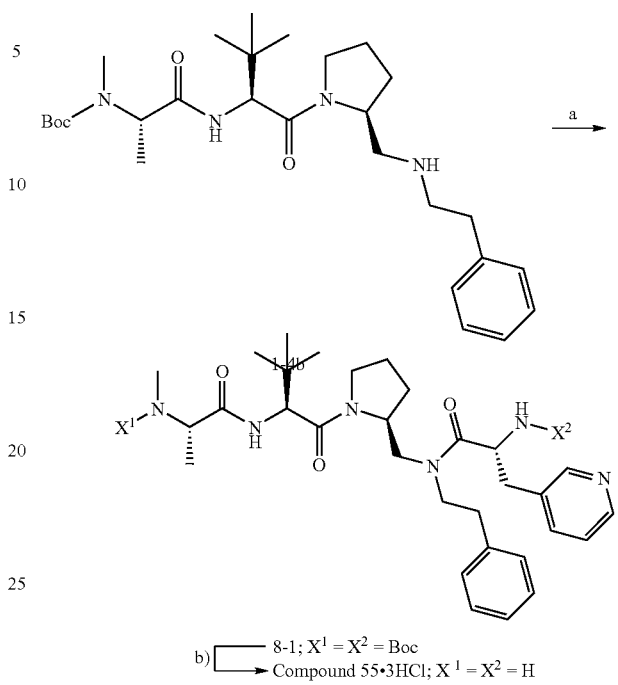

Step a)

To a solution of Boc-3-(3'-pyridyl)-D-alanine (102 mg, 0.38 mmol) in DMF were sequentially added DIPEA (240 μL, 1.4 mmol), HOBt (62 mg, 0.4 mmol) and HBTU (128 mg, 0.40 mmol). After stirring for 10 min 1-4b (146 mg, 0.3 mmol) was added and the reaction mixture was stirred overnight at room temperature. Water and ethyl acetate were added, the organic layer was separated, washed with 10% citric acid, saturated aqueous NaHCO₃ and brine, dried over MgSO₄, filtered and concentrated in vacuo. Purification by silica gel chromatography eluting with a hexane/EtOAc gradient provided the expected intermediate 8-1 as a white solid.

Step b)

4N HCl in 1,4-dioxane (5 mL) was added to 8-1 (163 mg, 0.20 mmol) at room temperature and the solution was stirred for 2 hrs at room temperature. Volatiles were removed under reduced pressure and the residue was triturated with diethyl ether to provide the expected compound 55.3HCl as a white solid. MS (m/z) M+1=551.4

9. Synthesis of Compound 59.HCl

Step A

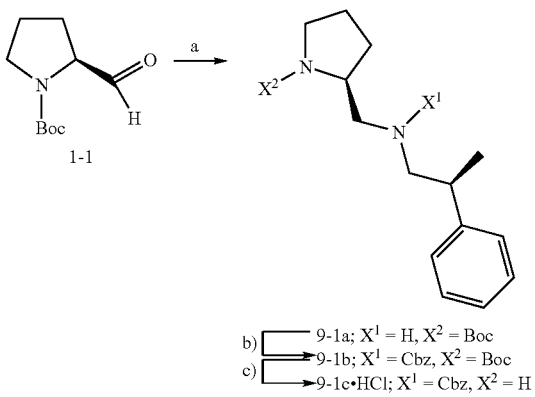

Step a)

To a solution of N-(tert-butoxycarbonyl)-L-prolinal 1-1 (1.37 g, 6.8 mmol) in methylene chloride (20 mL) was added (R)-β-Methylphenethylamine (1.0 mL, 6.9 mmol) and after stirring for 1 hr sodium triacetoxy-borohydride (2.3 g, 10.9 mmol) and methanol (10 mL) were added and the reaction mixture was then stirred at room temperature overnight. Saturated aqueous $NaHCO_3$ and ethyl acetate were added, the organic layer was separated, washed with brine, dried over $MgSO_4$, filtered and concentrated in vacuo. Purification by silica gel chromatography eluting with a hexane/EtOAc gradient provided the expected intermediate 9-1a as colorless oil. MS (m/z) M+1=319.2

Step b)

To a solution of 9-1a (2.5 g, 7.8 mmol) in methylene chloride (80 mL) cooled to 0° C. were sequentially added triethylamine (2.0 mL, 14.3 mmol), benzyl chloroformate (1.7 mL, 10.7 mmol) and the reaction mixture was stirred for 3 hrs at room temperature. Saturated aqueous $NaHCO_3$ and ethyl acetate were added, the organic layer was separated, washed with brine, dried over $MgSO_4$, filtered and concentrated in vacuo. Purification by silica gel chromatography eluting with a hexane/EtOAc gradient provided the expected intermediate 9-1b as colorless oil.

Step c)

4 N HCl in 1,4-dioxane (5 mL) was added to 9-1b (2.62 g, 5.8 mmol) at room temperature and the solution was stirred for 2 hrs. Volatiles were removed under reduced pressure and the residue was triturated with diethyl ether to provide the expected intermediate 9-1c.HCl as a white solid. MS (m/z) M+1=353.2

Step B

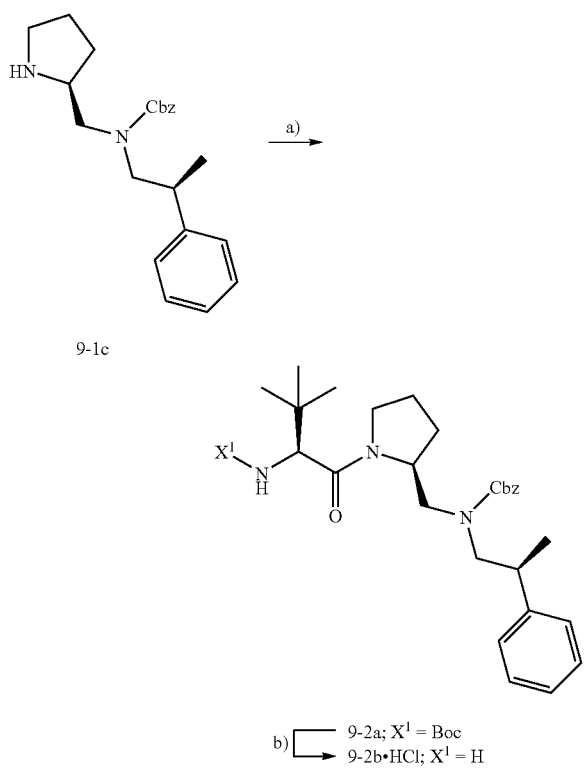

Step a)

To a solution of Boc-tBu-Gly-OH (310 mg, 1.3 mmol) in DMF were sequentially added DIPEA (970 µL, 5.6 mmol), HOBt (219 mg, 1.6 mmol) and HBTU (425 mg, 1.3 mmol). After stirring for 10 min 9-1c (428 mg, 1.1 mmol) was added and the reaction mixture was stirred overnight at room temperature. Water and ethyl acetate were added, the organic layer was separated, washed with 10% citric acid, saturated aqueous $NaHCO_3$ and brine, dried over $MgSO_4$, filtered and concentrated in vacuo. Purification by silica gel chromatography eluting with a hexane/EtOAc gradient provided the expected intermediate 9-2a as colorless oil.

Step b)

4 N HCl in 1,4-dioxane (5.0 mL) was added to 9-2a (523 mg, 0.9 mmol) at room temperature and the solution was stirred for 2 hrs. Volatiles were removed under reduced pressure and the residue was triturated with diethyl ether to provide the expected intermediate 9-2b.HCl as a white solid. MS (m/z) M+1=466.3.

Step C

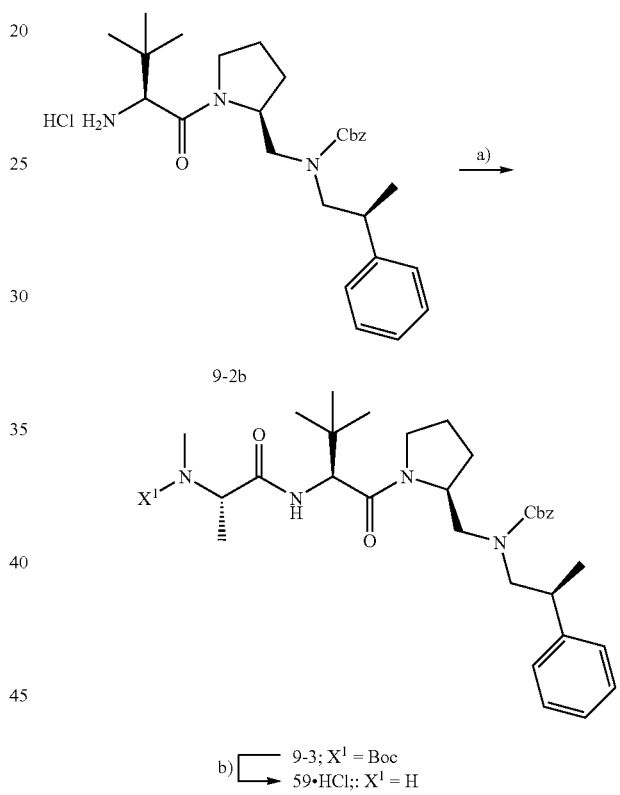

Step a)

To a solution of Boc-N-MeAla-OH (364 mg, 1.8 mmol) in DMF were sequentially added DIPEA (1.0 mL, 5.7 mmol), HOBt (372 mg, 2.7 mmol) and HBTU (556 mg, 1.8 mmol). After stirring for 10 min 9-2b (446 g, 0.9 mmol) was added and the reaction mixture was stirred overnight at room temperature. Water and ethyl acetate were added, the organic layer was separated, washed with 10% citric acid, saturated aqueous $NaHCO_3$ and brine, dried over $MgSO_4$, filtered and concentrated in vacuo. Purification by silica gel chromatography eluting with a hexane/EtOAc gradient provided the expected intermediate 9-3 as colorless oil.

Step b)

4 N HCl in 1,4-dioxane (4.0 mL) was added to 9-3 (130 mg, 0.2 mmol) at room temperature and the solution was stirred for 2 hrs. Volatiles were removed under reduced pressure and the residue was triturated with diethyl ether to provide the expected compound 59.HCl as a white solid. MS (m/z) M+1=551.3

10. Synthesis of Compound 15.HCl

Step A

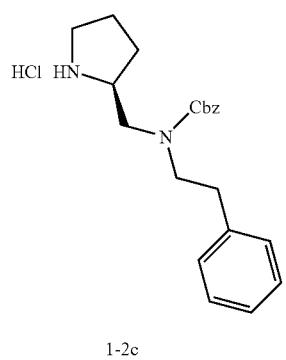

1-2c

Step B

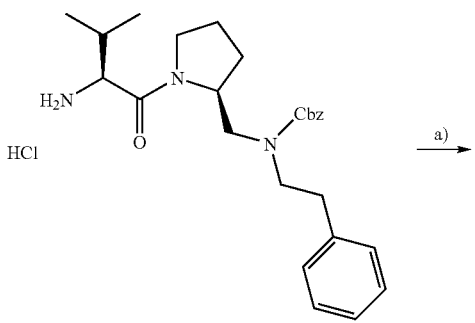

10-1b

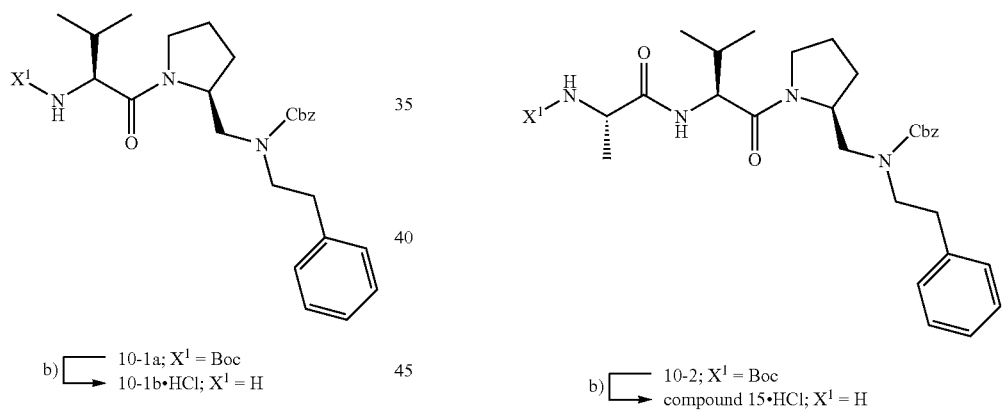

Step a)

To a solution of Boc-Val-OH (4.2 g, 19.2 mmol) in DMF were sequentially added DIPEA (13.2 mL, 73.3 mmol), HOBt (2.6 g, 19.2 mmol) and HBTU (7.3 g, 19.2 mmol). After stirring for 10 min 1-2c (5.0 g, 14.7 mmol) was added and the reaction mixture was stirred overnight at room temperature. Water and ethyl acetate were added, the organic layer was separated, washed with 10% citric acid, saturated aqueous NaHCO$_3$ and brine, dried over MgSO$_4$, filtered and concentrated in vacuo. Purification by silica gel chromatography eluting with a hexane/EtOAc gradient provided the expected intermediate 10-1a as colorless oil.

Step b)

4 N HCl in 1,4-dioxane (15 mL) was added to 10-1a (7.1 g, 13.2 mmol) at room temperature and the solution was stirred for 2 hrs. Volatiles were removed under reduced pressure and the residue was triturated with diethyl ether to provide the expected intermediate 10-1b.HCl as a white solid. MS (m/z) M+1=438.3

Step a)

To a solution of Boc-Ala-OH (3.9 g, 14.4 mmol) in DMF were sequentially added DIPEA (9.9 mL, 55.4 mmol), HOBt (1.9 g, 14.4 mmol) and HBTU (5.4 g, 14.4 mmol). After stirring for 10 min 10-1b (4.8 g, 11.1 mmol) was added and the reaction mixture was stirred overnight at room temperature. Water and ethyl acetate were added; the organic layer was separated, washed with 10% citric acid, saturated aqueous NaHCO$_3$ and brine, dried over MgSO$_4$, filtered and concentrated in vacuo. Purification by silica gel chromatography eluting with a hexane/EtOAc gradient provided the expected intermediate 10-2 as colorless oil.

Step b)

4 N HCl in 1,4-dioxane (5 mL) was added to 10-2 (1.0 g, 1.6 mmol) at room temperature and the solution was stirred for 2 hrs. Volatiles were removed under reduced pressure and the residue was triturated with diethyl ether to provide the expected compound 15.HCl as a white solid. MS (m/z) M+1=509.3

11. Synthesis of Compound 20.HCl
Step A

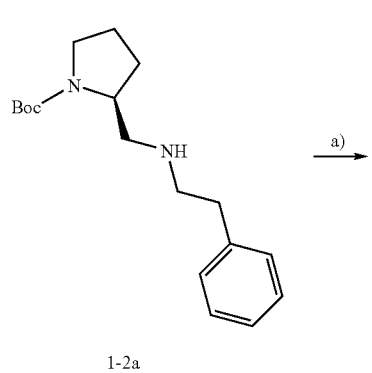

1-2a

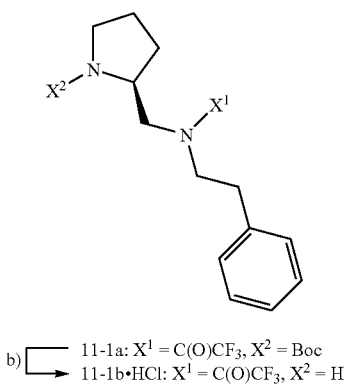

b) ┌── 11-1a: $X^1$ = C(O)CF$_3$, $X^2$ = Boc
   └→ 11-1b·HCl: $X^1$ = C(O)CF$_3$, $X^2$ = H

Step a)
To a solution of 1-2a (370 mg, 1.3 mmol) in methylene chloride (20 mL) cooled to 0° C. were sequentially added triethylamine (355 µL, 2.6 mmol), trifluoroacetic anhydride (270 µL, 1.9 mmol) DMAP (catalytic) and the reaction mixture was stirred for 3 hrs at room temperature. Saturated aqueous NaHCO$_3$ and ethyl acetate were added, the organic layer was separated, washed with brine, dried over MgSO$_4$, filtered and concentrated in vacuo. Purification by silica gel chromatography eluting with a hexane/EtOAc gradient provided the expected intermediate 11-1a as colorless oil.

Step b)
4N HCl in 1,4-dioxane (5 mL) was added to 11-1a (480 mg, 1.2 mmol) at room temperature and the solution was stirred for 2 hrs. Volatiles were removed under reduced pressure and the residue was triturated with diethyl ether to provide the expected intermediate 1'-1b.HCl as a white solid. MS (m/z) M+1=301.2

Step B

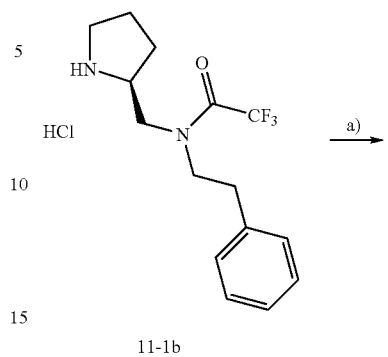

11-1b

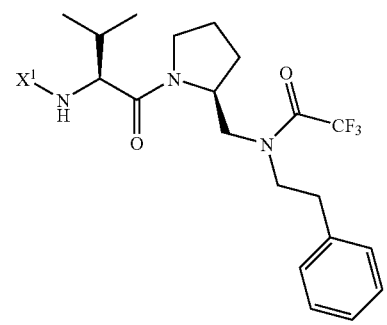

b) ┌── 11-2a: $X^1$ = Boc
   └→ 11-2b·HCl: $X^2$ = H

Step a)
To a solution of Boc-Val-OH (332 mg, 1.5 mmol) in methylene chloride were sequentially added DIPEA (844 µL, 4.7 mmol), HOBt (207 mg, 1.5 mmol) and EDC (294 mg, 1.5 mmol). After stirring for 10 min 11-1b.HCl (356 mg, 1.2 mmol) was added and the reaction mixture was stirred overnight at room temperature. Water and ethyl acetate were added, the organic layer was separated, washed with 10% citric acid, saturated aqueous NaHCO$_3$ and brine, dried over MgSO$_4$, filtered and concentrated in vacuo. Purification by silica gel chromatography eluting with a hexane/EtOAc gradient provided the expected intermediate 11-2a as colorless oil.

Step b)
4N HCl in 1,4-dioxane (3 mL) was added to 11-2a (389 mg, 0.9 mmol) at room temperature and the solution was stirred for 2 hrs. Volatiles were removed under reduced pressure and the residue was triturated with diethyl ether to provide the expected intermediate 11-2b.HCl as a white solid. MS (m/z) M+1=400.2

Step C

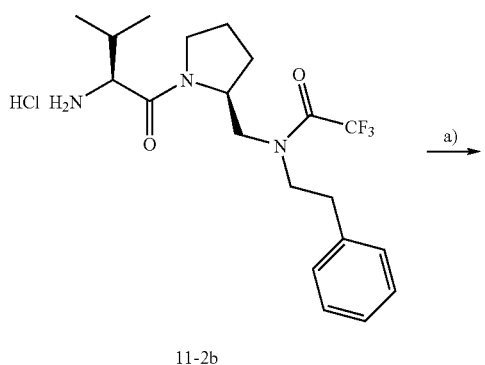

11-2b a)

12. Synthesis of Compound 9.HCl

Step A

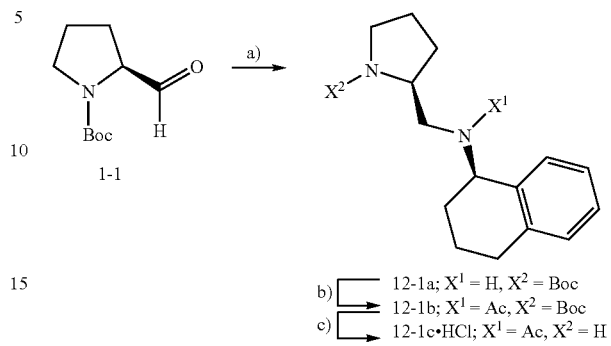

Step a)

To a solution of N-(tert-butoxycarbonyl)-L-prolinal 1-1 (4.0 g, 20.1 mmol) in methylene chloride (20 mL) was added (R)-(−)-1,2,3,4-tetrahydro-1-naphthylamine (2.9 g, 20.1 mmol) and after stirring for 1 hr sodium cyano-borohydride (1.9 g, 30.1 mmol) and methanol (10 mL) were added and the reaction mixture was then stirred at room temperature overnight. Saturated aqueous NaHCO$_3$ and ethyl acetate were added, the organic layer was separated, washed with brine, dried over MgSO$_4$, filtered and concentrated in vacuo. Purification by silica gel chromatography eluting with a hexane/EtOAc gradient provided the expected intermediate 12-1a as colorless oil. MS (m/z) M+1=331.2

Step b)

To a solution of 12-1a (5.2 g, 15.7 mmol) in methylene chloride (50 mL) cooled to 0° C. were sequentially added triethylamine (4.4 mL, 31.5 mmol), acetic anhydride (2.2 mL, 23.6 mmol), DMAP (catalytic) and the reaction mixture was stirred for 3 hrs at room temperature. Saturated aqueous NaHCO$_3$ and ethyl acetate were added, the organic layer was separated, washed with brine, dried over MgSO$_4$, filtered and concentrated in vacuo. Purification by silica gel chromatography eluting with a hexane/EtOAc gradient provided the expected intermediate 12-1b as colorless oil.

Step c)

4N HCl in 1,4-dioxane (5 mL) was added to 12-1b (4.50 g, 12.1 mmol) at room temperature and the solution was stirred for 2 hrs. Volatiles were removed under reduced pressure and the residue was triturated with diethyl ether to provide the expected intermediate 12-1c.HCl as a white solid. MS (m/z) M+1=273.2

Step B

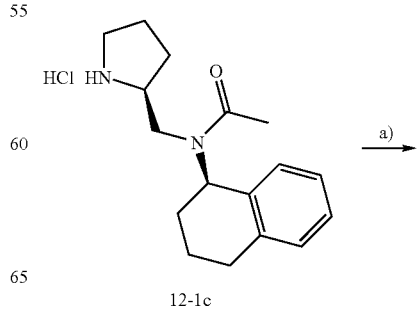

12-1c

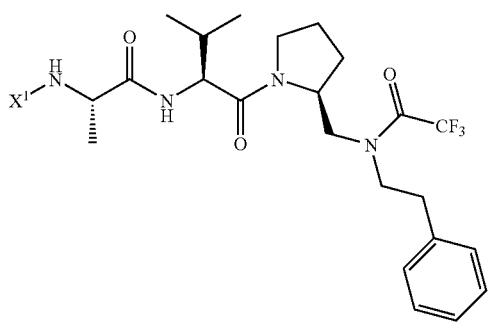

Step a)

To a solution of Boc-Ala-OH (113 mg, 0.6 mmol) in methylene chloride were sequentially added DIPEA (322 μL, 1.8 mmol), HOBt (77 mg, 0.6 mmol) and EDC (109 mg, 0.6 mmol). After stirring for 10 min 11-2b (180 mg, 0.4 mmol) was added and the reaction mixture was stirred overnight at room temperature. Water and ethyl acetate were added, the organic layer was separated, washed with 10% citric acid, saturated aqueous NaHCO$_3$ and brine, dried over MgSO$_4$, filtered and concentrated in vacuo. Purification by silica gel chromatography eluting with a hexane/EtOAc gradient provided the expected intermediate 11-3 as colorless oil.

Step b)

4N HCl in 1,4-dioxane (3 mL) was added to 11-3 (171 mg, 0.3 mmol) at room temperature and the solution was stirred for 2 hrs. Volatiles were removed under reduced pressure and the residue was triturated with diethyl ether to provide the expected compound 20.HCl as a white solid. MS (m/z) M+1=471.3

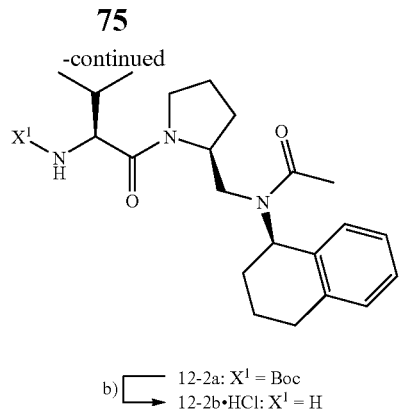

12-2a: X¹ = Boc
b) → 12-2b·HCl: X¹ = H

Step a)

To a solution of Boc-Val-OH (2.1 g, 9.7 mmol) in methylene chloride were sequentially added DIPEA (6.7 mL, 37.5 mmol), HOBt (1.3 g, 9.7 mmol) and EDC (1.8 g, 9.7 mmol). After stirring for 10 min 12-1c.HCl (2.0 g, 7.5 mmol) was added and the reaction mixture was stirred overnight at room temperature. Water and ethyl acetate were added, the organic layer was separated, washed with 10% citric acid, saturated aqueous NaHCO₃ and brine, dried over MgSO₄, filtered and concentrated in vacuo. Purification by silica gel chromatography eluting with a hexane/EtOAc gradient provided the expected intermediate 12-2a as colorless oil.

Step b)

4N HCl in 1,4-dioxane (5 mL) was added to 12-2a (2.82 g, 6.0 mmol) at room temperature and the solution was stirred for 2 hrs. Volatiles were removed under reduced pressure and the residue was triturated with diethyl ether to provide the expected intermediate 12-2b.HCl as a white solid. MS (m/z) M+1=371.3

Step C

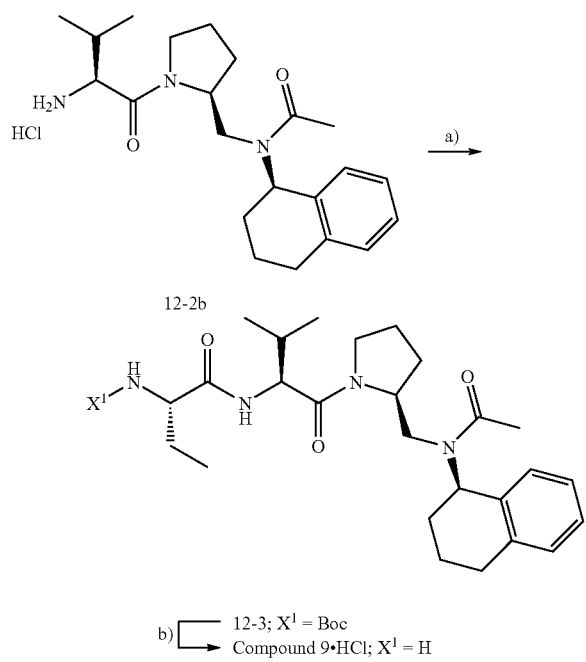

12-3; X¹ = Boc
b) → Compound 9·HCl; X¹ = H

Step a)

To a solution of Boc-Abu-OH (280 mg, 1.4 mmol) in methylene chloride were sequentially added DIPEA (950 µL, 5.3 mmol), HOBt (185 mg, 1.4 mmol) and EDC (262 mg, 1.4 mmol). After stirring for 10 min 12-2b.HCl (400 mg, 1.0 mmol) was added and the reaction mixture was stirred overnight at room temperature. Water and ethyl acetate were added, the organic layer was separated, washed with 10% citric acid, saturated aqueous NaHCO₃ and brine, dried over MgSO₄, filtered and concentrated in vacuo. Purification by silica gel chromatography eluting with a hexane/EtOAc gradient provided the expected intermediate 12-3 as colorless oil.

Step b)

4 N HCl in 1,4-dioxane (3 mL) was added to 12-3 (334 mg, 0.6 mmol) at room temperature and the solution was stirred for 2 hrs. Volatiles were removed under reduced pressure and the residue was triturated with diethyl ether to provide the expected compound 9.HCl as a white solid. MS (m/z) M+1=457.3

13. Synthesis of Intermediate 13-2b

Step A

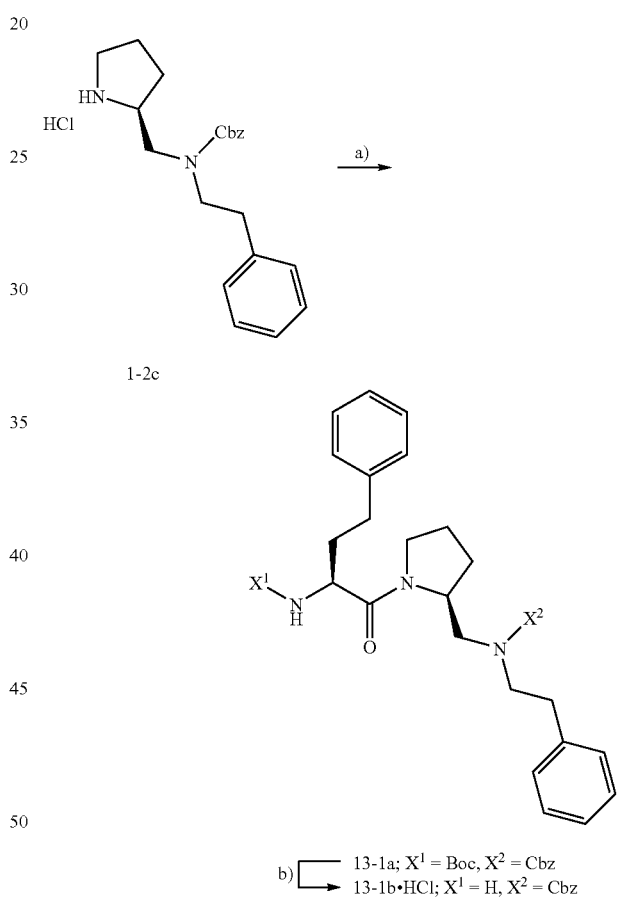

13-1a; X¹ = Boc, X² = Cbz
b) → 13-1b·HCl; X¹ = H, X² = Cbz

Step a)

To a solution of Boc-L-homophenylalanine (6.3 g, 22.5 mmol) in DMF cooled to 0° C. were sequentially added DIPEA (15 mL, 87 mmol), HOBt (3.0 g, 22.5 mmol) and HBTU (8.6 g, 22.5 mmol). After stirring for 5 min 1-2c (6.5 g, 17.3 mmol) was added and the reaction mixture was stirred overnight at room temperature. Water and ethyl acetate were added, the organic layer was separated, washed with 10% citric acid, saturated aqueous NaHCO₃ and brine, dried over anhydrous MgSO₄, filtered and concentrated in vacuo. Purification by silica gel chromatography eluting with a hexane/tetrahydrofuran gradient provided the expected intermediate 13-1a as a yellow solid.

Step b)

4N HCl in 1,4-dioxane (15 ml) was added to 13-1a (8.0 g, 13.3 mmol) and the solution was stirred for 3 hrs at room temperature. Volatiles were removed under reduced pressure and the residue was triturated with diethyl ether to provide the expected intermediate 13-1b.HCl as a white solid. MS (m/z) M+1=500.4.

Step B

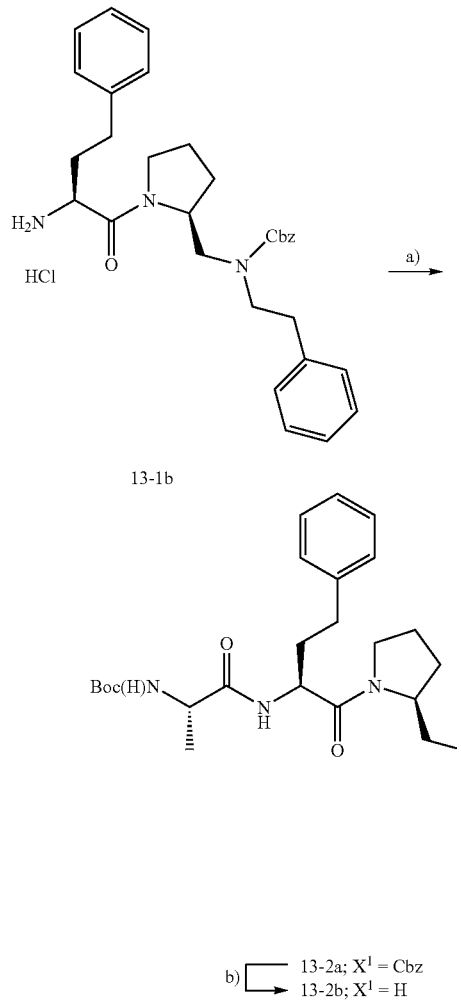

13-1b b) ⎡ 13-2a; X¹ = Cbz
   ⎣ 13-2b; X¹ = H

Step a)

To a solution of Boc-N-methyl-L-alanine (2.4 g, 11.9 mmol) in DMF cooled to 0° C. were sequentially added DIPEA (8 mL, 46 mmol), HOBt (1.6 g, 11.9 mmol) and HBTU (4.5 g, 11.9 mmol). After stirring for 5 min 13-1b.HCl (4.9 g, 9.1 mmol) was added and the reaction mixture was stirred overnight at room temperature. Water and ethyl acetate were added, the organic layer was separated, washed with 10% citric acid, saturated aqueous NaHCO₃ and brine, dried over anhydrous MgSO₄, filtered and concentrated in vacuo. Purification by silica gel chromatography eluting with a hexane/tetrahydrofuran gradient provided the expected intermediate 13-2a as a white solid.

Step b)

To a solution of 13-2a (3.3 g, 4.8 mmol) in anhydrous MeOH (100 ml) and stirred under N₂ was added 10% Pd/C (300 mg). The reaction mixture was purged with H₂ and stirred for 1 hr, then filtered through celite and the filtrate was concentrated in vacuo. Purification by silica gel chromatography eluting with a hexane/tetrahydrofuran gradient provided the expected intermediate 13-2b as colorless oil. MS (m/z) M+1=551.4.

14. Synthesis of Compound 108.HCl

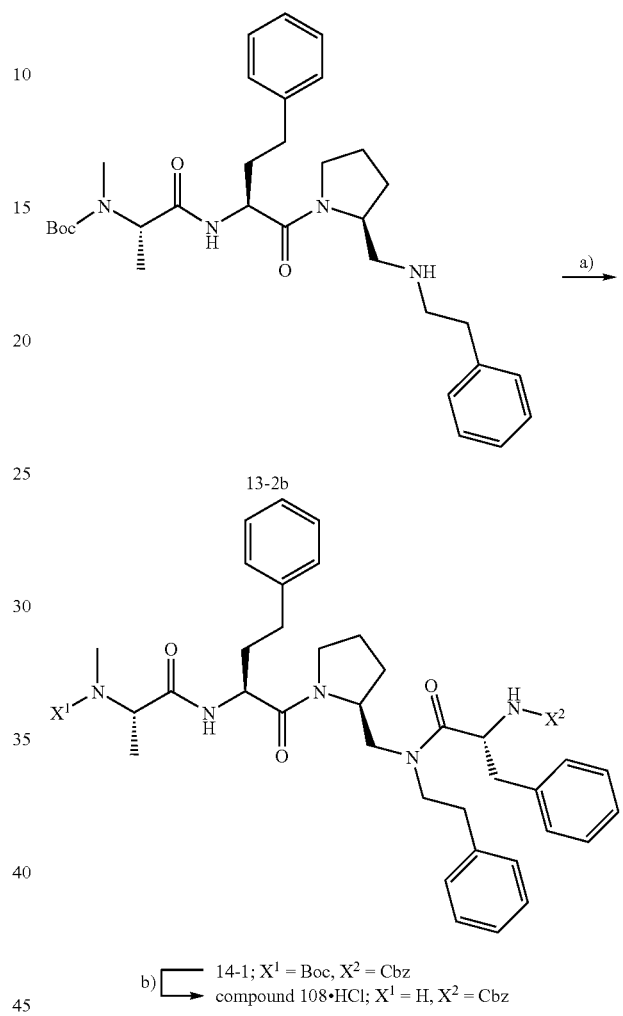

b) ⎡ 14-1; X¹ = Boc, X² = Cbz
   ⎣ compound 108·HCl; X¹ = H, X² = Cbz

Step a)

To a solution of N-Cbz-D-phenylalanine (521 mg, 1.74 mmol) in DMF cooled to 0° C. were sequentially added DIPEA (1.2 ml, 6.7 mmol), HOBt (235 mg, 1.74 mmol) and HBTU (660 mg, 1.74 mmol). After stirring for 5 min 13-2b (740 mg, 1.34 mmol) was added and the reaction mixture was stirred overnight at room temperature. Water and ethyl acetate were added, the organic layer was separated, washed with 10% citric acid, saturated aqueous NaHCO₃ and brine, dried over anhydrous MgSO₄, filtered and concentrated in vacuo. Purification by silica gel chromatography eluting with a hexane/tetrahydrofuran gradient provided the expected intermediate 14-1 as a white solid.

Step b)

4N HCl in 1,4-dioxane (2 mL) was added to 14-1 (150 mg, 0.18 mmol) and the solution was stirred for 2 hrs at room temperature. Volatiles were removed under reduced pressure and the residue was triturated with diethyl ether to provide the expected compound 108.HCl as a white solid. MS (m/z) M+1=732.4.

15. Synthesis of Compound 111.2HCl

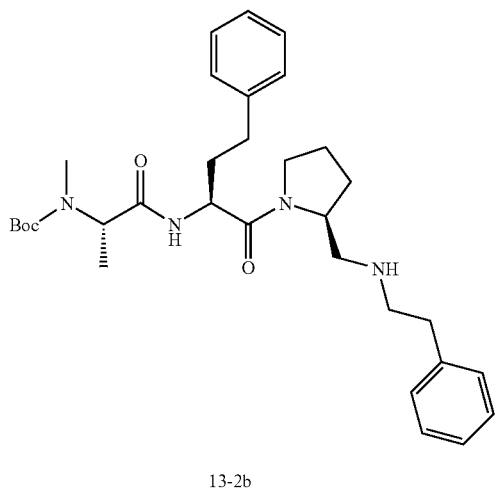

13-2b

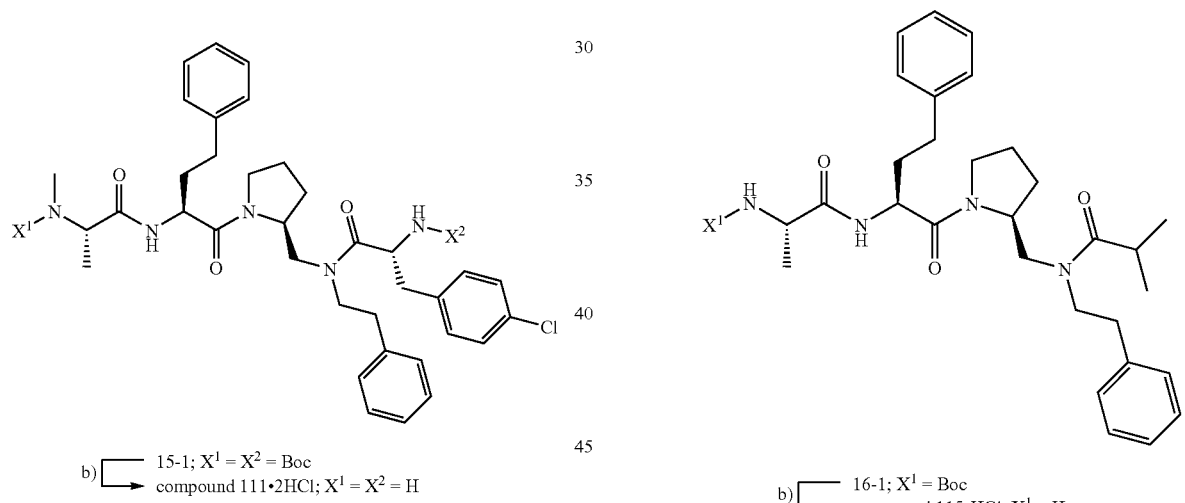

b) ⌈ 15-1; X¹ = X² = Boc
   ⌊ compound 111·2HCl; X¹ = X² = H

Step a)

To a solution of Boc-4-chloro-D-phenylalanine (71 mg, 0.24 mmol) in DMF cooled to 0° C. were sequentially added DIPEA (160 µl, 0.91 mmol), HOBt (32 mg, 0.24 mmol) and HBTU (90 mg, 0.24 mmol). After stirring for 5 min 13-2b (100 mg, 0.18 mmol) was added and the reaction mixture was stirred overnight at room temperature. Water and ethyl acetate were added, the organic layer was separated, washed with 10% citric acid, saturated aqueous NaHCO₃ and brine, dried over anhydrous MgSO₄, filtered and concentrated in vacuo. Purification by silica gel chromatography eluting with a hexane/tetrahydrofuran gradient provided the expected intermediate 15-1 as a white solid.

Step b)

4N HCl in 1,4-dioxane (2 ml) was added to 15-1 (143 mg, 0.17 mmol) and the solution was stirred for 2 hrs at room temperature. Volatiles were removed under reduced pressure and the residue was triturated with diethyl ether to provide the expected compound 111.2HCl as a white solid. MS (m/z) M+1=632.4.

16. Synthesis of Compound 115.HCl

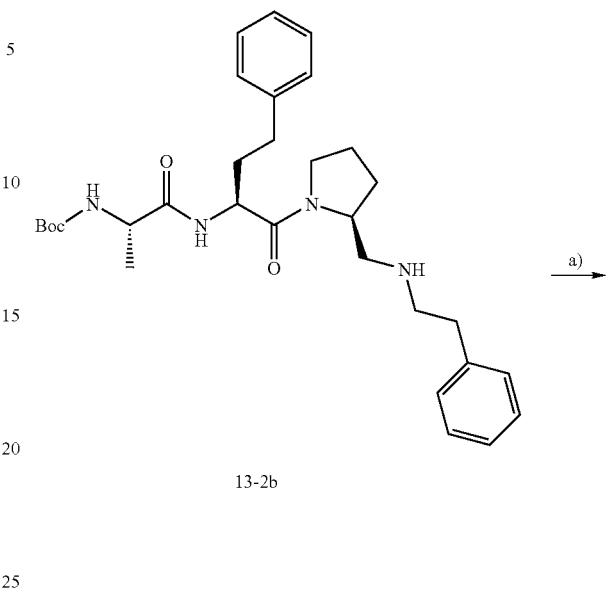

13-2b b) ⌈ 16-1; X¹ = Boc
   ⌊ compound 115·HCl; X¹ = H

Step a)

To a solution of 13-2b (200 mg, 0.36 mmol) in dichloromethane cooled to 0° C. were sequentially added DIPEA (160 µl, 0.91 mmol) isobutyryl chloride (38 µl, 0.36 mmol) and the reaction was then stirred for 3 hrs at room temperature. Aqueous NaHCO₃ and ethyl acetate were added, the organic layer was separated, washed with brine, dried over anhydrous MgSO₄, filtered and concentrated in vacuo. Purification by silica gel chromatography eluting with a hexane/tetrahydrofuran gradient provided the expected intermediate 16-1 as a white solid.

Step b)

4N HCl in 1,4-dioxane (3 ml) was added to 16-1 (200 mg, 0.36 mmol) and the solution was stirred for 2 hrs at room temperature. Volatiles were removed under reduced pressure and the residue was triturated with diethyl ether to provide the expected compound 115.HCl as a white solid. MS (m/z) M+1=521.4.

17. Synthesis of Intermediate 17-1

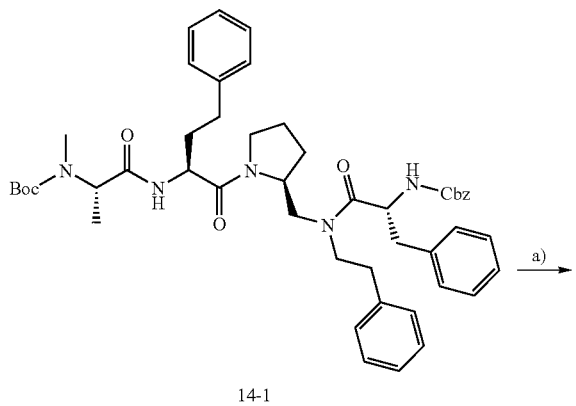

14-1

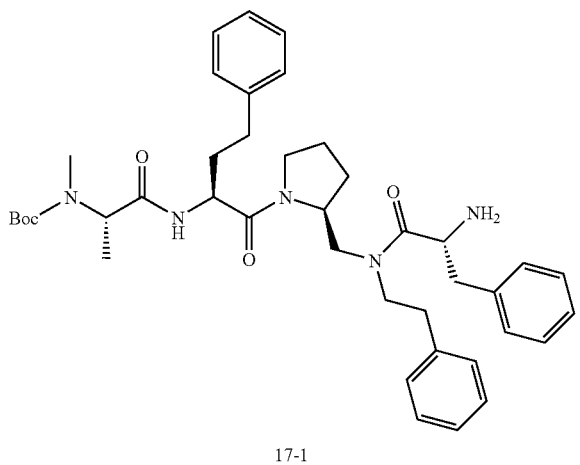

17-1

Step a)

To a solution of 14-1 (760 mg, 0.91 mmol) in anhydrous MeOH (20 ml) and stirred under $N_2$ was added 10% Pd/C (150 mg). The reaction mixture was purged with $H_2$ and stirred for 5 hrs, then filtered through celite and the filtrate was concentrated in vacuo to give the expected intermediate 17-1 as a white solid. MS (m/z) M+1=698.4.

18. Synthesis of Compound 109.HCl

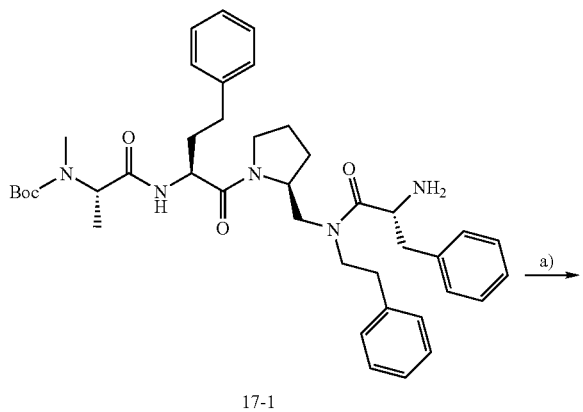

17-1

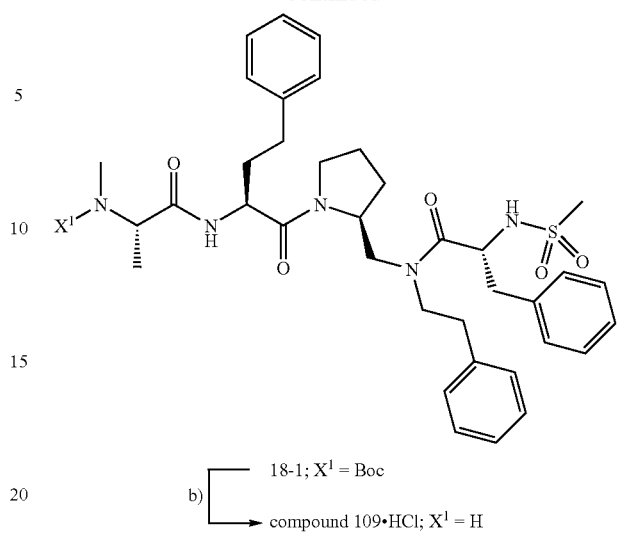

18-1; $X^1$ = Boc
compound 109·HCl; $X^1$ = H

Step a)

To a solution of 17-1 (125 mg, 0.18 mmol) in dichloromethane cooled to 0° C. were sequentially added TEA (75 μl, 0.18 mmol) and methanesulfonyl chloride (14 μl, 0.18 mmol) and the reaction was then stirred for 1 hr at room temperature. Aqueous $NaHCO_3$ and ethyl acetate were added, the organic layer was separated, washed with brine, dried over anhydrous $MgSO_4$, filtered and concentrated in vacuo. Purification by silica gel chromatography eluting with a hexane/ethyl acetate gradient provided the expected intermediate 18-1 as a white solid.

Step b)

4N HCl in 1,4-dioxane (2 ml) was added to 18-1 (80 mg, 0.10 mmol) and the solution was stirred for 1 hr at room temperature. Volatiles were removed under reduced pressure and the residue was triturated with diethyl ether to provide the expected compound 109.HCl as a white solid. MS (m/z) M+1=676.4

19. Synthesis of Compound 110.2TFA

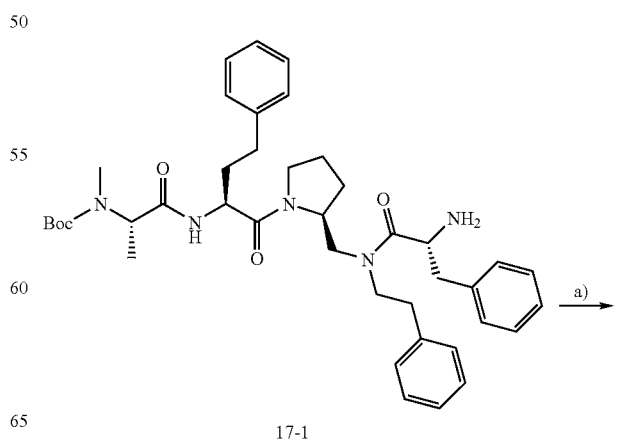

17-1

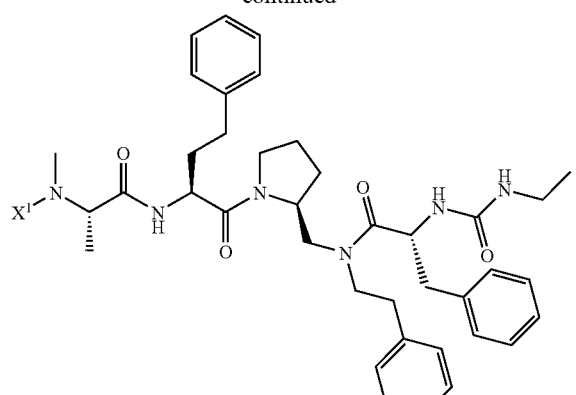

19-1; X¹ = Boc b) → compound 110·2TFA; X¹ = H

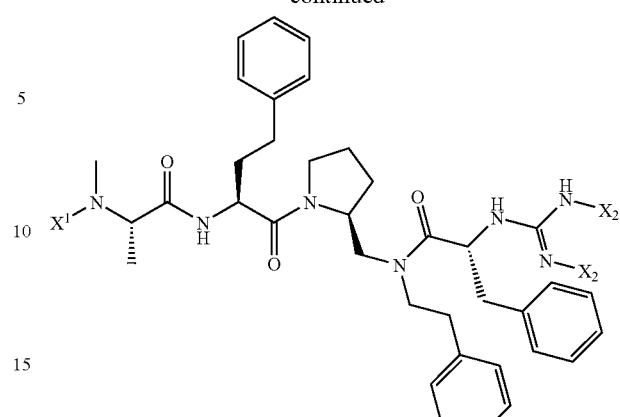

20-1; X¹ = X² = Boc b) → compound 167·2TFA; X¹ = X² = H

Step a)

To a solution of 17-1 (125 mg, 0.18 mmol) in tetrahydrofuran cooled to 0° C. was added ethylisocyanate (14 μl, 0.18 mmol) and the reaction was then stirred for 2 hrs at room temperature. Volatiles were removed under reduced pressure and the residue purified by silica gel chromatography eluting with a hexane/tetrahydrofuran gradient to provide the expected intermediate 19-1 as a white solid.

Step b)

Intermediate 19-1 was dissolved in a mixture of $CH_2Cl_2$ (0.8 mL) and TFA (0.2 mL). The solution was stirred for 2 hrs at room temperature. Volatiles were removed under reduced pressure and the residue was triturated with diethyl ether to provide the expected compound 110.2TFA as a white solid. MS (m/z) M+1=669.4

20. Synthesis of Compound 167.2TFA

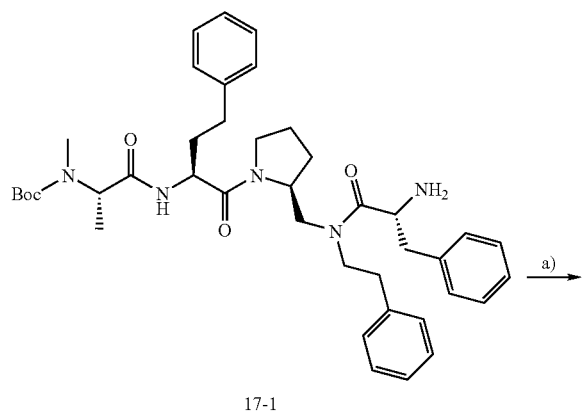

17-1

Step a)

To a solution of 17-1 (125 mg, 0.18 mmol) in dichloromethane cooled to 0° C. were sequentially added $NEt_3$ (27 μl, 0.19 mmol) and N—N'-di-Boc-1H-pyrazole-1-carboxamidine (58 mg, 0.18 mmol) and the reaction was then stirred for 2 hrs at room temperature. Volatiles were removed under reduced pressure and the residue purified by silica gel chromatography eluting with a hexane/ethyl acetate gradient to provide the expected intermediate 20-1 as a white solid.

Step b)

Intermediate 19-1 (159 mg, 0.17 mmol) was dissolved in a mixture of $CH_2Cl_2$ (1.0 mL) and TFA (1.0 mL). The solution was stirred for 2 hrs at room temperature. Volatiles were removed under reduced pressure and the residue was triturated with diethyl ether to provide the expected compound 167.2TFA as a white solid. MS (m/z) M+1=640.4

21. Synthesis of Intermediate 21-2b

Step A

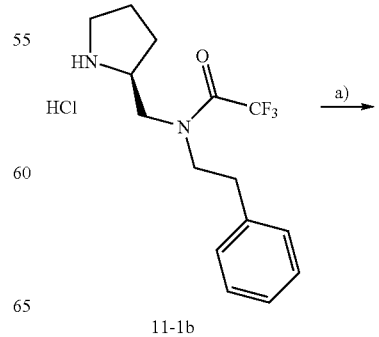

11-1b

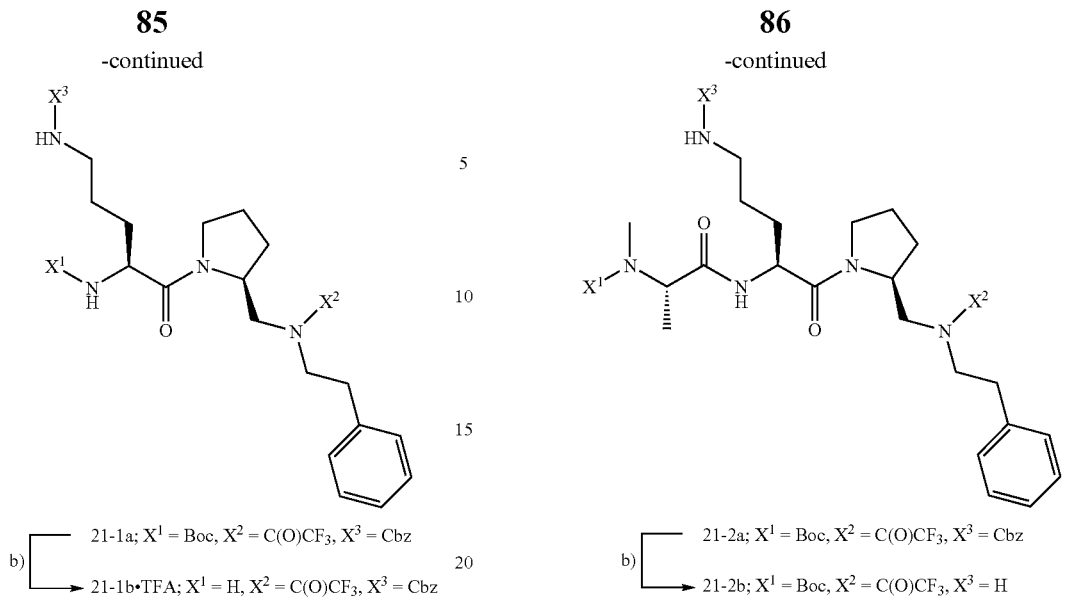

21-1a; $X^1$ = Boc, $X^2$ = C(O)CF$_3$, $X^3$ = Cbz
b)
21-1b·TFA; $X^1$ = H, $X^2$ = C(O)CF$_3$, $X^3$ = Cbz 21-2a; $X^1$ = Boc, $X^2$ = C(O)CF$_3$, $X^3$ = Cbz
b)
21-2b; $X^1$ = Boc, $X^2$ = C(O)CF$_3$, $X^3$ = H

Step a)

To a solution of Boc-Orn(Z)-OH (3.1 g, 8.5 mmol) in DMF cooled to 0° C. were sequentially added DIPEA (5.2 ml, 34.0 mmol), HOBt (1.42 g, 11.0 mmol) and HBTU (4.58 g, 12.0 mmol). After stirring for 5 min 1'-1b.HCl (3.0 g, 8.9 mmol) was added and the reaction mixture was stirred overnight at room temperature. Water and ethyl acetate were added, the organic layer was separated, washed with 10% citric acid, saturated aqueous NaHCO$_3$ and brine, dried over anhydrous MgSO$_4$, filtered and concentrated in vacuo. Purification by silica gel chromatography eluting with a hexane/tetrahydrofuran gradient provided the expected intermediate 21-1a as a white solid.

Step b)

Intermediate 21-1 was dissolved in a mixture of CH$_2$Cl$_2$ (5.0 mL) and TFA (5.0 mL). The solution was stirred for 2 hrs at room temperature. Volatiles were removed under reduced pressure and the residue was triturated with diethyl ether to provide the expected intermediate 21-1b.TFA as a white solid. MS (m/z) M+1=549.2

Step B

Step a)

To a solution of Boc-N-MeAla-OH (2.3 g, 11.4 mmol) in DMF cooled to 0° C. were sequentially added DIPEA (6.1 ml, 35.0 mmol), HOBt (1.8 g, 13.2 mmol) and HBTU (4.7 g, 12.3 mmol). After stirring for 5 min 11-1b.HCl (5.5 g, 8.5 mmol) was added and the reaction mixture was stirred overnight at room temperature. Water and ethyl acetate were added, the organic layer was separated, washed with 10% citric acid, saturated aqueous NaHCO$_3$ and brine, dried over anhydrous MgSO$_4$, filtered and concentrated in vacuo. Purification by silica gel chromatography eluting with a hexane/tetrahydrofuran gradient provided the expected intermediate 21-2a as a white solid.

Step b)

To a solution of 21-2a (1.0 g, 1.4 mmol) in anhydrous MeOH (20 mL) and stirred under N$_2$ was added 10% Pd/C (200 mg). The reaction mixture was purged with H$_2$ and stirred for 5 hrs. The reaction was then filtered through celite and the filtrate was concentrated in vacuo. Purified by silica gel chromatography eluting with a hexane/tetrahydrofuran gradient provided the expected intermediate 21-2b as a white solid. MS (m/z) M+1=600.4

22. Synthesis of Compound 157.HCl

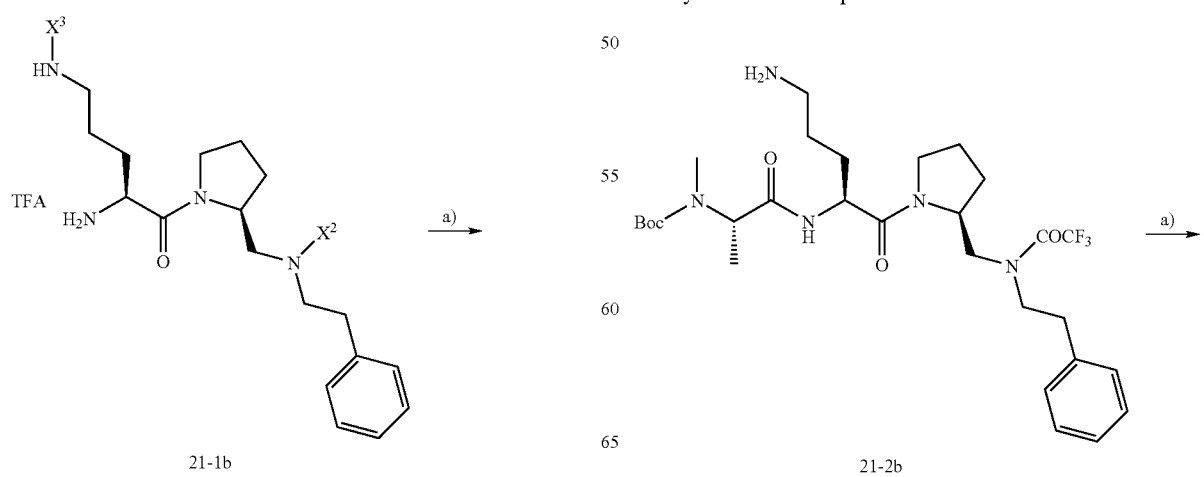

21-1b 21-2b

-continued

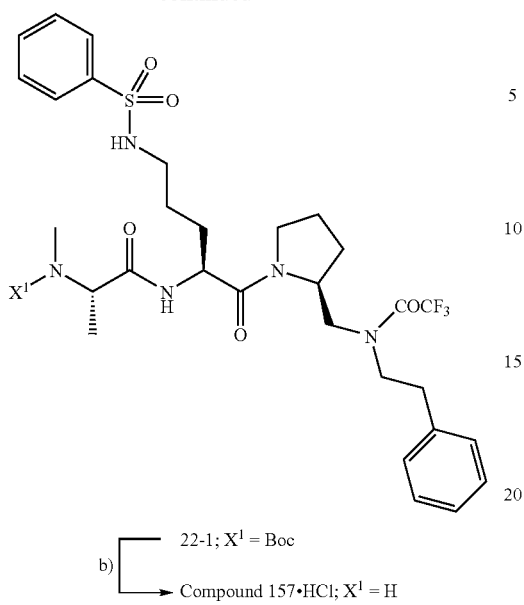

22-1; X¹ = Boc
b) ⟶ Compound 157·HCl; X¹ = H

Step a)

To a solution of 21-1b (100 mg, 0.17 mmol) in dichloromethane cooled to 0° C. were sequentially added DIPEA (89 μl, 0.5 mmol), benzenesulfonyl chloride (26 μl, 0.2 mmol) DMAP (catalytic) and the reaction was then stirred for 3 hrs at room temperature. Ethyl acetate and 10% citric acid were added, the organic layer was separated, washed with saturated aqueous NaHCO₃ and brine, dried over anhydrous MgSO₄, filtered and concentrated in vacuo. Purification by silica gel chromatography eluting with a hexane/tetrahydrofuran gradient provided intermediate 22-1 as a white solid.

Step b)

4N HCl in 1,4-dioxane (1 mL) was added to 22-1 (100 mg, 0.13 mmol) and the solution was stirred for 1 hr at room temperature. Volatiles were removed under reduced pressure and the residue was triturated with diethyl ether to provide compound 157.HCl as a white solid. MS (m/z) M+1=640.2.

23. Synthesis of Compound 158.2HCl

-continued

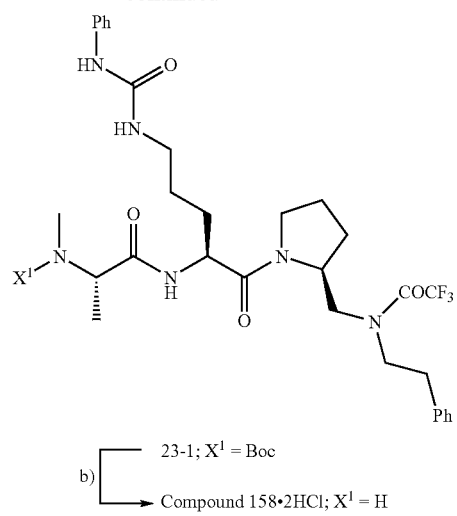

23-1; X¹ = Boc
b) ⟶ Compound 158·2HCl; X¹ = H

Step a)

To a solution of 21-2b (100 mg, 0.17 mmol) in dichloromethane cooled to 0° C. were sequentially added DiPEA (89 μl, 0.5 mmol) and phenylisocyanate (22 μl, 0.2 mmol), the reaction was then stirred for 16 hrs at room temperature. Ethyl acetate and 10% citric acid were added, the organic layer was separated, washed with saturated aqueous NaHCO₃ and brine, dried over anhydrous MgSO₄, filtered and concentrated in vacuo. Purification by silica gel chromatography eluting with a hexane/THF gradient provided intermediate 23-1 as a white solid.

Step b)

4N HCl in 1,4-dioxane (1 mL) was added to 23-1 (100 mg, 0.14 mmol) and the solution was stirred for 1 hr at room temperature. Volatiles were removed under reduced pressure and the residue was triturated with diethyl ether to provide compound 158.2HCl as a white solid. MS (m/z) M+1=619.4.

24. Synthesis of Compound 169

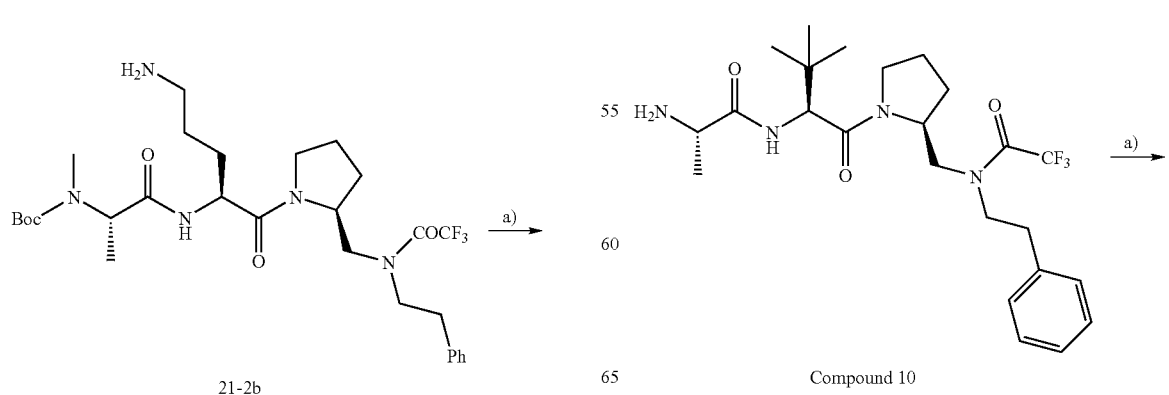

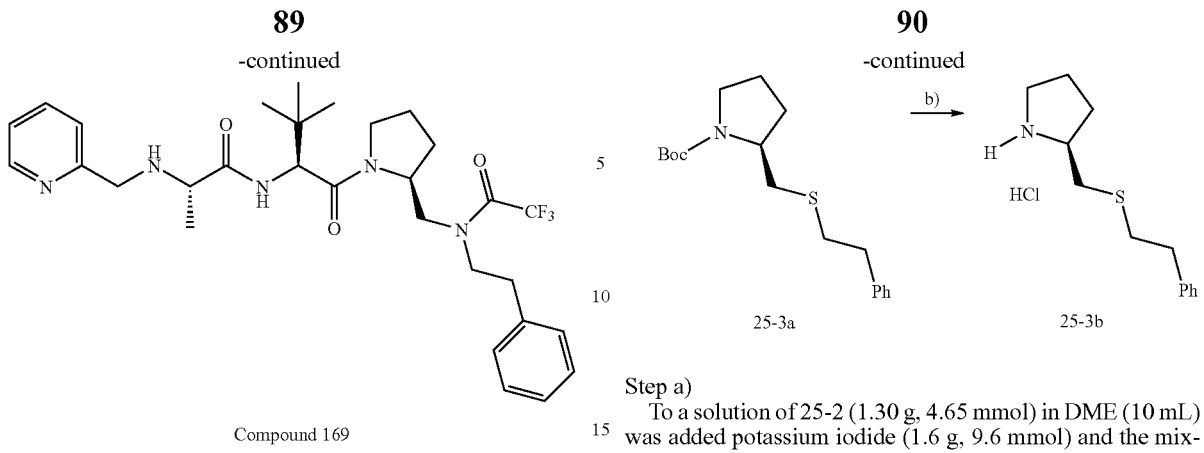

Compound 169

To a solution of compound 10 (100 mg, 0.19 mmol) in dichloromethane was added 2-pyridine carboxaldehyde (18 µl, 0.21 mmol). After stirring for 2 hrs at room temperature. Sodium triacetoxyborohydride (48 mg, 0.23 mmol) was added and the reaction mixture was stirred for 16 hrs at room temperature. Ethyl acetate and 10% citric acid were added, the organic layer was separated, washed with saturated aqueous NaHCO$_3$ and brine, dried over anhydrous MgSO$_4$, filtered and concentrated in vacuo. Purification by Amine-silica gel chromatography eluting with a hexane/tetrahydrofuran gradient provided compound 169 as a white solid. MS (m/z) M+1=576.4.

25. Synthesis of Compound 66

Step A

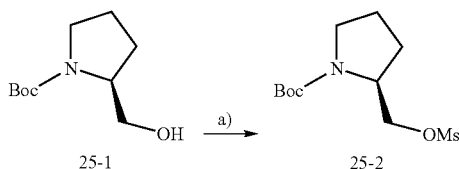 [SMILES: CC(C)(C)OC(=O)N1CCC[C@H]1CO ; CC(C)(C)OC(=O)N1CCC[C@H]1COS(C)(=O)=O]

To a solution of Boc-prolinol (2.13 g, 10.6 mmol) in dichloromethane (10 mL) were sequentially added triethylamine (3 mL, 21.5 mmol), methanesulfonic anhydride (2.88 g, 16.5 mmol), and 4-(N,N-dimethyl)aminopyridine (58 mg, 0.47 mmol). The reaction was stirred for 2 hrs at room temperature. Saturated aqueous NaHCO$_3$ was added, the organic layer was separated, washed with 10% citric acid and brine, dried over MgSO$_4$, filtered and concentrated in vacuo. Purification by silica gel chromatography, eluting with a hexane/ethyl acetate gradient, to provide intermediate 25-2 as colorless oil.

Step B

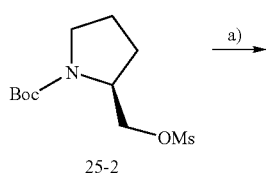

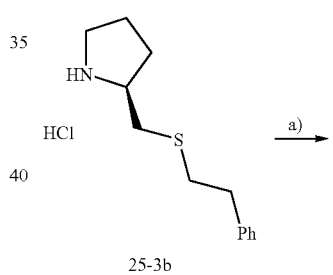

25-3a                     25-3b

Step a)

To a solution of 25-2 (1.30 g, 4.65 mmol) in DME (10 mL) was added potassium iodide (1.6 g, 9.6 mmol) and the mixture was stirred for 1 hr at room temperature. Benzenethiol (630 µL, 4.7 mmol) and sodium hydride (186 mg, 4.7 mmol) in DME (10 mL) were then added and the reaction was stirred overnight at room temperature. Water and ethyl acetate were added, the organic layer was separated, washed with saturated aqueous NaHCO$_3$ and brine, dried over MgSO$_4$, filtered and concentrated in vacuo. Purification by silica gel chromatography eluting with a hexane/ethyl acetate gradient to provide intermediate 25-3a as colorless oil.

Step b)

4N HCl in 1,4-dioxane (4 ml) was added to 25-3a (384 mg, 1.2 mmol) and the solution was stirred for 2 hrs at room temperature. Volatiles were removed under reduced pressure and the residue was triturated with diethyl ether to provide intermediate 25-3b.HCl as a white solid. MS (m/z) M+1=222.2

Step C

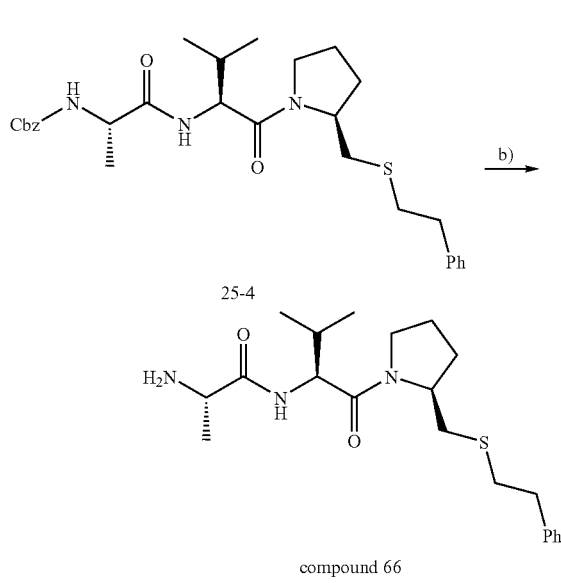

compound 66

Step a)

To a solution of Cbz-Ala-Val-OH (377 mg, 1.17 mmol) in DMF cooled to 0° C. were sequentially added DIPEA (515 µL, 2.96 mmol), HOBt (176 mg, 1.30 mmol) and HBTU (369 mg, 1.15 mmol). After stirring for 5 min 25-3b.HCl (153 mg, 0.59 mmol) was added and the reaction mixture was stirred overnight at room temperature. Water and ethyl acetate were added, the organic layer was separated, washed with 10% citric acid, saturated aqueous NaHCO$_3$ and brine, dried over anhydrous MgSO$_4$, filtered and concentrated in vacuo. Purification by silica gel chromatography eluting with a hexane/Ethyl acetate gradient provided intermediate 25-4 as a white solid.

Step b)

To a solution of 25-4 (150 mg, 0.28 mmol) in anhydrous MeOH (20 ml) and stirred under N$_2$ was added 10% Pd/C (210 mg). The reaction mixture was purged with H$_2$ and stirred for 3 hrs, then filtered through celite and the filtrate was concentrated in vacuo to provide the compound 66 as a white solid. MS (m/z) M+1=392.3

26. Synthesis of Compound 67

Step A

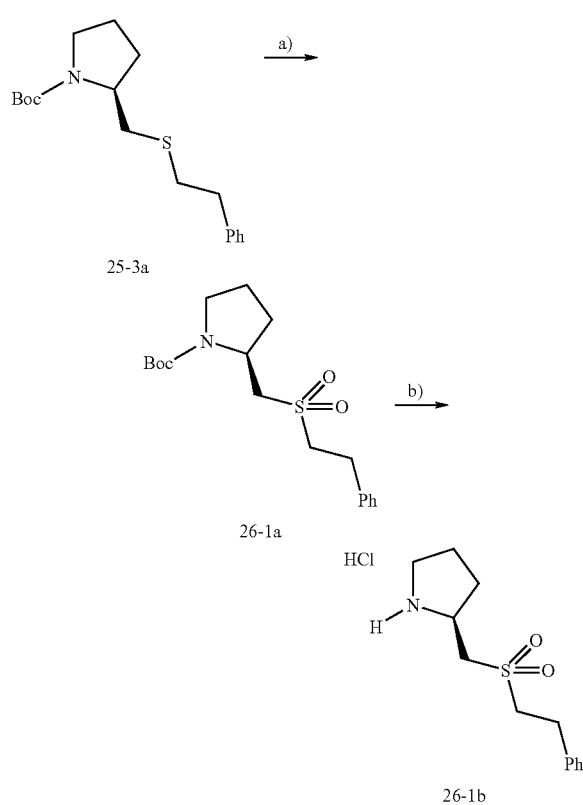

Step a)

To a solution of 25-3a (290 mg, 0.9 mmol) in dichloromethane (50 mL) cooled to 0° C. was added m-CPBA (523 mg, 2.29 mmol) and the reaction mixture was stirred overnight at room temperature. 10% aqueous Na$_2$SO$_3$ and ethyl acetate were added, the organic layer was separated, washed with saturated aqueous NaHCO$_3$ and brine, dried over MgSO$_4$, filtered and concentrated in vacuo. Purification by silica gel chromatography eluting with a hexane/EtOAc gradient provided the expected intermediate 26-1a as a white solid.

Step b)

4N HCl in 1,4-dioxane (4 ml) was added to 26-1a (335 mg, 0.94 mmol) and the solution was stirred for 2 hrs at room temperature. Volatiles were removed under reduced pressure and the residue was triturated with diethyl ether to provide the expected intermediate 26-1b.HCl as a white solid. MS (m/z) M+1=254.2

Step B

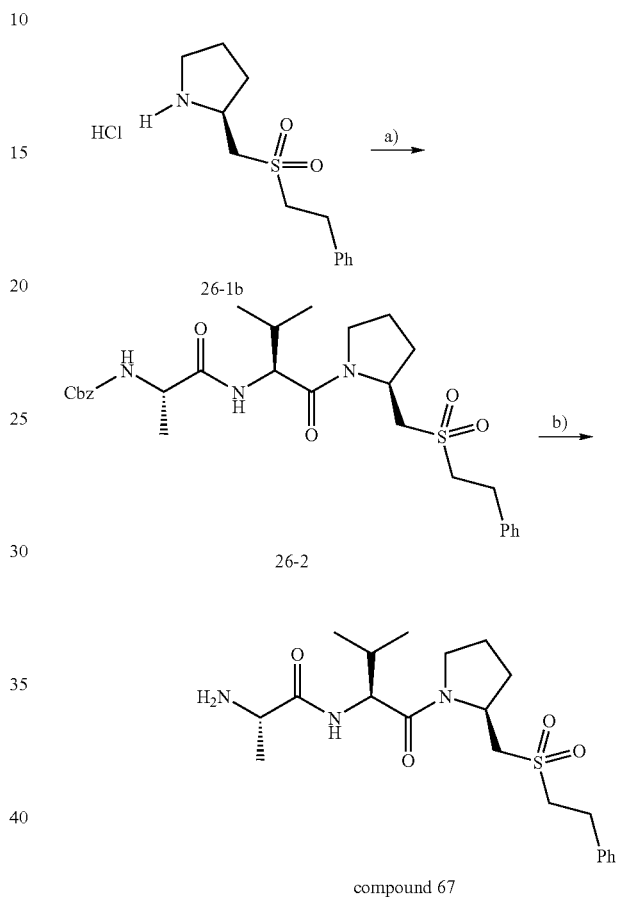

compound 67

Step a)

To a solution of Cbz-Ala-Val-OH (275 mg, 0.85 mmol) in DMF cooled to ° C. were sequentially added DIPEA (430 µL, 2.47 mmol), HOBt (122 mg, 0.90 mmol) and HBTU (275 mg, 0.85 mmol). After stirring for 5 min 26-1b.HCl (180 mg, 0.0.62 mmol) was added and the reaction mixture was stirred overnight at room temperature. Water and ethyl acetate were added, the organic layer was separated, washed with 10% citric acid, saturated aqueous NaHCO$_3$ and brine, dried over anhydrous MgSO$_4$, filtered and concentrated in vacuo. Purification by silica gel chromatography eluting with a hexane/Ethyl acetate gradient provided the expected intermediate 26-2b as a white solid.

Step b)

To a solution of 26-2b (155 mg, 0.28 mmol) in anhydrous MeOH (20 ml) added 10% Pd/C (58 mg). The reaction mixture was purged with H$_2$ and stirred for 3 hrs, then filtered through celite and the filtrate was concentrated in vacuo to provide compound 67 as a white solid. MS (m/z) M+1=424.2

Representative compounds of the present invention were prepared by simple modification of the above procedures and are illustrated in Table 1:

TABLE 1
| Compound # | Structure | MS m/z (M + H) |
|---|---|---|
| 1 | 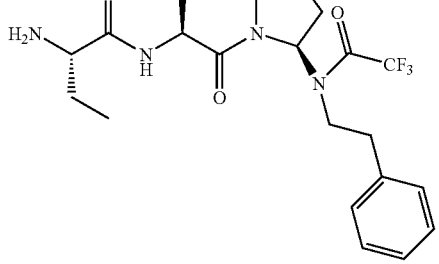 | 485.3 |
| 2 | 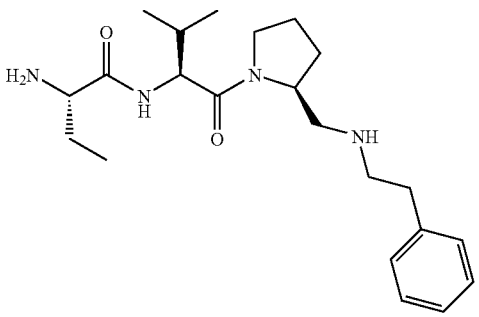 [SMILES: CC[C@H](N)C(=O)N[C@H](C(=O)N1CCC[C@H]1CNCCc1ccccc1)C(C)C] | 389.3 |
| 3 | 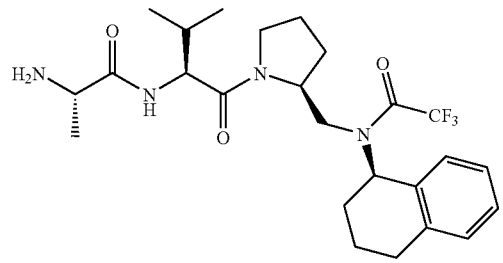 [SMILES: CC(C)[C@H](NC(=O)[C@H](C)N)C(=O)N1CCC[C@H]1CN(C(=O)C(F)(F)F)[C@@H]1CCCc2ccccc21] | 497.3 |
| 4 | 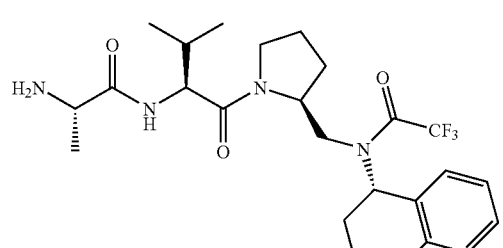 | 497.3 |
| 5 | 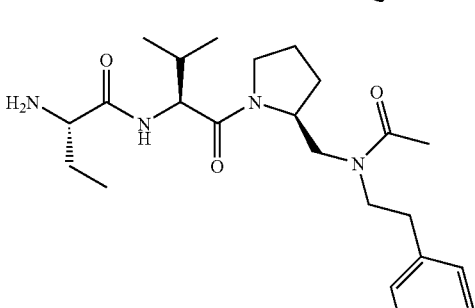 | 431.3 |

TABLE 1-continued
| Compound # | Structure | MS m/z (M + H) |
|---|---|---|
| 6 | 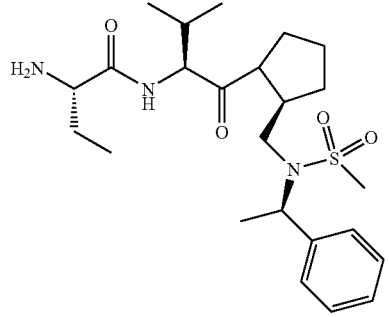 [SMILES: CC[C@H](N)C(=O)N[C@H](C(=O)C1CCC[C@H]1CN([C@H](C)c1ccccc1)S(C)(=O)=O)C(C)C] | 467.3 |
| 7 | 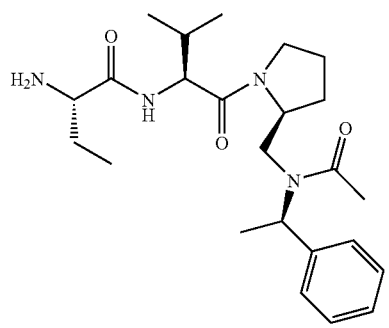 [SMILES: CC[C@H](N)C(=O)N[C@H](C(=O)N1CCC[C@H]1CN(C(C)=O)[C@H](C)c1ccccc1)C(C)C] | 431.4 |
| 8 | 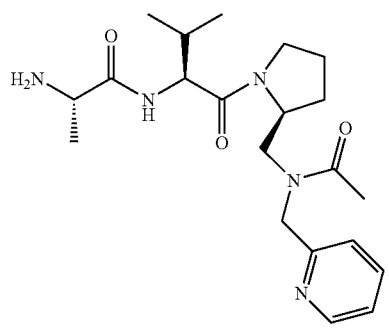 [SMILES: CC(=O)N(Cc1ccccn1)C[C@@H]1CCCN1C(=O)[C@@H](NC(=O)[C@H](C)N)C(C)C] | 404.2 |
| 9 | 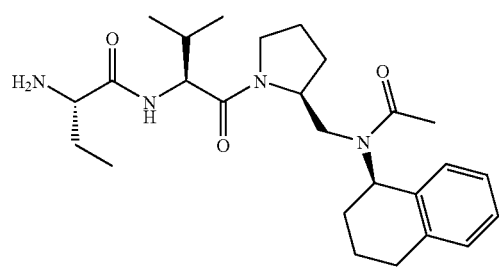 [SMILES: CC[C@H](N)C(=O)N[C@H](C(=O)N1CCC[C@H]1CN(C(C)=O)[C@@H]1CCCc2ccccc21)C(C)C] | 457.3 |

TABLE 1-continued

| Compound # | Structure | MS m/z (M + H) |
|---|---|---|
| 10 | 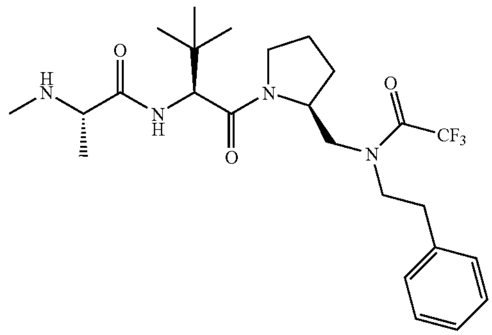 [SMILES: CN[C@@H](C)C(=O)N[C@H](C(=O)N1CCC[C@H]1CN(CCc1ccccc1)C(=O)C(F)(F)F)C(C)(C)C] | 499.3 |
| 11 | 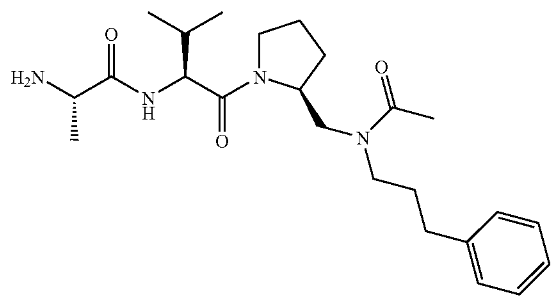 [SMILES: CC(=O)N(CCCc1ccccc1)C[C@@H]1CCCN1C(=O)[C@@H](NC(=O)[C@H](C)N)C(C)C] | 431.3 |
| 12 | 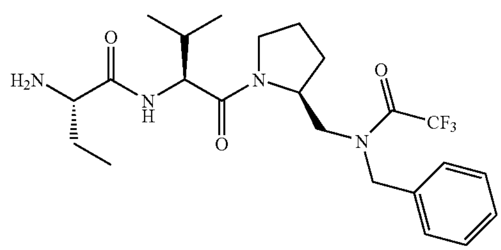 [SMILES: CC[C@H](N)C(=O)N[C@H](C(=O)N1CCC[C@H]1CN(Cc1ccccc1)C(=O)C(F)(F)F)C(C)C] | 471.3 |
| 13 | 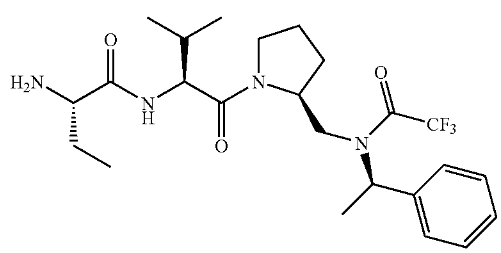 [SMILES: CC[C@H](N)C(=O)N[C@H](C(=O)N1CCC[C@H]1CN(C(=O)C(F)(F)F)[C@H](C)c1ccccc1)C(C)C] | 485.3 |
| 14 | 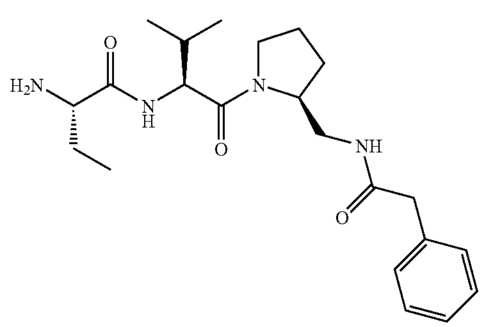 [SMILES: CC[C@H](N)C(=O)N[C@H](C(=O)N1CCC[C@H]1CNC(=O)Cc1ccccc1)C(C)C] | 403.3 |

TABLE 1-continued

| Compound # | Structure | MS m/z (M + H) |
|---|---|---|
| 15 | 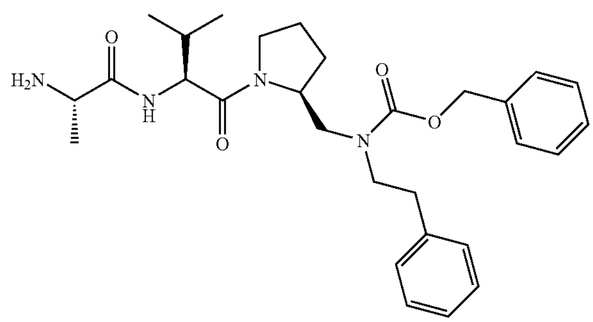 | 509.3 |
| 16 | 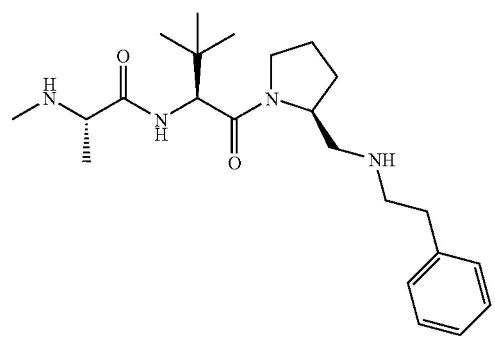 [SMILES: CN[C@@H](C)C(=O)N[C@H](C(=O)N1CCC[C@H]1CNCCc1ccccc1)C(C)(C)C] | 403.3 |
| 17 | 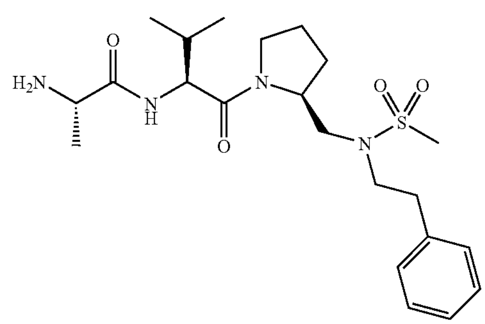 [SMILES: CC(C)[C@H](NC(=O)[C@H](C)N)C(=O)N1CCC[C@H]1CN(CCc1ccccc1)S(C)(=O)=O] | 453.3 |
| 18 | 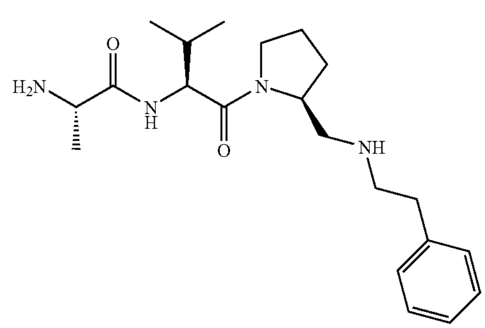 [SMILES: CC(C)[C@H](NC(=O)[C@H](C)N)C(=O)N1CCC[C@H]1CNCCc1ccccc1] | 375.3 |

TABLE 1-continued

| Compound # | Structure | MS m/z (M + H) |
|---|---|---|
| 19 | 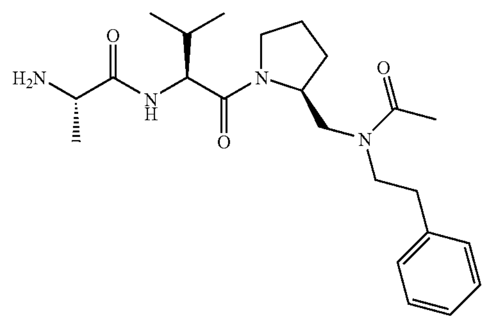 [SMILES: CC(=O)N(CCc1ccccc1)C[C@@H]1CCCN1C(=O)[C@@H](NC(=O)[C@H](C)N)C(C)C] | 417.3 |
| 20 | 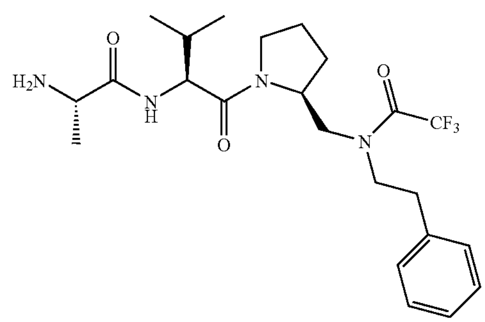 [SMILES: CC(C)[C@H](NC(=O)[C@H](C)N)C(=O)N1CCC[C@H]1CN(CCc1ccccc1)C(=O)C(F)(F)F] | 471.3 |
| 21 | 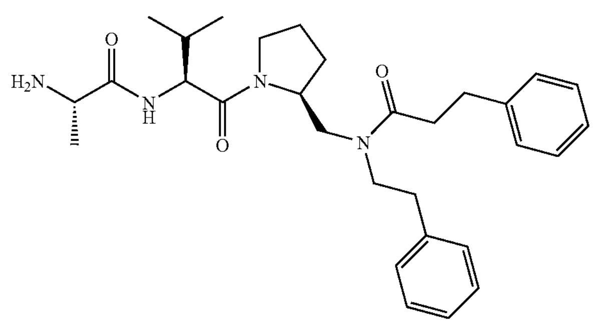 [SMILES: CC(C)[C@H](NC(=O)[C@H](C)N)C(=O)N1CCC[C@H]1CN(CCc1ccccc1)C(=O)CCc1ccccc1] | 507.4 |
| 22 | 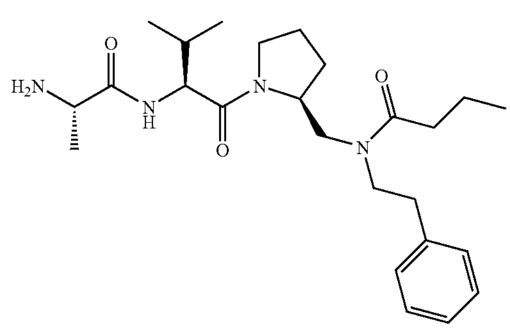 [SMILES: CCCC(=O)N(CCc1ccccc1)C[C@@H]1CCCN1C(=O)[C@@H](NC(=O)[C@H](C)N)C(C)C] | 445.3 |

TABLE 1-continued

| Compound # | Structure | MS m/z (M + H) |
|---|---|---|
| 23 | 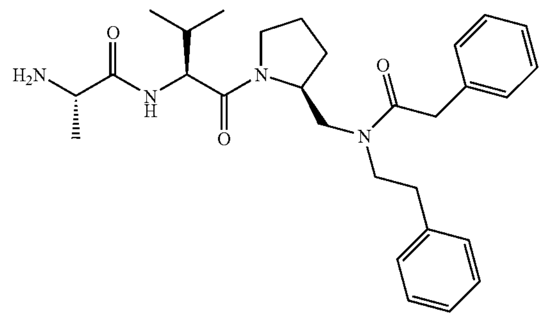 [SMILES: CC(C)[C@H](NC(=O)[C@H](C)N)C(=O)N1CCC[C@H]1CN(CCc1ccccc1)C(=O)Cc1ccccc1] | 493.3 |
| 24 | 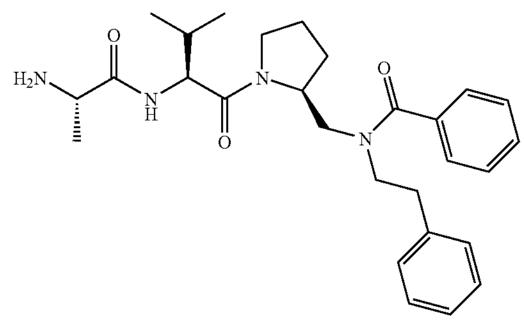 [SMILES: CC(C)[C@H](NC(=O)[C@H](C)N)C(=O)N1CCC[C@H]1CN(CCc1ccccc1)C(=O)c1ccccc1] | 479.3 |
| 25 | 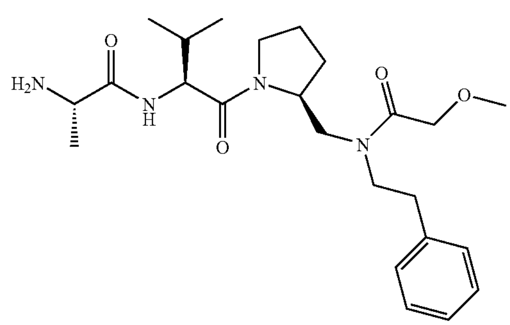 | 447.3 |
| 26 | 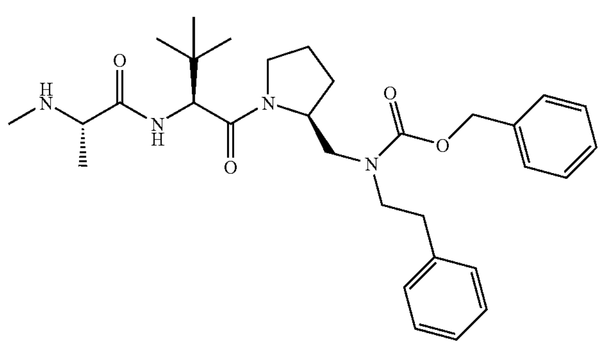 | 537.3 |

TABLE 1-continued

| Compound # | Structure | MS m/z (M + H) |
|---|---|---|
| 27 | 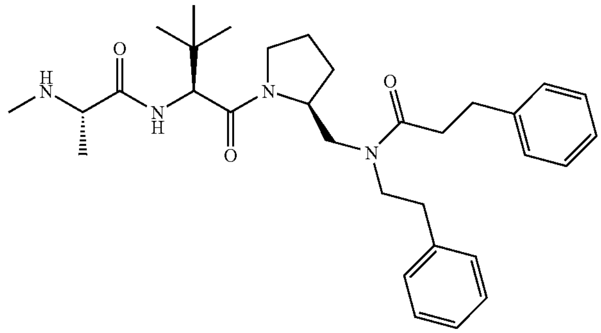 [SMILES: CN[C@@H](C)C(=O)N[C@H](C(=O)N1CCC[C@H]1CN(CCc1ccccc1)C(=O)OCc1ccccc1)C(C)(C)C] | 535.4 |
| 28 | 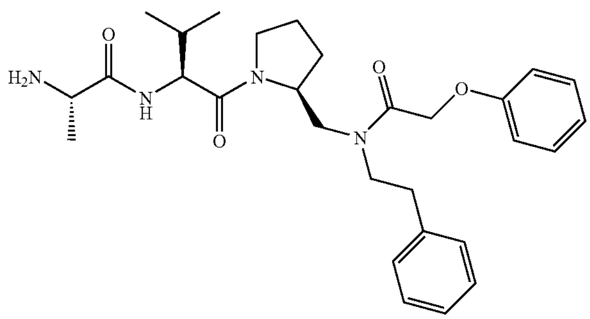 | 509.3 |
| 29 | 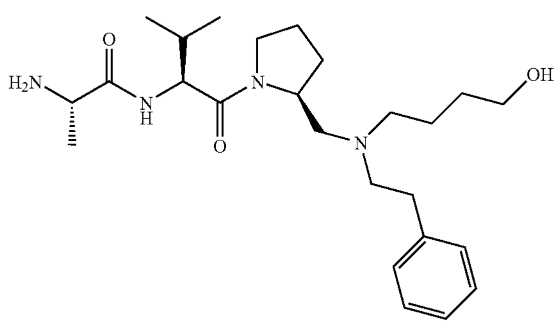 [SMILES: CC(C)[C@H](NC(=O)[C@H](C)N)C(=O)N1CCC[C@H]1CN(CCCCO)CCc1ccccc1] | 447.3 |
| 30 | 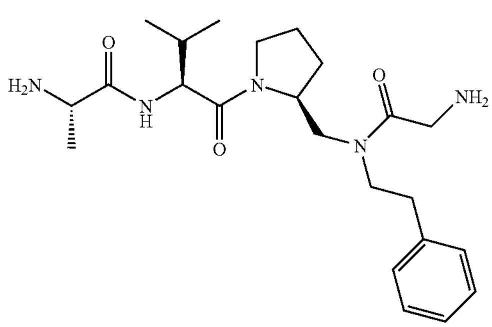 [SMILES: CC(C)[C@H](NC(=O)[C@H](C)N)C(=O)N1CCC[C@H]1CN(CCc1ccccc1)C(=O)CN] | 432.3 |

TABLE 1-continued

| Compound # | Structure | MS m/z (M + H) |
|---|---|---|
| 31 | 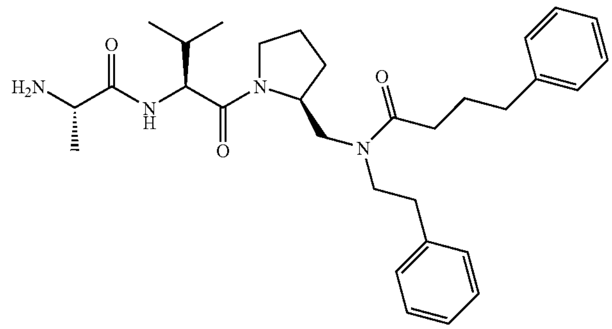 [SMILES: CC(C)[C@H](NC(=O)[C@H](C)N)C(=O)N1CCC[C@H]1CN(CCc1ccccc1)C(=O)CCCc1ccccc1] | 521.3 |
| 32 | 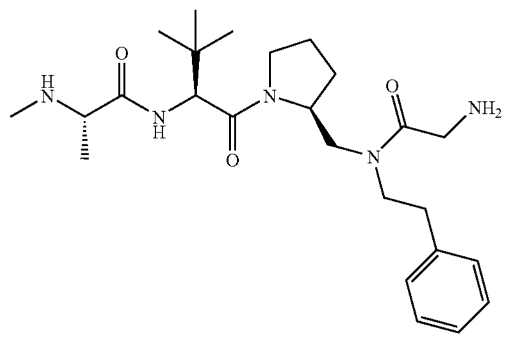 [SMILES: CN[C@@H](C)C(=O)N[C@H](C(=O)N1CCC[C@H]1CN(CCc1ccccc1)C(=O)CN)C(C)(C)C] | 460.3 |
| 33 | 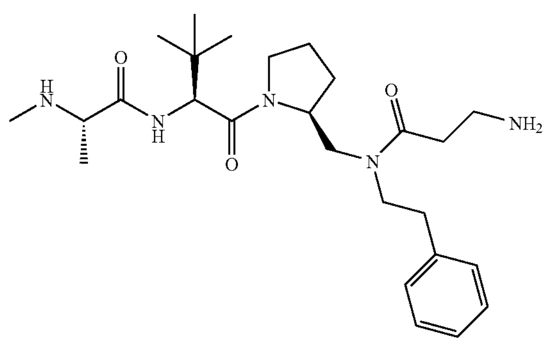 [SMILES: CN[C@@H](C)C(=O)N[C@H](C(=O)N1CCC[C@H]1CN(CCc1ccccc1)C(=O)CCN)C(C)(C)C] | 474.3 |
| 34 | 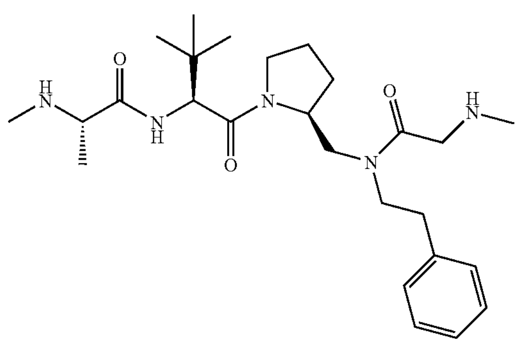 | 474.3 |

TABLE 1-continued

| Compound # | Structure | MS m/z (M + H) |
|---|---|---|
| 35 | 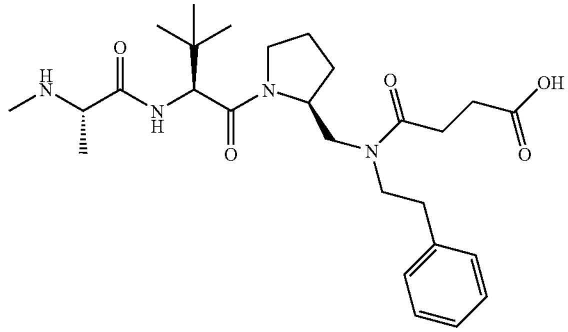 [SMILES: CN[C@@H](C)C(=O)N[C@H](C(=O)N1CCC[C@H]1CN(CCc1ccccc1)C(=O)CCC(=O)O)C(C)(C)C] | 503.1 |
| 36 | 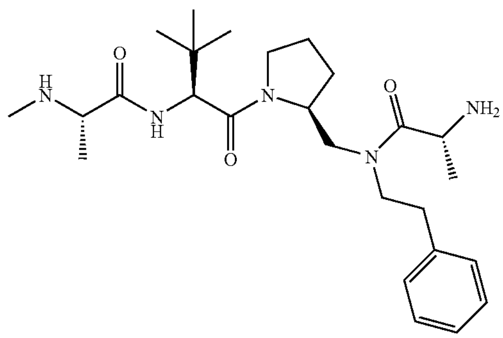 [SMILES: CN[C@@H](C)C(=O)N[C@H](C(=O)N1CCC[C@H]1CN(CCc1ccccc1)C(=O)[C@@H](C)N)C(C)(C)C] | 474.4 |
| 37 | 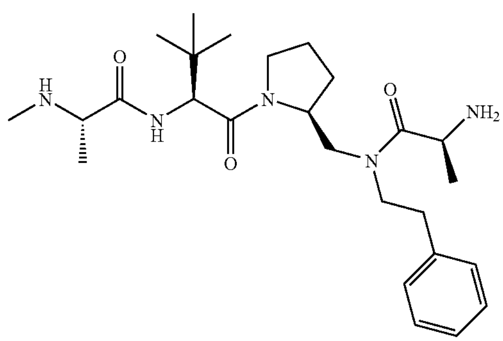 | 474.4 |
| 38 | 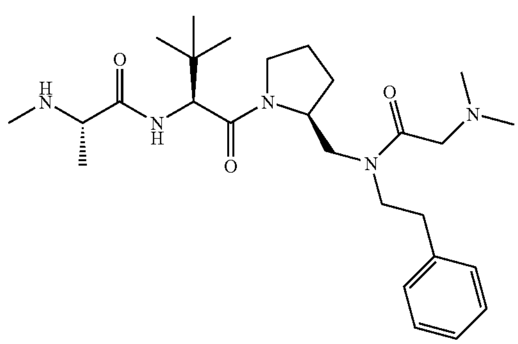 | 488.4 |

TABLE 1-continued
| Compound # | Structure | MS m/z (M + H) |
|---|---|---|
| 39 | 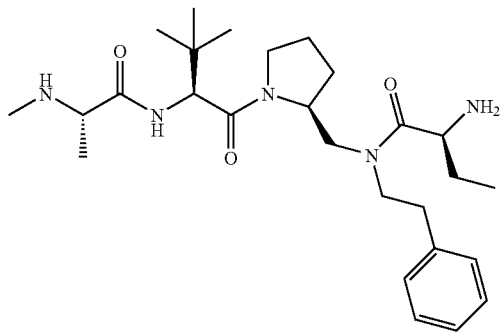 [SMILES: CC[C@H](N)C(=O)N(CCc1ccccc1)C[C@@H]1CCCN1C(=O)[C@@H](NC(=O)[C@H](C)NC)C(C)(C)C] | 488.4 |
| 40 | 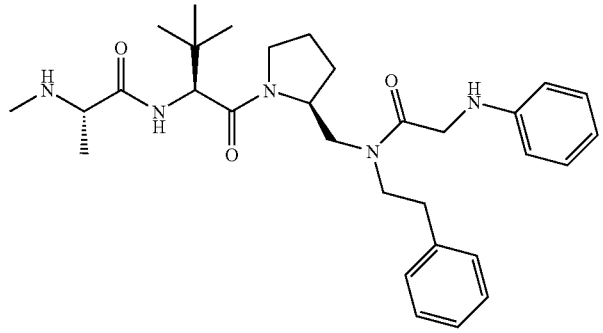 [SMILES: CN[C@@H](C)C(=O)N[C@H](C(=O)N1CCC[C@H]1CN(CCc1ccccc1)C(=O)CNc1ccccc1)C(C)(C)C] | 536.4 |
| 41 | 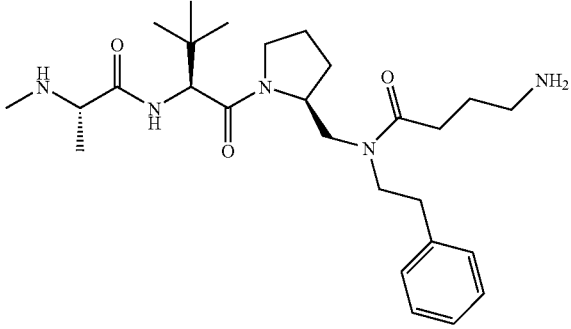 [SMILES: CN[C@@H](C)C(=O)N[C@H](C(=O)N1CCC[C@H]1CN(CCc1ccccc1)C(=O)CCCN)C(C)(C)C] | 488.4 |
| 42 | 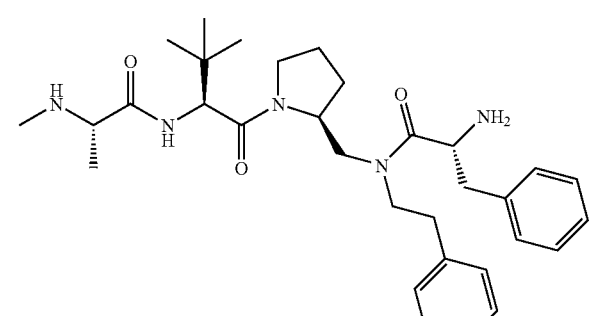 | 550.4 |

TABLE 1-continued

| Compound # | Structure | MS m/z (M + H) |
|---|---|---|
| 43 | 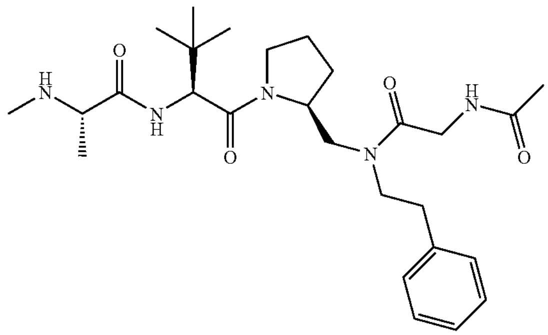 [SMILES: CN[C@@H](C)C(=O)N[C@H](C(=O)N1CCC[C@H]1CN(CCc1ccccc1)C(=O)CNC(C)=O)C(C)(C)C] | 502.4 |
| 44 | 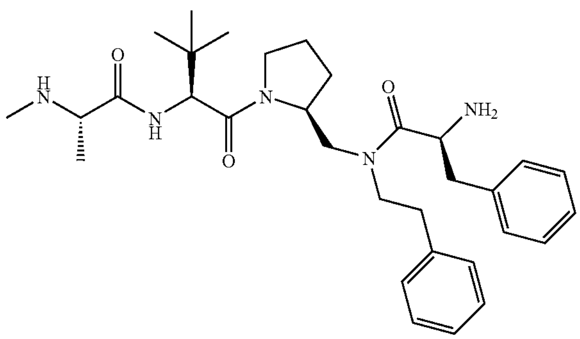 [SMILES: CN[C@@H](C)C(=O)N[C@H](C(=O)N1CCC[C@H]1CN(CCc1ccccc1)C(=O)[C@@H](N)Cc1ccccc1)C(C)(C)C] | 550.4 |
| 45 | 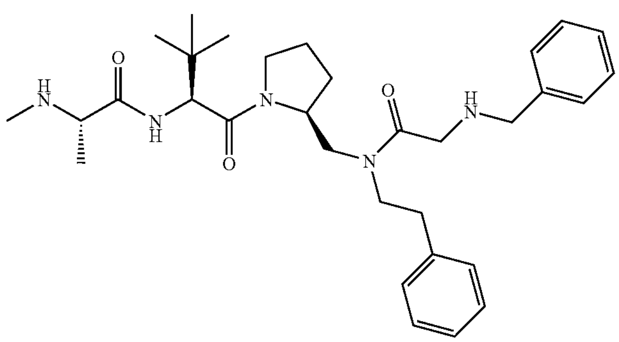 [SMILES: CN[C@@H](C)C(=O)N[C@H](C(=O)N1CCC[C@H]1CN(CCc1ccccc1)C(=O)CNCc1ccccc1)C(C)(C)C] | 550.4 |
| 46 | 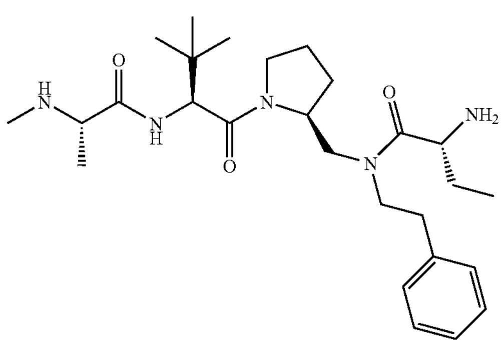 [SMILES: CC[C@@H](N)C(=O)N(CCc1ccccc1)C[C@@H]1CCCN1C(=O)[C@@H](NC(=O)[C@H](C)NC)C(C)(C)C] | 488.4 |

TABLE 1-continued

| Compound # | Structure | MS m/z (M + H) |
|---|---|---|
| 47 | 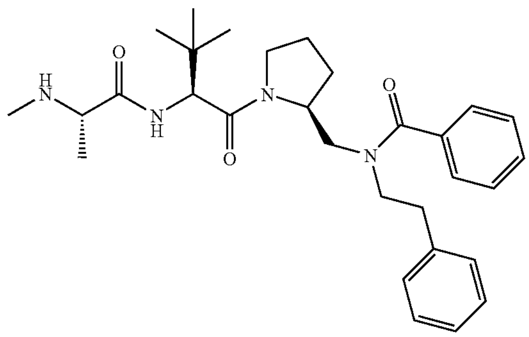 [SMILES: CN[C@@H](C)C(=O)N[C@H](C(=O)N1CCC[C@H]1CN(CCc1ccccc1)C(=O)c1ccccc1)C(C)(C)C] | 507.3 |
| 48 | 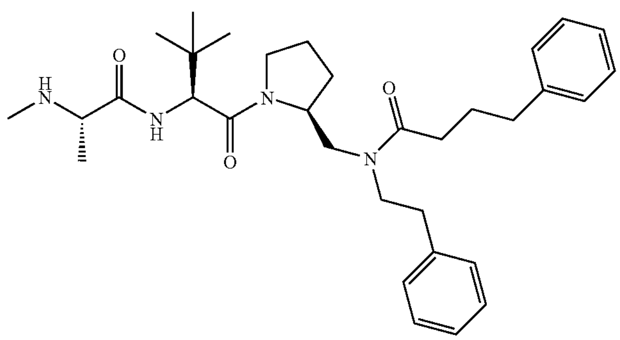 [SMILES: CN[C@@H](C)C(=O)N[C@H](C(=O)N1CCC[C@H]1CN(CCc1ccccc1)C(=O)CCCc1ccccc1)C(C)(C)C] | 549.4 |
| 49 | 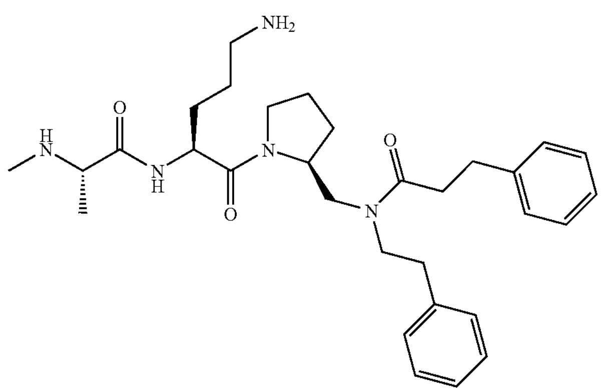 [SMILES: CN[C@@H](C)C(=O)N[C@@H](CCCN)C(=O)N1CCC[C@H]1CN(CCc1ccccc1)C(=O)CCc1ccccc1] | 536.4 |
| 50 | 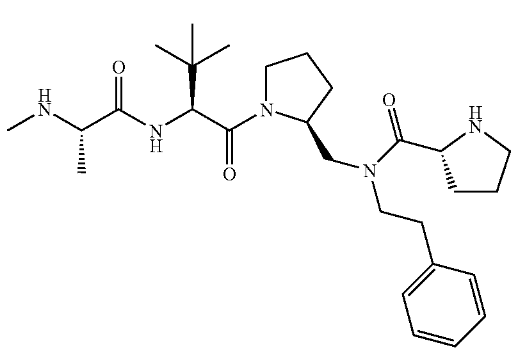 [SMILES: CN[C@@H](C)C(=O)N[C@H](C(=O)N1CCC[C@H]1CN(CCc1ccccc1)C(=O)[C@H]1CCCN1)C(C)(C)C] | 500.4 |

TABLE 1-continued

| Compound # | Structure | MS m/z (M + H) |
|---|---|---|
| 51 | 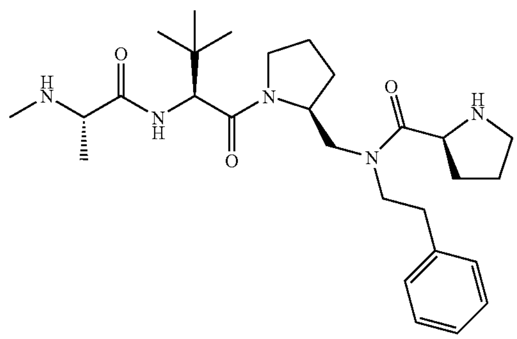 [SMILES: CN[C@@H](C)C(=O)N[C@H](C(=O)N1CCC[C@H]1CN(CCc1ccccc1)C(=O)[C@@H]1CCCN1)C(C)(C)C] | 500.4 |
| 52 | 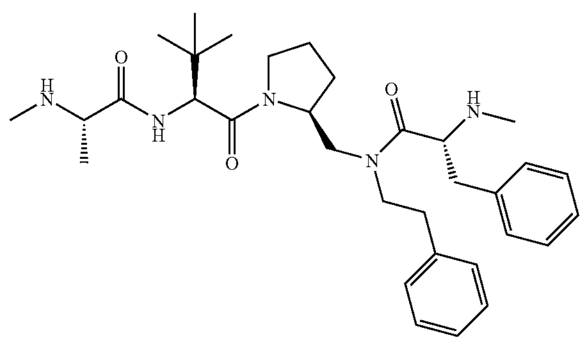 | 564.4 |
| 53 | 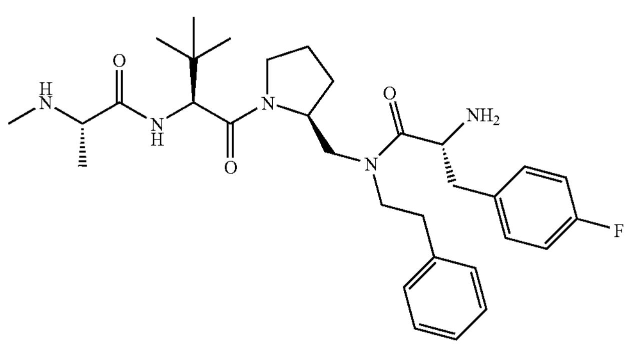 [SMILES: CN[C@@H](C)C(=O)N[C@H](C(=O)N1CCC[C@H]1CN(CCc1ccccc1)C(=O)[C@H](N)Cc1ccc(F)cc1)C(C)(C)C] | 568.4 |
| 54 | 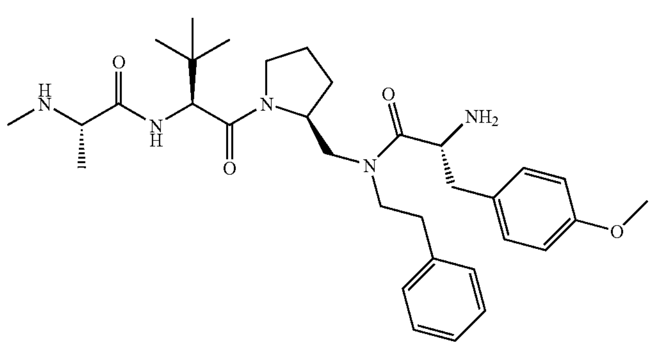 | 580.4 |

TABLE 1-continued

| Compound # | Structure | MS m/z (M + H) |
|---|---|---|
| 55 | 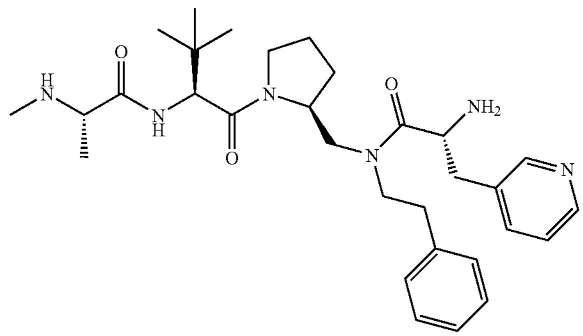 | 551.4 |
| 56 | 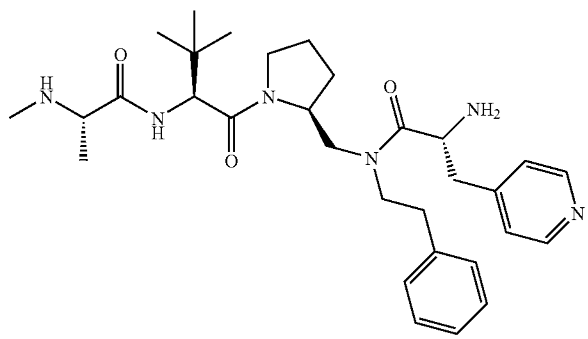 [SMILES: CN[C@@H](C)C(=O)N[C@H](C(=O)N1CCC[C@H]1CN(CCc1ccccc1)C(=O)[C@H](N)Cc1ccncc1)C(C)(C)C] | 551.4 |
| 57 | 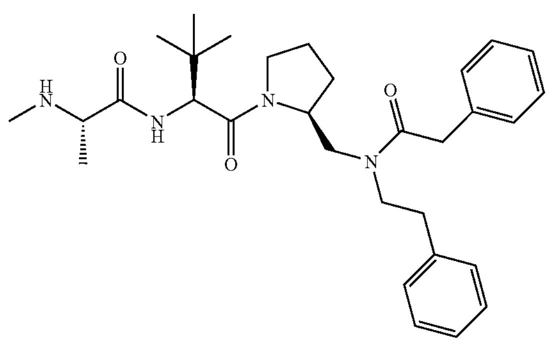 [SMILES: CN[C@@H](C)C(=O)N[C@H](C(=O)N1CCC[C@H]1CN(CCc1ccccc1)C(=O)Cc1ccccc1)C(C)(C)C] | 521.3 |
| 58 | 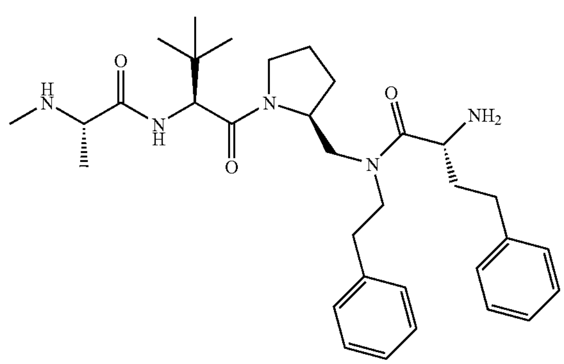 [SMILES: CN[C@@H](C)C(=O)N[C@H](C(=O)N1CCC[C@H]1CN(CCc1ccccc1)C(=O)[C@H](N)CCc1ccccc1)C(C)(C)C] | 564.4 |

TABLE 1-continued

| Compound # | Structure | MS m/z (M + H) |
|---|---|---|
| 59 | 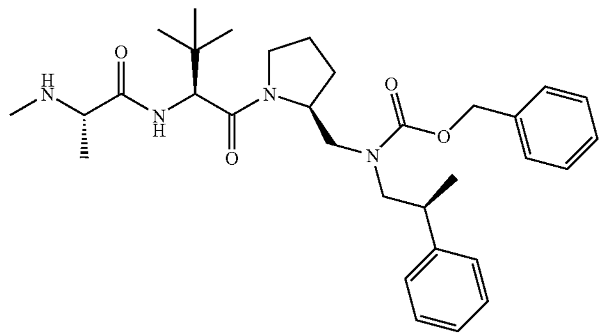 [SMILES: CN[C@@H](C)C(=O)N[C@H](C(=O)N1CCC[C@H]1CN(C[C@@H](C)c1ccccc1)C(=O)OCc1ccccc1)C(C)(C)C] | 551.3 |
| 60 | 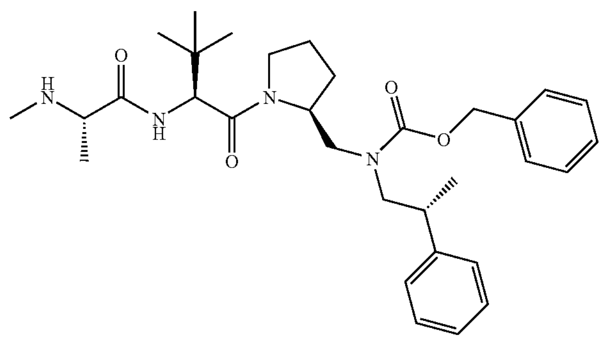 [SMILES: CN[C@@H](C)C(=O)N[C@H](C(=O)N1CCC[C@H]1CN(C[C@H](C)c1ccccc1)C(=O)OCc1ccccc1)C(C)(C)C] | 551.3 |
| 61 | 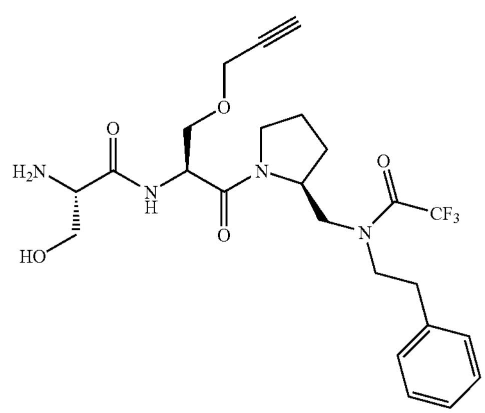 [SMILES: C#CCOC[C@H](NC(=O)[C@@H](N)CO)C(=O)N1CCC[C@H]1CN(CCc1ccccc1)C(=O)C(F)(F)F] | 513.2 |
| 62 | 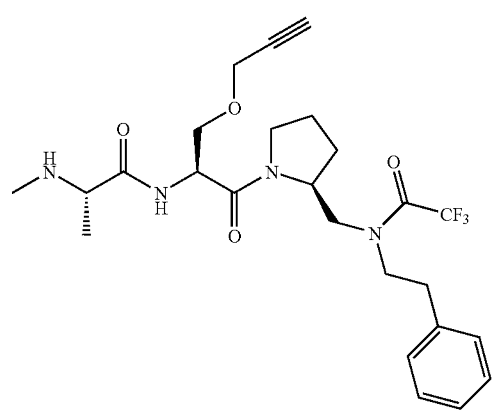 [SMILES: C#CCOC[C@H](NC(=O)[C@H](C)NC)C(=O)N1CCC[C@H]1CN(CCc1ccccc1)C(=O)C(F)(F)F] | 511.2 |

TABLE 1-continued

| Compound # | Structure | MS m/z (M + H) |
|---|---|---|
| 63 | 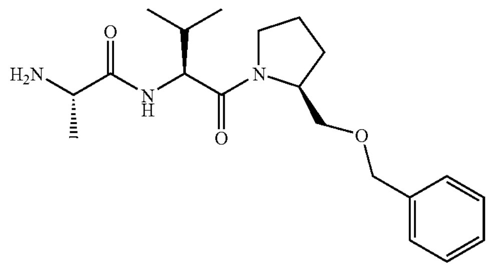 [SMILES: CC(C)[C@H](NC(=O)[C@H](C)N)C(=O)N1CCC[C@H]1COCc1ccccc1] | 362 |
| 64 | 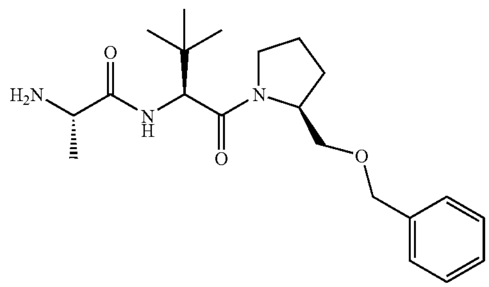 [SMILES: C[C@H](N)C(=O)N[C@H](C(=O)N1CCC[C@H]1COCc1ccccc1)C(C)(C)C] | 376 |
| 65 | 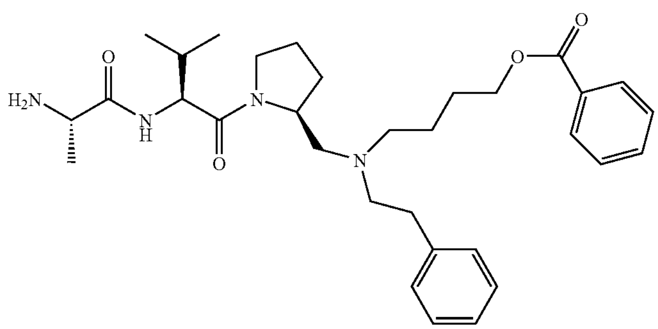 [SMILES: CC(C)[C@H](NC(=O)[C@H](C)N)C(=O)N1CCC[C@H]1CN(CCCCOC(=O)c1ccccc1)CCc1ccccc1] | 551.4 |
| 66 | 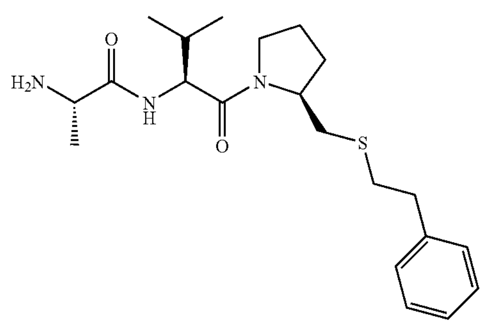 [SMILES: CC(C)[C@H](NC(=O)[C@H](C)N)C(=O)N1CCC[C@H]1CSCCc1ccccc1] | 392.3 |
| 67 | 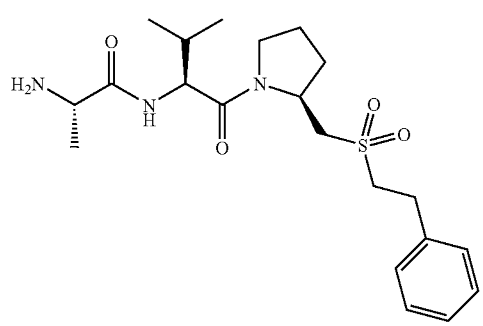 [SMILES: CC(C)[C@H](NC(=O)[C@H](C)N)C(=O)N1CCC[C@H]1CS(=O)(=O)CCc1ccccc1] | 424.2 |

TABLE 1-continued

| Compound # | Structure | MS m/z (M + H) |
|---|---|---|
| 68 | 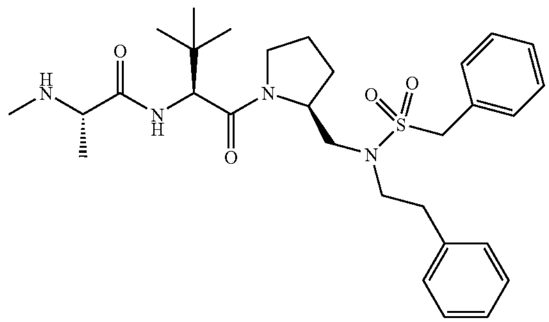 [SMILES: CN[C@@H](C)C(=O)N[C@H](C(=O)N1CCC[C@H]1CN(CCc1ccccc1)S(=O)(=O)Cc1ccccc1)C(C)(C)C] | 557.3 |
| 69 | 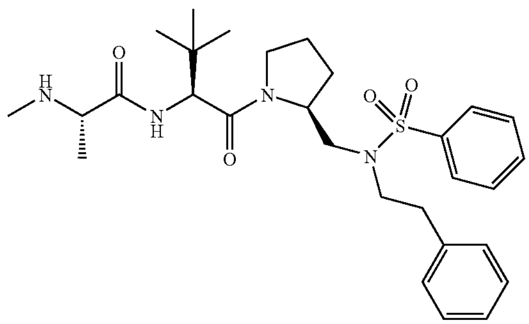 [SMILES: CN[C@@H](C)C(=O)N[C@H](C(=O)N1CCC[C@H]1CN(CCc1ccccc1)S(=O)(=O)c1ccccc1)C(C)(C)C] | 543.3 |
| 70 | 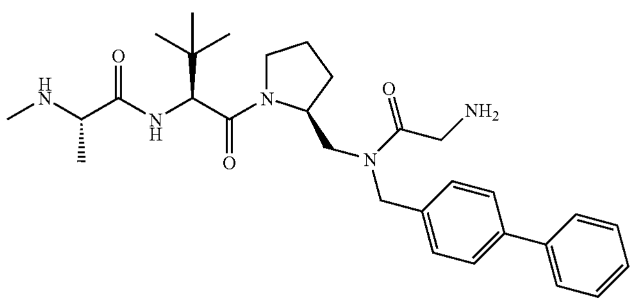 [SMILES: CN[C@@H](C)C(=O)N[C@H](C(=O)N1CCC[C@H]1CN(Cc1ccc(-c2ccccc2)cc1)C(=O)CN)C(C)(C)C] | 522.6 |
| 71 | 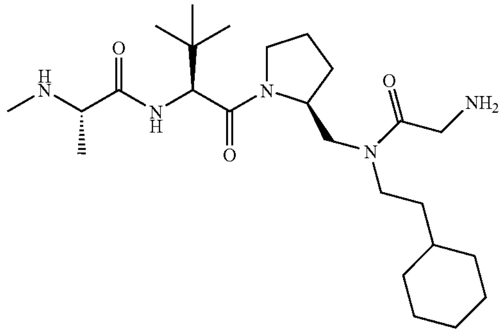 | 466.6 |

TABLE 1-continued

| Compound # | Structure | MS m/z (M + H) |
|---|---|---|
| 72 | 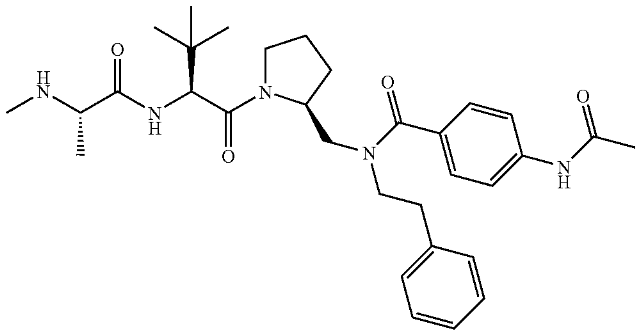 [SMILES: CN[C@@H](C)C(=O)N[C@H](C(=O)N1CCC[C@H]1CN(CCc1ccccc1)C(=O)c1ccc(NC(C)=O)cc1)C(C)(C)C] | 564.6 |
| 73 | 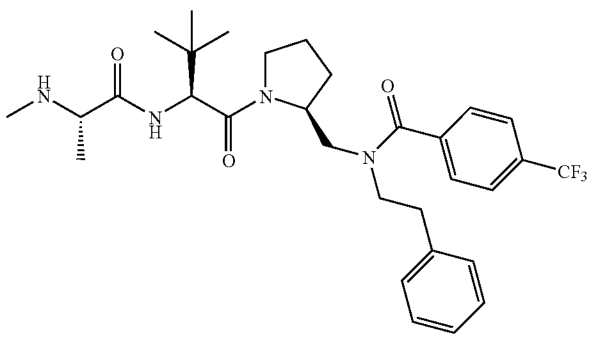 [SMILES: CN[C@@H](C)C(=O)N[C@H](C(=O)N1CCC[C@H]1CN(CCc1ccccc1)C(=O)c1ccc(C(F)(F)F)cc1)C(C)(C)C] | 575.6 |
| 74 | 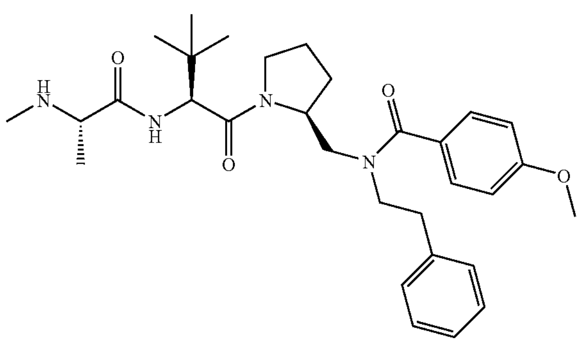 | 537.3 |
| 75 | 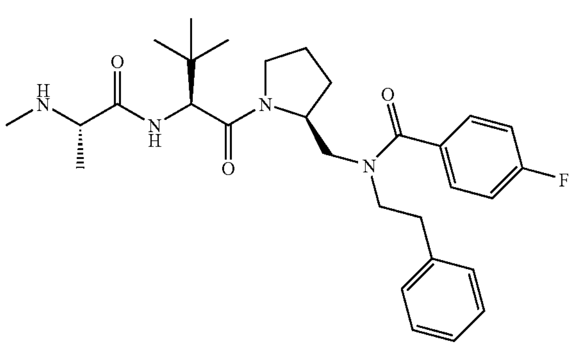 [SMILES: CN[C@@H](C)C(=O)N[C@H](C(=O)N1CCC[C@H]1CN(CCc1ccccc1)C(=O)c1ccc(F)cc1)C(C)(C)C] | 525.3 |

TABLE 1-continued
| Compound # | Structure | MS m/z (M + H) |
|---|---|---|
| 76 | 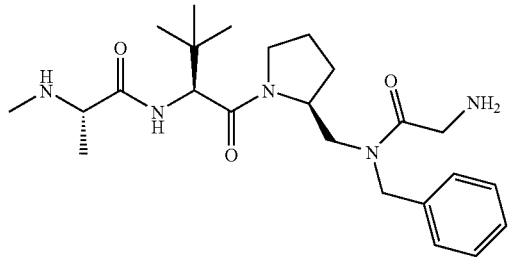 [SMILES: CN[C@@H](C)C(=O)N[C@H](C(=O)N1CCC[C@H]1CN(Cc1ccccc1)C(=O)CN)C(C)(C)C] | 446.5 |
| 77 | 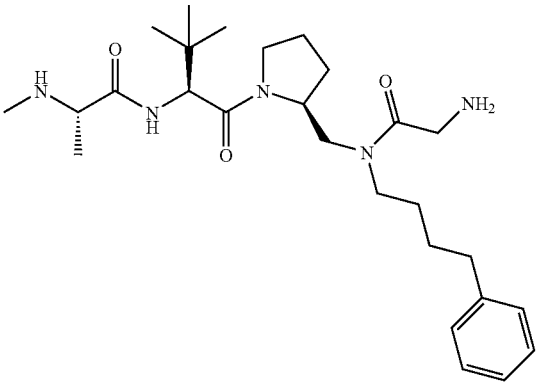 [SMILES: CN[C@@H](C)C(=O)N[C@H](C(=O)N1CCC[C@H]1CN(CCCCc1ccccc1)C(=O)CN)C(C)(C)C] | 488.6 |
| 78 | 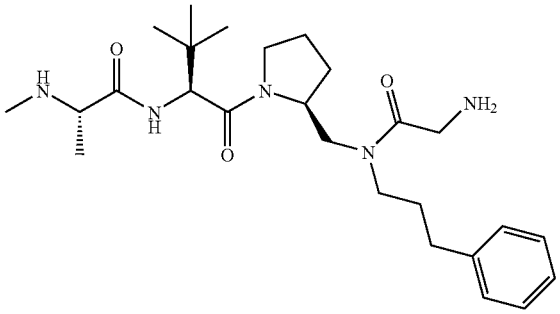 [SMILES: CN[C@@H](C)C(=O)N[C@H](C(=O)N1CCC[C@H]1CN(CCCc1ccccc1)C(=O)CN)C(C)(C)C] | 474.3 |
| 79 | 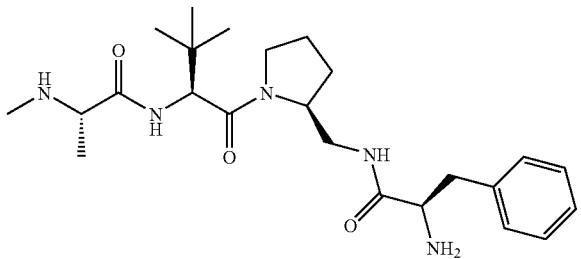 [SMILES: CN[C@@H](C)C(=O)N[C@H](C(=O)N1CCC[C@H]1CNC(=O)[C@H](N)Cc1ccccc1)C(C)(C)C] | 446.3 |

TABLE 1-continued
| Compound # | Structure | MS m/z (M + H) |
|---|---|---|
| 80 | 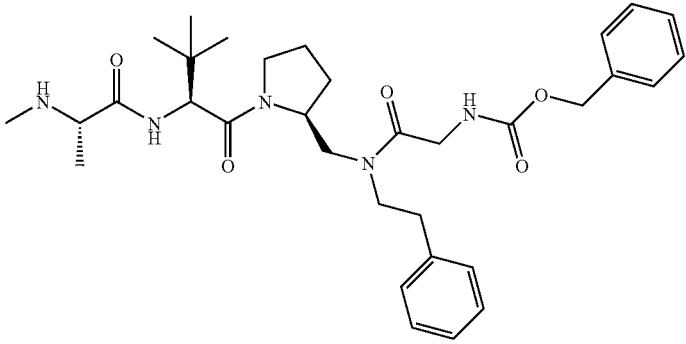 [SMILES: CN[C@@H](C)C(=O)N[C@H](C(=O)N1CCC[C@H]1CN(CCc1ccccc1)C(=O)CNC(=O)OCc1ccccc1)C(C)(C)C] | 594.4 |
| 81 | 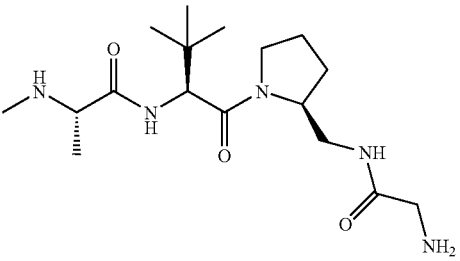 [SMILES: CN[C@@H](C)C(=O)N[C@H](C(=O)N1CCC[C@H]1CNC(=O)CN)C(C)(C)C] | 356.3 |
| 82 | 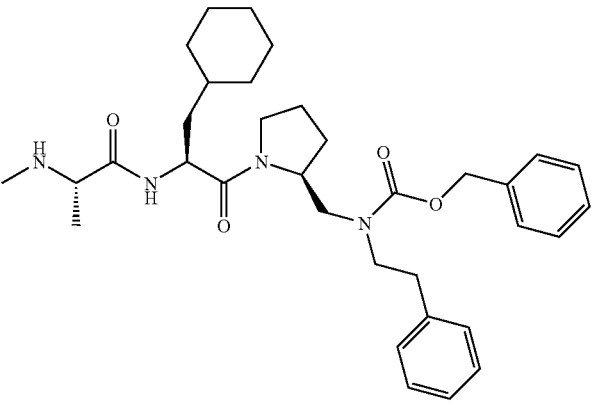 [SMILES: CN[C@@H](C)C(=O)N[C@@H](CC1CCCCC1)C(=O)N1CCC[C@H]1CN(CCc1ccccc1)C(=O)OCc1ccccc1] | 577.4 |
| 83 | 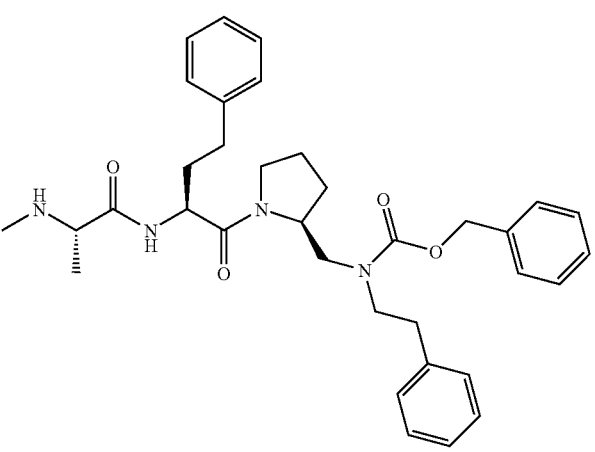 [SMILES: CN[C@@H](C)C(=O)N[C@@H](CCc1ccccc1)C(=O)N1CCC[C@H]1CN(CCc1ccccc1)C(=O)OCc1ccccc1] | 585.4 |

TABLE 1-continued

| Compound # | Structure | MS m/z (M + H) |
|---|---|---|
| 84 | 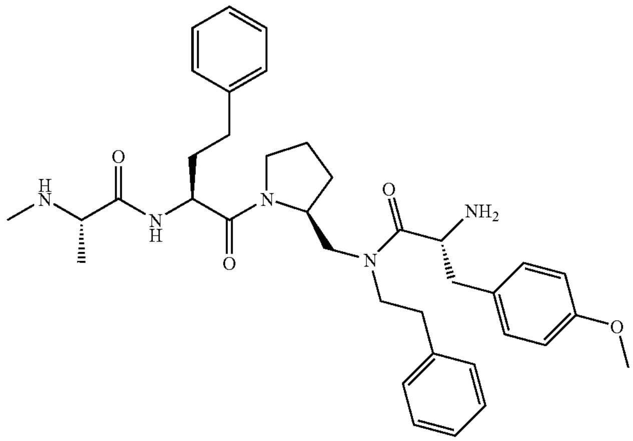 | 628.4 |
| 85 | 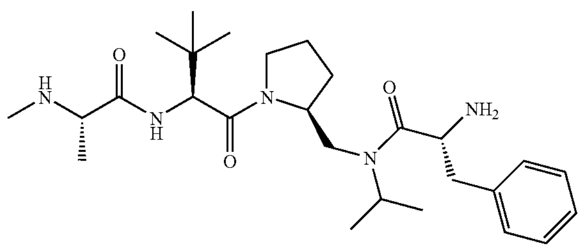 [SMILES: CN[C@@H](C)C(=O)N[C@H](C(=O)N1CCC[C@H]1CN(C(=O)[C@H](N)Cc1ccccc1)C(C)C)C(C)(C)C] | 488.4 |
| 86 | 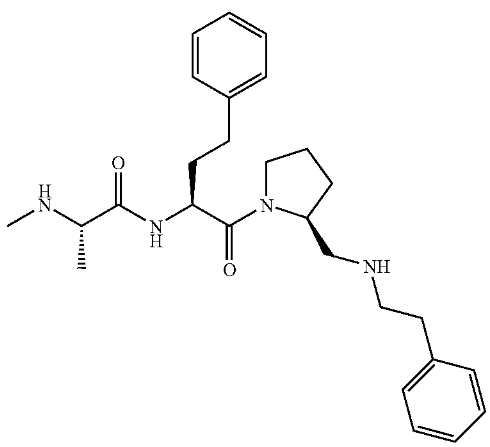 [SMILES: CN[C@@H](C)C(=O)N[C@@H](CCc1ccccc1)C(=O)N1CCC[C@H]1CNCCc1ccccc1] | 451.3 |
| 87 | 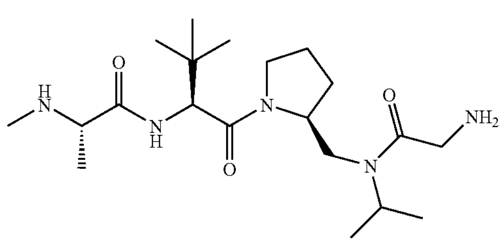 [SMILES: CN[C@@H](C)C(=O)N[C@H](C(=O)N1CCC[C@H]1CN(C(=O)CN)C(C)C)C(C)(C)C] | 398.3 |

TABLE 1-continued

| Compound # | Structure | MS m/z (M + H) |
|---|---|---|
| 88 | 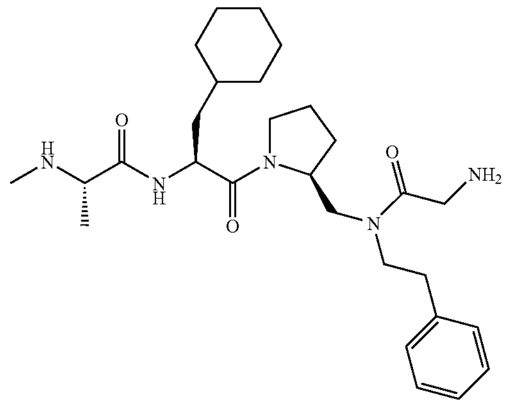 [SMILES: CN[C@@H](C)C(=O)N[C@@H](CC1CCCCC1)C(=O)N1CCC[C@H]1CN(CCc1ccccc1)C(=O)CN] | 500.4 |
| 89 | 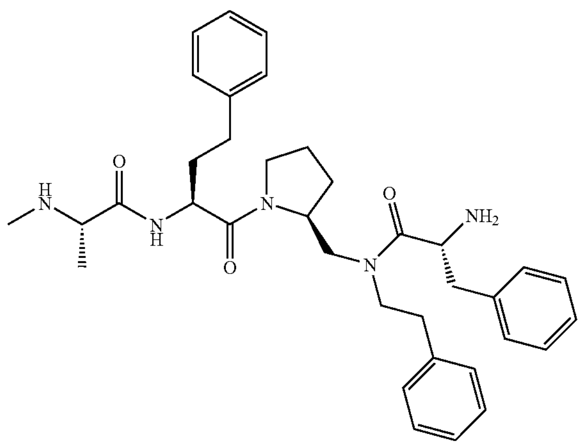 [SMILES: CN[C@@H](C)C(=O)N[C@@H](CCc1ccccc1)C(=O)N1CCC[C@H]1CN(CCc1ccccc1)C(=O)[C@H](N)Cc1ccccc1] | 598.4 |
| 90 | 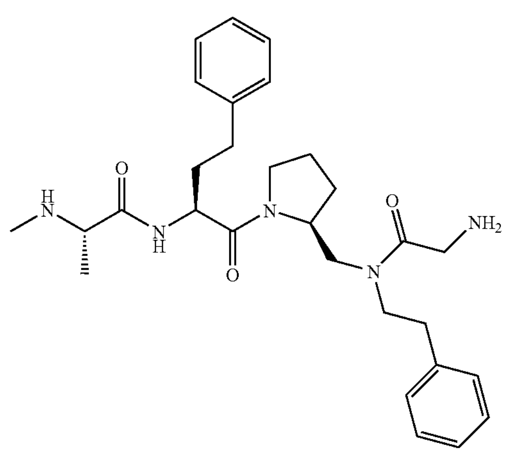 [SMILES: CN[C@@H](C)C(=O)N[C@@H](CCc1ccccc1)C(=O)N1CCC[C@H]1CN(CCc1ccccc1)C(=O)CN] | 508.4 |

TABLE 1-continued

| Compound # | Structure | MS m/z (M + H) |
|---|---|---|
| 91 | 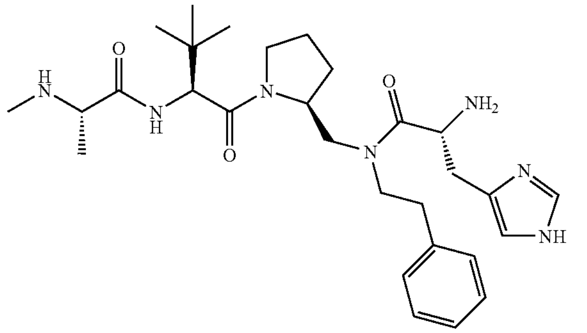 [SMILES: CN[C@@H](C)C(=O)N[C@H](C(=O)N1CCC[C@H]1CN(CCc1ccccc1)C(=O)[C@H](N)Cc1c[nH]cn1)C(C)(C)C] | 540.4 |
| 92 | 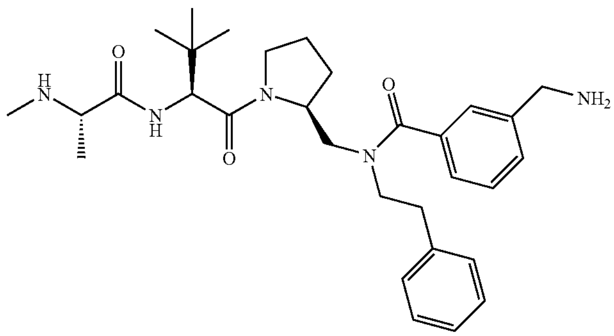 [SMILES: CN[C@@H](C)C(=O)N[C@H](C(=O)N1CCC[C@H]1CN(CCc1ccccc1)C(=O)c1cccc(CN)c1)C(C)(C)C] | 536.4 |
| 93 | 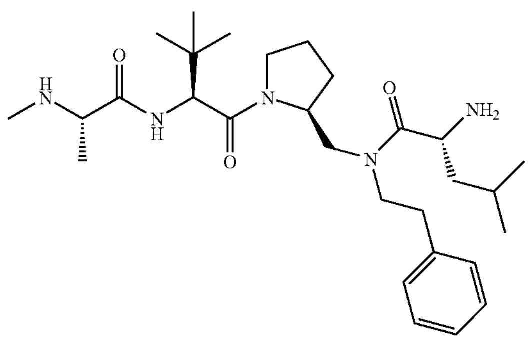 [SMILES: CN[C@@H](C)C(=O)N[C@H](C(=O)N1CCC[C@H]1CN(CCc1ccccc1)C(=O)[C@H](N)CC(C)C)C(C)(C)C] | 516.4 |
| 94 | 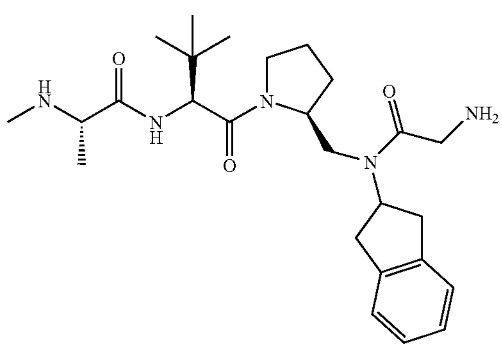 [SMILES: CN[C@@H](C)C(=O)N[C@H](C(=O)N1CCC[C@H]1CN(C(=O)CN)C1Cc2ccccc2C1)C(C)(C)C] | 472.3 |

TABLE 1-continued

| Compound # | Structure | MS m/z (M + H) |
|---|---|---|
| 95 | 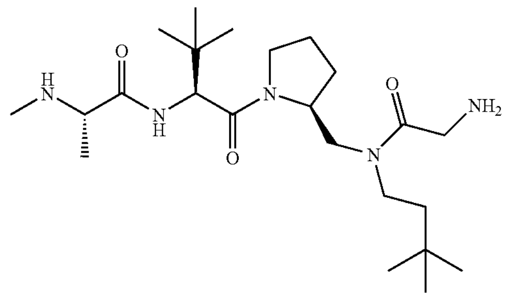 [SMILES: CN[C@@H](C)C(=O)N[C@H](C(=O)N1CCC[C@H]1CN(CCC(C)(C)C)C(=O)CN)C(C)(C)C] | 440.4 |
| 96 | 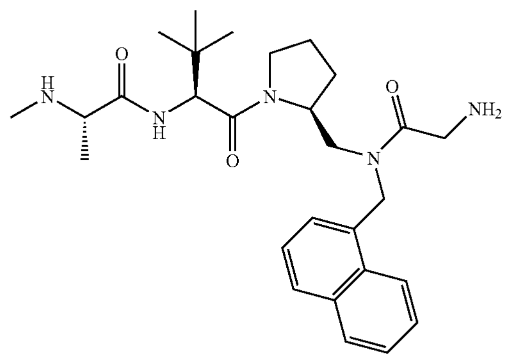 [SMILES: CN[C@@H](C)C(=O)N[C@H](C(=O)N1CCC[C@H]1CN(Cc1cccc2ccccc12)C(=O)CN)C(C)(C)C] | 496.3 |
| 97 | 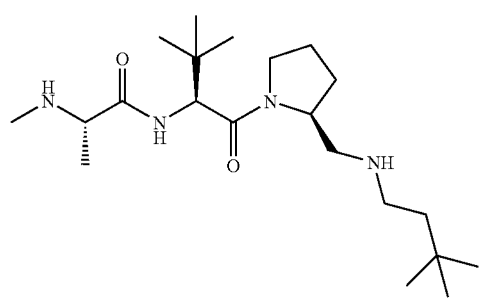 [SMILES: CN[C@@H](C)C(=O)N[C@H](C(=O)N1CCC[C@H]1CNCCC(C)(C)C)C(C)(C)C] | 383.3 |
| 98 | 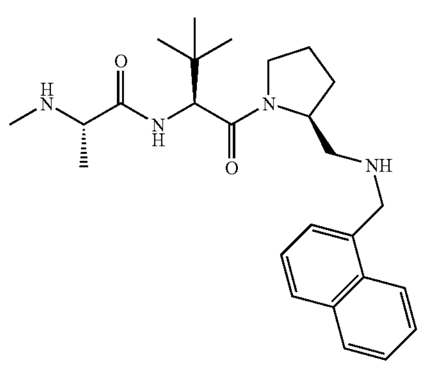 [SMILES: CN[C@@H](C)C(=O)N[C@H](C(=O)N1CCC[C@H]1CNCc1cccc2ccccc12)C(C)(C)C] | 439.3 |

TABLE 1-continued

| Compound # | Structure | MS m/z (M + H) |
|---|---|---|
| 99 | 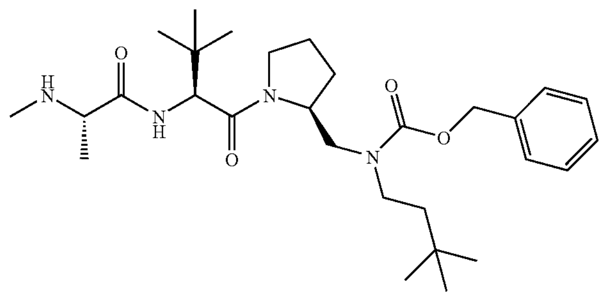 [SMILES: CN[C@@H](C)C(=O)N[C@H](C(=O)N1CCC[C@H]1CN(CCC(C)(C)C)C(=O)OCc1ccccc1)C(C)(C)C] | 517.4 |
| 100 | 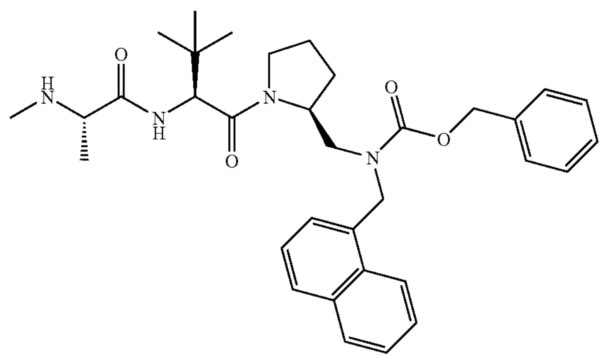 [SMILES: CN[C@@H](C)C(=O)N[C@H](C(=O)N1CCC[C@H]1CN(Cc1cccc2ccccc12)C(=O)OCc1ccccc1)C(C)(C)C] | 573.4 |
| 101 | 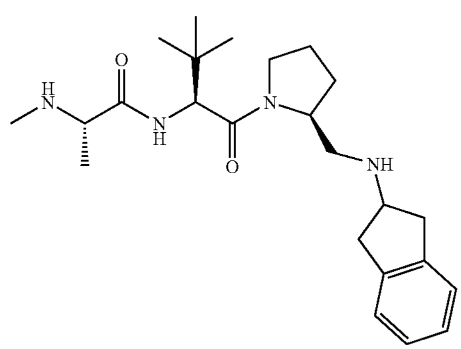 [SMILES: CN[C@@H](C)C(=O)N[C@H](C(=O)N1CCC[C@H]1CNC1Cc2ccccc2C1)C(C)(C)C] | 415.3 |
| 102 | 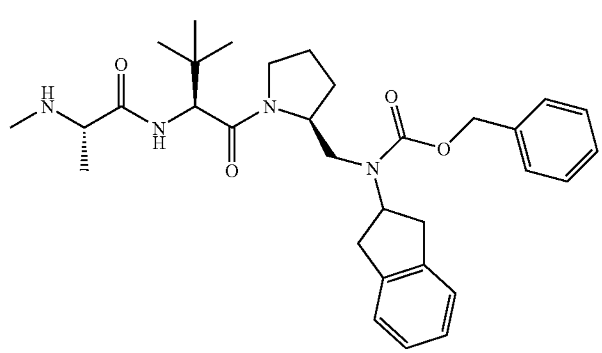 [SMILES: CN[C@@H](C)C(=O)N[C@H](C(=O)N1CCC[C@H]1CN(C(=O)OCc1ccccc1)C1Cc2ccccc2C1)C(C)(C)C] | 549.4 |

TABLE 1-continued

| Compound # | Structure | MS m/z (M + H) |
|---|---|---|
| 103 | 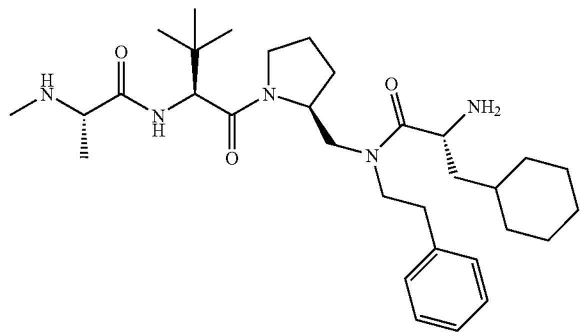 [SMILES: CN[C@@H](C)C(=O)N[C@H](C(=O)N1CCC[C@H]1CN(CCc1ccccc1)C(=O)[C@H](N)CC1CCCCC1)C(C)(C)C] | 556.4 |
| 104 | 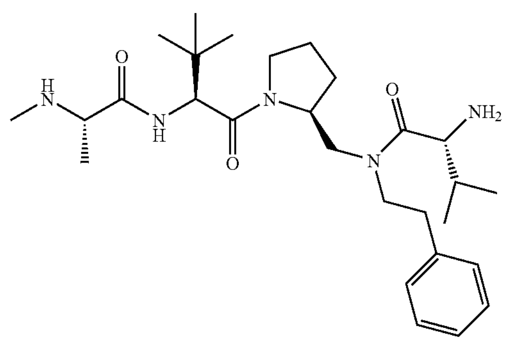 [SMILES: CN[C@@H](C)C(=O)N[C@H](C(=O)N1CCC[C@H]1CN(CCc1ccccc1)C(=O)[C@H](N)C(C)C)C(C)(C)C] | 502.5 |
| 105 | 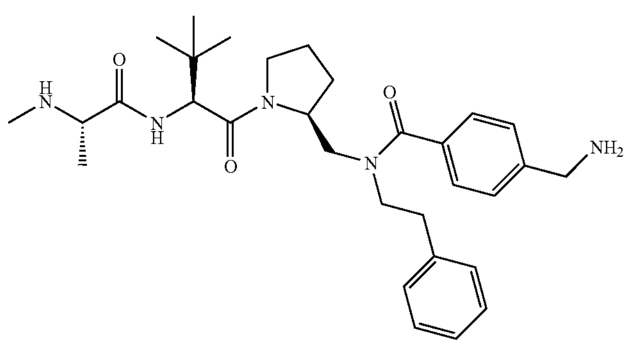 [SMILES: CN[C@@H](C)C(=O)N[C@H](C(=O)N1CCC[C@H]1CN(CCc1ccccc1)C(=O)c1ccc(CN)cc1)C(C)(C)C] | 536.4 |
| 106 | 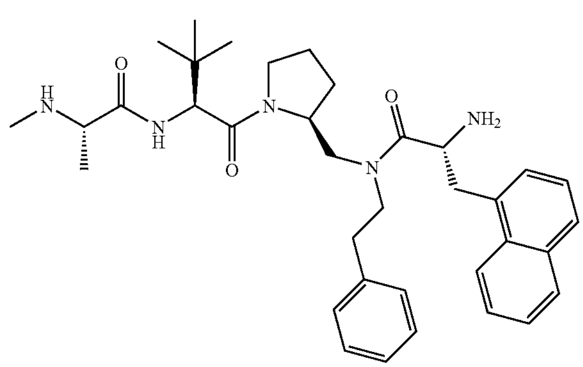 [SMILES: CN[C@@H](C)C(=O)N[C@H](C(=O)N1CCC[C@H]1CN(CCc1ccccc1)C(=O)[C@H](N)Cc1cccc2ccccc12)C(C)(C)C] | 600.4 |

TABLE 1-continued

| Compound # | Structure | MS m/z (M + H) |
|---|---|---|
| 107 | 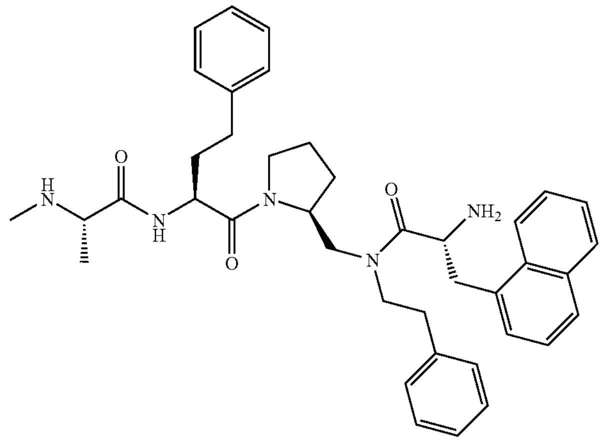 [SMILES: CN[C@@H](C)C(=O)N[C@@H](CCc1ccccc1)C(=O)N1CCC[C@H]1CN(CCc1ccccc1)C(=O)[C@H](N)Cc1cccc2ccccc12] | 648.4 |
| 108 | 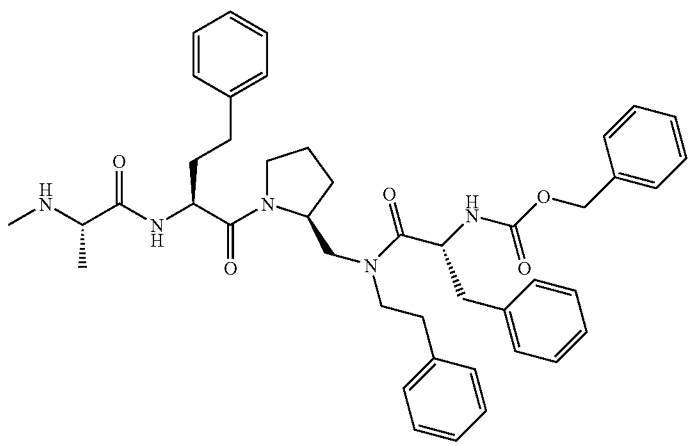 [SMILES: CN[C@@H](C)C(=O)N[C@@H](CCc1ccccc1)C(=O)N1CCC[C@H]1CN(CCc1ccccc1)C(=O)[C@@H](Cc1ccccc1)NC(=O)OCc1ccccc1] | 732.4 |
| 109 | 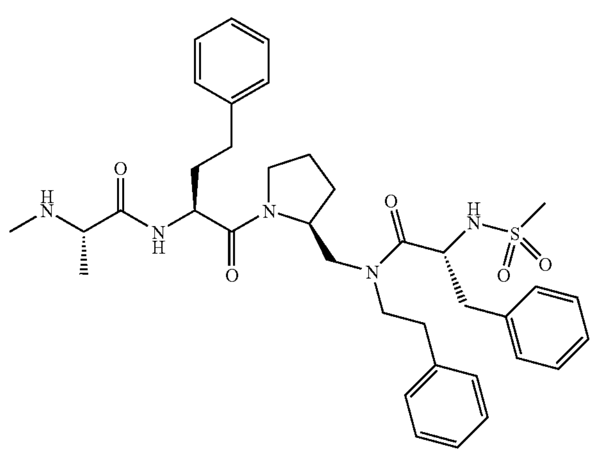 [SMILES: CN[C@@H](C)C(=O)N[C@@H](CCc1ccccc1)C(=O)N1CCC[C@H]1CN(CCc1ccccc1)C(=O)[C@@H](Cc1ccccc1)NS(C)(=O)=O] | 676.4 |

TABLE 1-continued

| Compound # | Structure | MS m/z (M + H) |
|---|---|---|
| 110 | 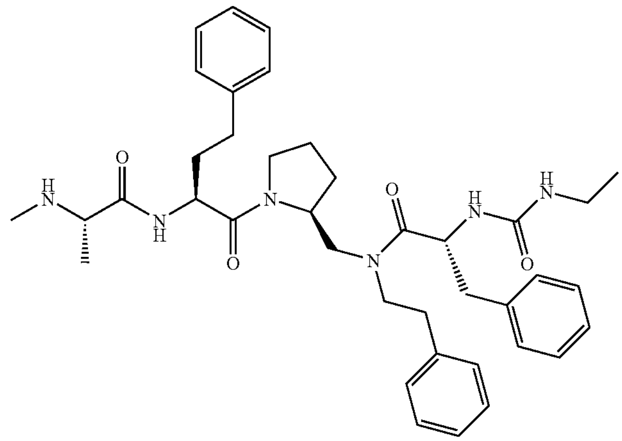 [SMILES: CCNC(=O)N[C@H](Cc1ccccc1)C(=O)N(CCc1ccccc1)C[C@@H]1CCCN1C(=O)[C@H](CCc1ccccc1)NC(=O)[C@H](C)NC] | 669.4 |
| 111 | 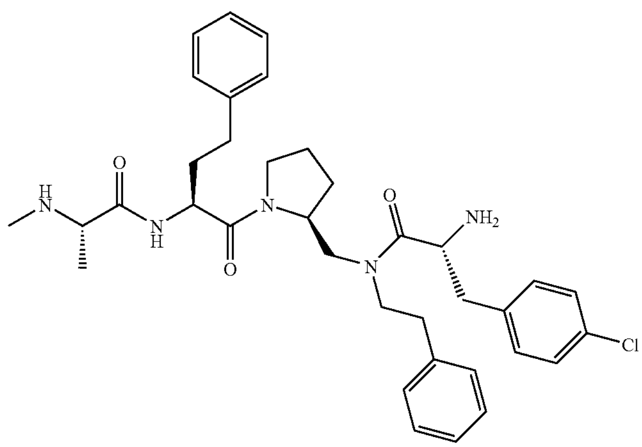 [SMILES: CN[C@@H](C)C(=O)N[C@@H](CCc1ccccc1)C(=O)N1CCC[C@H]1CN(CCc1ccccc1)C(=O)[C@H](N)Cc1ccc(Cl)cc1] | 632.4 |
| 112 | 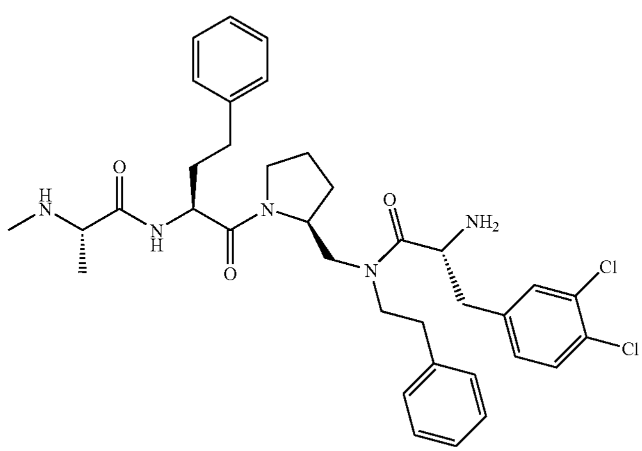 [SMILES: CN[C@@H](C)C(=O)N[C@@H](CCc1ccccc1)C(=O)N1CCC[C@H]1CN(CCc1ccccc1)C(=O)[C@H](N)Cc1ccc(Cl)c(Cl)c1] | 666.2 |

TABLE 1-continued

| Compound # | Structure | MS m/z (M + H) |
|---|---|---|
| 113 | 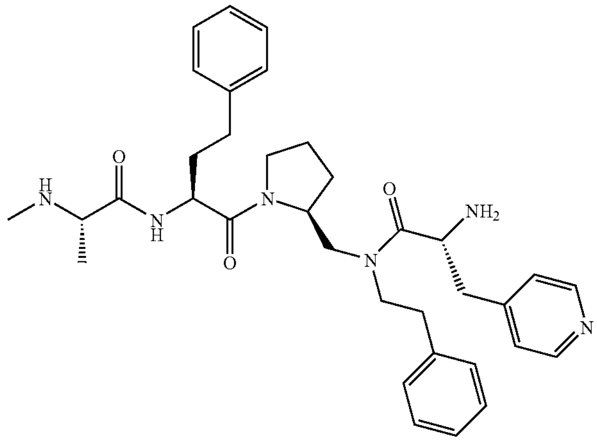 [SMILES: CN[C@@H](C)C(=O)N[C@@H](CCc1ccccc1)C(=O)N1CCC[C@H]1CN(CCc1ccccc1)C(=O)[C@H](N)Cc1ccncc1] | 599.4 |
| 114 | 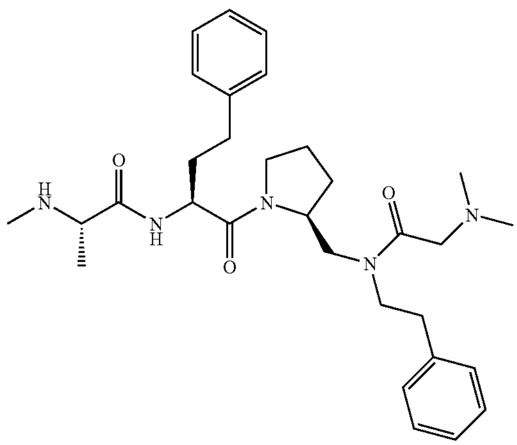 | 536.4 |
| 115 | 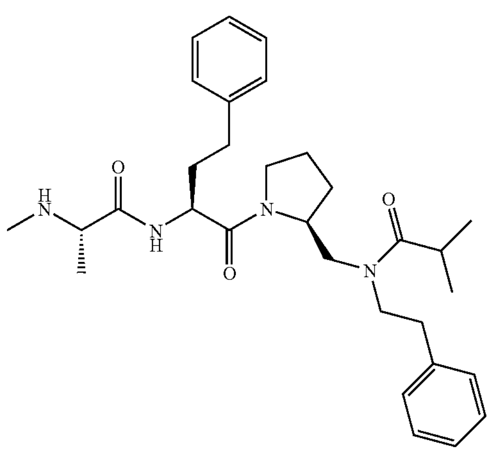 [SMILES: CN[C@@H](C)C(=O)N[C@@H](CCc1ccccc1)C(=O)N1CCC[C@H]1CN(CCc1ccccc1)C(=O)C(C)C] | 521.4 |

TABLE 1-continued

| Compound # | Structure | MS m/z (M + H) |
|---|---|---|
| 116 | 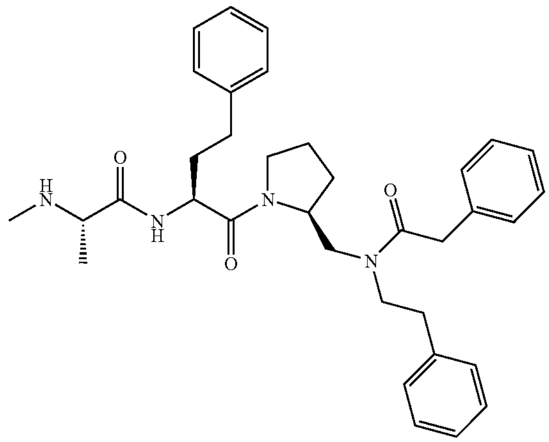 [SMILES: CN[C@@H](C)C(=O)N[C@@H](CCc1ccccc1)C(=O)N1CCC[C@H]1CN(CCc1ccccc1)C(=O)Cc1ccccc1] | 569.4 |
| 117 | 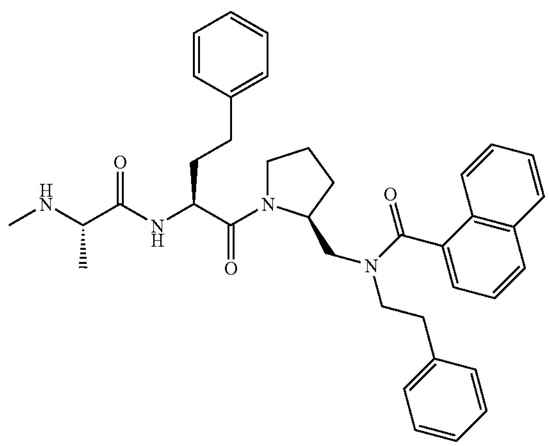 [SMILES: CN[C@@H](C)C(=O)N[C@@H](CCc1ccccc1)C(=O)N1CCC[C@H]1CN(CCc1ccccc1)C(=O)c1cccc2ccccc12] | 605.4 |
| 118 | 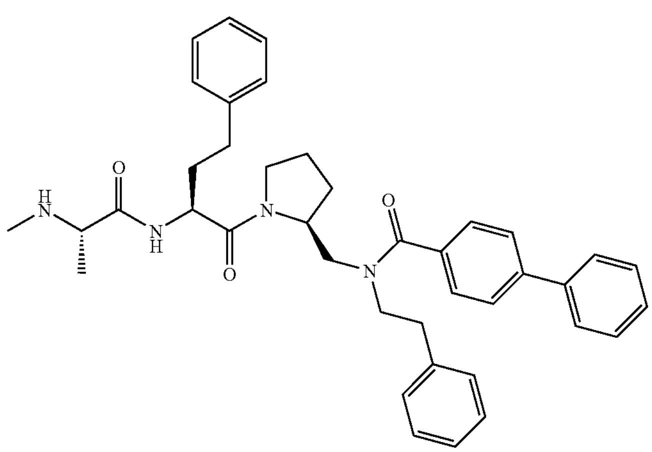 [SMILES: CN[C@@H](C)C(=O)N[C@@H](CCc1ccccc1)C(=O)N1CCC[C@H]1CN(CCc1ccccc1)C(=O)c1ccc(-c2ccccc2)cc1] | 631.4 |

US 8,575,113 B2
TABLE 1-continued
| Compound # | Structure | MS m/z (M + H) |
|---|---|---|
| 119 | 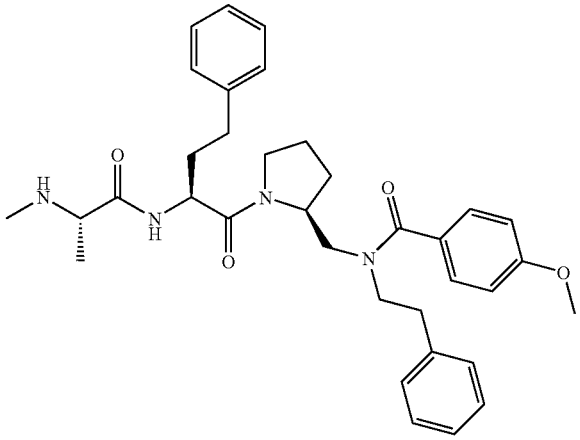 | 585.4 |
| 120 | 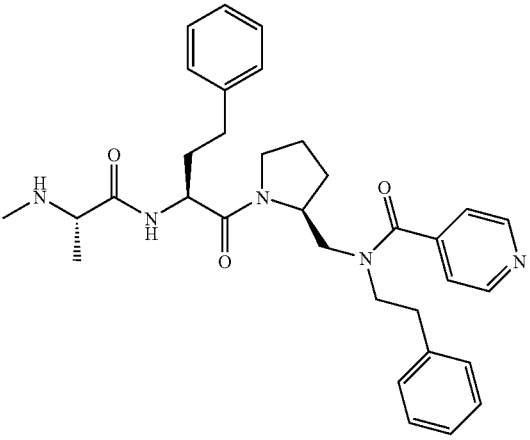 [SMILES: CN[C@@H](C)C(=O)N[C@@H](CCc1ccccc1)C(=O)N1CCC[C@H]1CN(CCc1ccccc1)C(=O)c1ccncc1] | 556.4 |
| 121 | 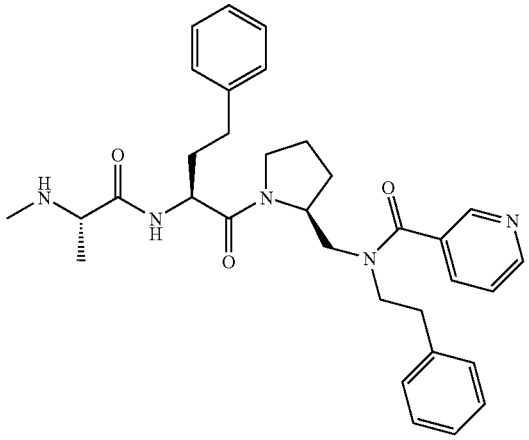 | 556.4 |

TABLE 1-continued

| Compound # | Structure | MS m/z (M + H) |
|---|---|---|
| 122 | 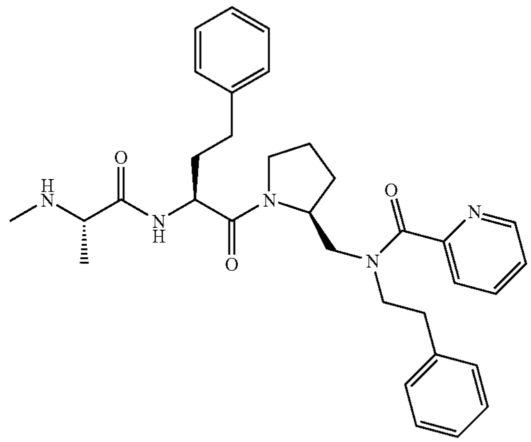 | 556.4 |
| 123 | 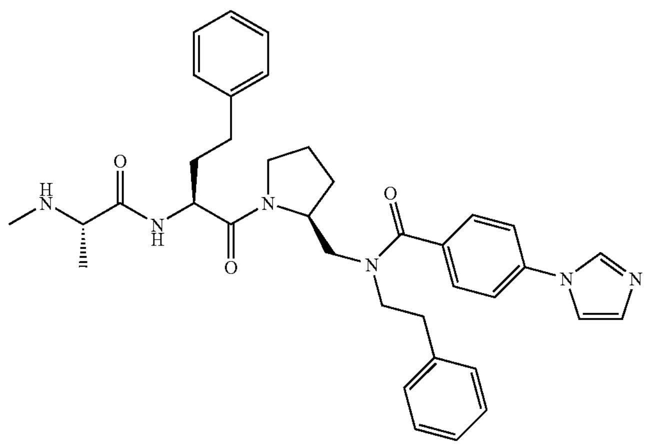 [SMILES: CN[C@@H](C)C(=O)N[C@@H](CCc1ccccc1)C(=O)N1CCC[C@H]1CN(CCc1ccccc1)C(=O)c1ccc(-n2ccnc2)cc1] | 621.4 |
| 124 | 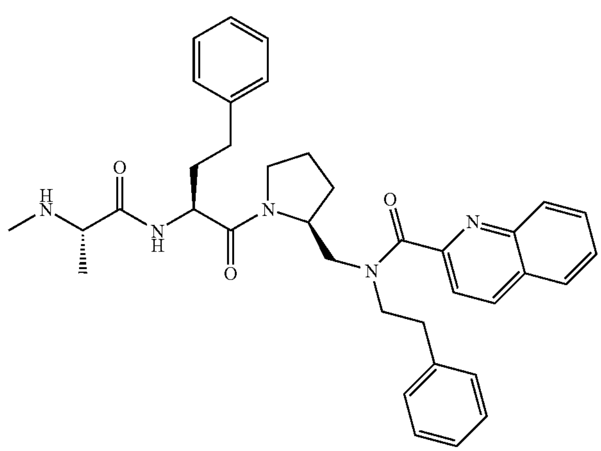 [SMILES: CN[C@@H](C)C(=O)N[C@@H](CCc1ccccc1)C(=O)N1CCC[C@H]1CN(CCc1ccccc1)C(=O)c1ccc2ccccc2n1] | 606.4 |

US 8,575,113 B2
TABLE 1-continued
| Compound # | Structure | MS m/z (M + H) |
|---|---|---|
| 125 | 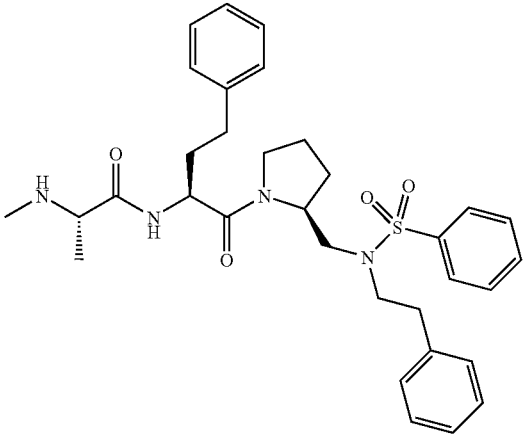 [SMILES: CN[C@@H](C)C(=O)N[C@@H](CCc1ccccc1)C(=O)N1CCC[C@H]1CN(CCc1ccccc1)S(=O)(=O)c1ccccc1] | 591.2 |
| 126 | 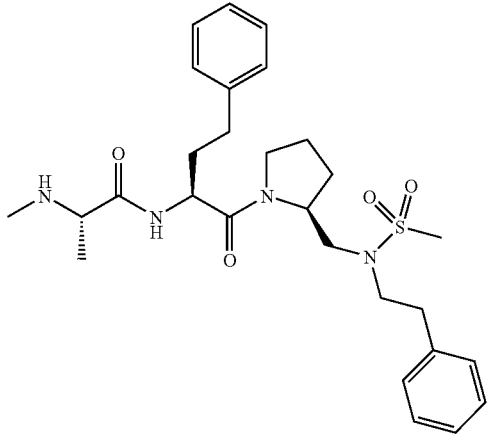 [SMILES: CN[C@@H](C)C(=O)N[C@@H](CCc1ccccc1)C(=O)N1CCC[C@H]1CN(CCc1ccccc1)S(C)(=O)=O] | 529.2 |
| 127 | 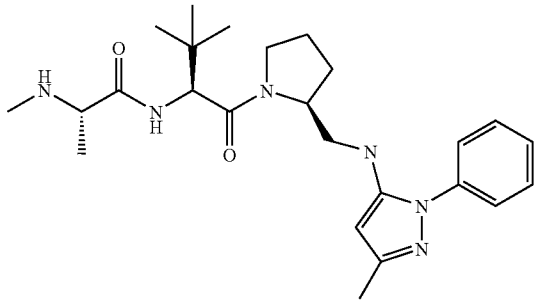 [SMILES: CN[C@@H](C)C(=O)N[C@H](C(=O)N1CCC[C@H]1CNc1cc(C)nn1-c1ccccc1)C(C)(C)C] | 455.4 |

TABLE 1-continued

| Compound # | Structure | MS m/z (M + H) |
|---|---|---|
| 128 | 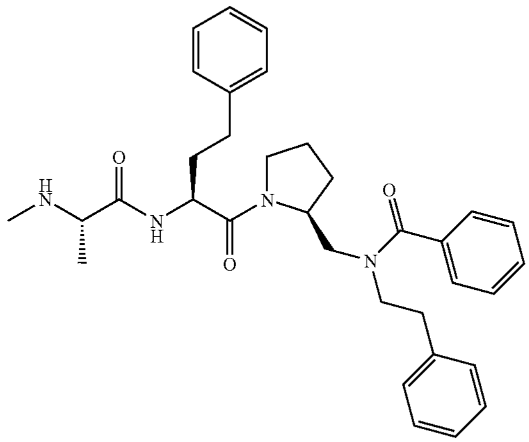 [SMILES: CN[C@@H](C)C(=O)N[C@@H](CCc1ccccc1)C(=O)N1CCC[C@H]1CN(CCc1ccccc1)C(=O)c1ccccc1] | 555.4 |
| 129 | 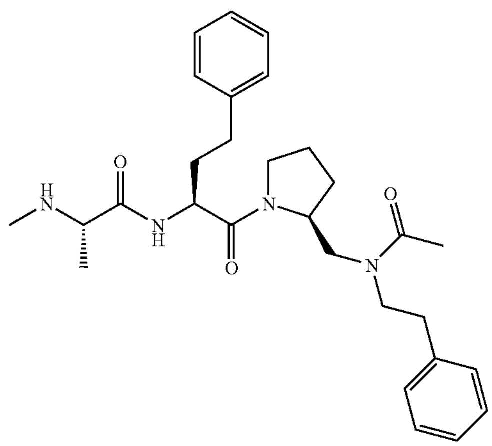 [SMILES: CN[C@@H](C)C(=O)N[C@@H](CCc1ccccc1)C(=O)N1CCC[C@H]1CN(CCc1ccccc1)C(C)=O] | 493.4 |
| 130 | 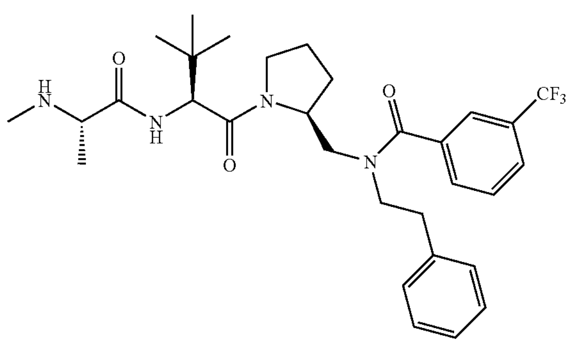 [SMILES: CN[C@@H](C)C(=O)N[C@H](C(=O)N1CCC[C@H]1CN(CCc1ccccc1)C(=O)c1cccc(C(F)(F)F)c1)C(C)(C)C] | 575.4 |
| 131 | 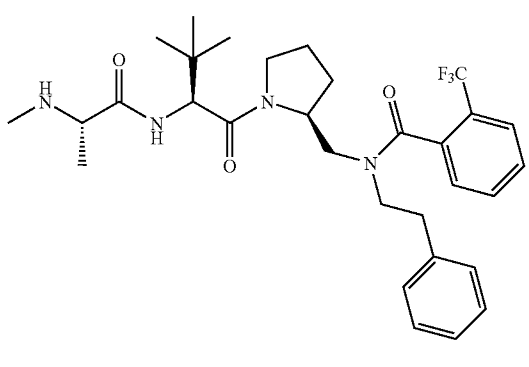 [SMILES: CN[C@@H](C)C(=O)N[C@H](C(=O)N1CCC[C@H]1CN(CCc1ccccc1)C(=O)c1ccccc1C(F)(F)F)C(C)(C)C] | 575.4 |

TABLE 1-continued

| Compound # | Structure | MS m/z (M + H) |
|---|---|---|
| 132 | 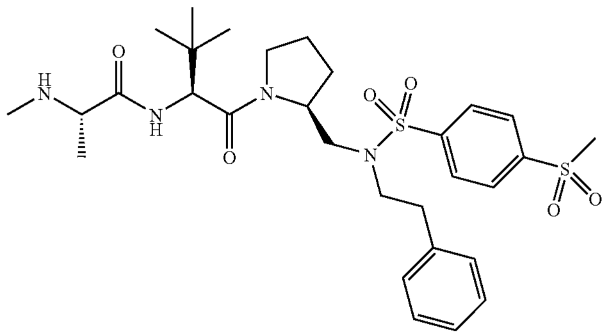 [SMILES: CN[C@@H](C)C(=O)N[C@H](C(=O)N1CCC[C@H]1CN(CCc1ccccc1)S(=O)(=O)c1ccc(S(C)(=O)=O)cc1)C(C)(C)C] | 621.4 |
| 133 | 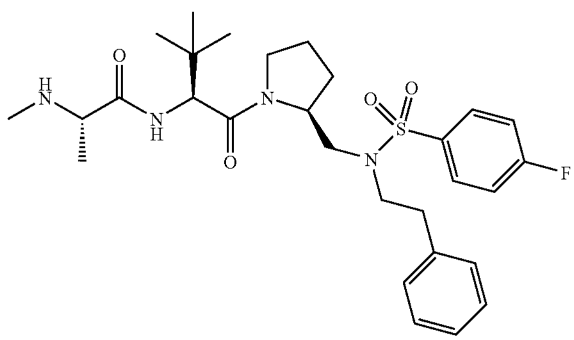 [SMILES: CN[C@@H](C)C(=O)N[C@H](C(=O)N1CCC[C@H]1CN(CCc1ccccc1)S(=O)(=O)c1ccc(F)cc1)C(C)(C)C] | 561.4 |
| 134 | 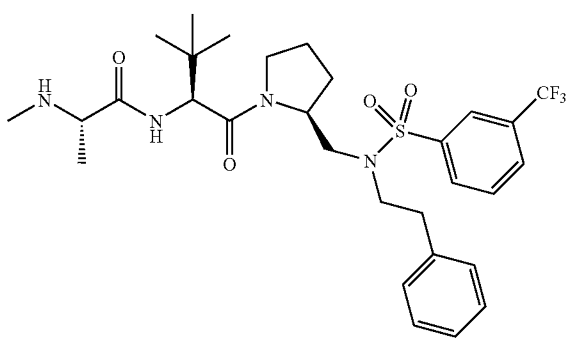 [SMILES: CN[C@@H](C)C(=O)N[C@H](C(=O)N1CCC[C@H]1CN(CCc1ccccc1)S(=O)(=O)c1cccc(C(F)(F)F)c1)C(C)(C)C] | 611.4 |
| 135 | 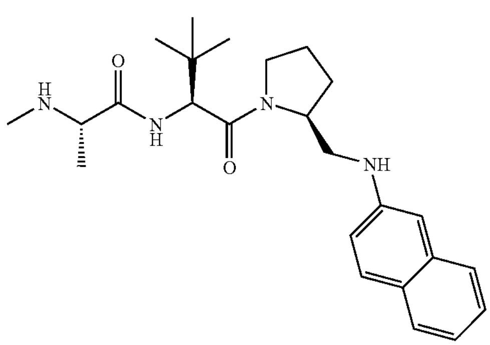 [SMILES: CN[C@@H](C)C(=O)N[C@H](C(=O)N1CCC[C@H]1CNc1ccc2ccccc2c1)C(C)(C)C] | 425.4 |

TABLE 1-continued

| Compound # | Structure | MS m/z (M + H) |
|---|---|---|
| 136 | 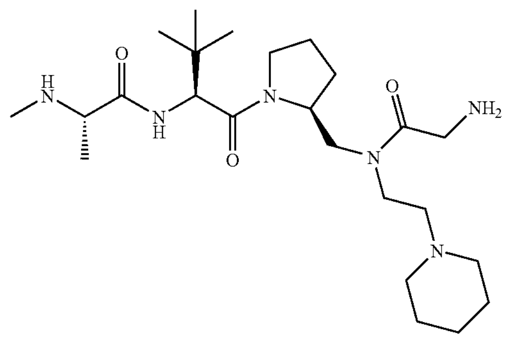 [SMILES: CN[C@@H](C)C(=O)N[C@H](C(=O)N1CCC[C@H]1CN(CCN1CCCCC1)C(=O)CN)C(C)(C)C] | 462.7 |
| 137 | 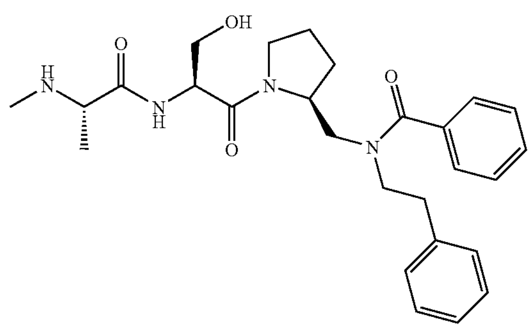 [SMILES: CN[C@@H](C)C(=O)N[C@@H](CO)C(=O)N1CCC[C@H]1CN(CCc1ccccc1)C(=O)c1ccccc1] | 481.4 |
| 138 | 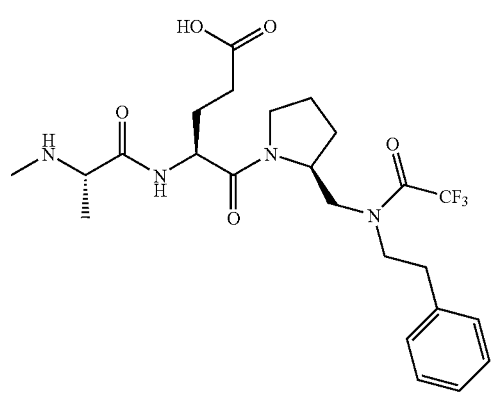 [SMILES: CN[C@@H](C)C(=O)N[C@@H](CCC(=O)O)C(=O)N1CCC[C@H]1CN(CCc1ccccc1)C(=O)C(F)(F)F] | 515.4 |
| 139 | 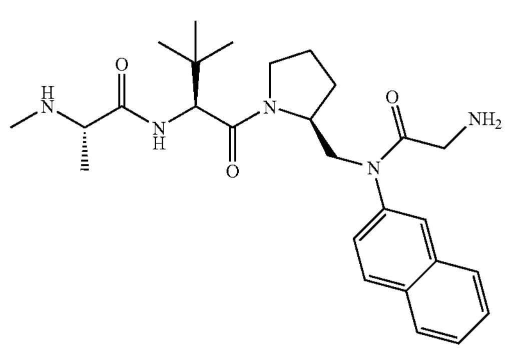 [SMILES: CN[C@@H](C)C(=O)N[C@H](C(=O)N1CCC[C@H]1CN(C(=O)CN)c1ccc2ccccc2c1)C(C)(C)C] | 482.4 |

TABLE 1-continued
| Compound # | Structure | MS m/z (M + H) |
|---|---|---|
| 140 | 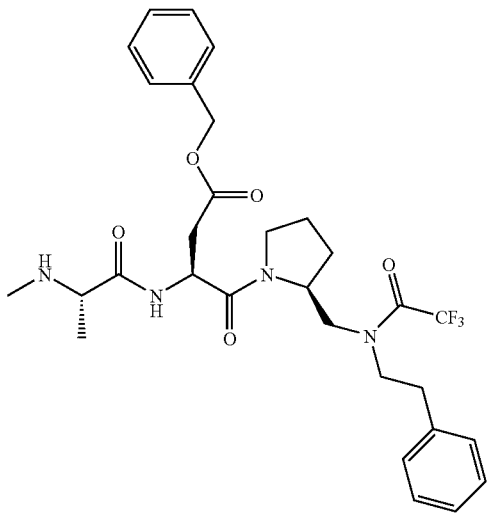 [SMILES: CN[C@@H](C)C(=O)N[C@@H](CC(=O)OCc1ccccc1)C(=O)N1CCC[C@H]1CN(CCc1ccccc1)C(=O)C(F)(F)F] | 591.6 |
| 141 | 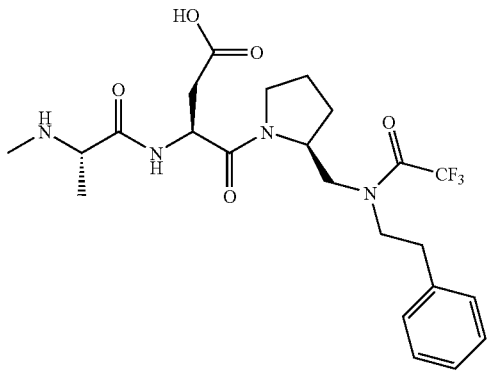 [SMILES: CN[C@@H](C)C(=O)N[C@@H](CC(=O)O)C(=O)N1CCC[C@H]1CN(CCc1ccccc1)C(=O)C(F)(F)F] | 501.2 |
| 142 | 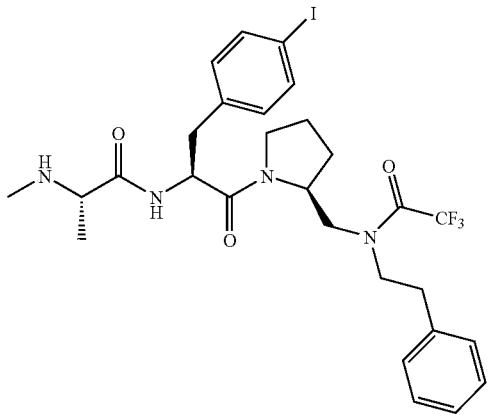 [SMILES: CN[C@@H](C)C(=O)N[C@@H](Cc1ccc(I)cc1)C(=O)N1CCC[C@H]1CN(CCc1ccccc1)C(=O)C(F)(F)F] | 659.2 |

TABLE 1-continued

| Compound # | Structure | MS m/z (M + H) |
|---|---|---|
| 143 | 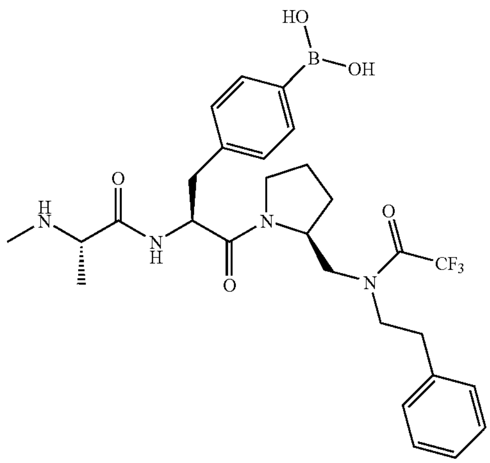 [SMILES: CN[C@@H](C)C(=O)N[C@@H](Cc1ccc(B(O)O)cc1)C(=O)N1CCC[C@H]1CN(CCc1ccccc1)C(=O)C(F)(F)F] | 577.2 |
| 144 | 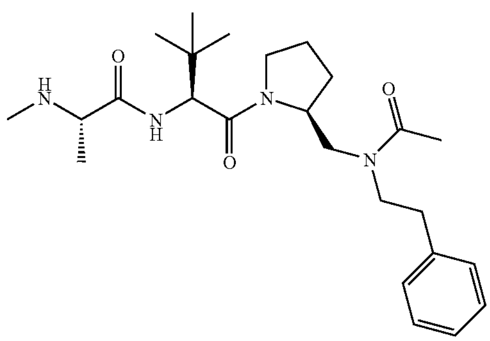 [SMILES: CN[C@@H](C)C(=O)N[C@H](C(=O)N1CCC[C@H]1CN(CCc1ccccc1)C(C)=O)C(C)(C)C] | 445.4 |
| 145 | 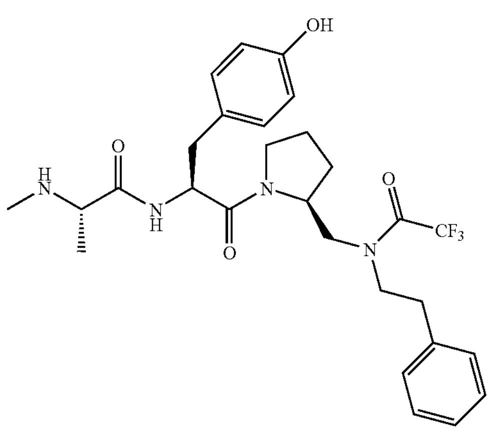 [SMILES: CN[C@@H](C)C(=O)N[C@@H](Cc1ccc(O)cc1)C(=O)N1CCC[C@H]1CN(CCc1ccccc1)C(=O)C(F)(F)F] | 549.2 |

TABLE 1-continued

| Compound # | Structure | MS m/z (M + H) |
|---|---|---|
| 146 | 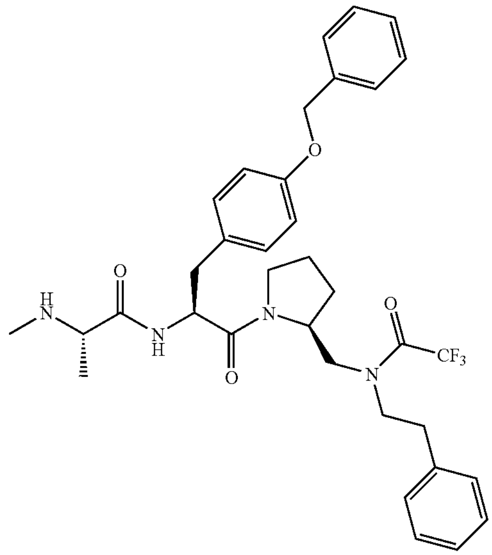 [SMILES: CN[C@@H](C)C(=O)N[C@@H](Cc1ccc(OCc2ccccc2)cc1)C(=O)N1CCC[C@H]1CN(CCc1ccccc1)C(=O)C(F)(F)F] | 639.3 |
| 147 | 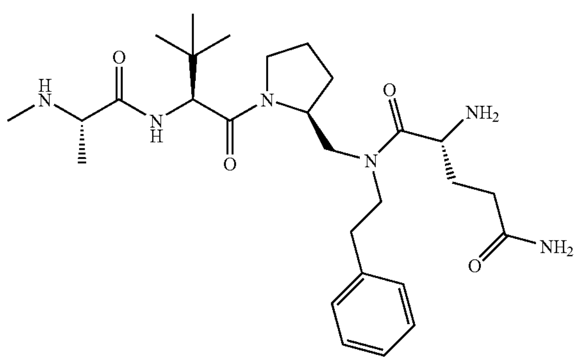 [SMILES: CN[C@@H](C)C(=O)N[C@H](C(=O)N1CCC[C@H]1CN(CCc1ccccc1)C(=O)[C@H](N)CCC(N)=O)C(C)(C)C] | 531.4 |
| 148 | 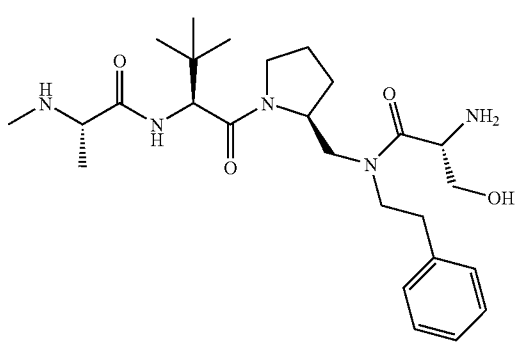 [SMILES: CN[C@@H](C)C(=O)N[C@H](C(=O)N1CCC[C@H]1CN(CCc1ccccc1)C(=O)[C@H](N)CO)C(C)(C)C] | 490.4 |

TABLE 1-continued

| Compound # | Structure | MS m/z (M + H) |
|---|---|---|
| 149 | 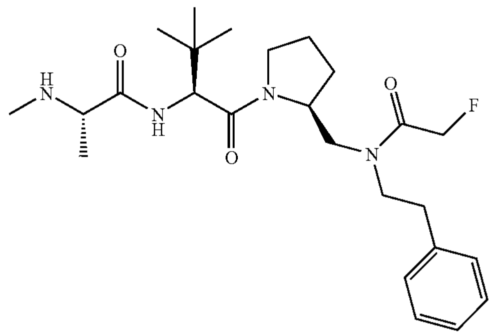 [SMILES: CN[C@@H](C)C(=O)N[C@H](C(=O)N1CCC[C@H]1CN(CCc1ccccc1)C(=O)CF)C(C)(C)C] | 463.4 |
| 150 | 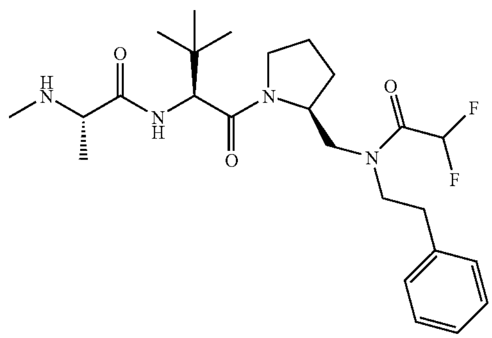 [SMILES: CN[C@@H](C)C(=O)N[C@H](C(=O)N1CCC[C@H]1CN(CCc1ccccc1)C(=O)C(F)F)C(C)(C)C] | 481.4 |
| 151 | 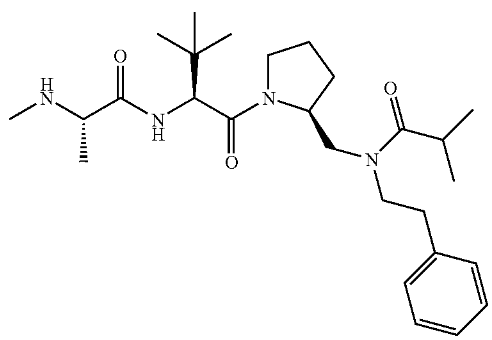 [SMILES: CN[C@@H](C)C(=O)N[C@H](C(=O)N1CCC[C@H]1CN(CCc1ccccc1)C(=O)C(C)C)C(C)(C)C] | 473.4 |
| 152 | 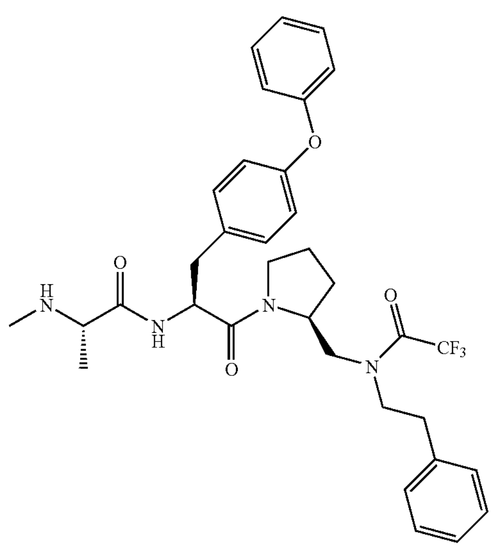 [SMILES: CN[C@@H](C)C(=O)N[C@@H](Cc1ccc(Oc2ccccc2)cc1)C(=O)N1CCC[C@H]1CN(CCc1ccccc1)C(=O)C(F)(F)F] | 625.4 |

TABLE 1-continued

| Compound # | Structure | MS m/z (M + H) |
|---|---|---|
| 153 | 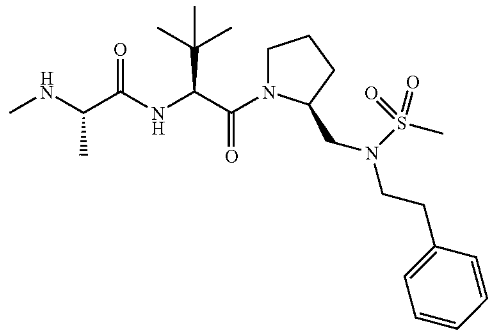 [SMILES: CN[C@@H](C)C(=O)N[C@H](C(=O)N1CCC[C@H]1CN(CCc1ccccc1)S(C)(=O)=O)C(C)(C)C] | 481.4 |
| 154 | 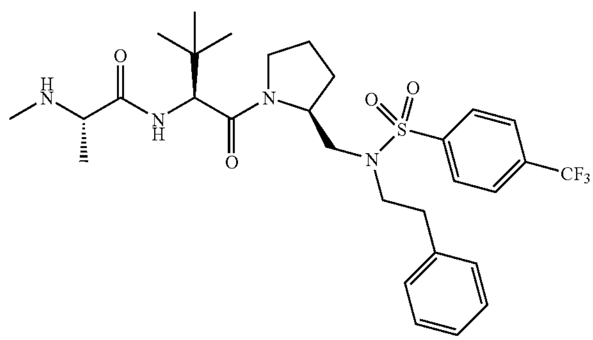 [SMILES: CN[C@@H](C)C(=O)N[C@H](C(=O)N1CCC[C@H]1CN(CCc1ccccc1)S(=O)(=O)c1ccc(C(F)(F)F)cc1)C(C)(C)C] | 611.2 |
| 155 | 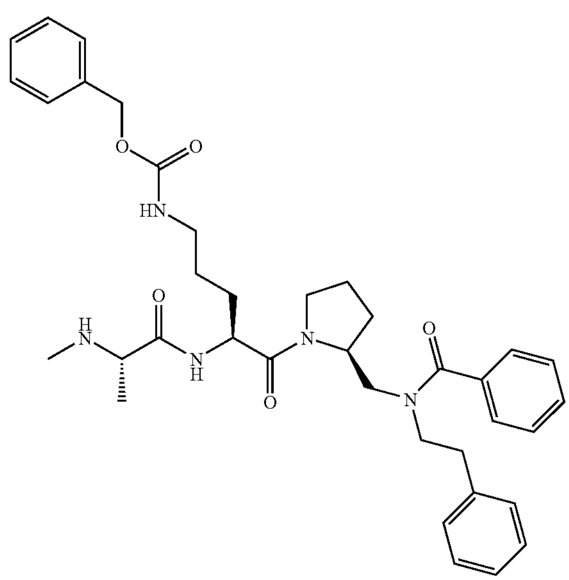 [SMILES: CN[C@@H](C)C(=O)N[C@@H](CCCNC(=O)OCc1ccccc1)C(=O)N1CCC[C@H]1CN(CCc1ccccc1)C(=O)c1ccccc1] | 642.4 |

TABLE 1-continued
| Compound # | Structure | MS m/z (M + H) |
|---|---|---|
| 156 | 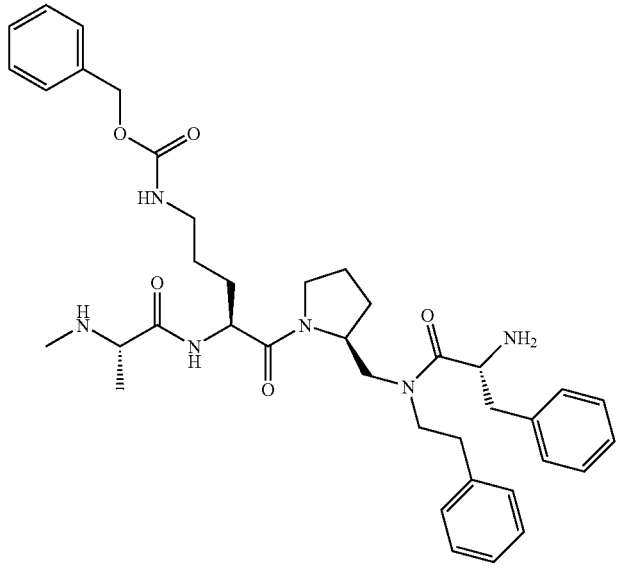 [SMILES: CN[C@@H](C)C(=O)N[C@@H](CCCNC(=O)OCc1ccccc1)C(=O)N1CCC[C@H]1CN(CCc1ccccc1)C(=O)[C@H](N)Cc1ccccc1] | 685.4 |
| 157 | 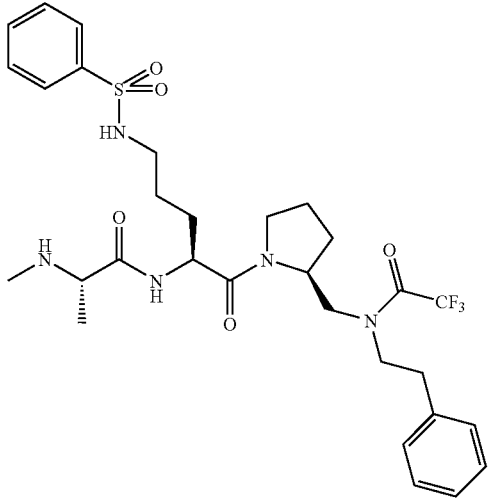 [SMILES: CN[C@@H](C)C(=O)N[C@@H](CCCNS(=O)(=O)c1ccccc1)C(=O)N1CCC[C@H]1CN(CCc1ccccc1)C(=O)C(F)(F)F] | 640.2 |

TABLE 1-continued

| Compound # | Structure | MS m/z (M + H) |
|---|---|---|
| 158 | 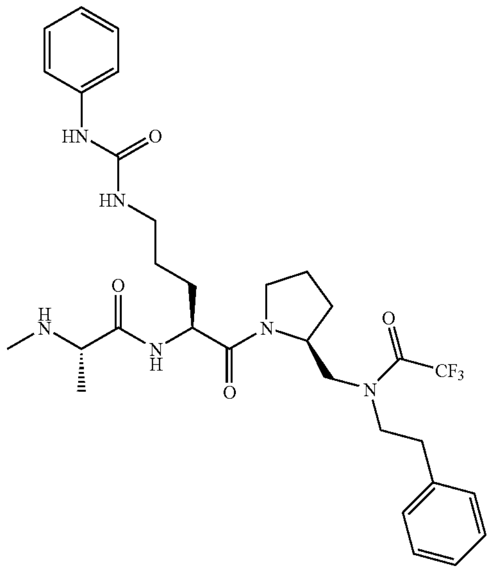 [SMILES: CN[C@@H](C)C(=O)N[C@@H](CCCNC(=O)Nc1ccccc1)C(=O)N1CCC[C@H]1CN(CCc1ccccc1)C(=O)C(F)(F)F] | 619.4 |
| 159 | 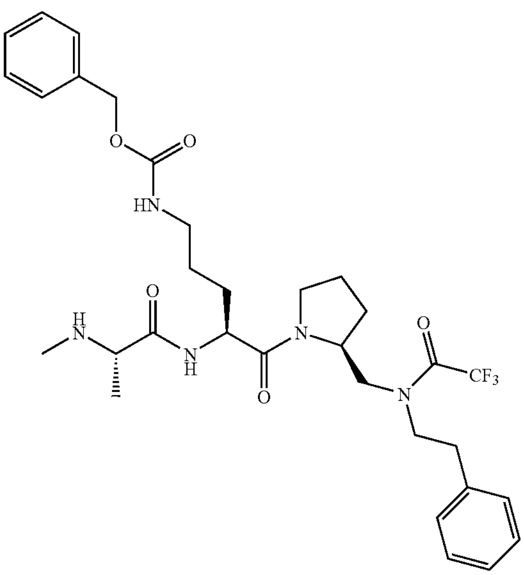 [SMILES: CN[C@@H](C)C(=O)N[C@@H](CCCNC(=O)OCc1ccccc1)C(=O)N1CCC[C@H]1CN(CCc1ccccc1)C(=O)C(F)(F)F] | 634.4 |
| 160 | 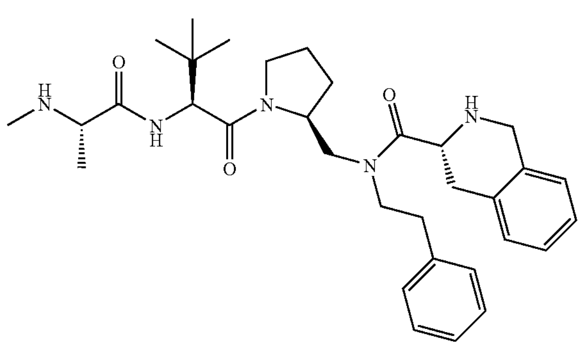 [SMILES: CN[C@@H](C)C(=O)N[C@H](C(=O)N1CCC[C@H]1CN(CCc1ccccc1)C(=O)[C@H]1Cc2ccccc2CN1)C(C)(C)C] | 562.4 |

TABLE 1-continued

| Compound # | Structure | MS m/z (M + H) |
|---|---|---|
| 161 | 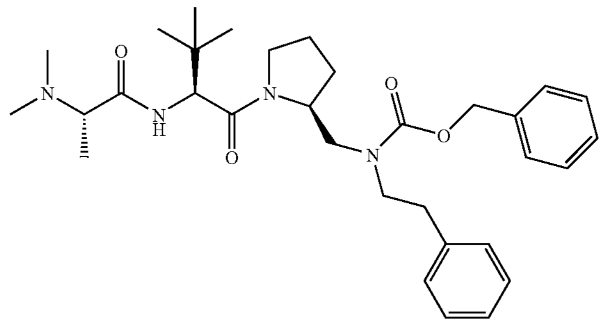 [SMILES: C[C@@H](C(=O)N[C@H](C(=O)N1CCC[C@H]1CN(CCc1ccccc1)C(=O)OCc1ccccc1)C(C)(C)C)N(C)C] | 551.4 |
| 162 | 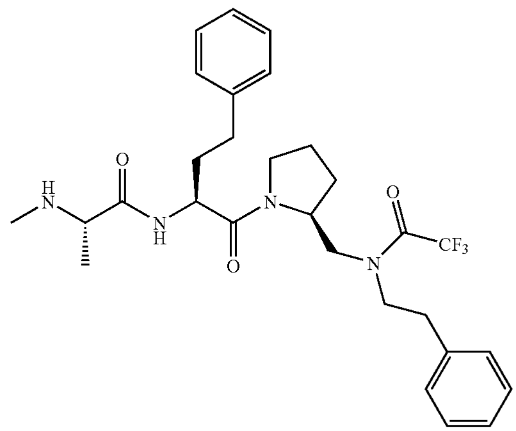 [SMILES: CN[C@@H](C)C(=O)N[C@@H](CCc1ccccc1)C(=O)N1CCC[C@H]1CN(CCc1ccccc1)C(=O)C(F)(F)F] | 547.2 |
| 163 | 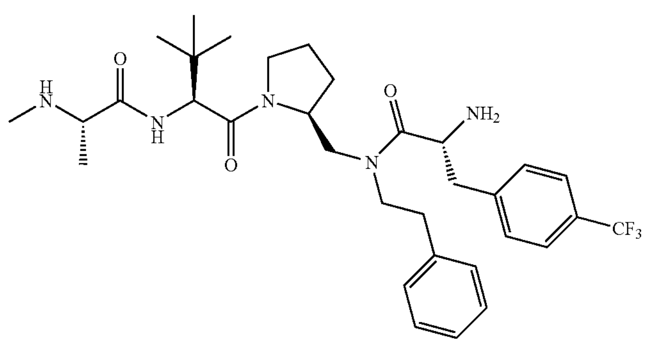 [SMILES: CN[C@@H](C)C(=O)N[C@H](C(=O)N1CCC[C@H]1CN(CCc1ccccc1)C(=O)[C@H](N)Cc1ccc(C(F)(F)F)cc1)C(C)(C)C] | 618.4 |
| 164 | 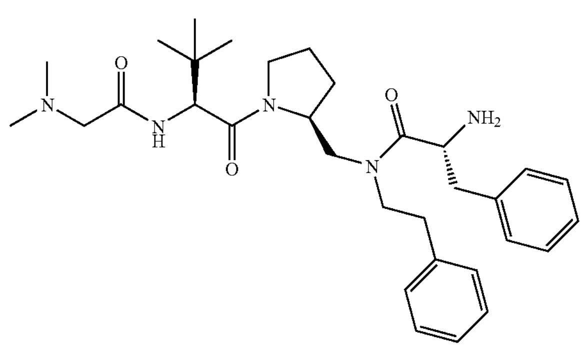 [SMILES: CN(C)CC(=O)N[C@H](C(=O)N1CCC[C@H]1CN(CCc1ccccc1)C(=O)[C@H](N)Cc1ccccc1)C(C)(C)C] | 550.4 |

TABLE 1-continued

| Compound # | Structure | MS m/z (M + H) |
|---|---|---|
| 165 | 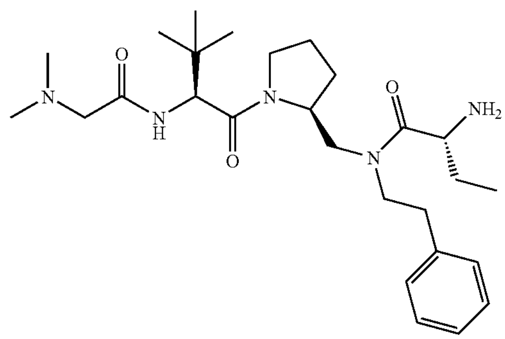 [SMILES: CC[C@@H](N)C(=O)N(CCc1ccccc1)C[C@@H]1CCCN1C(=O)[C@@H](NC(=O)CN(C)C)C(C)(C)C] | 488.4 |
| 166 | 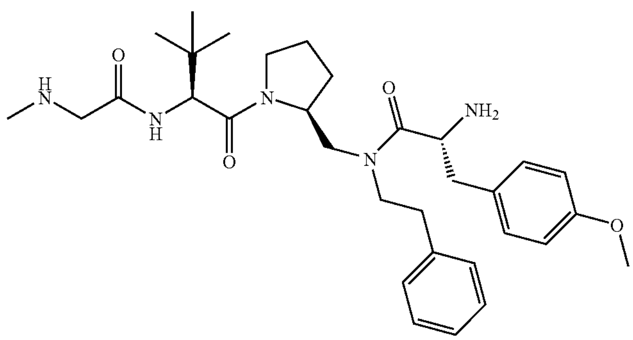 | 566.4 |
| 167 | 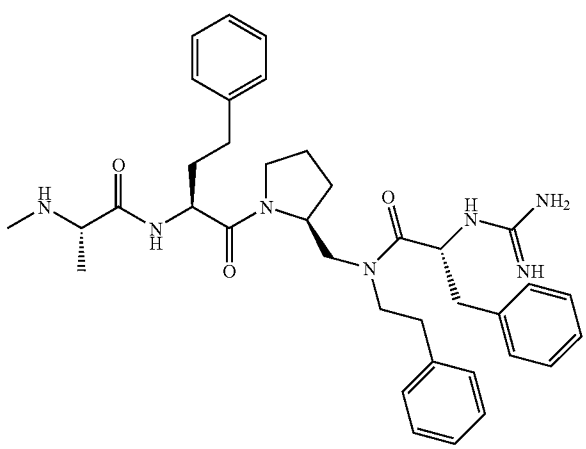 [SMILES: CN[C@@H](C)C(=O)N[C@@H](CCc1ccccc1)C(=O)N1CCC[C@H]1CN(CCc1ccccc1)C(=O)[C@@H](Cc1ccccc1)NC(=N)N] | 640.4 |
| 168 | 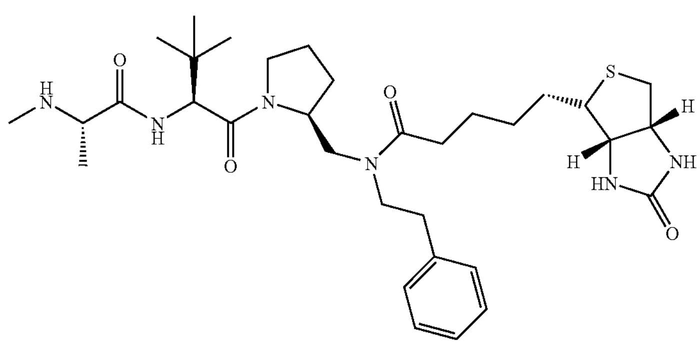 | 629.4 |

TABLE 1-continued
| Compound # | Structure | MS m/z (M + H) |
|---|---|---|
| 169 | 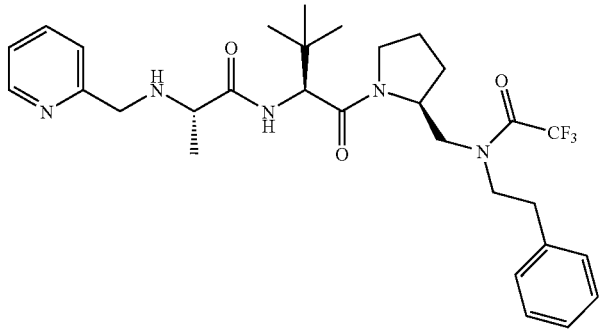 [SMILES: C[C@H](NCc1ccccn1)C(=O)N[C@H](C(=O)N1CCC[C@H]1CN(CCc1ccccc1)C(=O)C(F)(F)F)C(C)(C)C] | 576.4 |
| 170 | 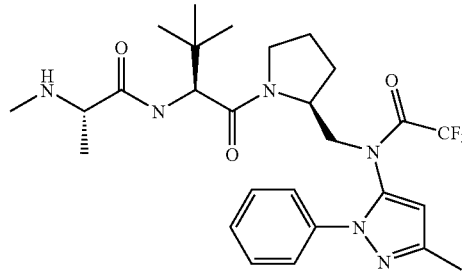 | 551.3 |
| 171 | 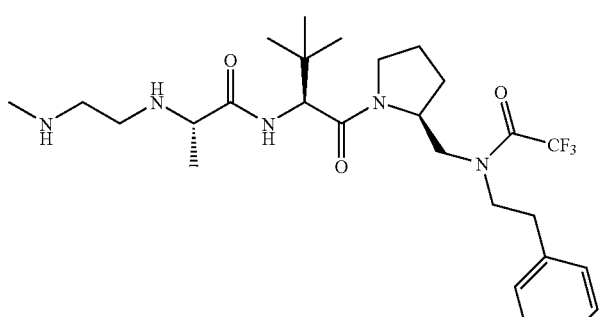 | 542.4 |
| 172 | 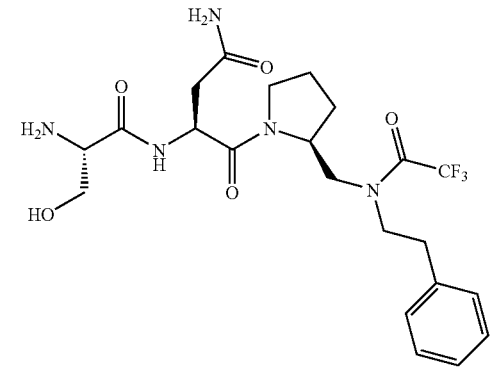 [SMILES: NC(=O)C[C@H](NC(=O)[C@@H](N)CO)C(=O)N1CCC[C@H]1CN(CCc1ccccc1)C(=O)C(F)(F)F] | 502.2 |

TABLE 1-continued

| Compound # | Structure | MS m/z (M + H) |
|---|---|---|
| 173 | 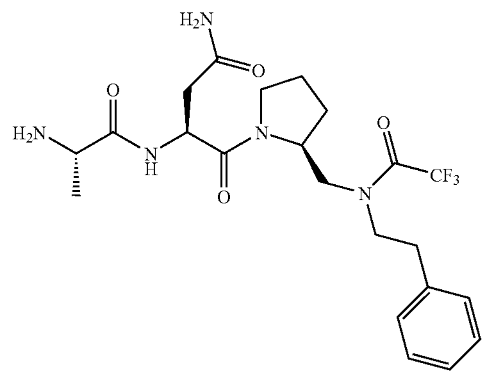 [SMILES: C[C@H](N)C(=O)N[C@@H](CC(N)=O)C(=O)N1CCC[C@H]1CN(CCc1ccccc1)C(=O)C(F)(F)F] | 486.2 |
| 174 | 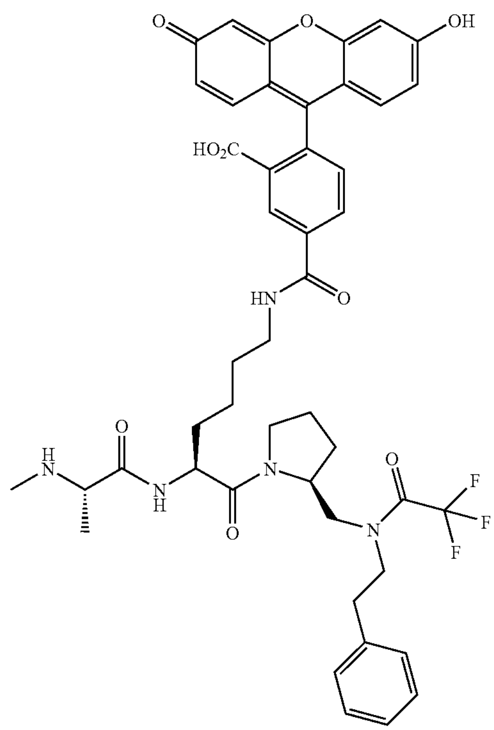 [SMILES: CN[C@@H](C)C(=O)N[C@@H](CCCCNC(=O)c1ccc(-c2c3ccc(=O)cc-3oc3cc(O)ccc23)c(C(=O)O)c1)C(=O)N1CCC[C@H]1CN(CCc1ccccc1)C(=O)C(F)(F)F] | 872.4 |
| 175 | 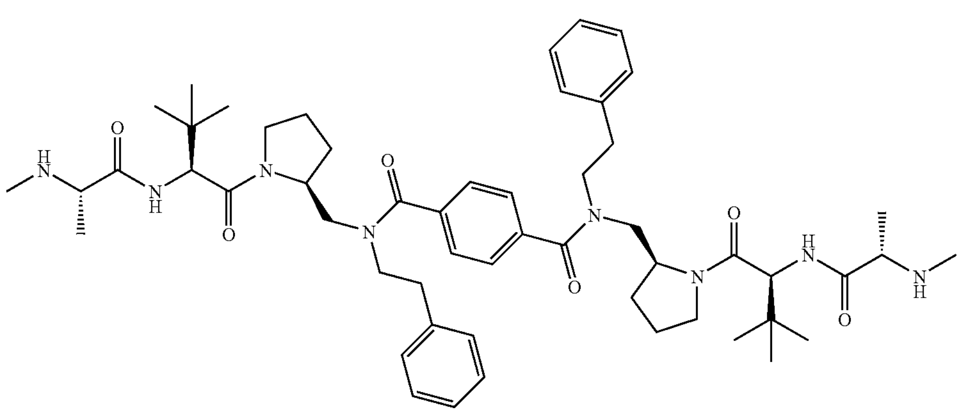 | 468.4 |

TABLE 1-continued

| Compound # | Structure | MS m/z (M + H) |
|---|---|---|
| 176 | 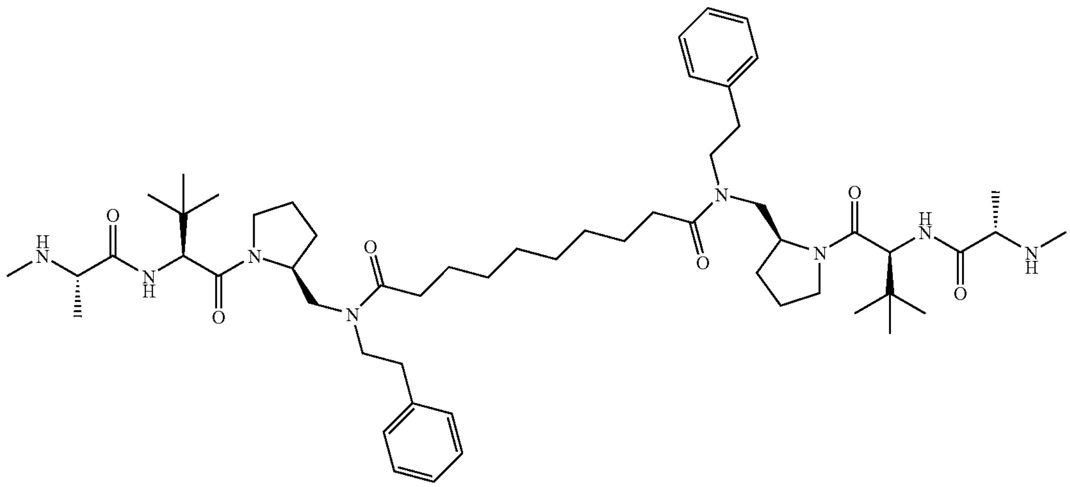 | 486.4 |
| 177 | 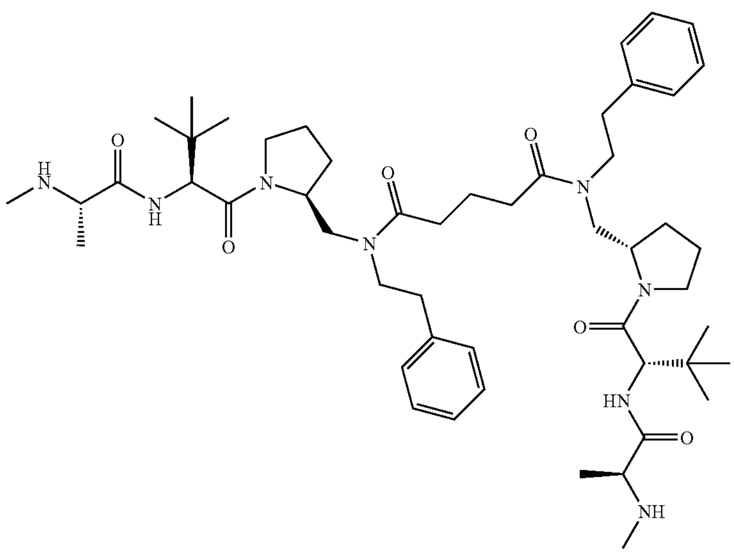 [SMILES: CN[C@@H](C)C(=O)N[C@H](C(=O)N1CCC[C@H]1CN(CCc1ccccc1)C(=O)CCCC(=O)N(CCc1ccccc1)C[C@@H]1CCCN1C(=O)[C@@H](NC(=O)[C@H](C)NC)C(C)(C)C)C(C)(C)C] | 451.4 |
| 178 | 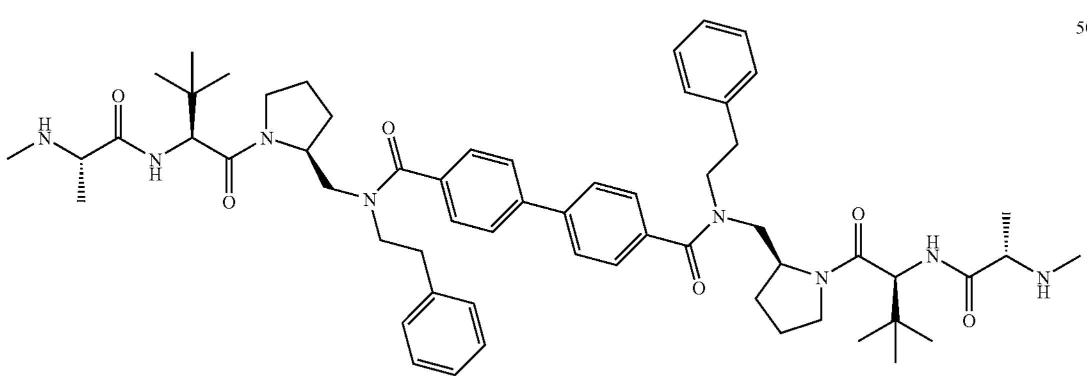 | 506.4 |

The following compounds in Tables 3, 4, and 5 may also be synthesized using the aforesaid synthetic methods or modifications thereof:
TABLE 3
Structure
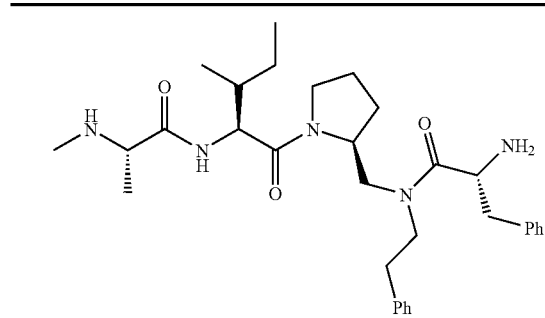
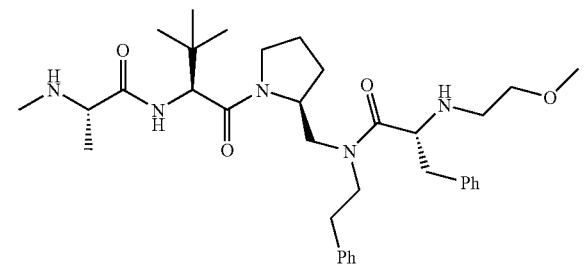
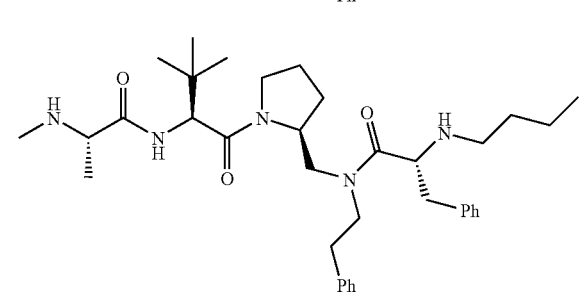
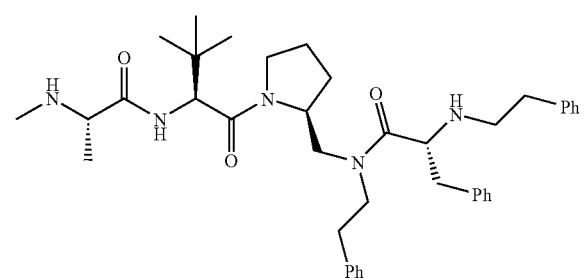 [SMILES: CN[C@@H](C)C(=O)N[C@H](C(=O)N1CCC[C@H]1CN(CCc1ccccc1)C(=O)[C@@H](Cc1ccccc1)NCCc1ccccc1)C(C)(C)C]
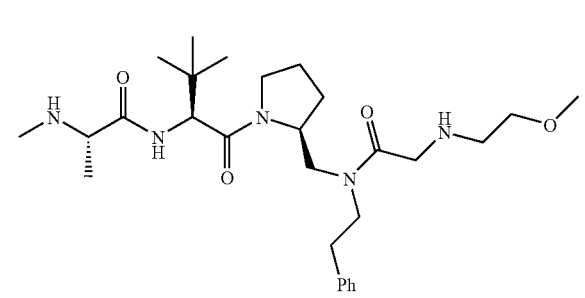
TABLE 3-continued
Structure
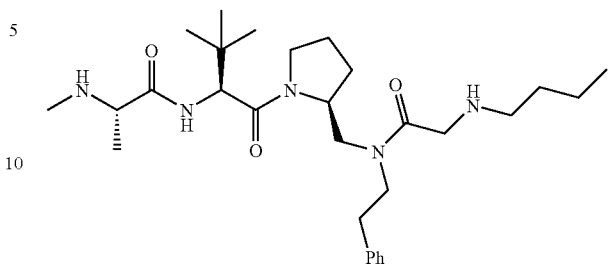
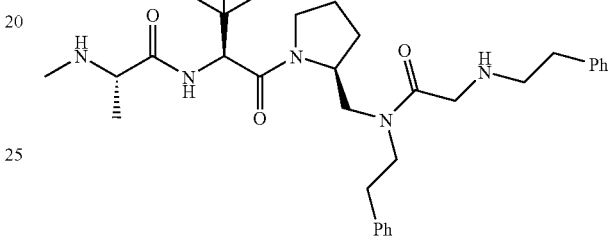
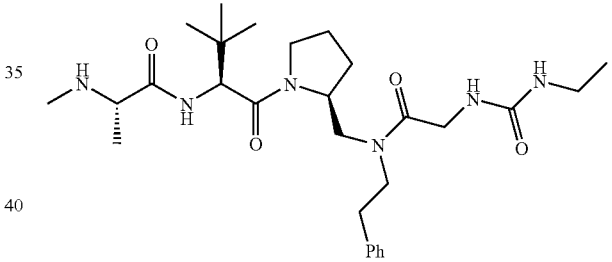
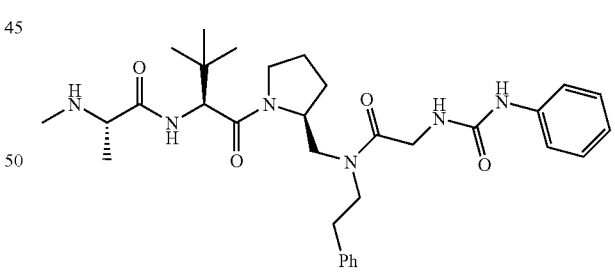
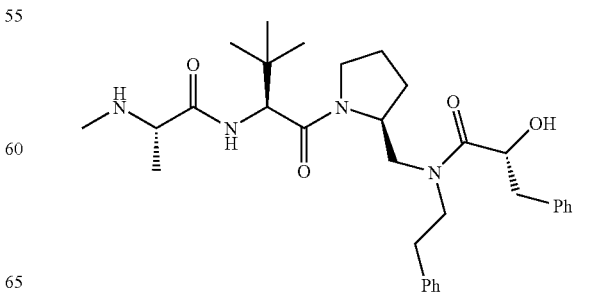

TABLE 3-continued
Structure
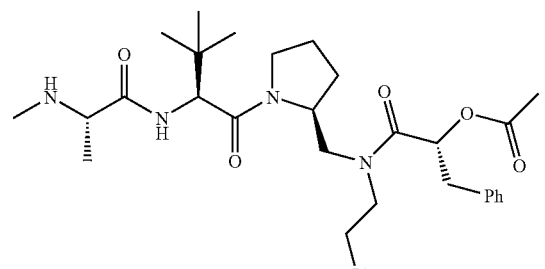
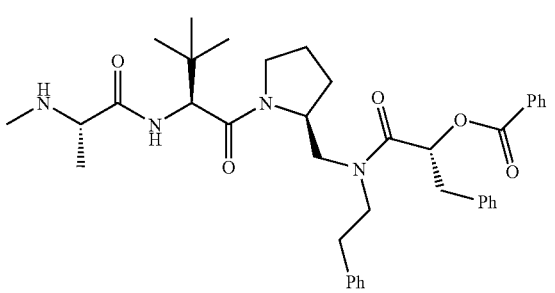 [SMILES: CN[C@@H](C)C(=O)N[C@H](C(=O)N1CCC[C@H]1CN(CCc1ccccc1)C(=O)[C@@H](Cc1ccccc1)OC(=O)c1ccccc1)C(C)(C)C]
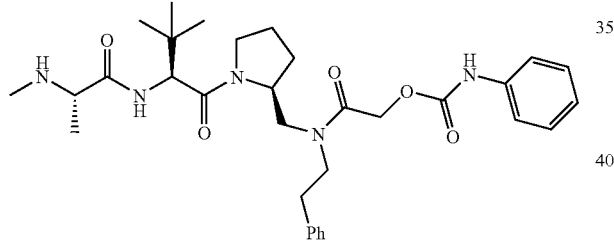
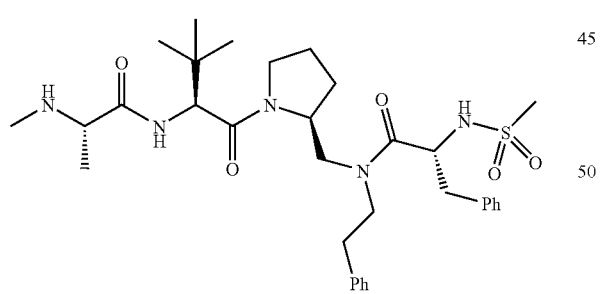
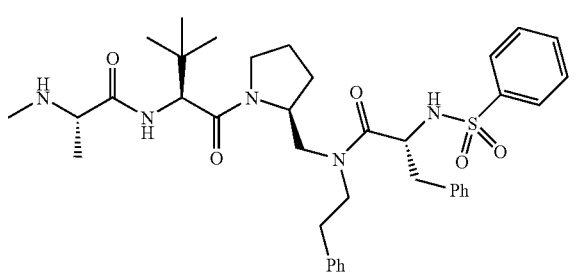 [SMILES: CN[C@@H](C)C(=O)N[C@H](C(=O)N1CCC[C@H]1CN(CCc1ccccc1)C(=O)[C@@H](Cc1ccccc1)NS(=O)(=O)c1ccccc1)C(C)(C)C]
TABLE 3-continued
Structure
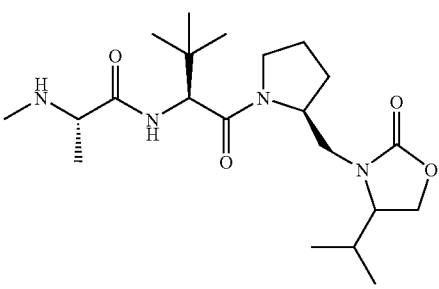 [SMILES: CN[C@@H](C)C(=O)N[C@H](C(=O)N1CCC[C@H]1CN1C(=O)OCC1C(C)C)C(C)(C)C]
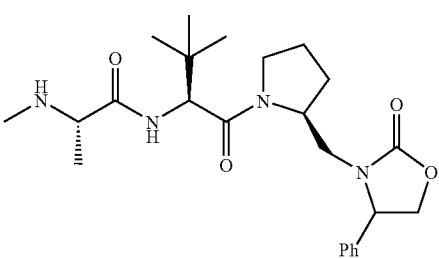 [SMILES: CN[C@@H](C)C(=O)N[C@H](C(=O)N1CCC[C@H]1CN1C(=O)OCC1c1ccccc1)C(C)(C)C]
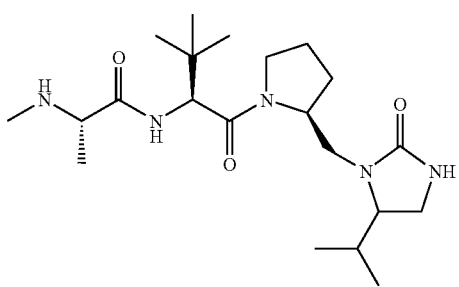 [SMILES: CN[C@@H](C)C(=O)N[C@H](C(=O)N1CCC[C@H]1CN1C(=O)NCC1C(C)C)C(C)(C)C]
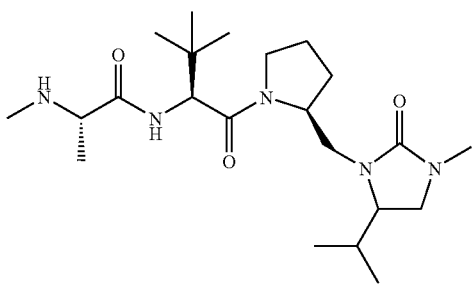
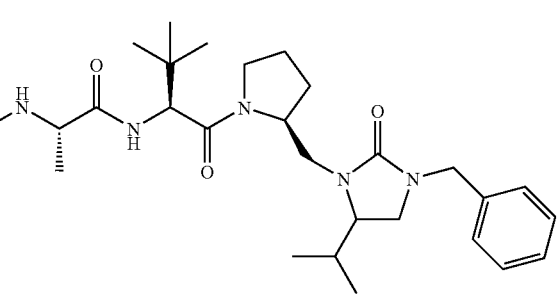

TABLE 3-continued
Structure
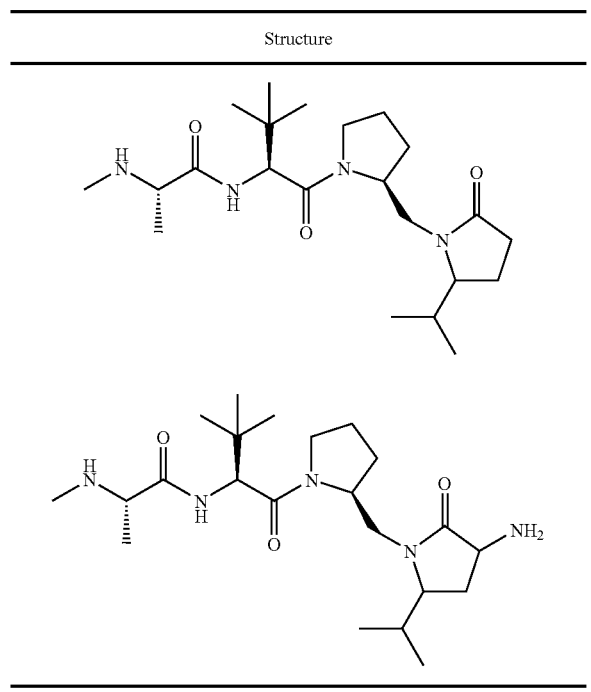
TABLE 4
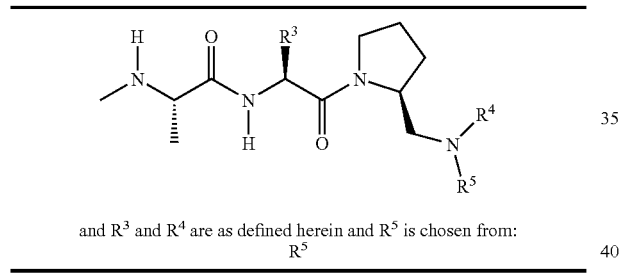
and R³ and R⁴ are as defined herein and R⁵ is chosen from:
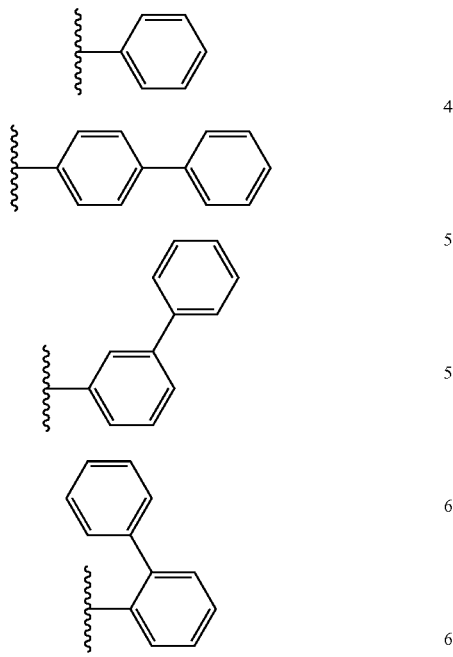
TABLE 4-continued
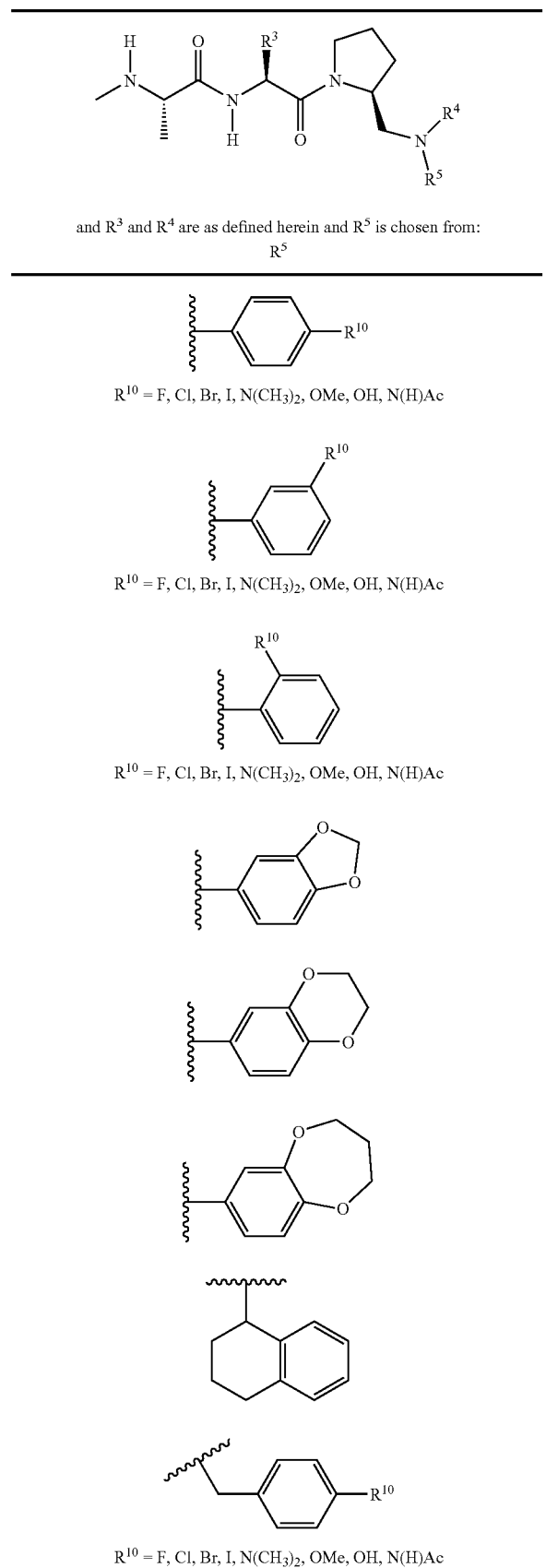

TABLE 4-continued

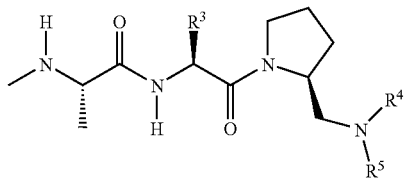

and R³ and R⁴ are as defined herein and R⁵ is chosen from:
R⁵

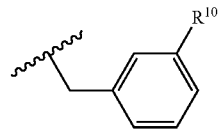

$R^{10}$ = F, Cl, Br, I, N(CH₃)₂, OMe, OH, N(H)Ac

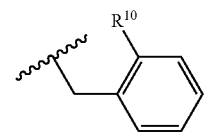

$R^{10}$ = F, Cl, Br, I, N(CH₃)₂, OMe, OH, N(H)Ac

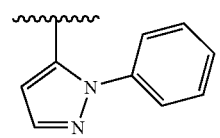 [SMILES: *c1ccnn1-c1ccccc1]

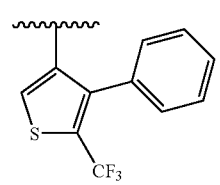 [SMILES: *c1csc(C(F)(F)F)c1-c1ccccc1]

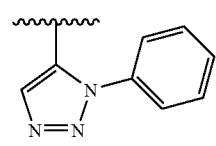 [SMILES: *c1cnnn1-c1ccccc1]

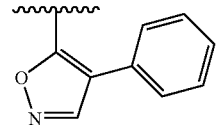 [SMILES: *c1oncc1-c1ccccc1]

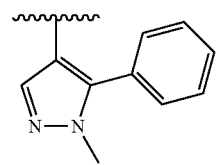 [SMILES: *c1cnn(C)c1-c1ccccc1]

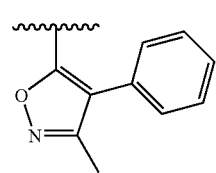 [SMILES: *c1onc(C)c1-c1ccccc1]

TABLE 4-continued

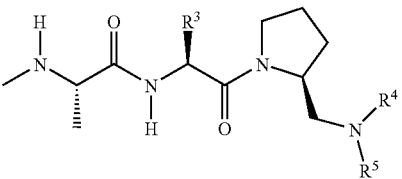

and R³ and R⁴ are as defined herein and R⁵ is chosen from:
R⁵

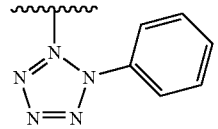

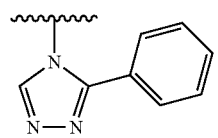 [SMILES: *n1cnnc1-c1ccccc1]

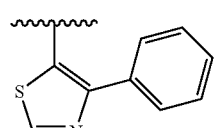

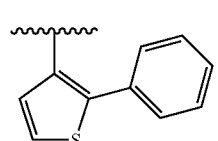

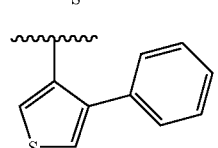

Assays

27. Molecular Constructs for Expression

GST-XIAP BIR3RING: XIAP coding sequence amino acids 246-497 cloned into PGEX2T1 via BamH1 and AVA I. The plasmid was transformed into *E. coli* DH5α for use in protein expression and purification.

GST-HIAP2 (cIAP-1) BIR 3: HIAP2 coding sequence from amino acids 251-363 cloned into PGex4T3 via BamH1 and XhoI. The plasmid was transformed into *E. coli* DH5α for use in protein expression and purification.

GST-HIAP1(cIAP-2) BIR 3: HIAP1 coding sequence from amino acids 236-349, cloned into PGex4T3 via BamH1 and XhoI. The plasmid was transformed into *E. coli* DH5α for use in protein expression and purification.

GST-linker BIR 2 BIR3Ring: XIAP coding sequence from amino acids 93-497 cloned into PGex4T1 via BamH1 and XhoI. Amino acids 93-497 were amplified from full length XIAP in pGex4t3, using the primers: TTAATAGGATCCAT-CAACGGCTTTTATC (SEQ ID NO: 7) and GCTGCATGT-GTGTCAGAGG (SEQ ID NO: 8), using standard PCR conditions. The PCR fragment was TA cloned into pCR-2.1 (invitrogen). Linker BIR 2 BIR 3Ring was subcloned into pGex4T1 by BamHI/XhoI digestion. The plasmid was transformed into *E. coli* DH5α for use in protein expression and purification.

GST-XIAP linker BIR 2: XIAP linker BIR 2 coding sequence from amino acids 93-497 cloned into pGex4T3 via BamHI and XhoI. The plasmid was transformed into *E. coli* DH5α for use in protein expression and purification.

28. Synthesis of Fluorescent Probe for FP Assay

A fluorescent peptide probe, Fmoc-Ala-Val-Pro-Phe-Tyr(t-Bu)-Leu-Pro-Gly(t-Bu)-Gly-OH (SEQ ID NO: 9) was prepared using standard Fmoc chemistry on 2-chlorotrityl chloride resin (Int. J. Pept. Prot. Res. 38:555-561, 1991). Cleavage from the resin was performed using 20% acetic acid in dichloromehane (DCM), which left the side chain still blocked. The C-terminal protected carboxylic acid was coupled to 4'-(aminomethy)fluorescein (Molecular Probes, A-1351; Eugene, Oreg.) using excess diisopropylcarbodiimide (DIC) in dimethylformamide (DMF) at room temperature and was purified by silica gel chromatography (10% methanol in DCM). The N-terminal Fmoc protecting group was removed using piperidine (20%) in DMF, and purified by silica gel chromatography (20% methanol in DCM, 0.5% HOAc). Finally, the t-butyl side chain protective groups were removed using 95% trifluoroacetic acid containing 2.5% water and 2.5% triisopropyl silane. The peptide obtained displayed a single peak by HPLC (>95% pure). Compound #174 was also used as a fluorescent probe in this assay.

29. Expression and Purification of Recombinant Proteins

A. Recombinant Proteins Expression

Glutathione S-transferase (GST) tagged proteins were expressed in *Escherichia coli* strains DH5-alpha. For expression of the XIAP-BIR's, cIAP-1, cIAP-2 and Livin transformed bacteria were cultured overnight at 37° C. in Luria Broth (LB) medium supplemented with 50 ug/ml of ampicillin. The overnight culture was then diluted 25 fold into fresh LB ampicillin supplemented media and bacteria were grown up to A600=0.6 then induced with 1 mM isopropyl-D-1-thiogalactopyranoside for 3 hours. Upon induction, cells were centrifuged at 5000 RPM for 10 minutes and the media was removed. Each pellet obtained from a 1 liter culture received 10 ml of lysis buffer (50 mM Tris-HCl, 200 mM NaCl, 1 mM DTT, 1 mM PMSF, 2 mg/ml of lysosyme), was incubated at 4° C. with gentle shaking. After 20 minutes of incubation, the cell suspension was placed at −80° C. overnight or until needed.

B. Purification of Recombinant Proteins

For purification of recombinant proteins, the IPTG-induced cell lysate was thaw and 100 ul of DNAase solution (100 ug/ml) was added to the cell lysate and incubated at 4° C. for 30 minutes with gentle rocking. Cell lysate was then passed four times through a Bio-Neb Cell disruptor device (Glas-col) set at 100 Psi with Nitrogen gas. The resulting cell extract was centrifuged at 4° C. at 15000 RPM in a SS-34 Beckman rotor for 30 minutes. The resulting supernatant from 500 ml cell culture was then mixed with 2 ml of glutathione-Sepharose beads (Pharmacia) for 1 hour at 4° C. Upon incubation, the beads were washed 3 times with 1× Tris-Buffered Saline (TBS). Elution of the retained proteins was done with 3 washes of 2 ml of 50 mM TRIS pH 8.0 containing 10 mM reduced glutathione. The eluted proteins were pooled and precipitated with 604 g/liter of ammonium sulfate and the resulting pellet re-suspended into an appropriate buffer. As judged by SDS-PAGE the purified proteins were >90% pure. The protein concentration of purified proteins was determined from the Bradford method.

His-tag proteins were expressed in the *E. Coli* strain in *E. coli* AD494 cells using a pet28ACPP32 construct. The soluble protein fraction was prepared as described above. For protein purification, the supernatant was purified by affinity chromatography using chelating-Sepharose (Pharmacia) charged with $NiSO_4$ according to the manufacturer's instructions. Purity of the eluted protein was >90% pure as determined by SDS-PAGE. The protein concentration of purified proteins was determined from the Bradford assay.

Binding Assay

30. Fluorescence Polarization-Based Competition Assay

For all assays, the fluorescence and fluorescence-polarization was evaluated using a Tecan Polarion instrument with the excitation filter set at 485 nm and the emission filter set at 535 nm. For each assay, the concentration of the target protein was first establish by titration of the selected protein in order to produce a linear dose-response signal when incubated alone in the presence of the fluorescent probe. Upon establishing these conditions, the compounds potency ($IC_{50}$) and selectivity, was assessed in the presence of a fix defined amount of target protein and fluorescent probe and a 10 point serial dilution of the selected compounds. For each $IC_{50}$ curve, the assays were run as followed: 25 ul/well of diluted compound in 50 mM MES buffer pH 6.5 were added into a black 96 well plate then 25 ul/well of bovine serum albumin (BSA) at 0.5 mg/ml in 50 mM MES pH 6.5. Auto-fluorescence for each compound was first assessed by performing a reading of the compound/BSA solution alone. Then 25 ul of the fluorescein probe diluted into 50 mM MES containing 0.05 mg/ml BSA were added and a reading to detect quenching of fluorescein signal done. Finally 25 ul/well of the target or control protein (GST—BIRs) diluted at the appropriate concentration in 50 mM MES containing 0.05 mg/ml BSA were added and the fluorescence polarization evaluated.

31. Determination of $IC_{50}$ and Inhibitory Constants

For each assay the relative polarization-fluorescence units were plotted against the final concentrations of compound and the $IC_{50}$ calculated using the Grad pad prism software and/or Cambridge soft. The ki value were derived from the calculated $IC_{50}$ value as described above and according to the equation described in Nikolovska-Coleska, Z. (2004) Anal Biochem 332, 261-273.

Compounds exemplified in Table 6 were tested and found to have $IC_{50}$s in the following ranges: A: >10 µM; B: <10 µM; C: <1 µM using the fluorescence polarization assay, as shown in Table 5. Each of the $IC_{50}$s was calculated from Graph Pad.

TABLE 6

| Cpd # | Bir3-RING XIAP | Bir3 cIAP-1 | Bir3 cIAP-2 |
|---|---|---|---|
| 1 | B | C | C |
| 2 | B | B | B |
| 3 | B | B | B |
| 4 | B | B | B |
| 5 | B | C | C |
| 6 | A | A | A |
| 7 | A | | |
| 8 | A | B | B |
| 9 | B | A | A |
| 10 | C | C | C |
| 11 | B | B | B |
| 12 | B | A | A |
| 13 | B | B | A |
| 14 | A | A | A |
| 15 | C | C | C |
| 16 | B | C | B |
| 17 | B | C | C |
| 18 | C | C | C |
| 19 | C | C | C |
| 20 | C | C | C |
| 21 | C | C | C |
| 22 | C | C | C |
| 23 | C | C | C |
| 24 | C | C | C |
| 25 | B | C | C |
| 26 | C | C | C |
| 27 | C | C | C |

TABLE 6-continued

| Cpd # | Bir3-RING XIAP | Bir3 cIAP-1 | Bir3 cIAP-2 |
|---|---|---|---|
| 28 | C | C | C |
| 29 | B | C | C |
| 30 | C | C | C |
| 31 | C | C | C |
| 32 | C | C | C |
| 33 | C | C | C |
| 34 | C | C | C |
| 35 | C | C | C |
| 36 | B | C | C |
| 37 | C | C | C |
| 38 | C | C | C |
| 39 | C | C | C |
| 40 | C | C | C |
| 41 | B | C | C |
| 42 | C | C | C |
| 43 | C | C | C |
| 44 | B | C | C |
| 45 | C | C | C |
| 46 | C | C | C |
| 47 | C | C | C |
| 48 | C | C | C |
| 49 | C | C | C |
| 50 | C | C | C |
| 51 | C | C | C |
| 52 | C | C | C |
| 53 | C | C | C |
| 54 | C | C | C |
| 55 | C | C | C |
| 56 | C | C | C |
| 57 | C | C | C |
| 58 | B | C | C |
| 59 | C | C | C |
| 60 | C | C | B |
| 61 | C | C | C |
| 63 | B | B | A |
| 64 | B | B | B |
| 65 | C | C | C |
| 66 | B | B | B |
| 67 | A | B | B |
| 68 | C | C | C |
| 69 | C | C | C |

32. Caspase-3 Linker BIR2 or Linker-BIR2-BIR3-RING Depression Assay

In order to determine the relative activity of the selected compound against BIR2, an in vitro assay was used where caspase-3 was inhibited by linker—BIR2 or linker BIR2—BIR3—RING of XIAP. Briefly, 1.5 ul of the enzyme, 0.25 uM to 2 uM of GST-Xiap fusion protein (GST-linker BIR2, GST-linker BIR2BIR3RING) were co-incubated with serial dilutions of compound (80 uM-0.04 uM). Caspase 3 activity was measured by overlaying 25 ul of a 0.4 mM DEVD-AMC solution. Final reaction volume was 100 ul. All dilutions were performed in caspase buffer (50 mM Hepes pH 7.4, 100 mM NaCl, 10% sucrose, 1 mM EDTA, 10 mM DTT, 0.1% CHAPS (Stennicke, H. R., and Salvesen, G. S. (1997). Biochemical characteristics of caspase-3, -6, -7, and -8. J. Biol. Chem. 272, 25719-25723)).

The fluorescent AMC released from the caspase-3 hydrolysis of the substrate was measured in a TECAN spectrophotometer at 360 nm excitation and 444 nm emission, on a kinetic cycle of 30 minutes with readings taken every 2 minutes. Caspase activity was calculated as $V_o$ of AMC fluorescence/sec. Caspase de-repression by our compounds were compared to caspase-3 alone and caspase 3 repressed by the presence of XIAP fusion protein.

33A: Pull-Down Assay

Compound #168 was dissolved in DMSO at 20 mM and used as the stock solution. Prior to the pull-down assay the compound 168-affinity-agarose beads were prepared as follows:

300 ul of avidine-agarose beads prepared as 50% slurry in buffer A were incubated with 40 ul compound 168 (2.5 mM final) for 6 hrs at 4° C. with shaking. Upon incubation the beads were washed 3 times with buffer A.

On the day of the pull-down assay, cells such as MDA-MB-231 or 293A were collected and lyzed with a buffer A containing 20 mM TrisHCl, 150 mM NaCl, 10% Glycerol 1% NP-40 and Protease inhibitor cocktail obtained from Sigma with a final protein concentration between 3 to 30 ug/ul.

For the pull-down assay, 60 ul of the compound 168-beads preparation were incubated with 300 ug cells lysate and 10 ul compound 107 (0.36 mM final) or as control with 10 ul of buffer A to get a final volume of 550 ul. The mixture was then incubated at 4 C over night with shaking. The following day, the beads were washed three times with the buffer A and the final bead pellet was re-suspended in 50 ul of 2× Leamli buffer. The samples were then centrifuged and the supernatant was collected for western blot analysis directed against XIAP of the other IAP's.

Alternatively a similar protocol was performed with AVPI-Biotin and IPVA-Biotin probes.

Results:

Using the compound 168-beads and AVPI-beads, XIAP BIR3 was pulled-down by Western-blot, according to Method 33A.

33B: Assay to Evaluate Direct IAP Binding Compounds

A direct IAP binding molecule is used to identify IAP binding compounds by contacting the test compound with an IAP protein which is either fixed or non-fixed on a solid support. The non-binding interacting molecules are washed away and the bound compounds are identified using analytical techniques that can either identify directly the compound such as mass spectrometry, surface plasma resonance or can a evaluate a change of conformation or structure in the target molecule induced by the test compound or using techniques that can monitor the molecular interaction between the test compound and the target molecule such as NMR and protein crystallography.

Cell-Free Assay

34. Caspase De-Repression Assay Using Cellular Extracts (Apoptosome)

100 ug of 293 cell S100 extract and 0.25 uM-2 uM of GST-Xiap fusion protein (GST—BIR 3RING, GST—linker BIR2BIR3RING) were co-incubated with serial dilutions of compound (0.02 uM-40 uM). Extracts were activated by adding 1 mM dATP, 0.1 mM ALLN, 133 ug Cytochrome C (final concentrations), and incubating at 37° C. for 25 minutes. All reactions and dilutions used S100 buffer (50 mM Pipes pH 7.0, 50 mM KCl, 0.5 mM EGTA pH 8.0, 2 mM $MgCl_2$ supplemented with 1/1000 dilutions of 2 mg/ml Cytochalisin B, 2 mg/ml Chymotstatin, Leupeptin, Pepstatin, Antipain, 0.1M PMSF, 1M DTT). Final reaction volume was 30 ul. Caspase-3 activity was measured by overlaying 30 ul of a 0.4 mM DEVD-AMC solution. AMC cleavage was measured in a TECAN spectrophotometer at 360 nm excitation and 444 nm emission, on a kinetic cycle of 1 hour with readings taken every 5 minutes. Caspase activity was calculated as $V_o$ of AMC fluorescence/sec. Caspase de-repression by our compounds were compared to fully activated extract and activated extract repressed by the presence of XIAP fusion protein.

Results:

Compounds were also tested in the apoptosome assay and the linker-BIR2/caspase-3 inhibition assay and found to have $IC_{50}$s in the following ranges: A: >10 µM; B: <10 µM; C: <1 µM, as shown in Table 7.

TABLE 7

| Cpd # | Apoptosome XIAP Bir3-RING | Apoptosome XIAP Bir2-Bir3-RING | Caspase-3 Bir2-Bir3-RING |
|---|---|---|---|
| 1 | A | | |
| 2 | A | A | |
| 3 | C | A | B |
| 4 | A | A | A |
| 5 | C | A | B |
| 6 | C | B | A |
| 7 | C | | A |
| 8 | C | A | A |
| 9 | C | A | A |
| 10 | B | A | A |
| 11 | C | | |
| 12 | C | A | A |
| 13 | B | A | A |
| 14 | B | A | A |
| 15 | B | A | A |
| 16 | C | A | A |
| 17 | C | A | A |
| 18 | C | A | A |
| 19 | C | A | A |
| 20 | C | A | A |
| 21 | C | A | A |
| 22 | C | A | A |
| 23 | C | A | A |
| 24 | C | | A |
| 25 | C | | A |
| 26 | A | | A |
| 27 | C | B | A |
| 28 | C | | A |
| 29 | C | B | A |
| 30 | C | A | A |
| 31 | C | A | A |
| 32 | C | | A |
| 33 | C | | A |
| 34 | C | | A |
| 35 | C | | A |

35. Cell Culture and Cell Death Assays

A. Cell Culture

MDA-MD-231 (breast) and H460 (lung) cancer cells were cultured in RPMI1640 media supplemented with 10% FBS and 100 units/mL of Penicillin and Steptomycin.

B. Assays

Survival assays were routinely done on MDA-MB-231 and H460 cells. Cells were seeded in 96 well plates at a respective density of 5000 and 2000 cells per well and incubated at 37° C. in presence of 5% $CO_2$ for 24 hours. Selected compounds were diluted into the media at various concentration ranging from 0.01 uM up to 100 uM. Diluted compounds were added onto the MDA-MB-231 cells. For H460 cells, the compounds were added either alone or in presence of 3 ng/ml of TRAIL. After 72 hours cellular viability was evaluated by MTS based assays. A solution of [3-(4,5-dimethylthiazol-2-yl)-5-(3-carboxymethoxyphenyl)-2-(4-sulfophenyl)-2H-tetrazolium, inner salt; MTS] was added onto cells for a period of 1 to 4 hours. Upon incubation the amount of converted MTS was evaluated using a Tecan spectrophotometer set at 570 nm.

Results:

Various compounds, including compounds 16, 42, 44, 45, 48, 52, 53, 75, 84 and 89, were tested in the MDA-MB-231 breast derived cell line and found to have $EC_{50}$ of <5 μM. Similarly, compounds of this instant invention also demonstrated synergistic killing of H460 breast derived cell line with TRAIL, demonstrating $EC_{50}$s of <10 μM. Also, various compounds 175, 176, 177 and 178 were tested against SKOV-3 cell line, and found to have $EC_{50}$ of <5 μM.

36. Cellular Biochemistry:

A. Detection of XIAP and PARP/Caspase-3/Caspase-9

Detection of cell expressed XIAP and PARP were done by western blotting. Cells were plated at 300 000 cells/well in a 60 mm wells (6 wells plate dish). The next day the cells were treated with selected compound at the indicated concentration. 24 hours later cells the trypsinized cells, pelleted by centrifugation at 1800 rpm at 4° C. The resulting pellet was rinsed twice with cold TBS. The final washed pellet of cells was the lysed with 250 ul Lysis buffer (NP-40, glycerol, 1% of a protease inhibitor cocktail (Sigma)), placed at 4° C. for 25 min with gentle shaking. The cells extract was centrifuged at 4° C. for 10 min at 10 000 rpm. Both the supernatant and the pellet were kept for western blotting analysis as described below. From the supernatant, the protein content was evaluated and about 50 ug of protein was fractionated onto a 10% SDS-PAGE. Pellets were washed with the lysis buffer and re-suspend into 50 ul of Lamelli buffer 1×, boiled and fractionated on SDS-PAGE. Upon electrophoresis each gel was electro-transferred onto a nitrocellulose membrane at 0.6 A for 2 hours. Membrane non-specific sites were blocked for 1 hours with 5% Skim milk in TBST (TBS containing 0.1% (v/v) Tween-20) at room temperature. For protein immunodetection, membranes were incubated overnight with primary antibodies raised against XIAP clone 48 obtained from Becton-Dickison) or PARP: obtained from Cell signal or caspase-3 or caspase-9 primary antibodies were incubated at 4° C. with shaking at dilutions as follows:

XIAP clone 80 (Becton-Dickinson) . . . 1/2500

PARP (Cell Signal) . . . 1/2500

Caspase 3 (Sigma) . . . 1/1500

Caspase 9 (Upstate) . . . 1/1000

Upon overnight incubation, the membranes received three washes of 15 min in TBST then were incubated for 1 hour at room temperature in the presence of a secondary antibody coupled with HRP-enzyme (Chemicon) and diluted at 1/5 000. Upon incubation each membrane were washed three times with TBST and the immunoreactive bands were detected by addition of a luminescent substrate (ECL kit Amersham) and capture of signal on a X-RAY film for various time of exposure. Active compounds were shown to induce the cleavage of PARP and XIAP as well as to translocate XIAP into an insoluble compartment.

37. Hollow Fiber Model

Hollow fiber in vivo model were used to demonstrate in vivo efficacy of selected compounds against selected cell lines as single agent therapy or in combination with selected cytotoxic agents. At day 1, selected cell lines were cultured and the fiber filled at a cell density of about 40,000 cells/fiber. At the day of operation (day 4), three fibers are implanted sub-cutaneous into 28-35 Nu/Nu CD-1 male mice. On day 5, mice start to receive daily injection via sub-cutaneous route of control vehicle or vehicle containing the selected compound at the appropriate concentration and/or injection of cytotoxic agent via intra-peritoneal route. Upon 7 days of non-consecutive treatments, the animals are sacrificed, each fiber is removed and the metabolic viability of the remaining cells determined by MTT assay. Efficacy of the compound is define as the difference between the vehicle-treated animal and the animal treated with the compound alone or the compound given in combination of the cytotoxic agent Compound 54 bis-HCl demonstrated a reduction in MTT signal according to Method 37.

38. Combination Anti-Cancer Therapy In Vivo with Taxotere and BIR Domain Binding Compounds Groups (n=9-10/grp):

Saline/Saline (n=9)

Taxotere (30 mg/kg, ip)/Saline (n=9)

Taxotere (30 mg/kg, ip)/compound 56 (2×5 mg/kg, sc) (n=10)

Female CD-1 nude mice (approximately 20-25 g) were subcutaneously injected with 1×10$^6$ $^H$460 cells in the right flank. Animals were balanced into groups based on tumor size and drug therapy began when tumors were ~30-50 mm$^3$. Animals that had no tumor or that were deemed outliers because of excessive tumor size at this time were removed from the study. The remaining animals received Taxotere (or equivalent volume of vehicle) at 30 mg/kg, ip 2 times, one week apart. The compound was given two times per day (at 10 mg/kg, sc, approximately 6 hrs apart), starting at the time of Taxotere, and continuing daily for the duration of the experiment. If dehydration occurred, animals received sc fluids (0.5 ml). Tumor size was measured three times per week. Health assessments were performed at the time of the compound's delivery.

Results:

At a cumulative dose of 20 mg/kg, sc per day compound 54 bis-HCl had anti-tumor activity in combination with Taxotere. The compound 54 bis-HCl resulted in tumor suppression when combined with the chemotherapy agent Taxotere.

Without wishing to be bound by theory, we believe that the compounds of the present invention bind within the BIR domains of the IAPs. More specifically, compounds of the instant invention bind XIAP and prevent the interaction of the activated caspases with XIAP. Specifically, our data supports the notion that the compounds of the present invention can significantly reduce or essentially eliminate the interaction of XIAP with active caspase-9 and with active caspase-3. Since caspase-7 can also bind to the BIR2 site of XIAP, it is possible that the compounds can also prevent activated caspase-7 from binding to XIAP. Thus one possible mechanism of action of the compounds is to bind to the BIR motif and prevent the interaction with the caspase. In doing so the ratio of active/non-bound caspase in the cells is believed to increase and prime the cells to apoptosis. Alternatively, the compounds of the present invention may bind to the IAPs and modify the global protein conformation and thus modulate its half-life or again prevent XIAP from binding to other proteins. For IAPs having RING domain/E3 ligase activity, the mechanism of action of the compounds may be to prevent the interaction of yet other unknown protein to interact with IAP domains and possibly preventing or inducing the ubiquination of these proteins.

24. Pharmacokinetic Studies

Selected compounds were dissolved into normal saline (0.9% NaCl) at 10 mg/ml and injected at 40 mg/Kg under sub-cutaneous route of administration. At each selected time point, blood sample of three mice were taken and the plasma fraction was prepared and kept frozen until analysis by liquid chromatography/electrospray mass spectrometry (LC/MS). At the day of analysis, plasma samples were thawed and extracted by liquid-liquid extraction procedure using 75% acetonitrile-water solution. Each extracted sample was analyzed for the presence of the selected compound on an Agilent 1100 LC/MS equipped with a C18 reverse-phase column. Quantitation of the compound in the plasma was done relatively to a plasma standard curve using of the selected compound. Upon determining the plasma concentration for each time point, the calculated area under the curve (AUC) and the peak at maximum concentration ($C_{max}$) were calculated using Kinetica Version 4.2 software (Innaphase).

Select compounds of the instant invention were shown to display pharmaceutically acceptable aqueous solubility and PK parameters when administered SC, IV, or PO.

Other Embodiments

From the foregoing description, it will be apparent to one of ordinary skill in the art that variations and modifications may be made to the invention described herein to adapt it to various usages and conditions. Such embodiments are also within the scope of the present invention.

All publications mentioned in this specification are hereby incorporated by reference.

All literature, patents, published patent applications cited herein are hereby incorporated by reference.

While specific embodiments have been described, those skilled in the art will recognize many alterations that could be made within the spirit of the invention, which is defined solely according to the following claims:

We claim:

1. A method of inhibiting apoptosis in a cell comprising contacting the cell with a compound of Formula 1.2a,

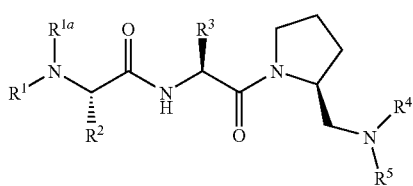

wherein:

n is 0 or 1;

m is 0, 1, or 2;

Y is NH, O or S;

$R^1$ is $C_1$-$C_6$ optionally substituted with one $R^6$ substituent, $R^{1a}$ is
  1) H, or
  2) $C_1$-$C_6$ alkyl optionally substituted with one $R^6$ substituent;

$R^2$ is $C_1$-$C_6$ optionally substituted with one or more halogens;

$R^3$ is $C_1$-$C_6$ alkyl optionally substituted with one $R^6$ substituent;

$R^4$ is
  1) H
  2) —C(O)(O)$_n$—$R^{11}$,
  3) —C(=Y)NR$^8$R$^9$, or
  4) —S(O)$_2$—$R^{11}$ $R^5$ is
  1) $C_1$-$C_6$ alkyl,
  2) aryl,
  3) heteroaryl,
  4) $C_1$-$C_7$ cycloalkyl, or
  5) heterocyclyl;

wherein the alkyl and cycloalkyl are optionally substituted with one or more $R^6$ substituents;

and wherein the aryl, heteroaryl, and heterocyclyl are optionally substituted with one or more $R^{10}$ substituents;

$R^6$ is:
  1) halogen,
  2) haloalkyl,
  3) $C_1$-$C_6$ alkyl,
  4) $C_3$-$C_7$ cycloalkyl,
  5) aryl,
  6) heteroaryl,
  7) heterocyclyl,
  8) —OR$^7$,
  9) —S(O)$_m$R$^7$,
  10) —NR$^8$R$^9$,
  11) —COR$^7$,
  12) —C(O)OR$^7$
  13) —OC(O)R$^7$,
  14) —SC(O)R$^7$,
  15) —CONR$^8$R$^9$,
  16) —S(O)$_2$NR$^8$R$^9$, or
  17) —NC(=Y)NR$^8$R$^9$ wherein the aryl, heteroaryl, and heterocyclyl are optionally substituted with one or more $R^{10}$ substituents;

$R^7$ is:
  1) H,
  2) haloalkyl,
  3) $C_1$-$C_6$ alkyl,
  4) $C_3$-$C_7$ cycloalkyl,
  5) aryl,
  6) heteroaryl,
  7) heterocyclyl, or
  8) —C(=Y)NR$^8$R$^9$, wherein the alkyl and cycloalkyl are optionally substituted with one or more $R^6$ substituents, and the aryl, heteroaryl, and heterocyclyl, are optionally substituted with one or more $R^{10}$ substituents;

$R^8$ and $R^9$ are each independently
  1) H,
  2) haloalkyl,
  3) $C_1$-$C_6$ alkyl,
  4) $C_3$-$C_7$ cycloalkyl,
  5) aryl,
  6) heteroaryl,
  7) heterocyclyl,
  8) —C(O)R$^{11}$,
  9) —C(O)YR$^{11}$, or
  10) —SO$_2$R$^{11}$, wherein the alkyl and cycloalkyl are optionally substituted with one or more $R^6$ substituents, and wherein the aryl, heteroaryl, and heterocyclyl are optionally substituted with one or more $R^{10}$ substituents;

or $R^8$ and $R^9$ together with the nitrogen atom to which they are bonded form a five, six, or seven membered heterocyclic ring optionally substituted with one or more $R^6$ substituents;

$R^{10}$ is
  1) halogen,
  2) NO$_2$,
  3) CN,
  4) $C_1$-$C_6$ alkyl,
  5) $C_3$-$C_7$ cycloalkyl,
  6) haloalkyl,
  7) —OR$^7$,
  8) —NR$^8$R$^9$,
  9) —SR$^7$,
  10) —COR$^7$,
  11) —C(O)OR$^7$,
  12) —S(O)$_m$R$^7$,
  13) —CONR$^8$R$^9$, or
  14) —SO$^2$NR$^8$R$^9$, wherein the alkyl is optionally substituted with one or more $R^6$ substituents;

and $R^{11}$ is
  1) haloalkyl,
  2) $C_1$-$C_6$ alkyl,
  3) $C_3$-$C_7$ cycloalkyl,
  4) aryl,
  5) heteroaryl, 6) heterocyclyl, or
7) heterobicyclyl,
wherein the alkyl and cycloalkyl are optionally substituted with one or more $R^6$ substituents;
and wherein the aryl, heteroaryl, and heterocyclyl are optionally substituted with one or more $R^{10}$ substituents;
or a salt thereof
wherein the cell is a breast cancer cell, lung cancer cell, or ovarian cancer cell.

2. The method of claim 1, wherein the cell is in a subject, and the cell is contacted with the compound of Formula I or salt thereof by administering the compound of Formula I or salt thereof to the subject.

3. The method of claim 2, further comprising administering to the subject a chemotherapeutic agent prior to, simultaneously with, or after administration of the compound of Formula I or salt thereof.

4. The method of claim 2, further comprising administering to the subject death receptor agonist prior to, simultaneously with, or after administration of the compound of Formula I or salt thereof.

5. The method of claim 3, wherein the death receptor agonist is TRAIL.

6. The method of claim 3, in which the death receptor agonist is administered in an amount that produces a synergistic effect.

7. The method of claim 2, in which the subject is a human.

8. The method of claim 1, wherein the compound is a pharmaceutically acceptable salt.

9. The method of claim 1, wherein $R^5$ is a $C_{1-3}$ alkyl optionally substituted with one $R^6$ substituent, and $R^6$ is selected from aryl, heteroaryl, and heterocyclyl, optionally substituted with one or more $R^{10}$ substituents.

10. The method of claim 1, wherein $R^5$ is a $C_{1-3}$ alkyl substituted with one $R^6$ substituent, and $R^6$ is phenyl optionally substituted with one or more $R^{10}$ substituents.

11. The method of claim 1, wherein
$R^4$ is $C(O)(O)_n-R^{11}$, wherein n=0;
and $R^{11}$ is
1) heteroaryl,
2) heterocyclyl, or
3) heterobicyclyl;
wherein the heteroaryl, heterocyclyl, and heterobicyclyl are optionally substituted with one or more $R^{10}$ substituents.

12. The method of claim 1, wherein $R^4$ is $C(O)(O)_n-R^{11}$; $R^{11}$ is aryl optionally substituted with one or more $R^{10}$ substituents; and n=0.

13. The method of claim 1, wherein $R^4$ is $C(O)(O)_n-R^{11}$; $R^{11}$ is heteroaryl optionally substituted with one or more $R^{10}$ substituents; and n=0.

14. The method of claim 1, wherein $R^4$ is $C(O)(O)_n-R^{11}$; $R^{11}$ is $C_{1-6}$ alkyl optionally substituted with one or more $R^6$ substituents; and n=0.

15. The method of claim 14, wherein $R^6$ is selected from the group consisting of $C_{1-6}$ alkyl, aryl, $NR^8R^9$, $NR^8S(O)_2R^{11}$, $C(O)OR^7$, and $NC(Y)NR^8R^9$, wherein the aryl is optionally substituted with one or more $R^{10}$ substituents.

16. The method of claim 15, wherein
$R^6$ is $NR^8R^9$;
$R^8$ is hydrogen; and
$R^9$ is
1) haloalkyl,
2) $C_1-C_6$ alkyl,
3) $C_3-C_7$ cycloalkyl,
4) aryl,
5) heteroaryl,
6) heterocyclyl,
7) heterobicyclyl,
8) $-C(O)R^{11}$,
9) $-C(O)Y-R^{11}$, or
10) $-S(O)_2-R^{11}$;
wherein the alkyl and cycloalkyl are optionally substituted with one or more $R^6$ substituents;
and wherein the aryl, heteroaryl, heterocyclyl, and heterobicyclyl are optionally substituted with one or more $R^{10}$ substituents.

17. The method of claim 1, wherein $R^{1a}$ is H and $R^1$ is a $C_1-C_3$ alkyl.

18. The method of claim 1, wherein $R^2$ is a $C_1-C_3$ alkyl.

19. The method of claim 1, wherein $R^3$ is a $C_1-C_6$ alkyl optionally substituted with one or more $R^6$ substituents.

20. The method of claim 1, wherein the compound is:

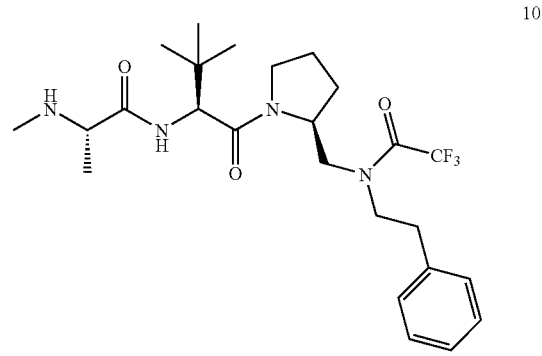

10

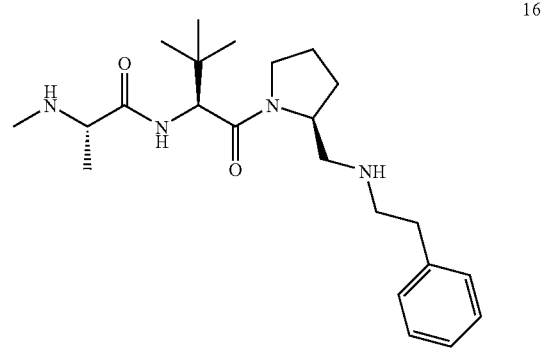

16

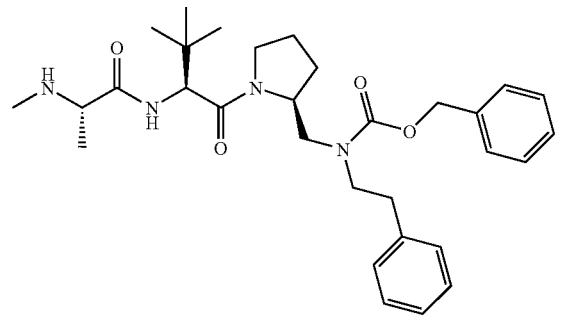

26

27
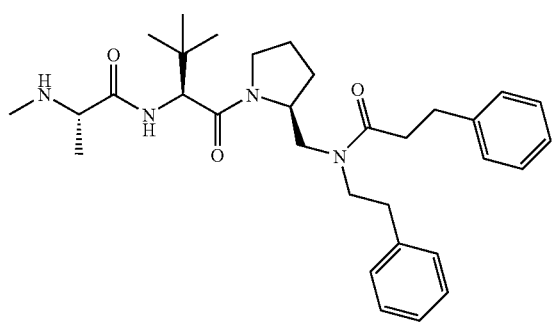
28
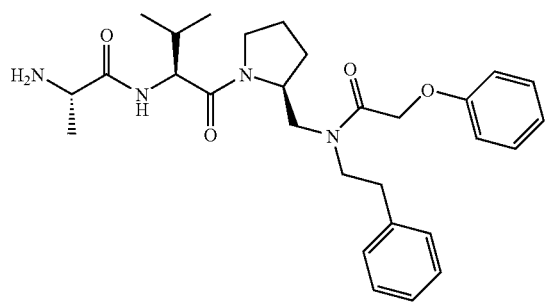
32
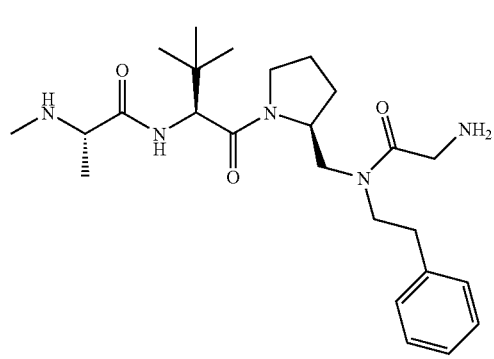
33
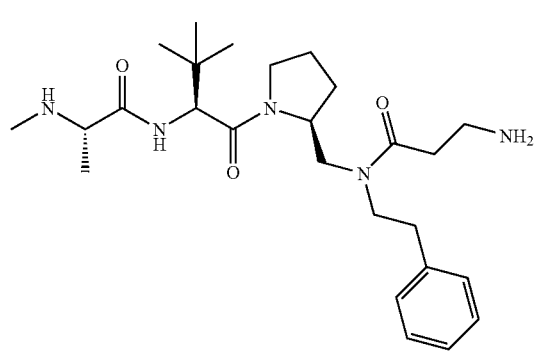
34
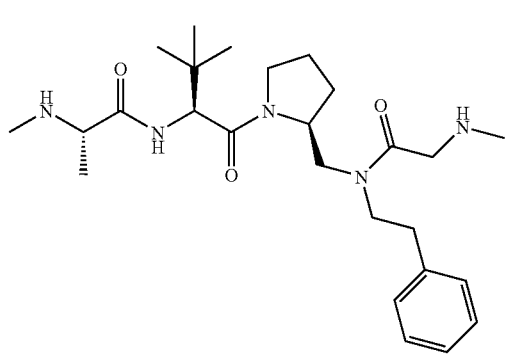
35
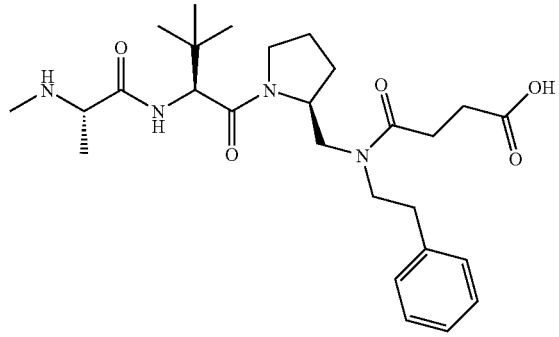
36
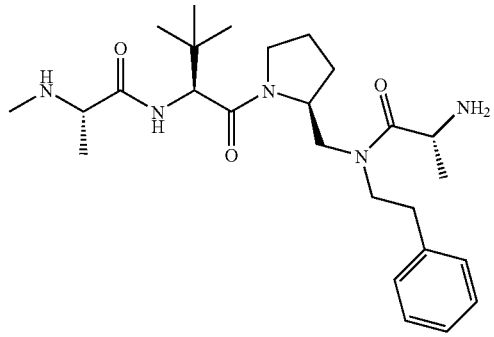
37
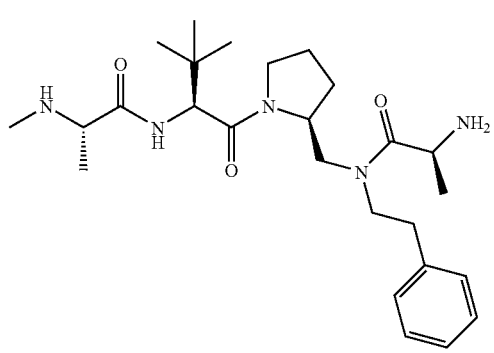

38
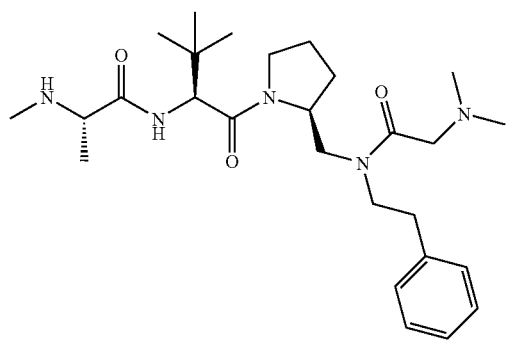
39
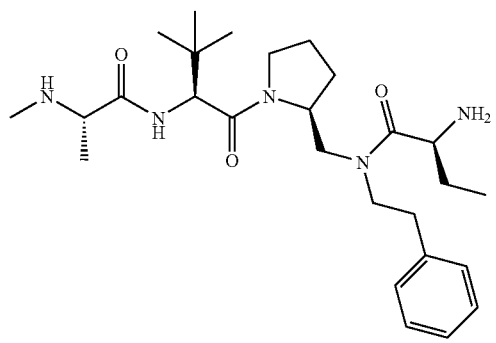
40
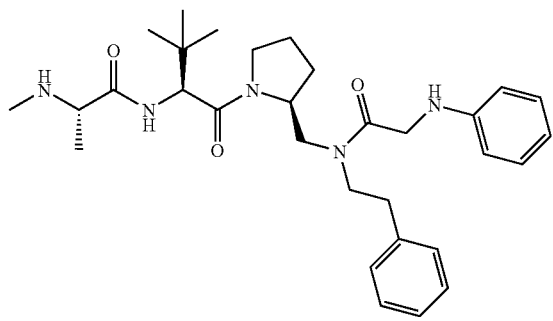
41
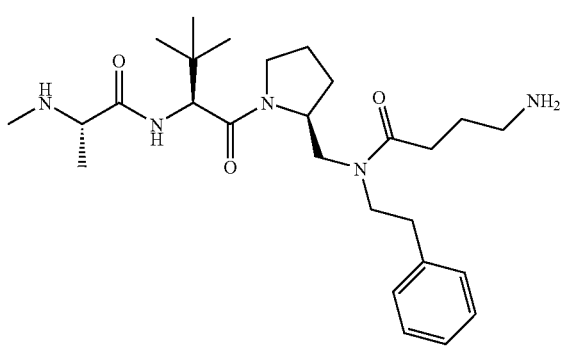
42
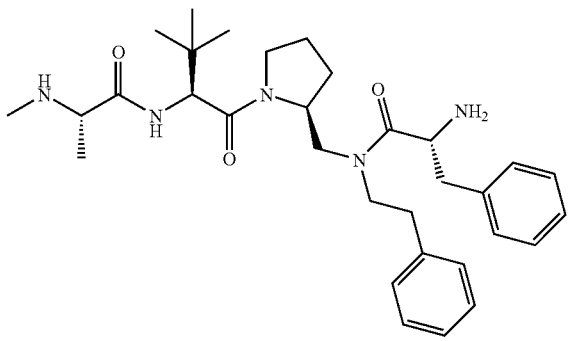
43
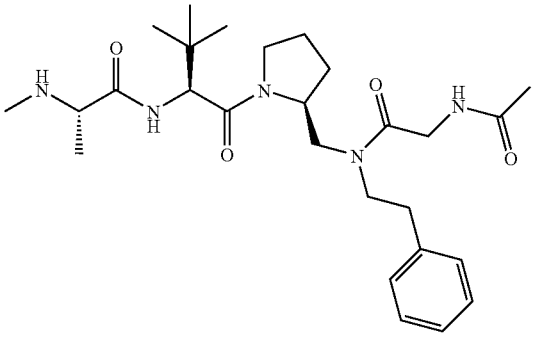
44
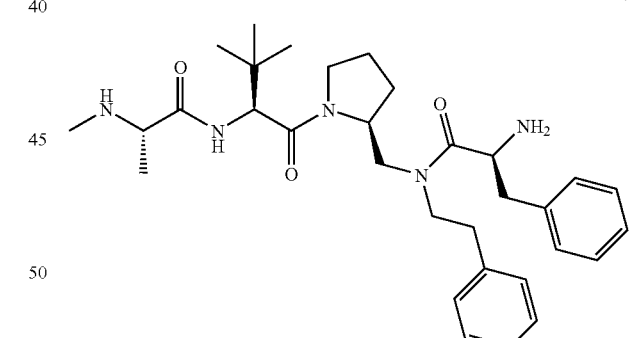
45
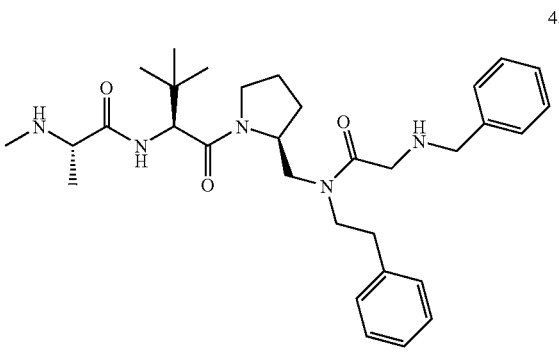

227
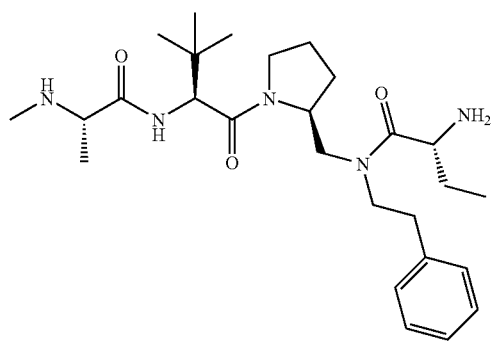
46
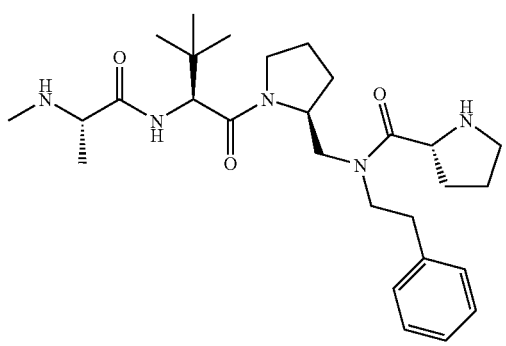
50
47
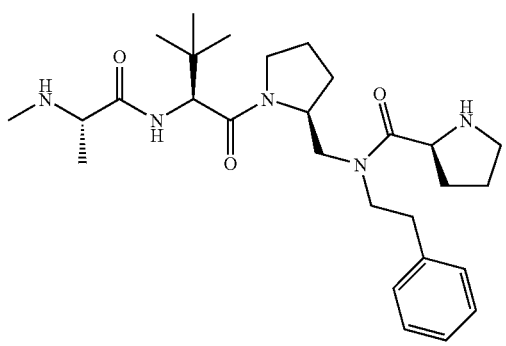
51
228
48
52
49
53

54
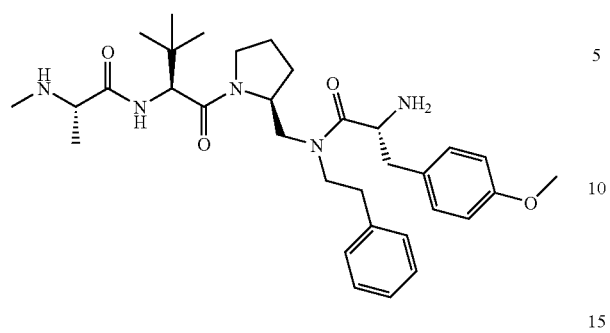
55
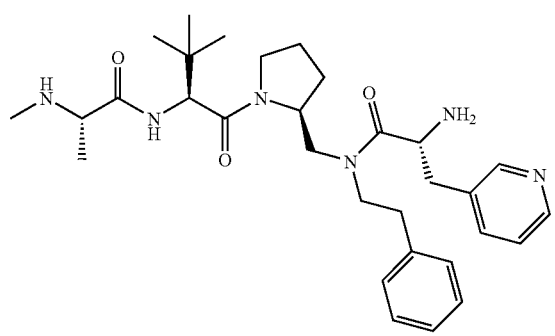
56
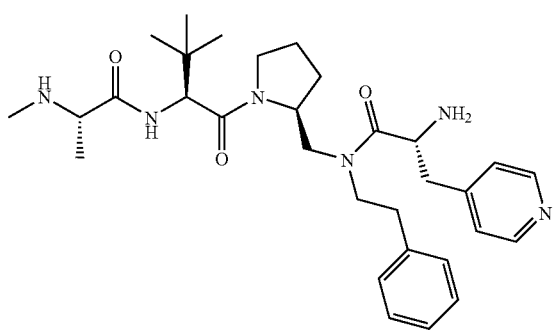
57
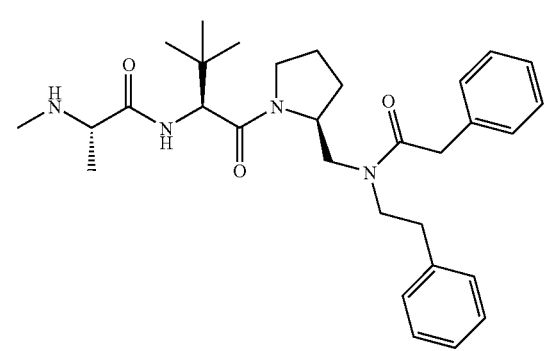
58
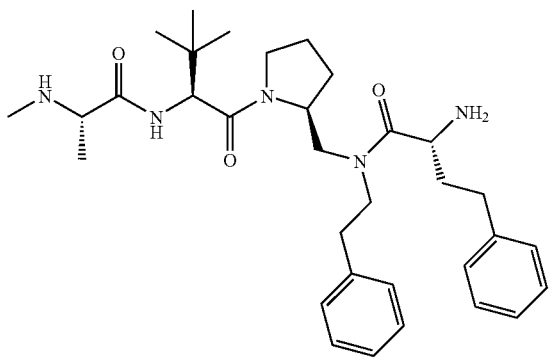
59
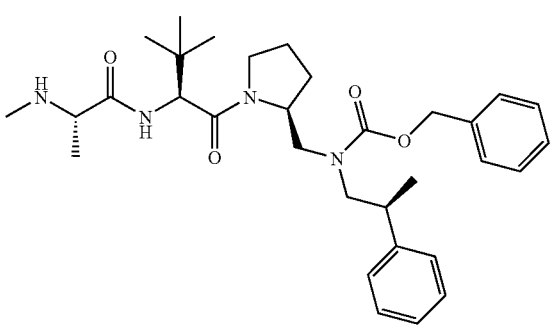
60
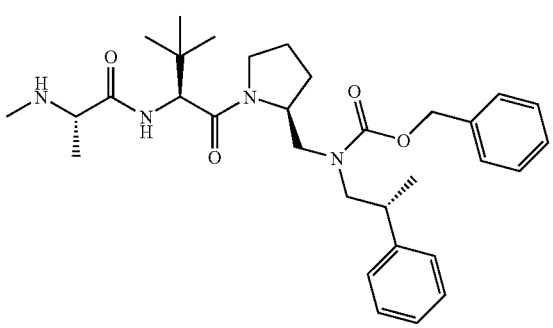
69
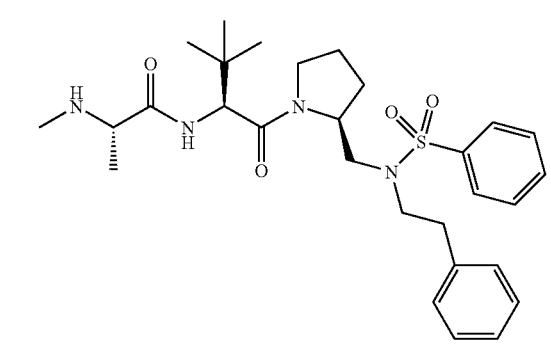

231
-continued
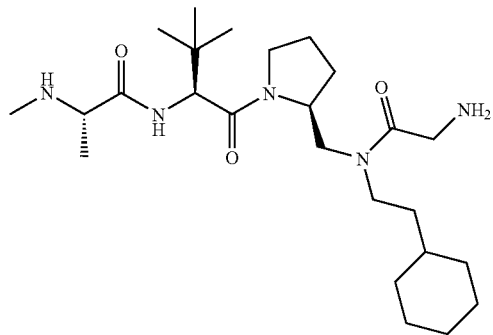
71
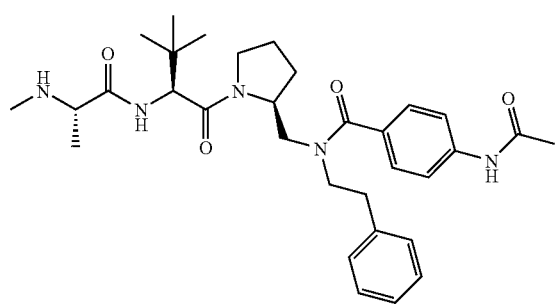
72
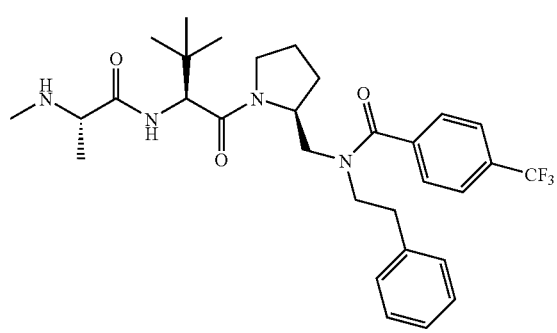
73
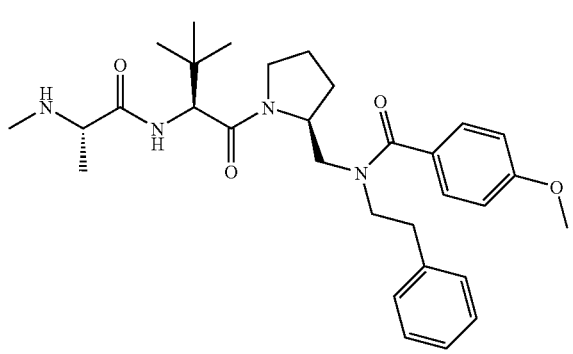
74
232
-continued
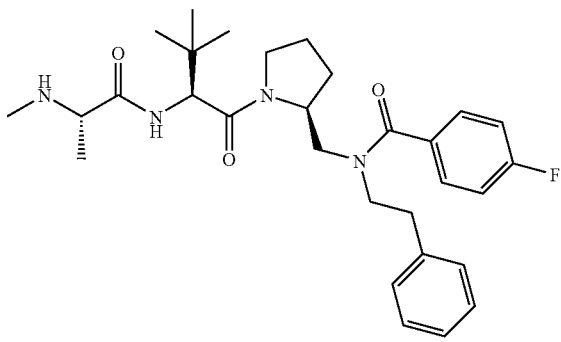
75
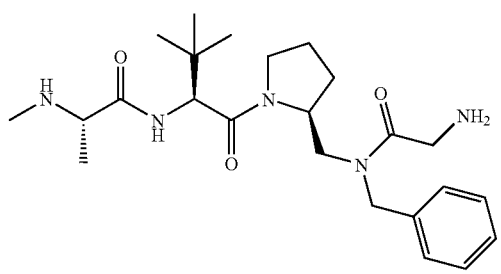
76
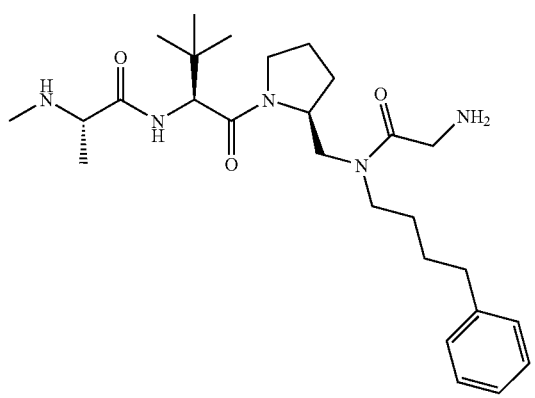
77
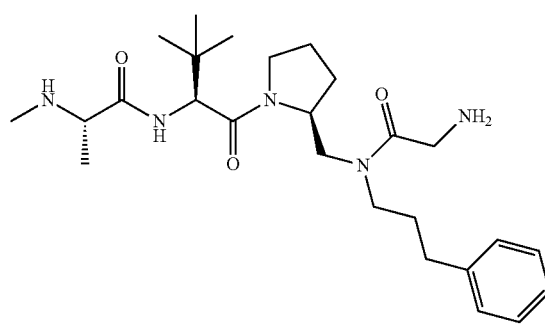
78

233
-continued
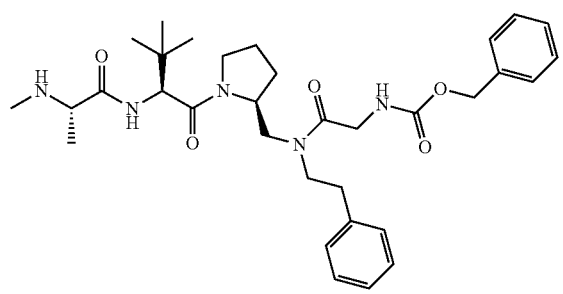
80
82
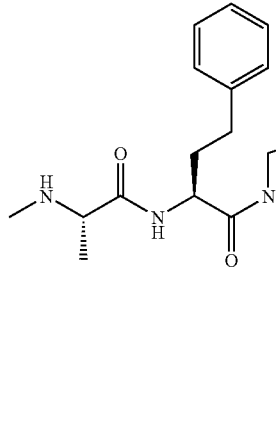
83
84
234
-continued
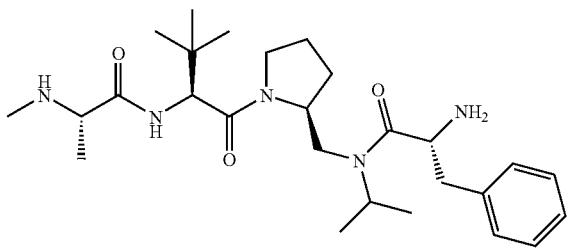
85
86
87
88
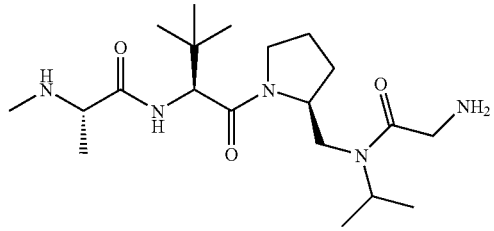
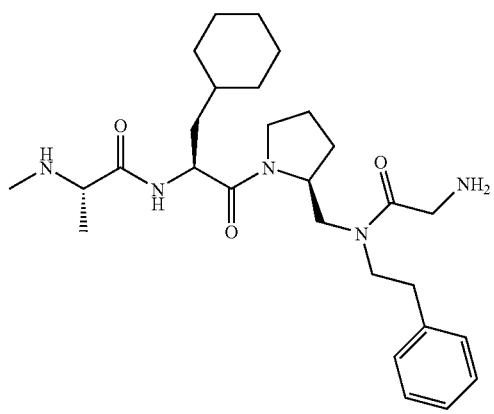

235 -continued

89

90

91

92

236 -continued

93

94

95

96

97 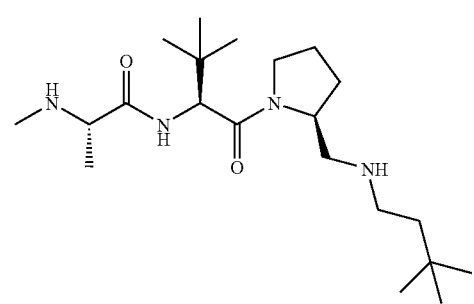
98 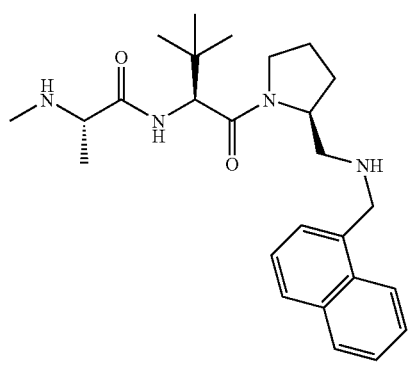
99 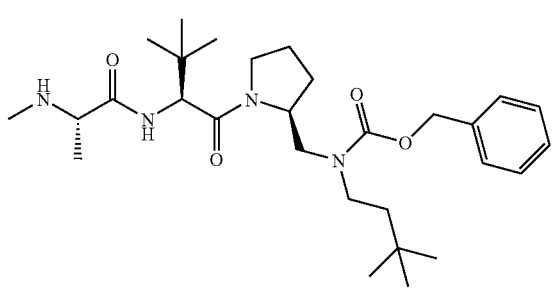
100 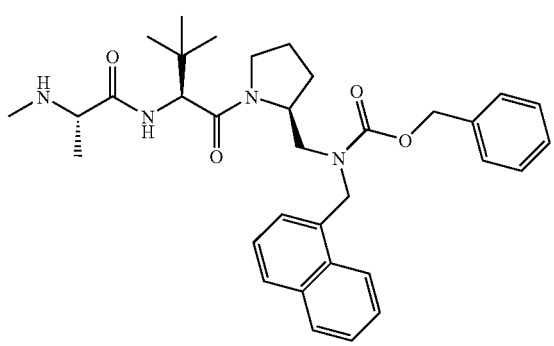
101 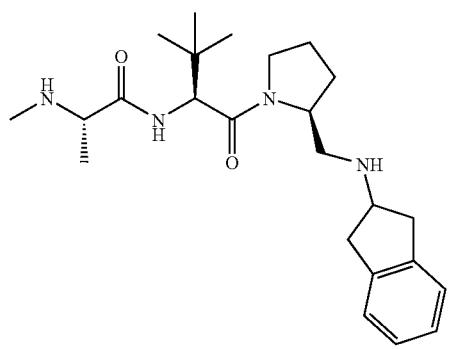
102 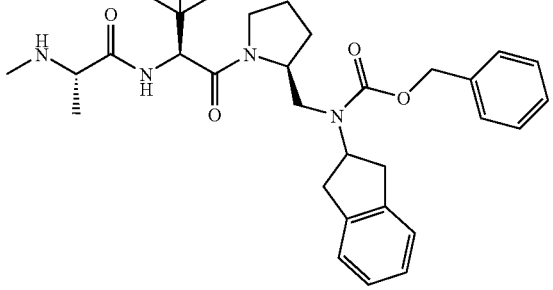
103 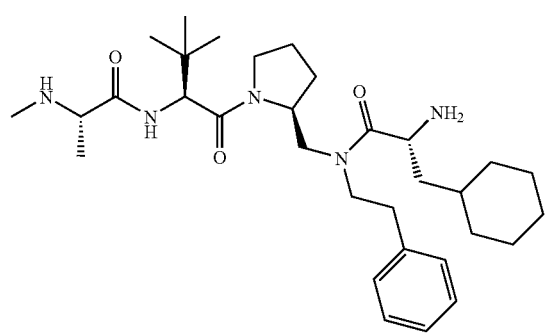
104 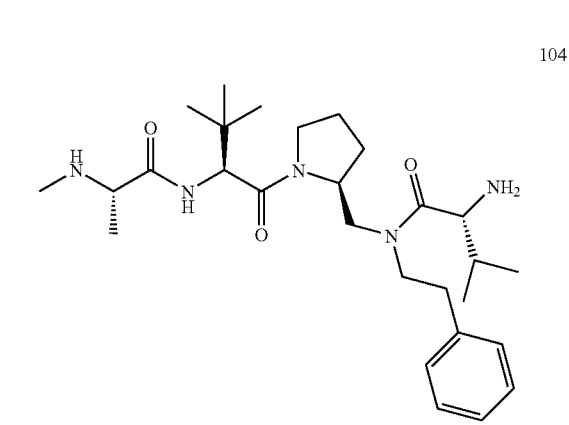
105 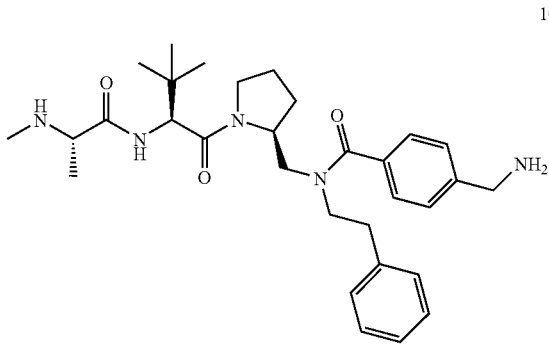

106
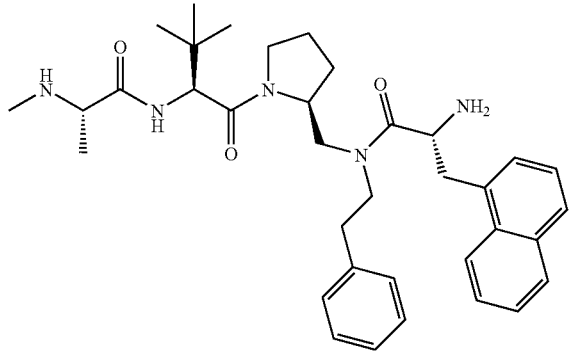
107
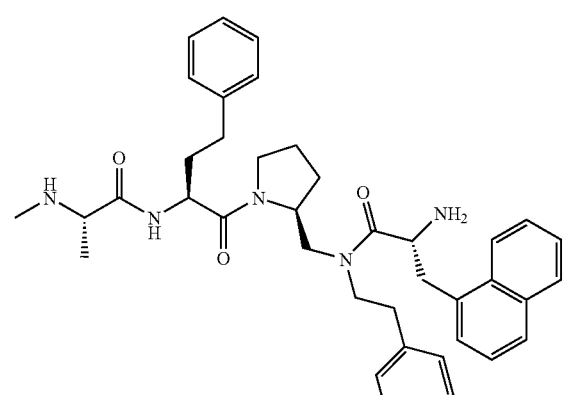
108
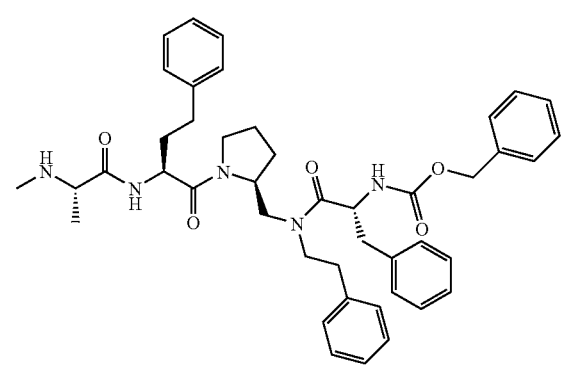
109
110
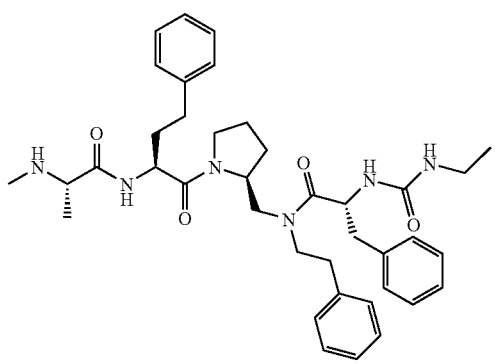
111
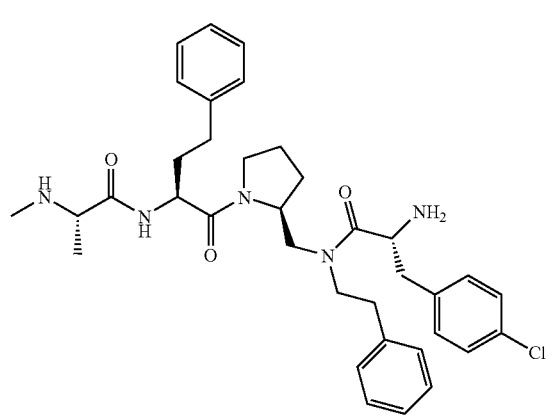
112
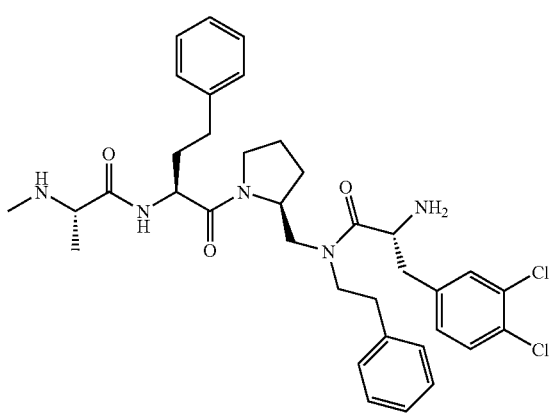

113
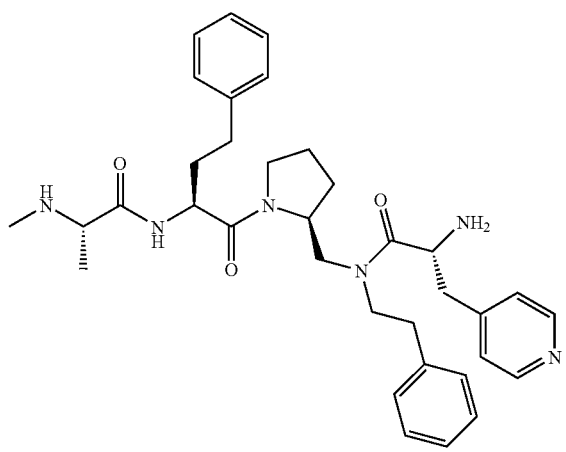
114
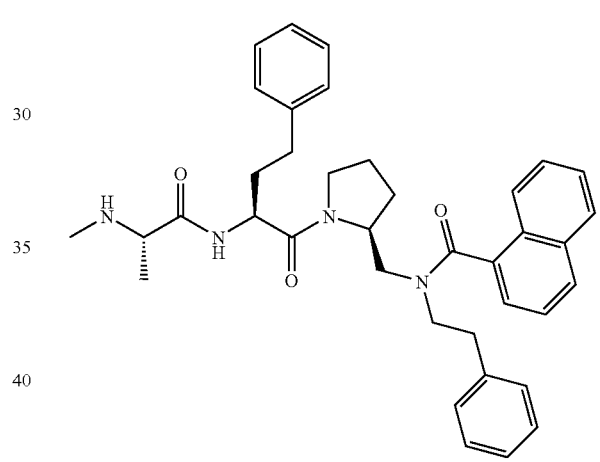
115
116
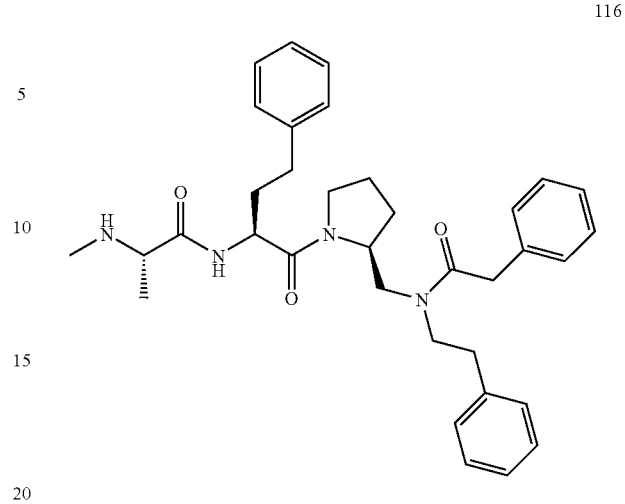
117
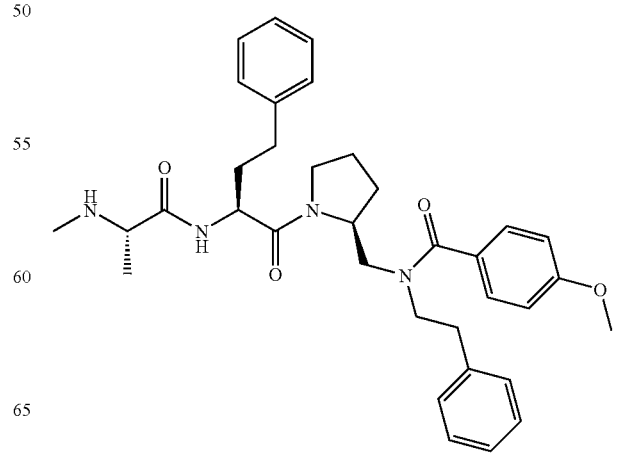
119

243
-continued
120
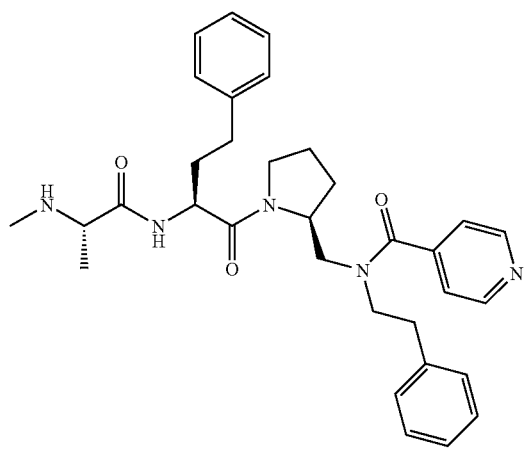
121
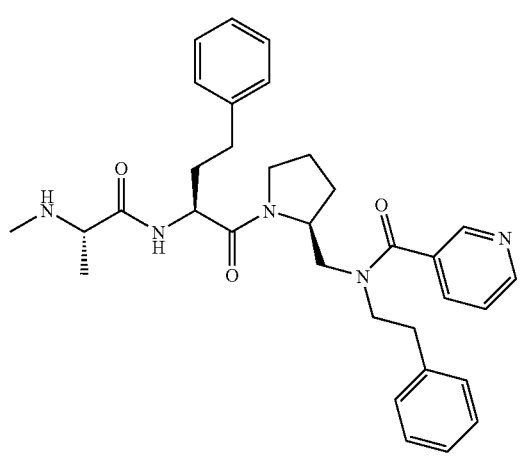
122
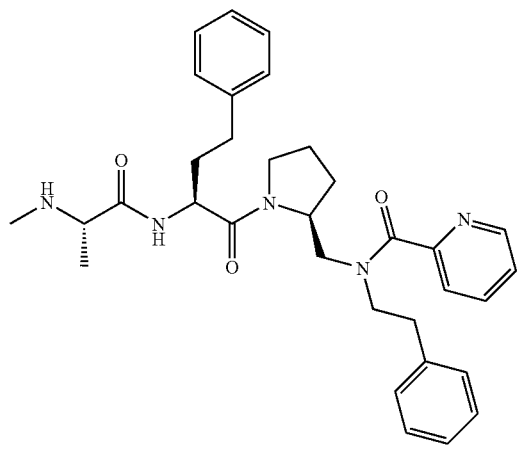
244
-continued
124
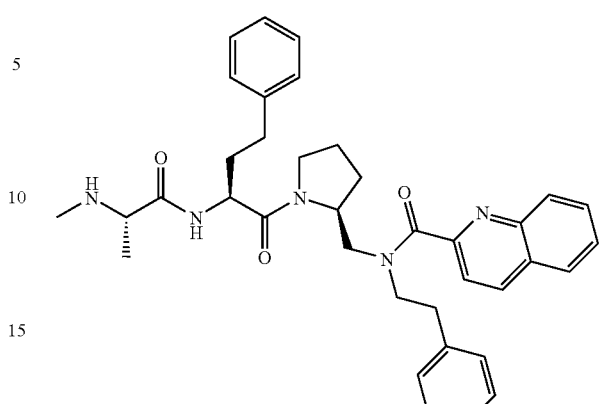
125
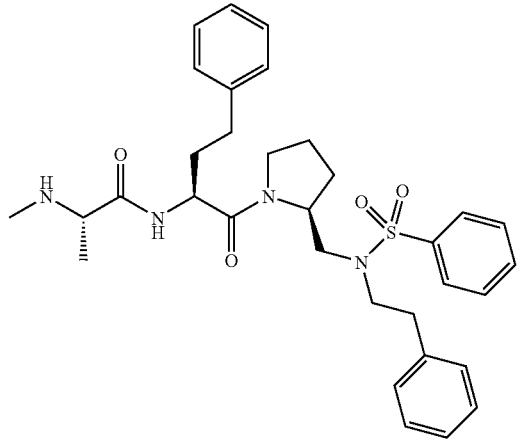
128
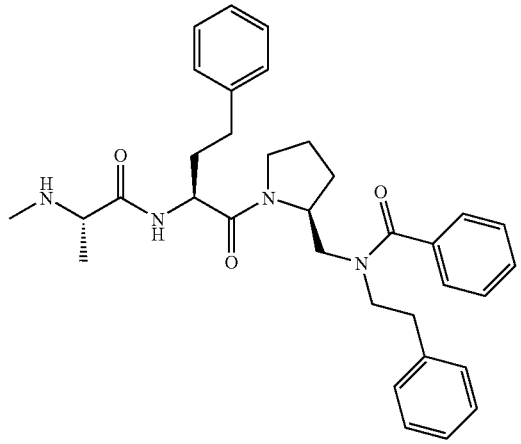

129
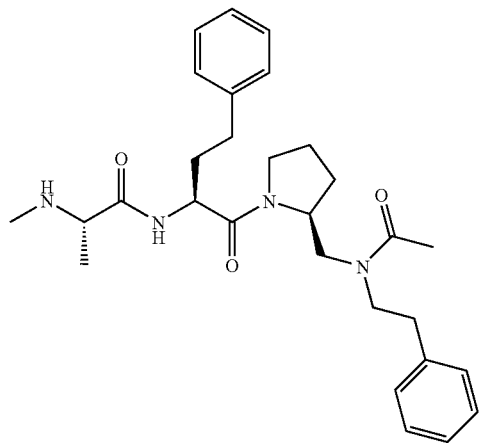
130
133
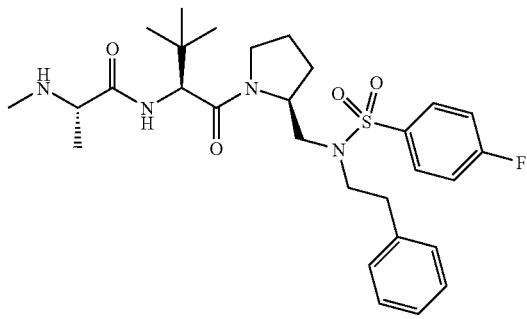
134
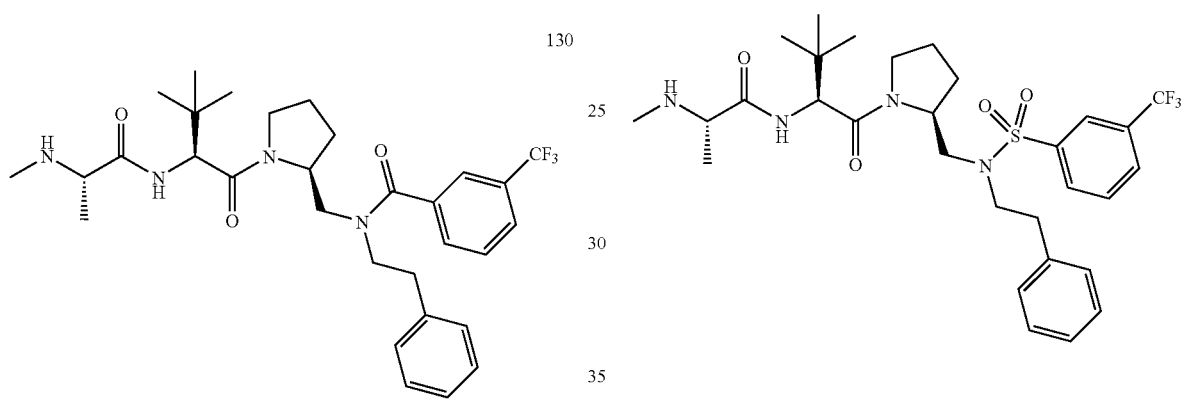
131
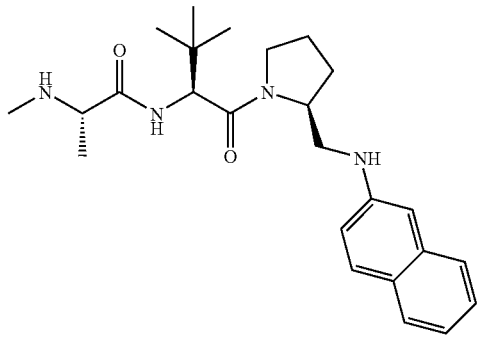
135
132
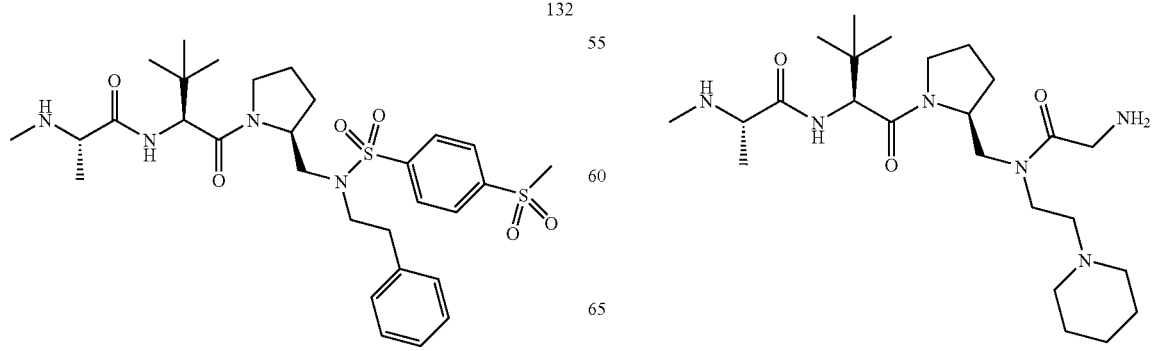
136

137
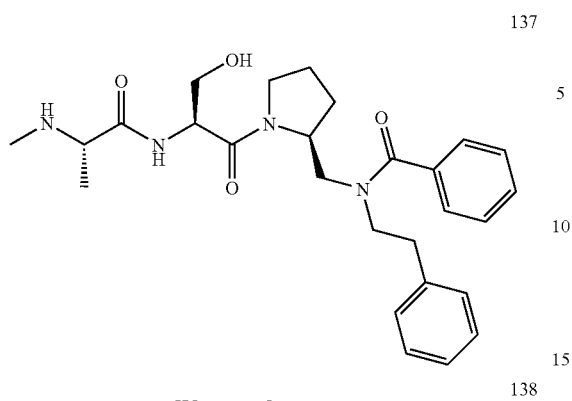
141
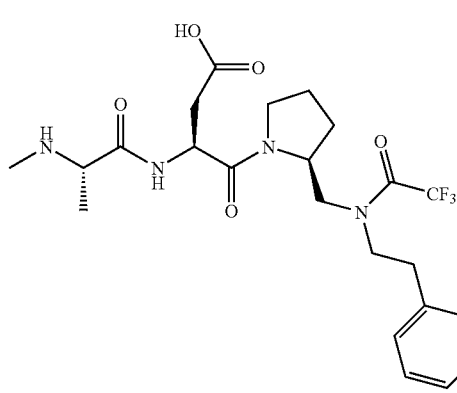
138
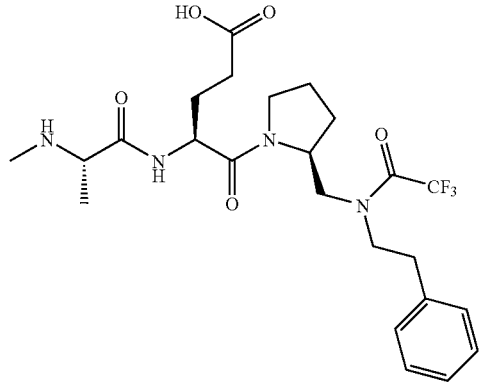
142
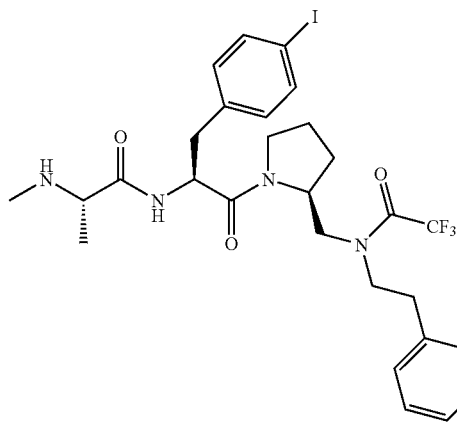
139
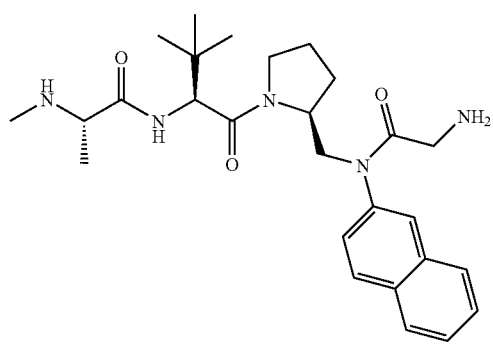
144
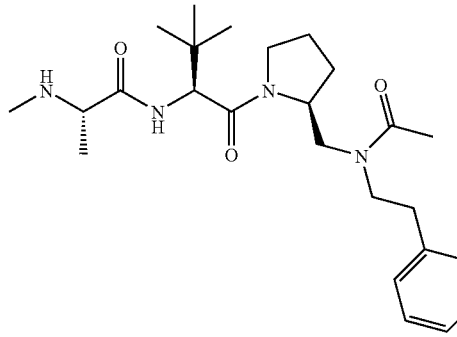
140
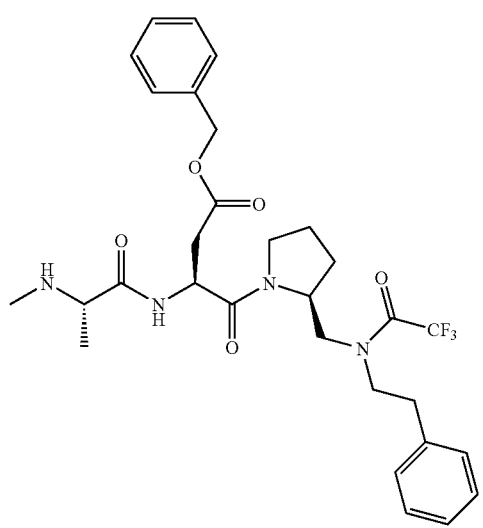
145
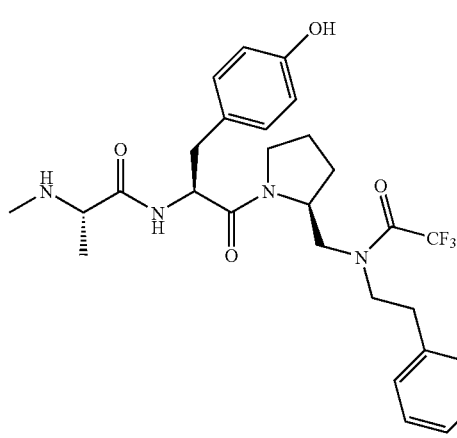

146
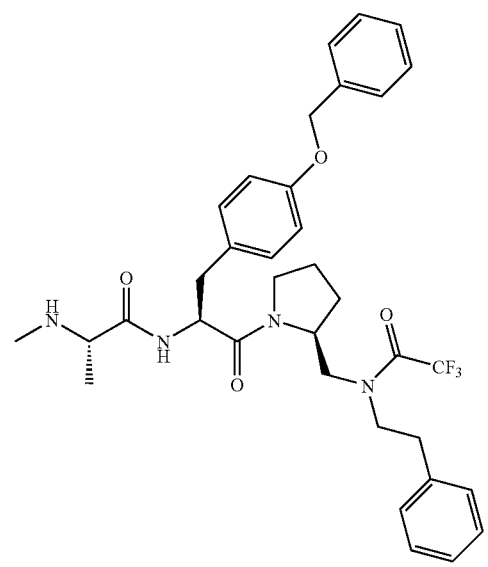
147
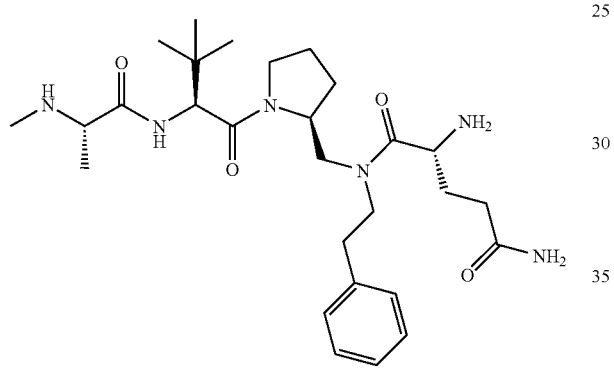
148
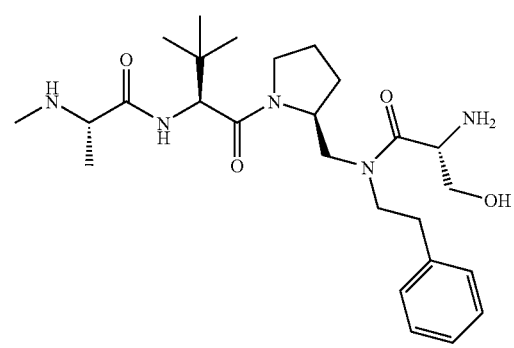
149
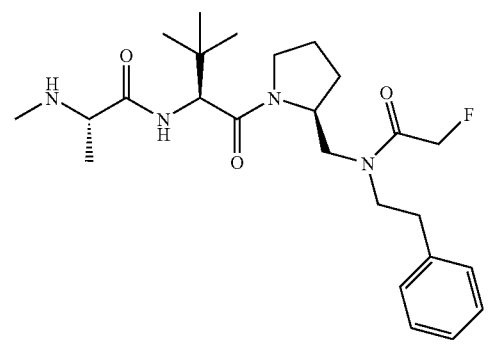
150
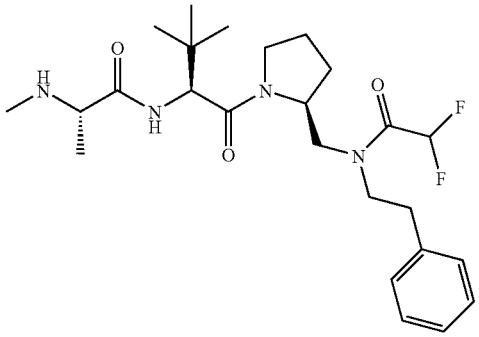
151
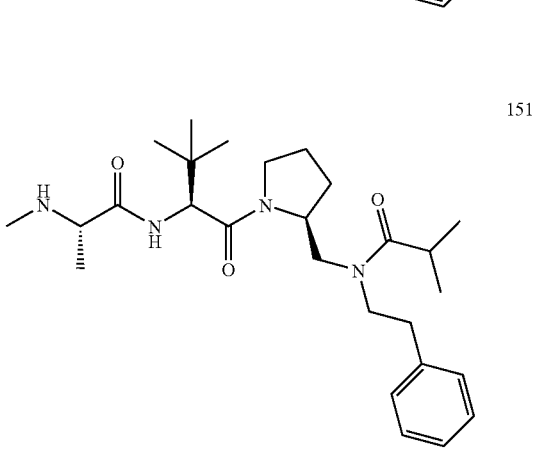
152
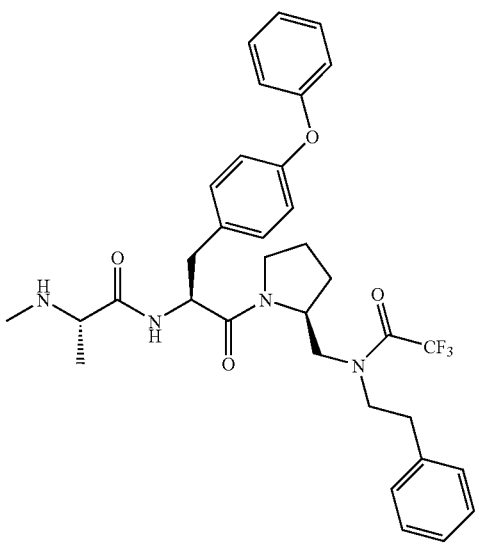
154
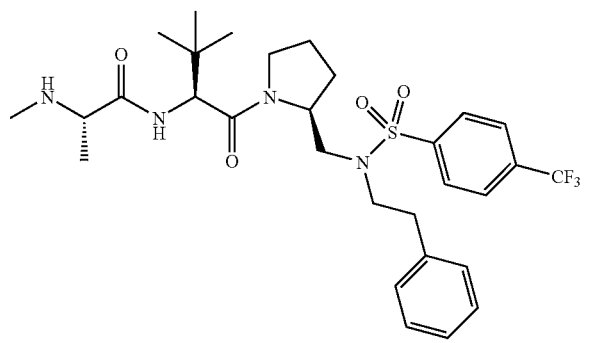

251
-continued
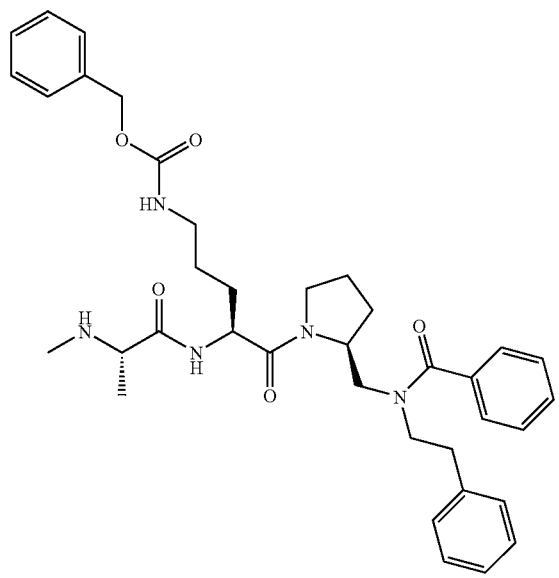
155
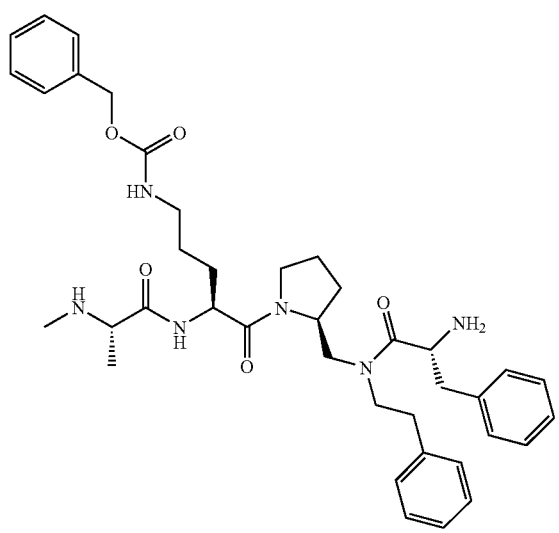
156
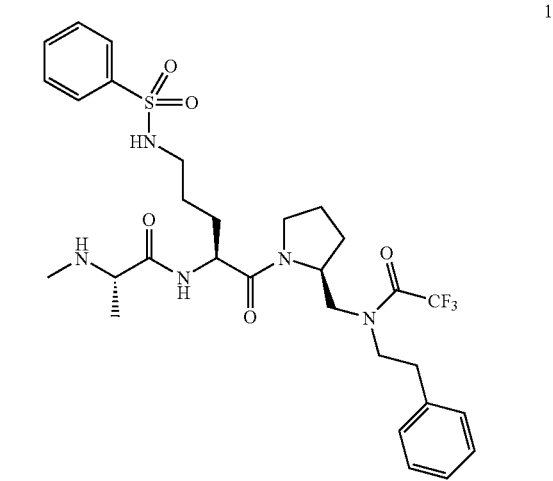
157
252
-continued
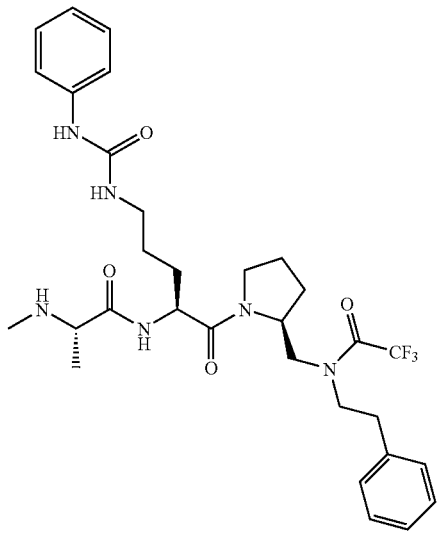
158
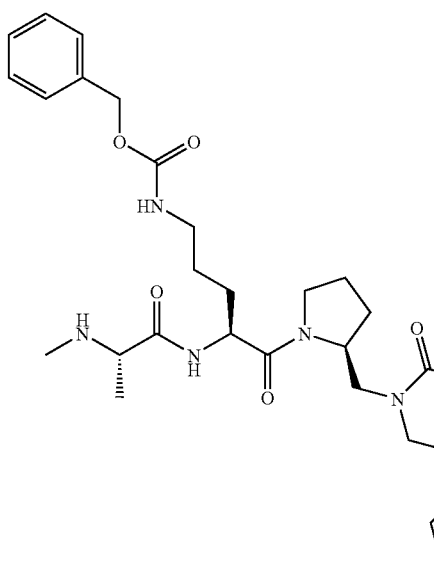
159
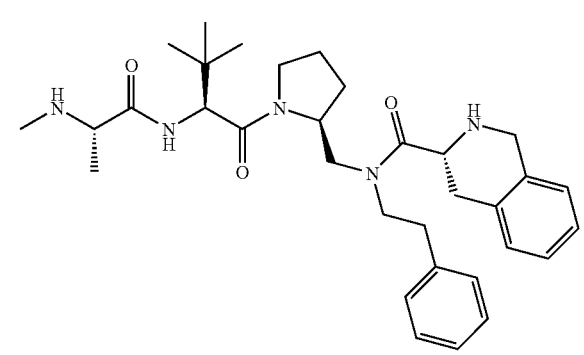
160

253
-continued
161
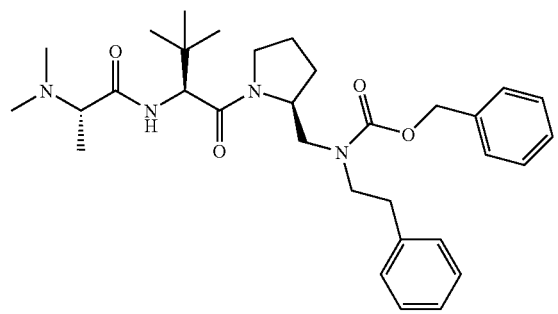
162
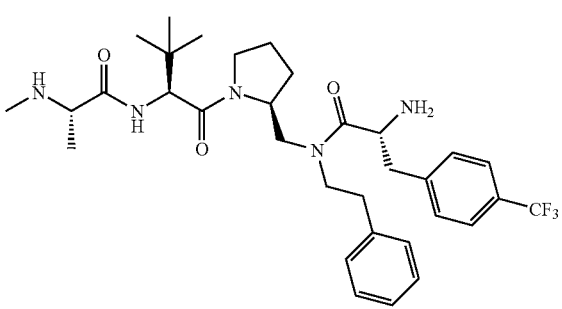
163
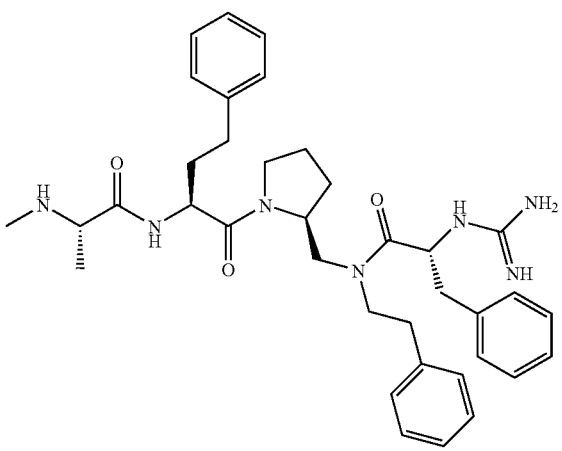
167
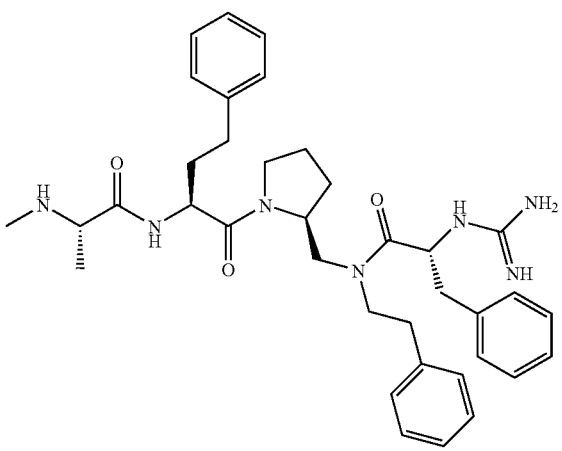
254
-continued
169
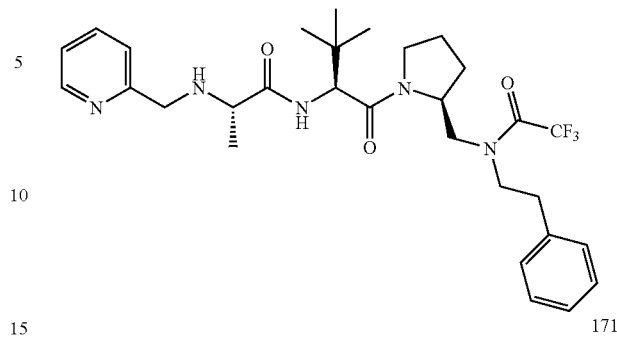
171
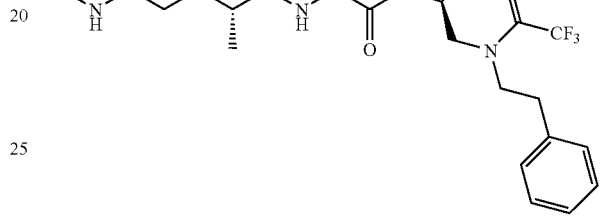
or a salt thereof.
21. The method of claim 1, wherein the compound is:
120
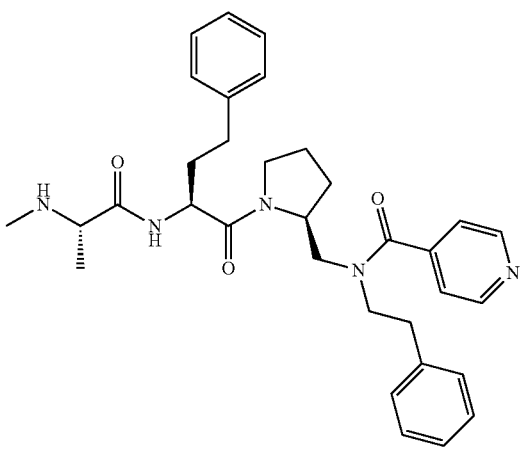
121
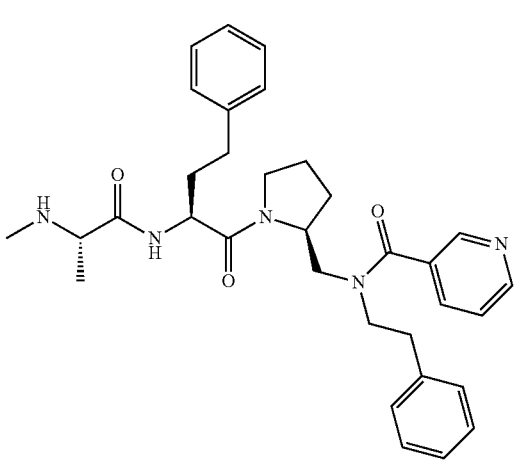

-continued
122
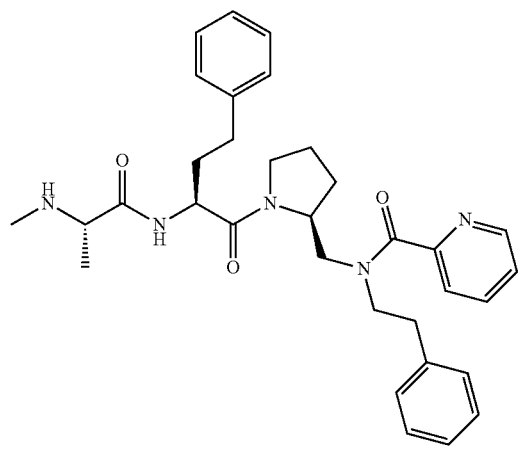
or
123
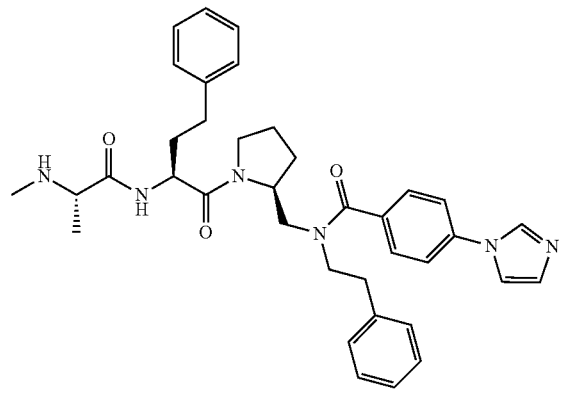
or
124
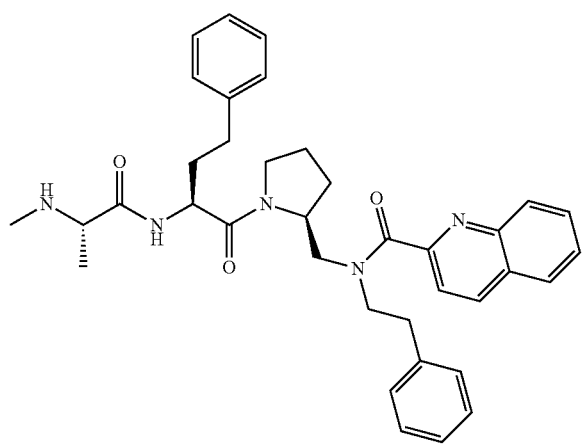
or a salt thereof.
22. The method of claim 1, wherein the compound is:
32
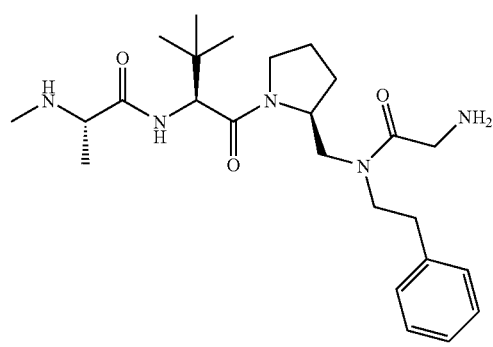
34
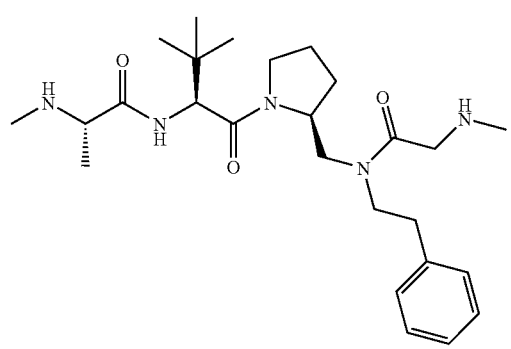
36
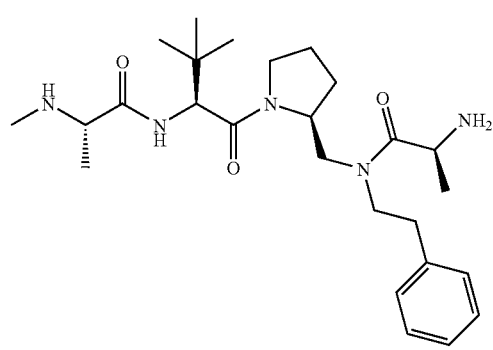
37

38
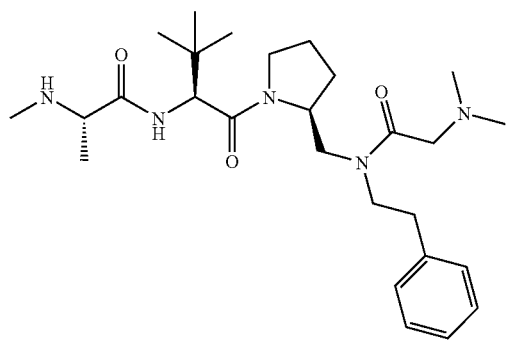
39
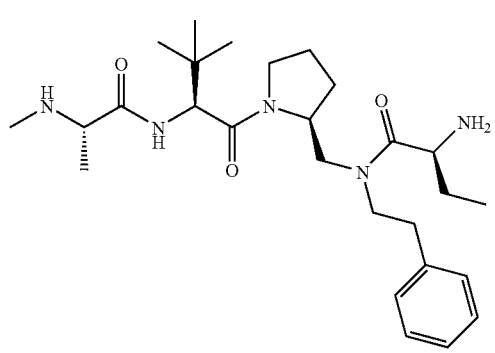
41
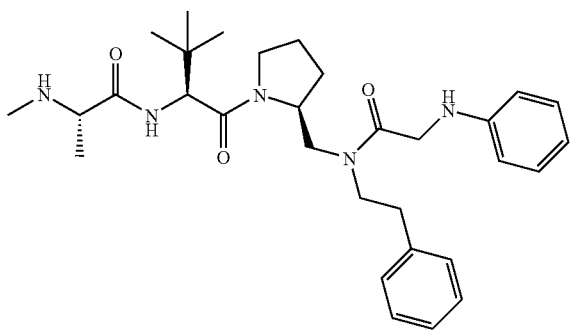
42
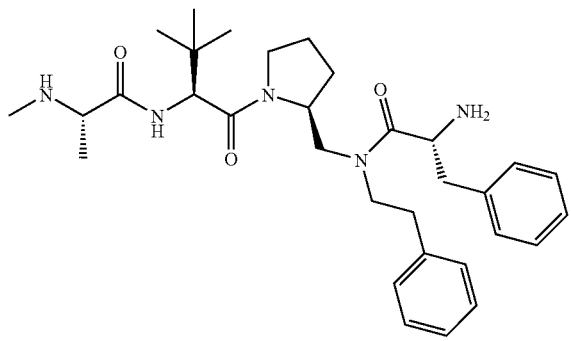
43
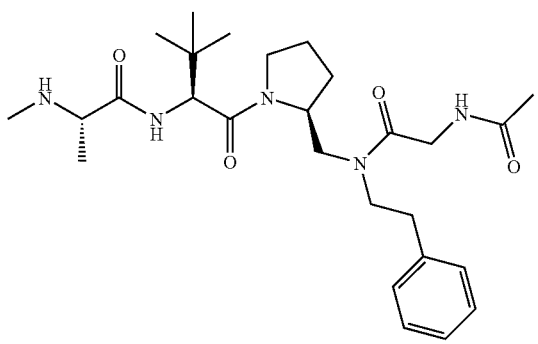
44
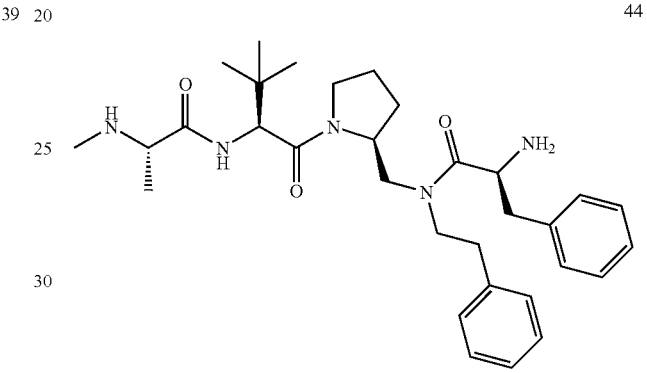
45
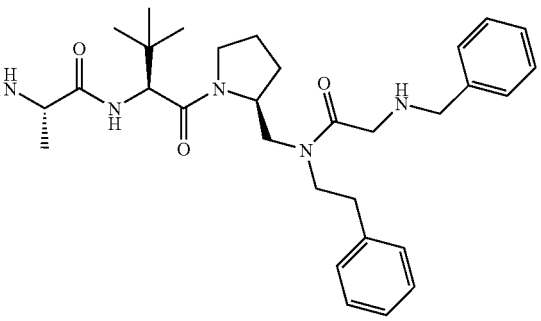
46
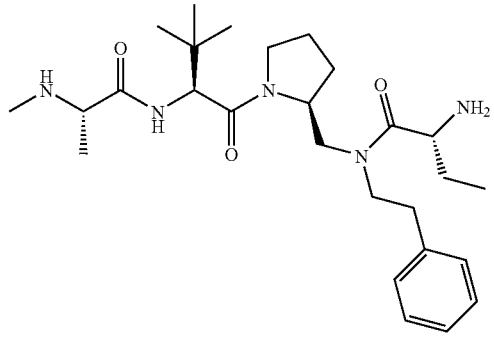

259
-continued
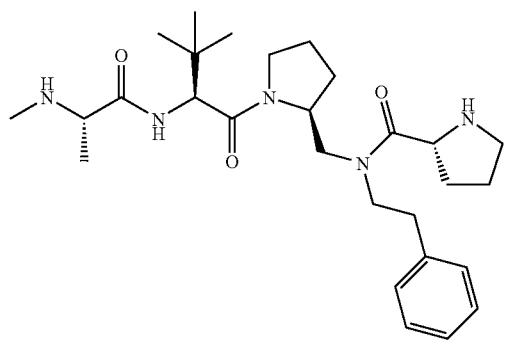
50
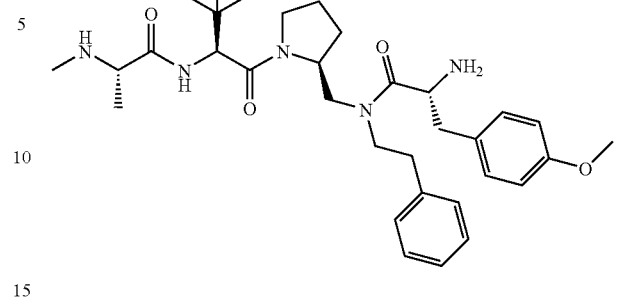
54
51
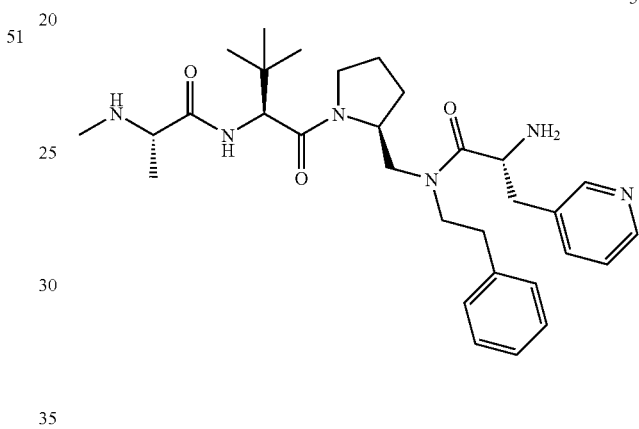
55
52
56
53
58
260
-continued 70
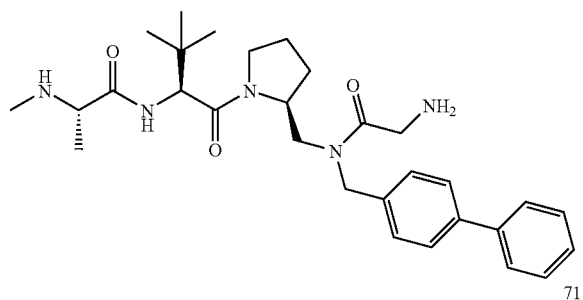
71
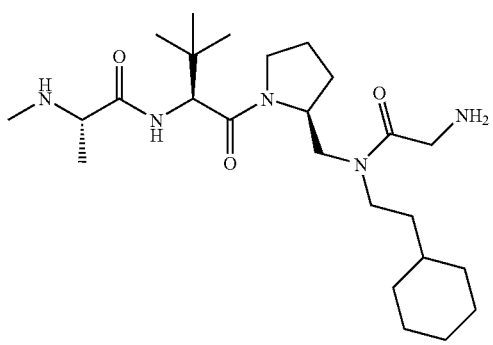
76
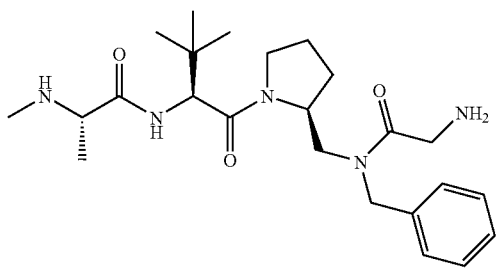
77
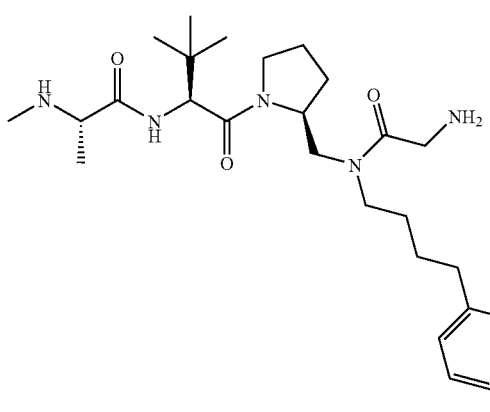
78
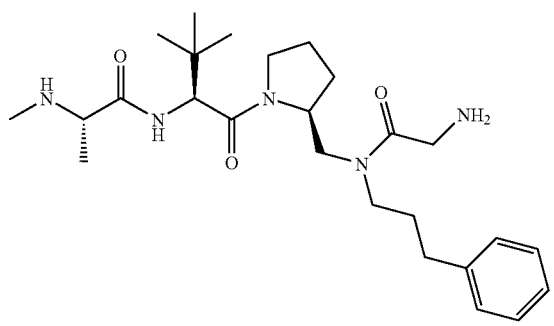
80
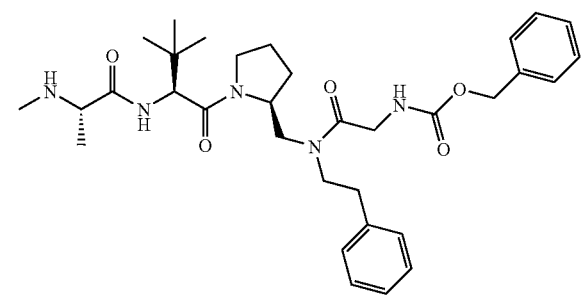
84
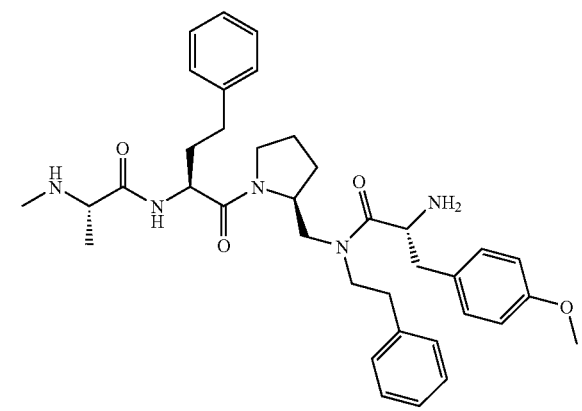
85
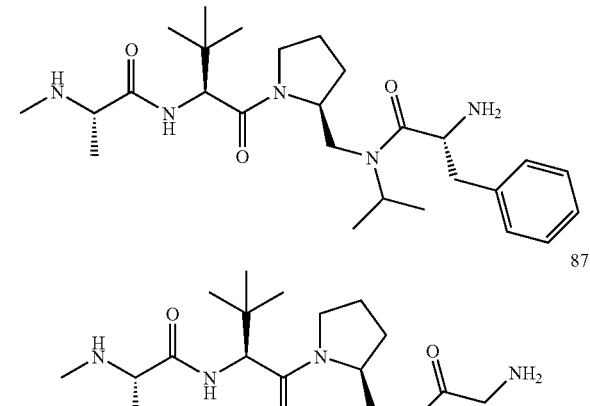
87
88
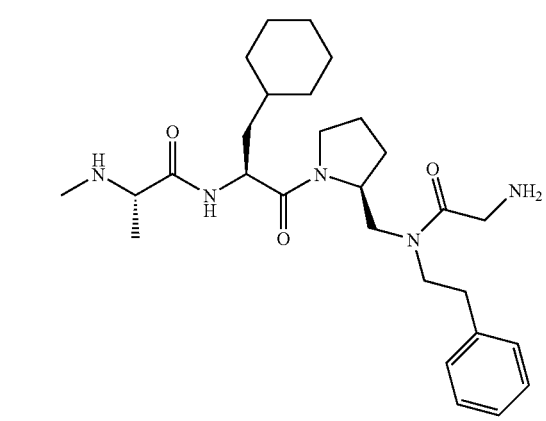

89
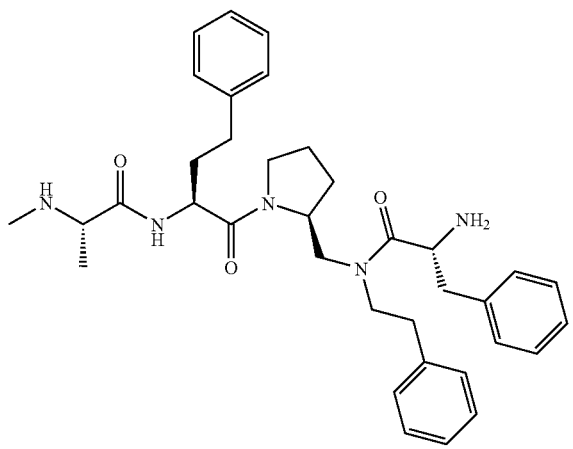
90
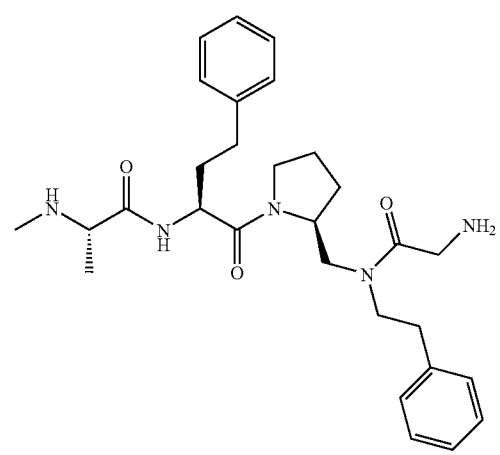
91
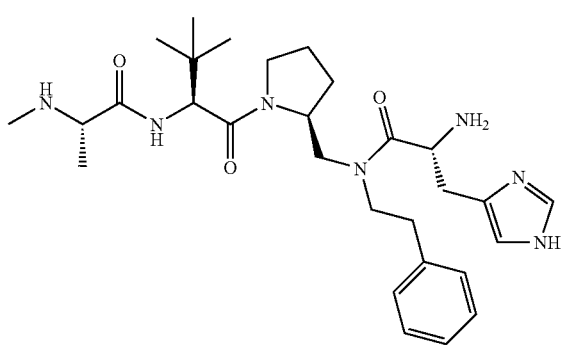
93
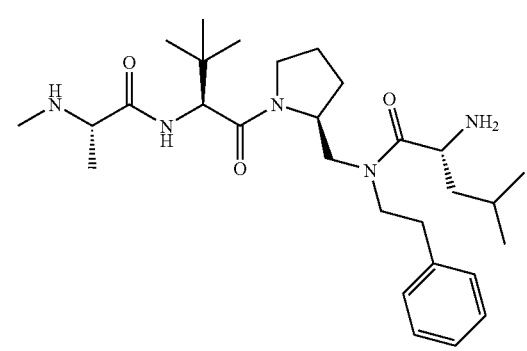
94
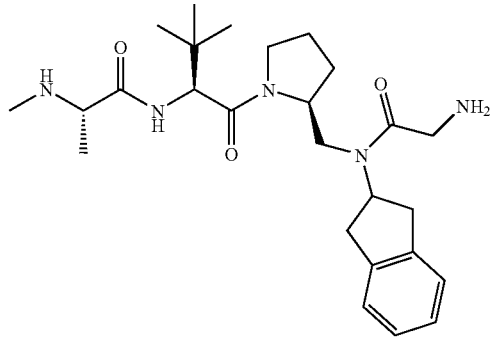
95
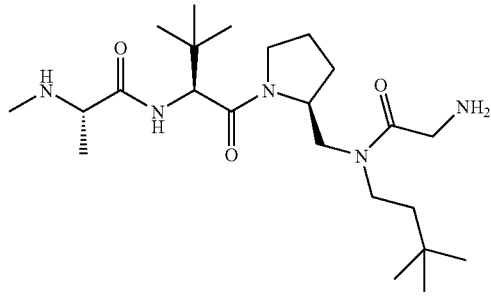
96
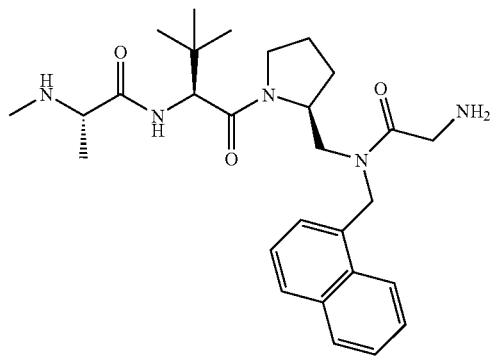
103
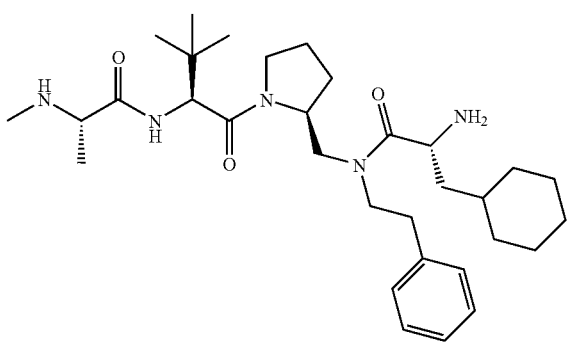

104
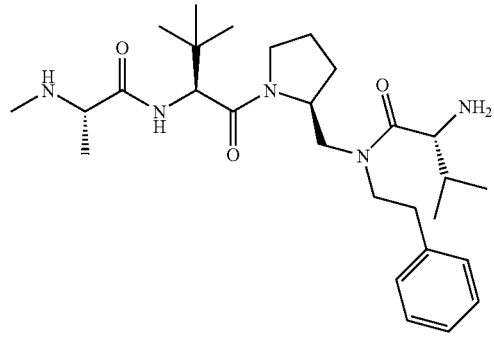
106
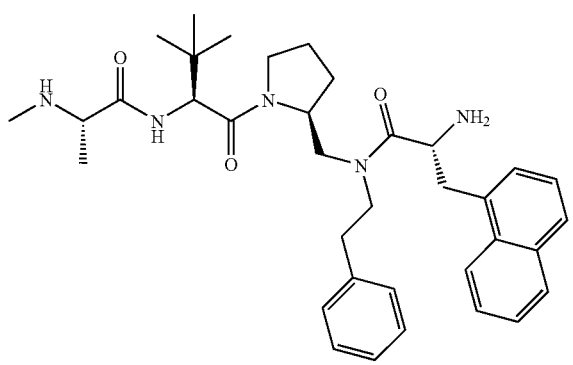
107
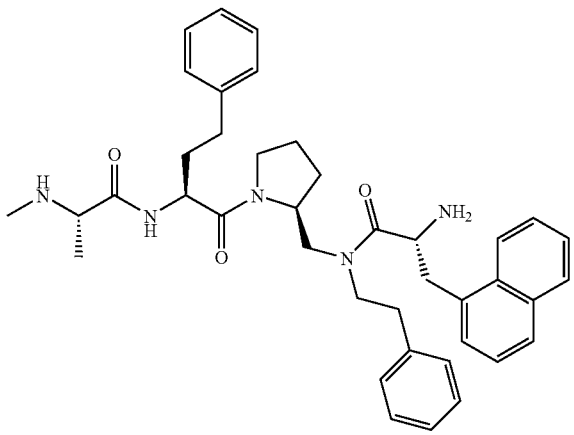
108
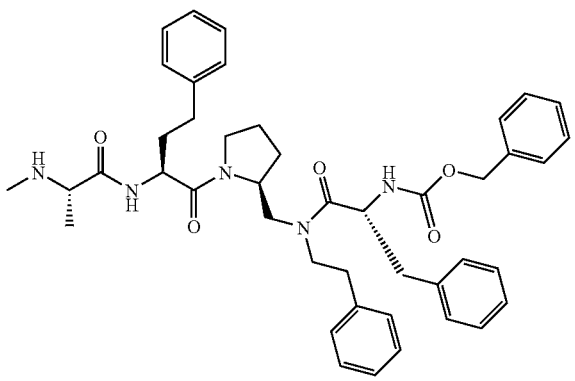
109
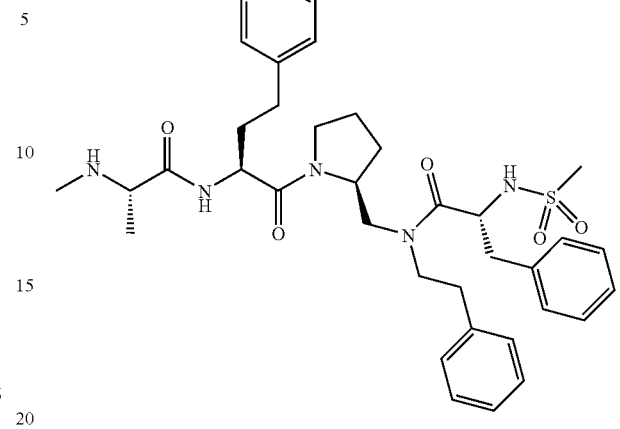
110
111
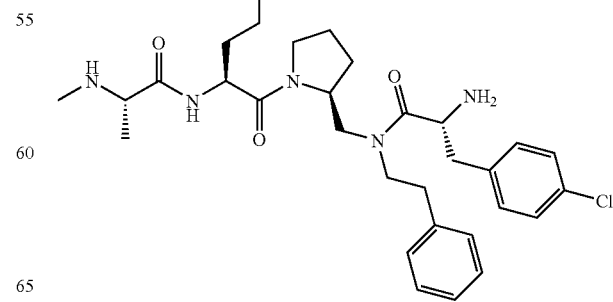

267
112
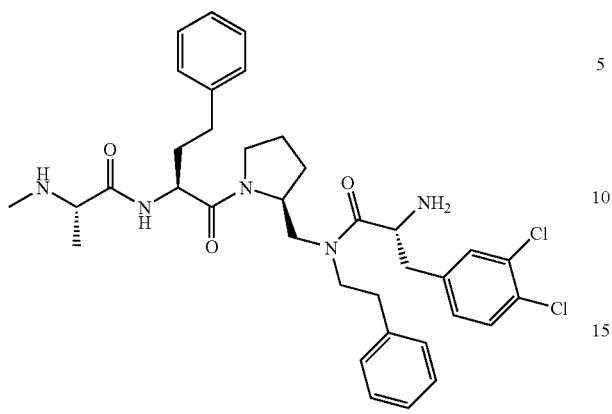
113
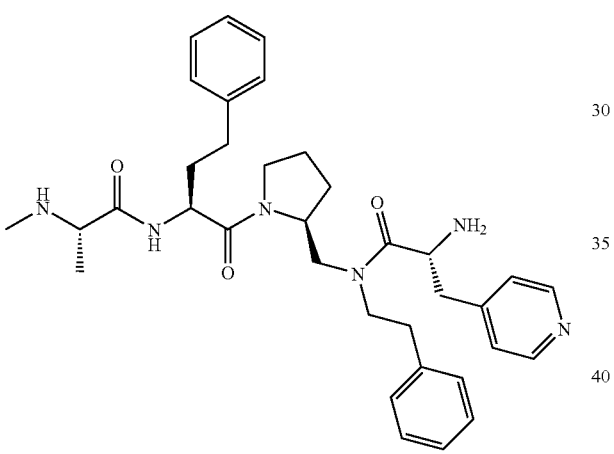
114
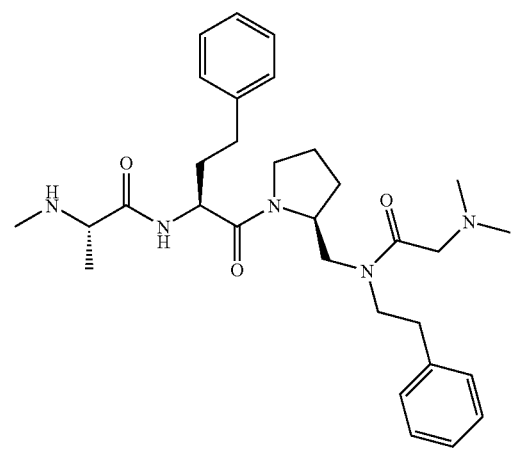
268
136
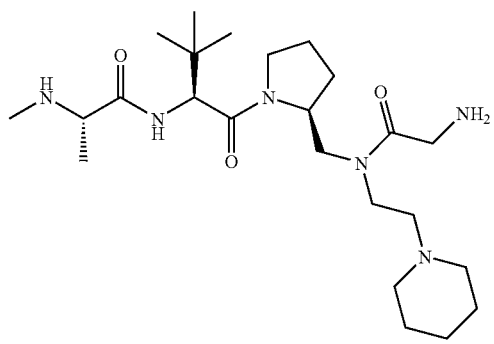
139
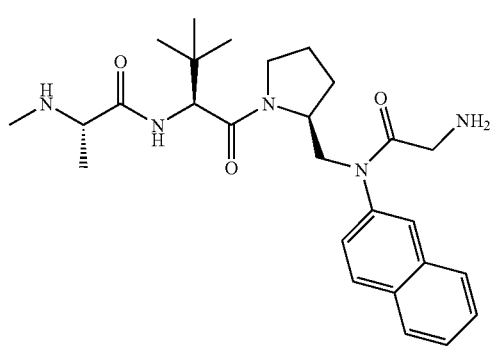
147
148
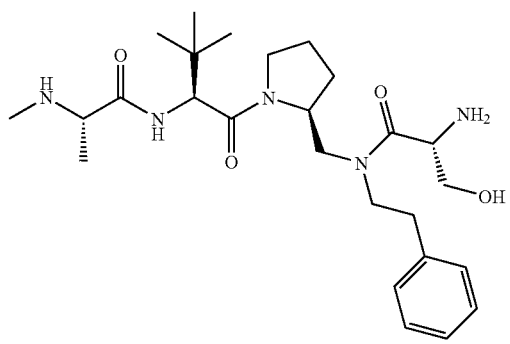

156
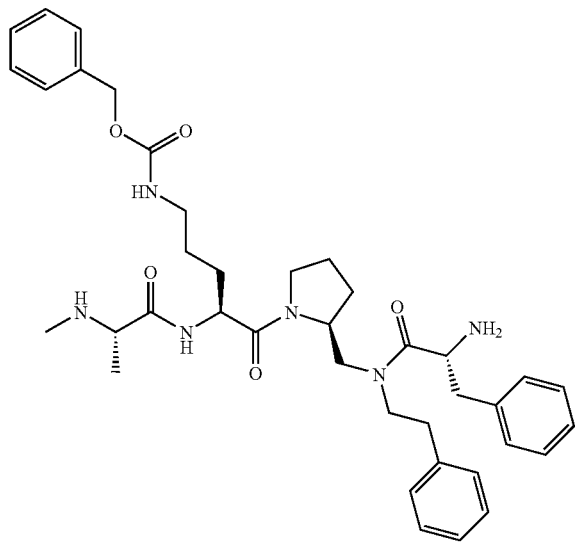
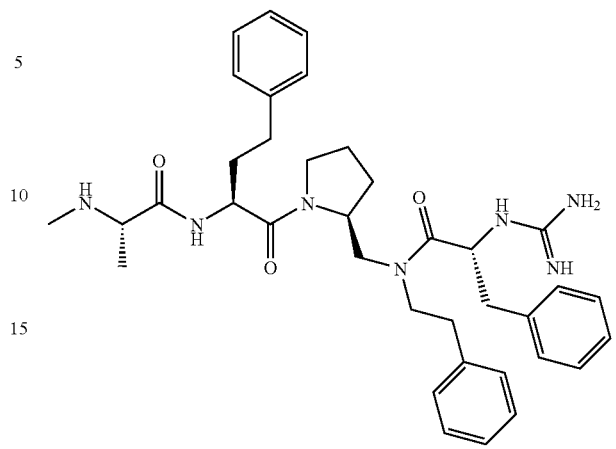
or a salt thereof.
23. The method of claim 1, wherein the compound is:
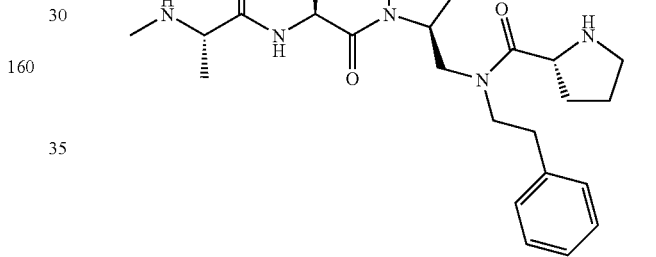
or
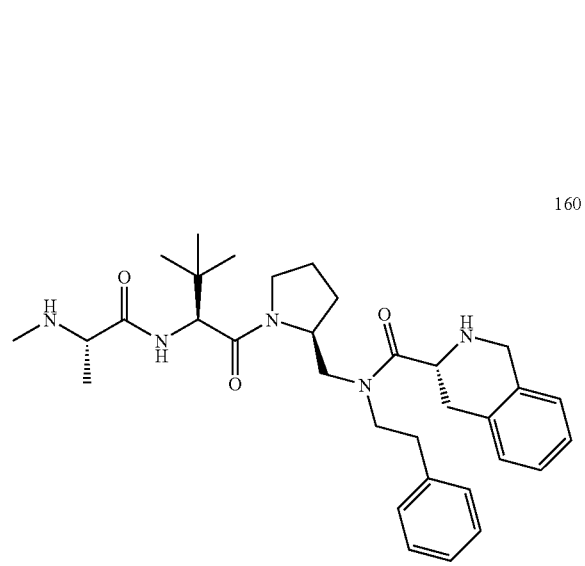
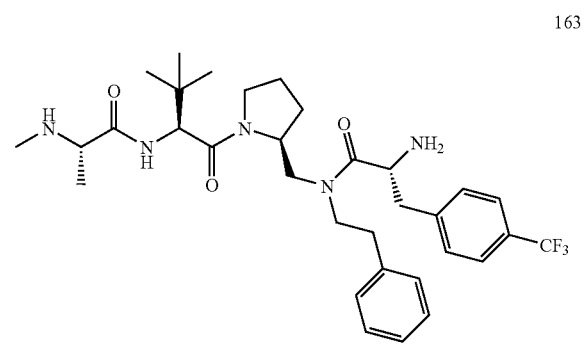
or a salt thereof.

24. The method of claim 1, wherein the compound is:
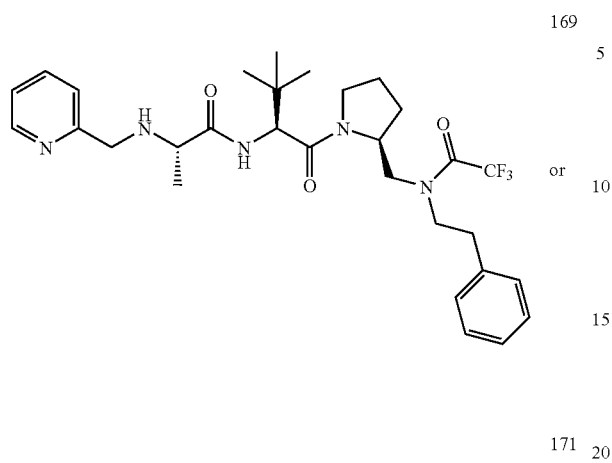
169
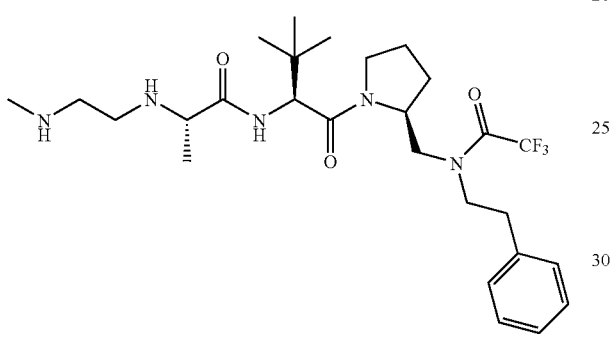
171
or a salt thereof.
25. The method of claim 1, wherein the compound is:
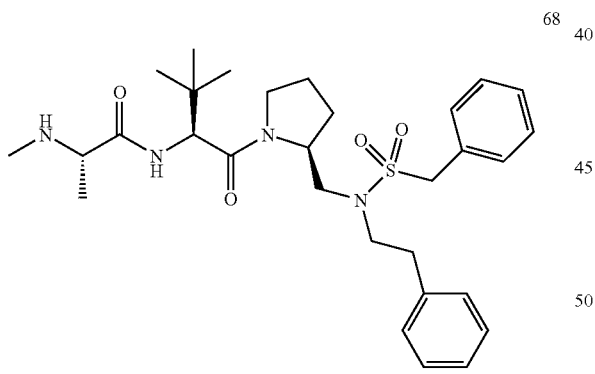
68
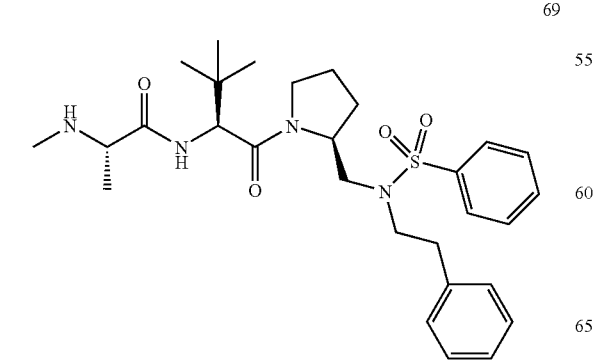
69
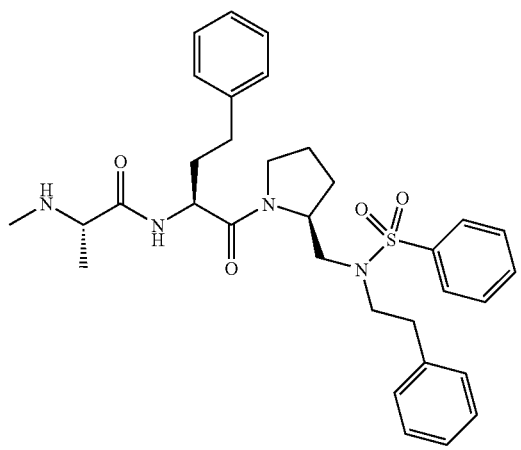
125
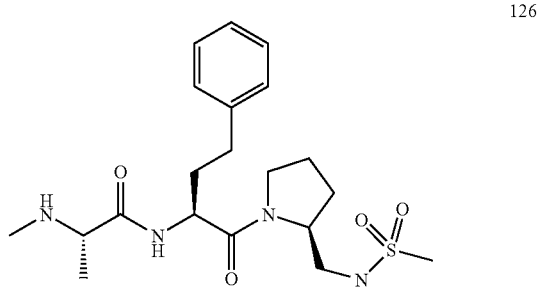
126
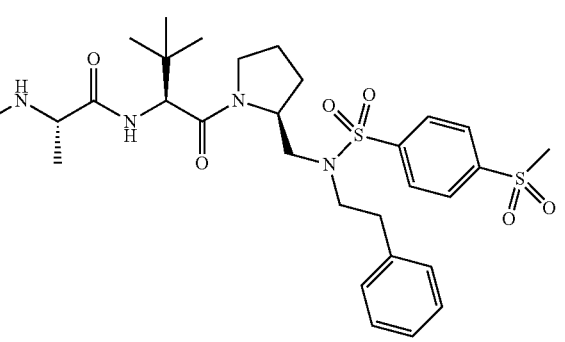
132

273
-continued
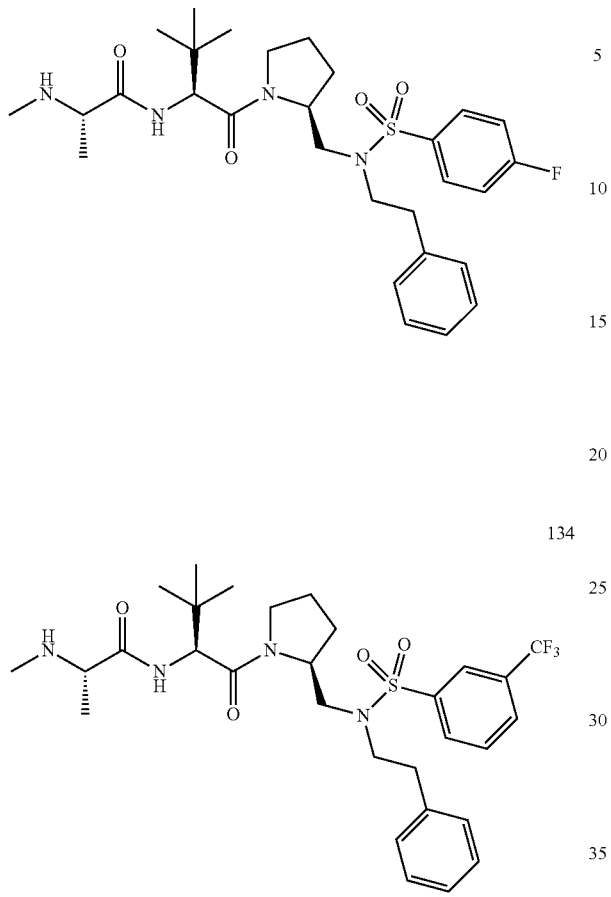
274
-continued
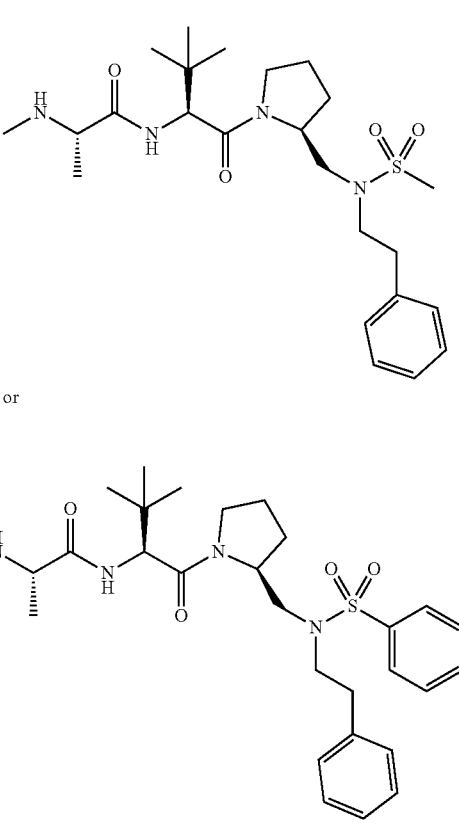
or a salt thereof.
* * * * *